US007579488B2

(12) United States Patent
Lu et al.

(10) Patent No.: US 7,579,488 B2
(45) Date of Patent: Aug. 25, 2009

(54) VITAMIN D RECEPTOR MODULATORS

(75) Inventors: Jianliang Lu, Fishers, IN (US); Tianwei Ma, Carmel, IN (US); Sunil Nagpal, Carmel, IN (US); Quanrong Shen, Fishers, IN (US); Alan M. Warshawsky, Carmel, IN (US); Jason Matthew Ochoada, Greenwood, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 250 days.

(21) Appl. No.: 10/579,563

(22) PCT Filed: Nov. 16, 2004

(86) PCT No.: PCT/US2004/035529

§ 371 (c)(1),
(2), (4) Date: May 12, 2006

(87) PCT Pub. No.: WO2005/051938

PCT Pub. Date: Jun. 9, 2005

(65) Prior Publication Data

US 2007/0106095 A1    May 10, 2007

Related U.S. Application Data

(60) Provisional application No. 60/523,905, filed on Nov. 20, 2003.

(51) Int. Cl.
*C07D 307/87* (2006.01)
*C07D 307/00* (2006.01)

(52) U.S. Cl. .................................... 549/462
(58) Field of Classification Search ............... 549/462, 549/469
See application file for complete search history.

(56) References Cited

U.S. PATENT DOCUMENTS

| | | | |
|---|---|---|---|
| 6,218,430 | B1 | 4/2001 | Allegretto et al. |
| 6,706,725 | B1 | 3/2004 | Bernardon |
| 2006/0094778 | A1 | 5/2006 | Nagpal et al. |
| 2006/0135484 | A1 | 6/2006 | Nagpal et al. |
| 2006/0287536 | A1 | 12/2006 | Dahnke et al. |
| 2006/0293385 | A1 | 12/2006 | Gajewski et al. |
| 2007/0105951 | A1 | 5/2007 | Gajewski et al. |
| 2007/0106095 | A1 | 5/2007 | Lu et al. |
| 2007/0149810 | A1 | 6/2007 | Lu et al. |
| 2007/0225377 | A1 | 9/2007 | Flatt et al. |

FOREIGN PATENT DOCUMENTS

| | | |
|---|---|---|
| WO | WO 2004/048309 | 6/2004 |
| WO | WO 2005/051893 | 6/2005 |
| WO | WO 2006/069153 | 6/2006 |
| WO | WO 2006/069154 | 6/2006 |

OTHER PUBLICATIONS

Roger Bouillion, et al., Structure-Function Relationships in the Vitamin D Endocrine System, Endocrine Review, Apr. 2005, pp. 200-257, vol. 16, No.2.

Marcus F. Boehm, et al, Novel nonsecpsteroidal vitamin D mimics exert VDR-modulating activities with less calcium mobilization than 1,25-dihydroxyvitamin $D_3$, Chemistry & Biology, 1999, pp. 265-275, vol. 6, No. 5.

Sunil Nagpal, et al., Vitamin D Analogs: Mechanism of Action and Therapeutic Applications, Current Medicinal Chemistry, 2001, pp. 1661-1679, vol. 8, No. 13.

Boehm, M. F. et al: "Novel Nonsecosteroidal Vitamin D Mimics Exert VDR-Modulating Activities With Less Calcium Mobilization Than 1, 25-Dihydroxyvitamin D3" Chemistry and Biology, Current Biology, London, GB, vol. 6, No. 5, Apr. 6, 1999, pp. 265-275, XP000852987.

Nagpal, S. et al: "Vitamin D Analogs: Mechanism of action and Therapeutic Applications" Current Medicinal Chemistry, Bentham Science Publishers BV, BE, vol. 8 No. 13, Nov. 2001, pp. 1661-1679, XP009003249.

Bouillon R., et al. Endocrine Rev. 1995, 200-257, vol. 16.

Masahiko Inouye, Toshiyuki Miyake, Masaru Furusyo, Hiroyuki Nakazumi: "Molecular recognition of beta-Ribofuranosides by synthetic polypyridine_macrocyclic receptors" J.Am. Chem. Soc. vol. 117, 1995, pp. 12416-12425, XP001206518.

Ping Huang, John Ramphal, James Wei, Congxin Liang, Bahija Jallal, Gerald McMahon and Cho Tang: "Structure-based design and discovery of novel inhibitors of protein tyrosine phosphatases" Bioorganic & Medicinal Chemistry, vol. 11, 2003, pp. 1835-1849, XP001206517.

Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.

Swann et al. "Structure-Based Design of Selective Agonists for a Rickets-Associated Mutant of the Vitamin D Receptor" *J. Am. Chem. Soc.* 2002 13795-13805, vol. 124.

Basak, et al., "Comparative effects of calcipotriol and betamethasone 17-valerate solution in the treatment of seborrhoeic dermatitis of the scalp," *European Academy of Dermatology and Venereology JEADV*, vol. 15, pp. 77-92 (2001).

Böhm, et al., "Disseminated superficial actinic porokeratosis: Treatment with topical tacalcitol," *Journal of the American Academy of Dermatology*, vol. 40, pp. 479-480 (1999).

Cunningham, et al., "Topical calcipotriene for morphea/linear scleroderma," *Journal of the American Academy of Dermatology*, vol. 39, pp. 211-215 (1998).

(Continued)

*Primary Examiner*—D. Margaret Seaman
*Assistant Examiner*—Nizal S Chandrakumar
(74) *Attorney, Agent, or Firm*—James B. Myers

(57) ABSTRACT

The present invention relates to novel, non-secosteroidal, phenyl-benzofuran compounds with vitamin D receptor (VDR) modulating activity that are less hypercalcemic than 1α,25 dihydroxy vitamin D3. These compounds are useful for treating bone disease and psoriasis.

17 Claims, No Drawings

OTHER PUBLICATIONS

Harrison, "Disseminated superficial actinic porokeratosis responding to calcipotriol," *Clinical Exp. Dermatol*, vol. 19, No. 1, p. 95 (1994).

Lin, et al., "The pleiotropic actions of vitamin D," *BioEssays*, vol. 26, pp. 21-28 (2003).

Sapadin, et al., "Treatment of Scleroderma," *Arch Dermatology*, vol. 138, pp. 99-105 (2002).

Sato, et al., "Epidermal Growth Factor and 1α,25-Dihydroxyvitamin $D_3$ Suppress Kipogenesis in Hamster Sebaceous Gland Cells In Vitro," *The Society of Investigative Dermatology*, vol. 117, pp. 965-970 (2001).

Zinser, et al., "Vitamin $D_3$ receptor ablation sensitizes skin to chemically induced tumorigenesis," *Carcinogenesis*, vol. 23, No. 12, pp. 2103-2109 (2002).

VITAMIN D RECEPTOR MODULATORS

This application is submitted as a United States national phase entry, pursuant to 35 U.S.C. §371, of PCT/US2004/035529, filed on 16 Nov. 2004, which claims the benefit of U.S. provisional patent application Ser. No. 60/523,905, filed 20 Nov. 2003, which is incorporated by reference herein.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,25(OH)$_2$D$_3$) acts upon a wide variety of tissues and cells both related to and unrelated to calcium and phosphate homeostasis.

The activity 1α,25-dihydroxyvitamin D3 in various systems suggests wide clinical applications. However, use of conventional VDR ligands is hampered by their associated toxicity, namely hypercalcemia (elevated serum calcium). Currently, 1α,25(OH)$_2$D$_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,25(OH)$_2$D$_3$) show increased separation of binding affinity on VDR from hypercalcemic activity.

Chemical modifications of 1α,25(OH)$_2$D$_3$ have yielded analogs with attenuated calcium mobilization effects (R. Bouillon et. al., Endocrine Rev. 1995, 16, 200-257). One such analog, Dovonex® (pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefits from VDR mediated biological activity is psoriasis. Psoriasis is one of the most common dermatologic diseases and is a chronic inflammatory skin condition characterized by erythematous, sharply demarcated papules and rounded plaques, covered by silvery micaceous scale.

Synthetic VDR ligands with reduced calcemic potential have been synthesized. For example, a class of bis-phenyl compounds stated to mimic 1α,25-dihydroxyvitamin $D_3$ is described in U.S. Pat. No. 6,218,430 and the article; "Novel nonsecosteroidal vitamin D mimics exert VDR-modulating activities with less calcium mobilization than 1α,25-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002.

There remains a need for improved treatments using alternative or improved pharmaceutical agents that mimic 1α,25-dihydroxyvitamin $D_3$ to stimulate bone formation, restore bone quality, and treat other diseases without the attendant disadvantage of hypercalcemia.

SUMMARY OF THE INVENTION

Novel compounds having a phenyl-benzofuran nucleus of Formula "(FP)", "(PF)", or (PF6) have been found effective as Vitamin D Receptor modulators (VDRM):

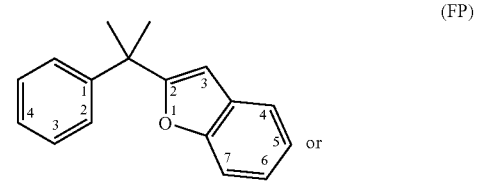

(FP)

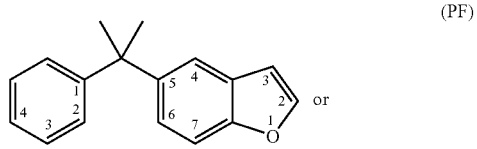

(PF)

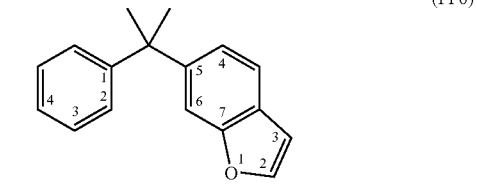

(PF6)

Compounds of the invention with VDR modulating activities are represented by formulae (IA)

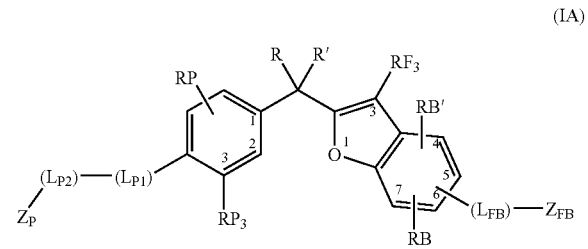

(IA)

wherein the variables R, R', RP, RP$_3$, L$_{P1}$, L$_{P2}$, Z$_P$, RB, RB', RF$_3$, L$_{FB}$ and Z$_{FB}$ are as hereinafter defined.

Compounds of the invention with VDR modulating activities are also represented by formulae (IB)

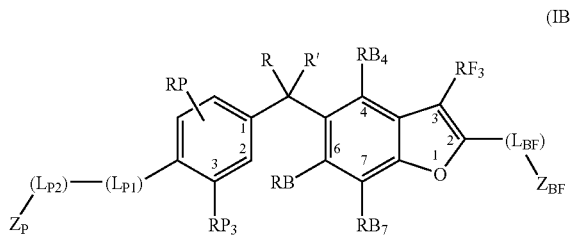
(IB)

wherein the variables R, R', RP, RP$_3$, L$_{P1}$, L$_{P2}$, Z$_P$, RB$_7$, RB, RB$_4$, RF$_3$, L$_{BF}$ and Z$_{BF}$ are as hereinafter defined.

Compounds of the invention with VDR modulating activities are also represented by formulae (IC)

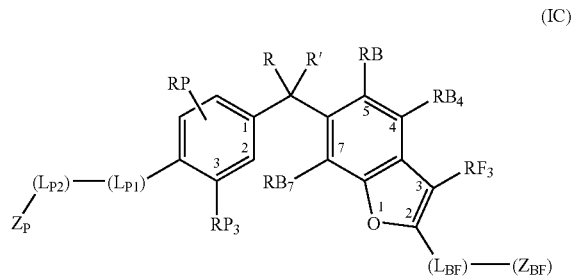
(IC)

wherein the variables R, R', RP, RP$_3$, L$_{P1}$, L$_{P2}$, Z$_P$, RB$_7$, RB, RB$_4$, RF$_3$, L$_{BF}$ and Z$_{BF}$ In another aspect, the present invention is directed towards pharmaceutical compositions containing pharmaceutically effective amounts of compounds of formulae IA, IB, IC or a pharmaceutically acceptable salt or a prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of formulae IA, IB, or IC alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of formulae IA, IB, or IC alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of formulae IA, IB, or IC alone or together with pharmaceutically effective amounts of co-agents conventionally used for the treatment of prostate cancer.

Another aspect of the invention is to use the compounds of formulae IA, IB, or IC to treat disease states responsive to Vitamin D receptor ligands.

Another aspect of the invention is the prevention and treatment of acne, actinic keratosis, alopecia, Alzheimer's disease, autoimmune induced diabetes, benign prostatic hyperplasia, bladder cancer, bone fracture healing, breast cancer, Crohn's disease, prostate cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, psoriasis, renal osteodystrophy, rheumatoid arthritis, scleroderma, seborrheic dermatitis, skin cancer, systemic lupus erythematosis, skin cell damage from Mustard vesicants, ulcerative colitis, and wrinkles, by administering to a mammal in need thereof a pharmaceutically effective amount of a compound of Formulae IA, IB, or IC.

DETAILED DESCRIPTION OF THE INVENTION

Definitions:

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound of the invention" refers to a compound represented by Formulae IA, IB, or IC or as set out as products of the Examples or synthesis schemes described herein.

The term, "Active Ingredient" means a compound of the invention.

The term, "Mustard" is inclusive of both sulfur mustards and nitrogen mustards, either alone or in any combination. Examplary of such compounds are the vesicants; bis(2-chloroethyl)sulfide (Chemical Agent Symbol HD), Cl(CH$_2$)$_2$S(CH$_2$)$_2$Cl 1,2-bis(2-chloroethylthio)ethane (Chemical Agent Symbol Q), Cl(CH$_2$)$_2$S(CH$_2$)$_2$S(CH$_2$)$_2$Cl; bis(2-chloroethylthioethyl)ether, Cl(CH$_2$)$_2$S(CH$_2$)$_2$O(CH$_2$)$_2$S(CH$_2$)$_2$Cl (Chemical Agent Symbol T); tris(2-chloroethyl)amine (Chemical Agent Symbol HN3) N(CH$_2$CH$_2$Cl)$_3$; N-methyl-2,2'-dichlorodiethylamine (Chemical Agent Symbol NH2); and 2,2'-dichlorotriethylamine, CH$_3$CH$_2$N(CH$_2$CH$_2$Cl)$_2$ (Chemical Agent Symbol NH1).

The term, "(Acidic Group)" means an organic group that acts as a proton donor capable of hydrogen bonding. Illustrative of an (Acidic Group) is a group selected from the following:

—C(O)OH,

-5-tetrazolyl,

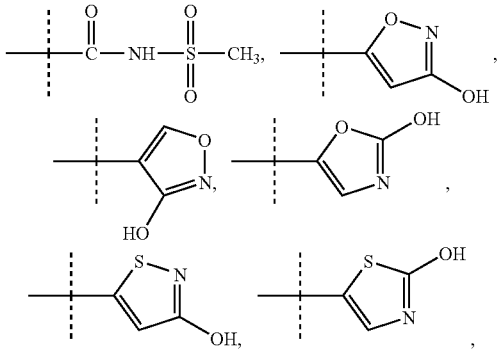

-continued

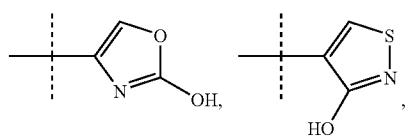

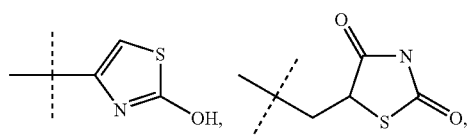

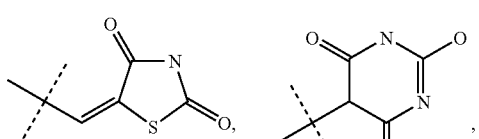

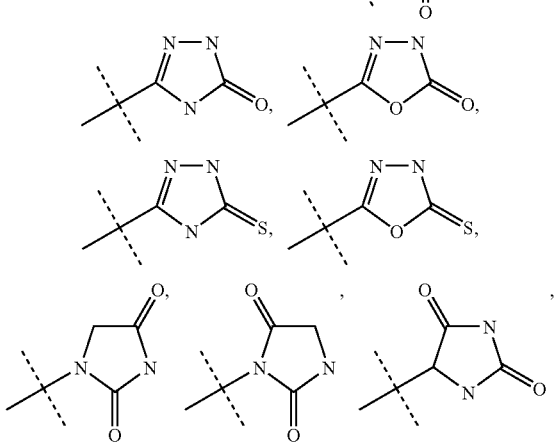

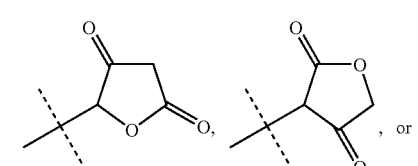

The term, "-1,3-thiazolidine-2,4-dione-5-ethylidene", refers to the radical represented by the structural formula:

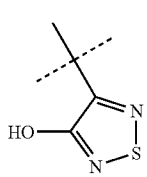

The term, "—CH₂—C(O)—N-pyrrolidine" refers to the radical represented by the structural formula:

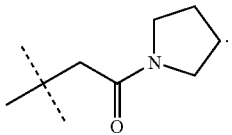

The term, "—CH₂—N-pyrrolidin-2-one" refers to the radical represented by the structural formula:

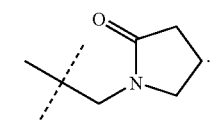

The term, "—CH₂-(1-methylpyrrolidin-2-one-3-yl)" refers to the organic radical represented by the structural formula:

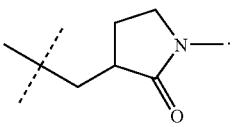

The term, "1,3,4-oxadiazolin-2-one-5-yl" refers to the organic radical represented by the structural formula:

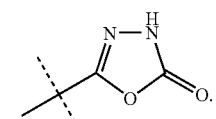

The term, "1,3,4-oxadiazolin-2-thione-5-yl" refers to the organic radical represented by the structural formula:

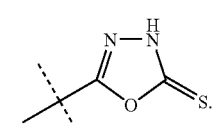

The term, "imidazolidine-2,4-dione-5-yl" refers to the organic radical represented by the structural formula:

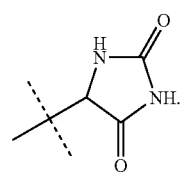

The term, "isoxazol-3-ol-5-yl" refers to the organic radical represented by the structural formula:

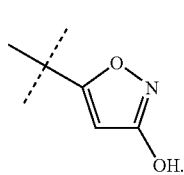

The dotted line symbol crossing a solid line representing a bond

means that the bond so marked is the bond of attachment.

The term, "mammal" includes humans.

The term "halo" refer to fluorine, chlorine, bromine, and iodine.

The term "sulfonate" refers to the group

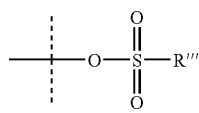

where R''' is $C_1$-$C_5$ alkyl, $C_1$-$C_5$ fluoroalkyl,

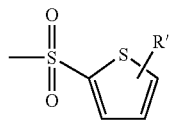

where R' is —$CO_2H$, —$CO_2R'''$, —OH, —$CF_3$, or $C_1$-$C_5$ alkyl.

The term "sulfonamide" refers to the group methyl, ethyl, branched $C_3$-$C_5$ alkyl,

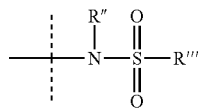

where R" is H, $C_1$-$C_5$ alkyl, $C_1$-$C_5$ fluoroalkyl, or

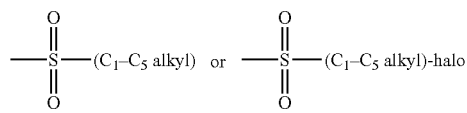

where R''' is $C_1$-$C_5$ alkyl, $C_1$-$C_5$ fluoroalkyl,

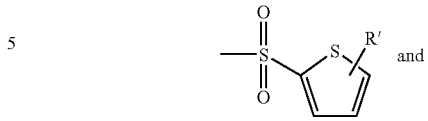

where R' is —CO2H, —CO2R''', —OH, —CF3, or $C_1$-$C_5$ alkyl.

The term, "$C_{1-3}$ alkyl" refers to an alkyl group selected from methyl, ethyl, n-propyl, and isopropyl.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl, ethyl, n-propyl, from 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The abbreviation, "Me" means methyl.

The abbreviation, "Et" means ethyl.

The abbreviation, "iPr" means 1-methylethyl.

The abbreviation, "tBu" means 1,1-dimethylethyl.

The term, "terminal hydroxyalkyl" is a group selected from 3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
1-hydroxycycloalkenyl; and
1-hydroxycycloalkyl.

The term, "3-methyl-3-hydroxypentyl" refers to the radical having the structural formula:

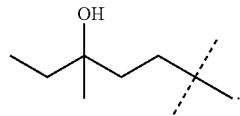

The term, "3-methyl-3-hydroxypentenyl" refers to the radical having the structural formula (both cis and trans isomers):

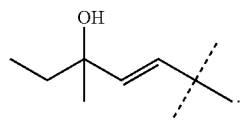

The term, "3-methyl-3-hydroxypentynyl" refers to the radical having the structural formula:

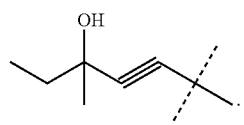

The term, "3-ethyl-3-hydroxypentyl" refers to the radical having the structural formula:

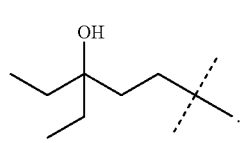

The term, "3-ethyl-3-hydroxypentenyl" refers to the radical having the structural formula (both cis and trans isomers):

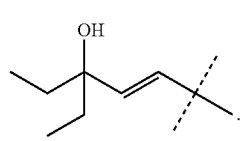

The term, "3-ethyl-3-hydroxypentynyl" refers to the radical having the structural formula:

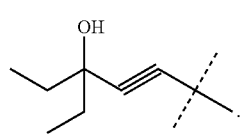

The term, "3-propyl-3-hydroxypentyl" refers to the radical having the structural formula:

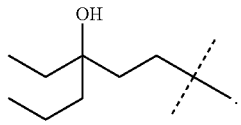

The term, "3-propyl-3-hydroxypentenyl" refers to the radical having the structural formula (both cis and trans isomers):

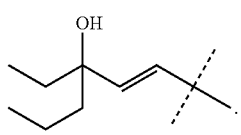

The term, "3-propyl-3-hydroxypentynyl" refers to the radical having the structural formula:

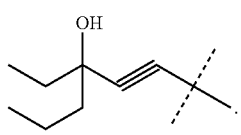

The term, "3-ethyl-3-hydroxy-4-methylpentyl" refers to the radical having the structural formula:

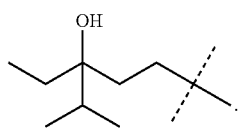

The term, "3-ethyl-3-hydroxy-4-methylpentenyl" refers to the radical having the structural formula (both cis and trans isomers):

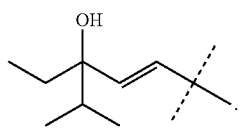

The term, "3-ethyl-3-hydroxy-4-methylpentynyl" refers to the radical having the structural formula:

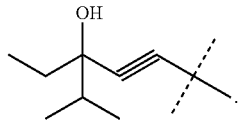

The term, "1-hydroxy-2-methyl-1-(methylethyl)propyl" refers to the radical having the structural formula:

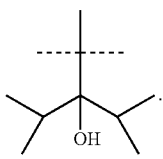

The term, "3-methyl-3-hydroxy-4,4-dimethylpentyl" refers to the radical having the structural formula:

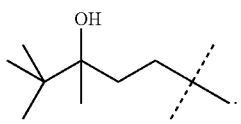

The term, "3-methyl-3-hydroxy-4,4-dimethylpentenyl." refers to the radical having the structural formula (both cis and trans isomers):

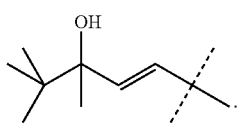

The term, "3-methyl-3-hydroxy-4,4-dimethylpentynyl" refers to the radical having the structural formula:

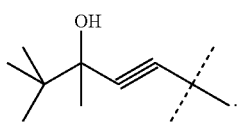

The term, "3-ethyl-3-hydroxy-4,4-dimethylpentyl" refers to the radical having the structural formula:

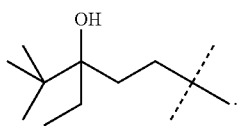

The term, "3-ethyl-3-hydroxy-4,4-dimethylpentenyl" refers to the radical having the structural formula (both cis and trans isomers):

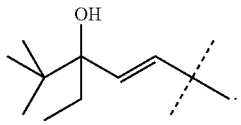

The term, "3-ethyl-3-hydroxy-4,4-dimethylpentynyl" refers to the radical having the structural formula:

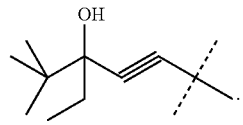

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

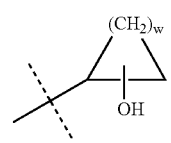

where w is an integer from 1 to 6 and the hydroxyl radical is substituted on any ring carbon atom.

The term "1-hydroxycycloalkyl" refers to a radical having the general structural formula:

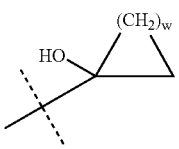

Examples of 1-hydroxycycloalkyl radicals are 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The abbreviation, "Me" means methyl.
The abbreviation, "Et" means ethyl.
The abbreviation, "iPr" means 1-methylethyl.
The abbreviation, "nPr" means n-propyl.
The abbreviation, "3Me3OH-Pentyl" means 3-methyl-3-hydroxypentyl.
The abbreviation, "3Me3OH-Pentenyl" means 3-methyl-3-hydroxypentenyl
The abbreviation, "3Me3OH-Pentynyl" means 3-methyl-3-hydroxypentynyl
The abbreviation, "3Et3OH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl
The abbreviation, "3Pr3OH-Pentyl" means 3-propyl-3-hydroxypentyl.
The abbreviation, "3Pr3OH-Pentenyl" means 3-propyl-3-hydroxypentenyl.
The abbreviation, "3Pr3OH-Pentynyl" means 3-propyl-3-hydroxypentynyl.
The abbreviation, "3Et3OH4Me-Pentyl" means 3-ethyl-3-hydroxy-4-methylpentyl.
The abbreviation, "3Et3OH4Me-Pentenyl" means 3-ethyl-3-hydroxy-4-methylpentenyl,
The abbreviation, "3Et3OH4Me-Pentynyl" means 3-ethyl-3-hydroxy-4-methylpentynyl.

The abbreviation, "1OH2Me1MeEt-Propyl" means 1-hydroxy-2-methyl-1-(methylethyl)propyl.

Compounds of the Invention:

The compounds of the invention with vitamin receptor modulating (VDRM) activity are represented by formula (IA) or a pharmaceutically acceptable salt or a prodrug derivative thereof:

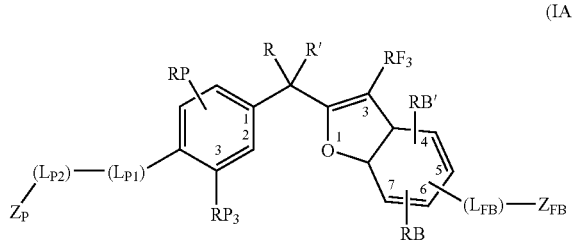

(IA)

wherein

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

$RP_3$ and RB are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

RP, $RP_3$, and RB' are independently selected from hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, or $C_3$-$C_5$ cycloalkenyl;

($L_{P1}$), ($L_{P2}$), and ($L_{FB}$) are divalent linking groups independently selected from the group consisting of

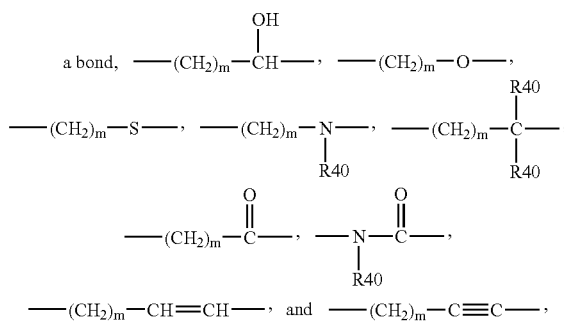

where m is 0, 1, or 2, and each R40 is independently hydrogen, $C_1$-$C_5$ alkyl, or $C_1$-$C_5$ fluoroalkyl;

$Z_P$ is
branched $C_3$-$C_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
1-hydroxycycopentenyl,
1-hydroxycyclohexenyl, 1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
2-oxocyclohexyloxy
2-oxocyclohexylmethyl
3-methyl-2-oxocyclohexyloxy
3-methyl-2-oxocyclohexylmethyl
3,3-dimethyl-2-oxocyclohexyloxy
3,3-dimethyl-2-oxocyclohexylmethyl
2-hydroxycyclohexyloxy
2-hydroxycyclohexylmethyl
3-methyl-2-hydroxycyclohexyloxy
3-methyl-2-hydroxycyclohexylmethyl
3,3-dimethyl-2-hydroxycyclohexyloxy
3,3-dimethyl-2-hydroxycyclohexylmethyl
1-hydroxycycloheptyl, or
1-hydroxycyclooctyl;

provided, however, that when
$Z_P$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl, or
1-hydroxy-2-methyl-1-(methylethyl)propyl;
   then ($L_{P1}$) and ($L_{P2}$) combine as a bond;

$Z_{FB}$ is selected from
—O—($C_1$-$C_5$ alkyl),
—O—($C_2$-$C_5$ alkenyl),
—O—($C_3$-$C_5$ cycloalkyl),
—O—($C_3$-$C_5$ cycloalkenyl), —O—(C$_1$-C$_5$ hydroxyalkyl),
—O—(C$_1$-C$_5$ fluoroalkyl),
—O—(C$_1$-C$_5$ alkyl)-phenyl,
—O—(C$_1$-C$_5$ alkyl)-(O)—(C$_1$-C$_5$ alkyl),
—O—(C$_1$-C$_5$ alkyl) NH$_2$,
—O—(C$_1$-C$_5$ alkyl)-NH—(C$_1$-C$_5$ alkyl)$_2$,
—O—(C$_1$-C$_5$ alkyl)-C(O)—NH$_2$,
—O—(C$_1$-C$_5$ alkyl)-C(O)—NH—(C$_1$-C$_5$ alkyl),
—O—(C$_1$-C$_5$ alkyl)-C(O)—N—(C$_1$-C$_5$ alkyl)$_2$,
—O—(C$_1$-C$_5$ alkyl)-C(O)—OH,
—O—(C$_1$-C$_5$ alkyl)-C(O)—NH-5-tetrazolyl,
—O—(C$_1$-C$_5$ alkyl)-C(O)—(C$_1$-C$_5$ alkyl),
—O—(C$_1$-C$_5$ alkyl)-C(O)—(O—C$_1$-C$_5$ alkyl),
—O—(C$_1$-C$_5$ alkyl)-NH$_2$,
—O—(C$_1$-C$_5$ alkyl)-NH—(C$_1$-C$_5$ alkyl),
—O—(C$_1$-C$_5$ alkyl)-N—(C$_1$-C$_5$ alkyl)$_2$,
—O—(C$_1$-C$_5$ alkyl)-NH—SO$_2$—(C$_1$-C$_5$ alkyl),
—O—(C$_1$-C$_5$ alkyl)-N-pyrrolidin-2-one,
—O—(C$_1$-C$_5$ alkyl)-N-pyrrolidine,
—O—(C$_1$-C$_5$ alkyl)-(1-methylpyrrolidin-2-one-3-yl),
—O—(C$_1$-C$_5$ alkyl)-SO$_2$—(C$_1$-C$_5$ alkyl,) —O—(C$_1$-C$_5$ alkyl)-SO$_2$—NH$_2$,
—O—(C$_1$-C$_5$ alkyl)-SO$_2$—NH—(C$_1$-C$_5$ alkyl),
—O—(C$_1$-C$_5$ alkyl)-SO$_2$—N—(C$_1$-C$_5$ alkyl)$_2$,
—O—(C$_1$-C$_5$ alkyl)-SO$_2$—(C$_1$-C$_5$ alkyl),
—O—(C$_1$-C$_5$ alkyl)-S(O)—(C$_1$-C$_5$ alkyl,) —O—(C$_1$-C$_5$ alkyl)-S(O)—NH$_2$,
—O—(C$_1$-C$_5$ alkyl)-S(O)—NH—(C$_1$-C$_5$ alkyl),
—O—(C$_1$-C$_5$ alkyl)-S(O)—N—(C$_1$-C$_5$ alkyl)$_2$,
—O—(C$_1$-C$_5$ alkyl)-S(O)—(C$_1$-C$_5$ alkyl),
—O—(C$_1$-C$_5$ alkyl)-P(O)—(O—C$_1$-C$_5$ alkyl)$_2$,
—O—(C$_1$-C$_5$ alkyl)-5-tetrazolyl,
—O—CH$_2$—CO$_2$H,
—O—CH$_2$-5-tetrazolyl,
—O—(C$_1$-C$_5$ alkyl),
—O—C(O)—NH$_2$,
—O—C(O)—N—(CH$_3$)$_2$,
—O—C(S)—N—(CH$_3$)$_2$,
—O—C(O)—O—(C$_1$-C$_5$ alkyl),
—O-(5-tetrazolyl),
—O—SO$_2$—(C$_1$-C$_5$ alkyl,)
—O—SO$_2$—NH$_2$,
—O—SO$_2$—NH—(C$_1$-C$_5$ alkyl),
—O—SO$_2$—N—(C$_1$-C$_5$ alkyl)$_2$,
—O—S(O)—(C$_1$-C$_5$ alkyl,)
—O—S(O)—NH$_2$,
—O—S(O)—NH—(C$_1$-C$_5$ alkyl),
—O—S(O)—N—(C$_1$-C$_5$ alkyl)$_2$,
—S—(C$_1$-C$_5$ alkyl),
—S—(C$_2$-C$_5$ alkenyl),
—S—(C$_3$-C$_5$ cycloalkyl),
—S—(C$_3$-C$_5$ cycloalkenyl),
—S—(C$_1$-C$_5$ fluoroalkyl),
—S—(C$_1$-C$_5$ hydroxyalkyl),
—S—(C$_1$-C$_5$ alkyl)-phenyl,
—S—(C$_1$-C$_5$ alkyl)-O—(C$_1$-C$_5$ alkyl),
—S—(C$_1$-C$_5$ alkyl)-C(O)—OH,
—S—(C$_1$-C$_5$ alkyl)-C(O)—(C$_1$-C$_5$ alkyl),
—S—(C$_1$-C$_5$ alkyl)-C(O)—O—(C$_1$-C$_5$ alkyl),
—S—(C$_1$-C$_5$ alkyl)-C(O)—NH$_2$,
—S—(C$_1$-C$_5$ alkyl)-C(O)—NH—(C$_1$-C$_5$ alkyl),
—S—(C$_1$-C$_5$ alkyl)-C(O)—N—(C$_1$-C$_5$ alkyl)$_2$,
—S—(C$_1$-C$_5$ alkyl) NH$_2$,
—S—(C$_1$-C$_5$ alkyl)-NH—(C$_1$-C$_5$ alkyl),
—S—(C$_1$-C$_5$ alkyl)-N—(C$_1$-C$_5$ alkyl)$_2$,
—S—(C$_1$-C$_5$ alkyl)-NH—SO$_2$—(C$_1$-C$_5$ alkyl),
—S—(C$_1$-C$_5$ alkyl)-N-pyrrolidin-2-one,
—S—(C$_1$-C$_5$ alkyl)-N-pyrrolidine,
—S—(C$_1$-C$_5$ alkyl)-(1-methylpyrrolidin-2-one-3-yl),
—S—(C$_1$-C$_5$ alkyl)-SO$_2$—(C$_1$-C$_5$ alkyl),
—S—(C$_1$-C$_5$ alkyl)-SO$_2$—NH$_2$,
—S—(C$_1$-C$_5$ alkyl)-SO$_2$—NH—(C$_1$-C$_5$ alkyl),
—S—(C$_1$-C$_5$ alkyl)-SO$_2$—N—(C$_1$-C$_5$ alkyl)$_2$,
—S—(C$_1$-C$_5$ alkyl)-SO$_2$—(C$_1$-C$_5$ alkyl),
—S—(C$_1$-C$_5$ alkyl)-P(O)—(O—C$_1$-C$_5$ alkyl)$_2$,
—S—(C$_1$-C$_5$ alkyl)-5-tetrazolyl,
—S—(C$_1$-C$_5$ alkyl)-S(O)—(C$_1$-C$_5$ alkyl),
—S—(C$_1$-C$_5$ alkyl)-S(O)—NH$_2$,
—S—(C$_1$-C$_5$ alkyl)-S(O)—NH—(C$_1$-C$_5$ alkyl),
—S—(C$_1$-C$_5$ alkyl)-S(O)—N—(C$_1$-C$_5$ alkyl)$_2$,
—S—(C$_1$-C$_5$ alkyl)-S(O)—(C$_1$-C$_5$ alkyl),
—SO$_2$—(C$_1$-C$_5$ alkyl),
—SO$_2$—(C$_2$-C$_5$ alkenyl),
—SO$_2$—(C$_3$-C$_5$ cycloalkyl),
—SO$_2$—(C$_3$-C$_5$ cycloalkenyl),
—SO$_2$—(C$_1$-C$_5$ hydroxyalkyl),
—SO$_2$—(C$_1$-C$_5$ fluoroalkyl),
—SO$_2$—(C$_1$-C$_5$)-phenyl,
—SO$_2$—NH$_2$,
—SO$_2$—NH—(C$_1$-C$_5$ alkyl),
—SO$_2$—NH—CH$_2$—C(O)OH,
—SO$_2$—NH—CH$_2$—C(O)(O—C$_1$-C$_5$ alkyl),
—SO$_2$—NH—(C$_1$-C$_5$ alkyl)-C(O)OH,
—SO$_2$—NH—(C$_1$-C$_5$ alkyl)-C(O)(O—C$_1$-C$_5$ alkyl),
—SO$_2$—NHC(O)—(C$_3$-C$_6$ cycloalkyl),
—SO$_2$—NH—C(O)—(C$_1$-C$_5$ alkyl),
—SO$_2$—N—(C$_1$-C$_5$ alkyl)$_2$,
—SO$_2$—(C$_1$-C$_5$ alkyl)-O—(C$_1$-C$_5$ alkyl),
—SO$_2$—(C$_1$-C$_5$ alkyl)-C(O)—(C$_1$-C$_5$ alkyl),
—SO$_2$—(C$_1$-C$_5$ alkyl) NH$_2$,
—SO$_2$—(C$_1$-C$_5$ alkyl)-NH—(C$_1$-C$_5$ alkyl),
—SO$_2$—(C$_1$-C$_5$ alkyl)-N—(C$_1$-C$_5$ alkyl)$_2$,
—SO$_2$—(C$_1$-C$_5$ alkyl)-C(O)—NH$_2$,
—SO$_2$—(C$_1$-C$_5$ alkyl)-C(O)—NH—(C$_1$-C$_5$ alkyl),
—SO$_2$—(C$_1$-C$_5$ alkyl)-C(O)—N—(C$_1$-C$_5$ alkyl)$_2$,
—SO$_2$—(C$_1$-C$_5$ alkyl)-NH—SO$_2$—(C$_1$-C$_5$ alkyl),
—SO$_2$—(C$_1$-C$_5$ alkyl)-N-pyrrolidin-2-one,
—SO$_2$—(C$_1$-C$_5$ alkyl)-N-pyrrolidine,
—SO$_2$—(C$_1$-C$_5$ alkyl)-(1-methylpyrrolidin-2-one-3-yl),
—SO$_2$—(C$_1$-C$_5$ alkyl)-C(O)—O—(C$_1$-C$_5$ alkyl),
—SO$_2$—(C$_1$-C$_5$ alkyl)-C(O)—OH,
—SO$_2$—(C$_1$-C$_5$ alkyl)-5-tetrazolyl,
—SO$_2$—(C$_1$-C$_5$ alkyl)-SO$_2$—(C$_1$-C$_5$ alkyl),
—SO$_2$—(C$_1$-C$_5$ alkyl)-SO$_2$—NH$_2$,
—SO$_2$—(C$_1$-C$_5$ alkyl)-SO$_2$—NH—(C$_1$-C$_5$ alkyl),
—SO$_2$—(C$_1$-C$_5$ alkyl)-SO$_2$—N—(C$_1$-C$_5$ alkyl)$_2$,
—SO$_2$—(C$_1$-C$_5$ alkyl)-SO$_2$—(C$_1$-C$_5$ alkyl),
—SO$_2$—(C$_1$-C$_5$ alkyl)-P(O)—(O—C$_1$-C$_5$ alkyl)$_2$,
—SO$_2$—(C$_1$-C$_5$ alkyl),
—SO$_2$—(C$_2$-C$_5$ alkenyl),
—SO$_2$—(C$_3$-C$_5$ cycloalkyl),
—SO$_2$—(C$_3$-C$_5$ cycloalkenyl),
—SO$_2$—(C$_1$-C$_5$ hydroxyalkyl),
—SO$_2$—(C$_1$-C$_5$ fluoroalkyl),
—SO$_2$—(C$_1$-C$_5$)-phenyl,
—SO$_2$—N=CHN(C$_1$-C$_5$ alkyl)$_2$,
—S(O)—NH$_2$,
—S(O)—NH—(C$_1$-C$_5$ alkyl),
—S(O)—NH—CH$_2$—C(O)OH  —S(O)—NH—(C$_1$-C$_5$ alkyl)-C(O)OH,
—S(O)—NH—CH$_2$—C(O)(O—C$_1$-C$_5$ alkyl),
—S(O)—NH—(C$_1$-C$_5$ alkyl)-C(O)(O—C$_1$-C$_5$ alkyl),
—S(O)HC(O)—(C$_3$-C$_6$ cycloalkyl),
—S(O)—NH—C(O)—(C$_1$-C$_5$ alkyl), —S(O)—N—(C$_1$-C$_5$ alkyl)$_2$,
—S(O)—(C$_1$-C$_5$ alkyl)-O—(C$_1$-C$_5$ alkyl),
—S(O)—(C$_1$-C$_5$ alkyl)-C(O)—(C$_1$-C$_5$ alkyl),
—S(O)(C$_1$-C$_5$ alkyl)-C(O)—(O—C$_1$-C$_5$ alkyl),
—S(O)—(C$_1$-C$_5$ alkyl)-NH—(C$_1$-C$_5$ alkyl),
—S(O)—(C$_1$-C$_5$ alkyl)-N—(C$_1$-C$_5$ alkyl)$_2$,
—S(O)—(C$_1$-C$_5$ alkyl)-C(O)—NH$_2$,
—S(O)—(C$_1$-C$_5$ alkyl)-C(O)—NH—(C$_1$-C$_5$ alkyl),
—S(O)—(C$_1$-C$_5$ alkyl)-C(O)—N—(C$_1$-C$_5$ alkyl)$_2$,
—S(O)—(C$_1$-C$_5$ alkyl)-NH—SO$_2$—(C$_1$-C$_5$ alkyl),
—S(O)—(C$_1$-C$_5$ alkyl)-NH—S(O)—(C$_1$-C$_5$ alkyl),
—S(O)—(C$_1$-C$_5$ alkyl)-N-pyrrolidin-2-one,
—S(O)—(C$_1$-C$_5$ alkyl)-N-pyrrolidine,
—S(O)—(C$_1$-C$_5$ alkyl)-(1-methylpyrrolidin-2-one-3-yl),
—S(O)—(C$_1$-C$_5$ alkyl)-C(O)—(O—C$_1$-C$_5$ alkyl),
—S(O)—(C$_1$-C$_5$ alkyl)-C(O)—OH,
—S(O)—(C$_1$-C$_5$ alkyl)-5-tetrazolyl,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-SO$_2$—NH$_2$,
—S(O)—(C$_1$-C$_5$ alkyl)-S(O)—NH$_2$,
—S(O)—(C$_1$-C$_5$ alkyl)-SO$_2$—NH—(C$_1$-C$_5$ alkyl),
—S(O)—(C$_1$-C$_5$ alkyl)-S(O)—NH—(C$_1$-C$_5$ alkyl),
—S(O)—(C$_1$-C$_5$ alkyl)-SO$_2$—N—(C$_1$-C$_5$ alkyl)$_2$,
—S(O)—(C$_1$-C$_5$ alkyl)-S(O)—N—(C$_1$-C$_5$ alkyl)$_2$,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-P(O)—(O—C$_1$-C$_5$ alkyl)$_2$,
—S(O)—N=CHN(C$_1$-C$_5$ alkyl)$_2$,
—NHC(S)NH$_2$,
—NHC(S)NH—(C$_1$-C$_5$ alkyl),
—NHC(S)N—(C$_1$-C$_5$ alkyl)$_2$,
—NHC(S)NH—(C$_2$-C$_5$ alkenyl),
—NHC(S)NH—(C$_3$-C$_5$ cycloalkyl),
—NHC(S)NH—(C$_3$-C$_5$ cycloalkenyl),
—NHC(S)NH—(C$_1$-C$_5$ fluoroalkyl),
—NHC(S)NH—C$_1$-C$_5$ hydroxyalkyl,
—NHC(S)NH—C$_1$-C$_5$ fluoroalkyl),
—NHC(S)NH-phenyl,
—NHC(S)NH—(C$_1$-C$_5$ alkyl)-C(O)—OH,
—NHC(S)NH—(C$_1$-C$_5$ alkyl)-O—(C$_1$-C$_5$ alkyl),
—NHC(S)NH—(C$_1$-C$_5$ alkyl)-C(O)—(C$_1$-C$_5$ alkyl),
—NHC(S)NH—(C$_1$-C$_5$ alkyl)-C(O)—(O—C$_1$-C$_5$ alkyl),
—NHC(S)NH—(C$_1$-C$_5$ alkyl)-NH$_2$,
—NHC(S)NH—(C$_1$-C$_5$ alkyl)-NH—(C$_1$-C$_5$ alkyl),
—NHC(S)NH—(C$_1$-C$_5$ alkyl)-N—(C$_1$-C$_5$ alkyl)$_2$,
—NHC(S)NH—(C$_1$-C$_5$ alkyl)-C(O)—NH$_2$,
—NHC(S)NH—(C$_1$-C$_5$ alkyl)-C(O)—NH—(C$_1$-C$_5$ alkyl),
—NHC(S)NH—(C$_1$-C$_5$ alkyl)-C(O)—N—(C$_1$-C$_5$ alkyl)$_2$,
—NHC(S)NH—(C$_1$-C$_5$ alkyl)-NH—SO$_2$—(C$_1$-C$_5$ alkyl),
—NHC(S)NH—(C$_1$-C$_5$ alkyl)-NH—S(O)—(C$_1$-C$_5$ alkyl),
—NHC(S)NH—(C$_1$-C$_5$ alkyl)-N-pyrrolidin-2-one,
—NHC(S)NH—(C$_1$-C$_5$ alkyl)-N-pyrrolidine,
—NHC(S)NH—(C$_1$-C$_5$ alkyl)-(1-methylpyrrolidin-2-one-3-yl),
—NHC(S)NH—(C$_1$-C$_5$ alkyl)-5-tetrazolyl,
—NHC(S)NH—(C$_1$-C$_5$ alkyl)-SO$_2$—(C$_1$-C$_5$ alkyl),
—NHC(S)NH—(C$_1$-C$_5$ alkyl)-SO$_2$—NH$_2$,
—NHC(S)NH—(C$_1$-C$_5$ alkyl)-SO$_2$—NH—(C$_1$-C$_5$ alkyl),
—NHC(S)NH—(C$_1$-C$_5$ alkyl)-SO$_2$—N—(C$_1$-C$_5$ alkyl)$_2$,
—NHC(S)NH—(C$_1$-C$_5$ alkyl)-S(O)—(C$_1$-C$_5$ alkyl),
—NHC(S)NH—(C$_1$-C$_5$ alkyl)-S(O)—NH$_2$,
—NHC(S)NH—(C$_1$-C$_5$ alkyl)-S(O)—NH—(C$_1$-C$_5$ alkyl),
—NHC(S)NH—(C$_1$-C$_5$ alkyl)-S(O)—N—(C$_1$-C$_5$ alkyl)$_2$,
—NHC(S)NH—(C$_1$-C$_5$ alkyl)-P(O)—(O—C$_1$-C$_5$ alkyl)$_2$,
—NHC(O)NH$_2$,
—NHC(O)NH—(C$_1$-C$_5$ alkyl),
—NHC(O)N—(C$_1$-C$_5$ alkyl)$_2$,
—NHC(O)NH—(C$_2$-C$_5$ alkenyl),
—NHC(O)NH—(C$_3$-C$_5$ cycloalkyl),
—NHC(O)NH—(C$_3$-C$_5$ cycloalkenyl),
—NHC(O)NH—(C$_1$-C$_5$ hydroxyalkyl),
—NHC(O)NH—(C$_1$-C$_5$ fluoroalkyl),
—NHC(O)NH-phenyl,
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-O—(C$_1$-C$_5$ alkyl),
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C1-C$_5$ alkyl)$_2$,
—NHC(O)NH—(C$_1$-C$_5$ alkyl)-C(O)—NH$_2$,
—NHC(O)NH—(C$_1$-C$_5$ alkyl)-C(O)—NH—(C$_1$-C$_5$ alkyl),
—NHC(O)NH—(C$_1$-C$_5$ alkyl)-C(O)—N—(C$_1$-C$_5$ alkyl)$_2$,
—NHC(O)NH—(C$_1$-C$_5$ alkyl)-C(O)—(C$_1$-C$_5$ alkyl),
—NHC(O)NH—(C$_1$-C$_5$ alkyl)-NH—SO$_2$—(C$_1$-C$_5$ alkyl),
—NHC(O)NH—(C$_1$-C$_5$ alkyl)-N-pyrrolidin-2-one,
—NHC(O)NH—(C$_1$-C$_5$ alkyl)-N-pyrrolidine,
—NHC(O)NH—(C$_1$-C$_5$ alkyl)-(1-methylpyrrolidin-2-one-3-yl),
—NHC(O)NH—(C$_1$-C$_5$ alkyl)-C(O)—OH,
—NHC(O)NH—(C$_1$-C$_5$ alkyl)-C(O)—O—(C$_1$-C$_5$ alkyl),
—NHC(O)NH—(C$_1$-C$_5$ alkyl)-5-tetrazolyl,
—NHC(O)NH—(C$_1$-C$_5$ alkyl)-SO$_2$—(C$_1$-C$_5$ alkyl),
—NHC(O)NH—(C$_1$-C$_5$ alkyl)-SO$_2$—NH$_2$,
—NHC(O)NH—(C$_1$-C$_5$ alkyl)-SO$_2$—NH—(C$_1$-C$_5$ alkyl),
—NHC(O)NH—(C$_1$-C$_5$ alkyl)-SO$_2$—N—(C$_1$-C$_5$ alkyl)$_2$,
—NHC(O)NH—(C$_1$-C$_5$ alkyl)-P(O)—O—(C$_1$-C$_5$ alkyl)$_2$,
—NH$_2$,
—NH—(C$_1$-C$_5$ alkyl),
—NH—CH$_2$—C(O)OH,
—N—(C$_1$-C$_5$ alkyl)$_2$,
—NH—C(O)—NH$_2$,
—NH—C(O)—NH—(C$_1$-C$_5$ alkyl),
—NH—C(O)—N—(C$_1$-C$_5$ alkyl)$_2$,
—NH—C(O)—(C$_1$-C$_5$ alkyl),
—NH—SO$_2$—(C$_1$-C$_5$ alkyl),
—NH—S(O)—(C$_1$-C$_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me,
—C(O)CH$_2$CH$_2$S(O)Et,
—C(O)CH$_2$CH$_2$S(O)$_2$Me,
—C(O)CH$_2$CH$_2$S(O)$_2$Et,
—C(O)CH(Me)CH$_2$CO$_2$H,
—C(O)CH(Me)CH$_2$CO$_2$Me,
—C(O)CH(Me)CH$_2$CO$_2$Et,
—C(O)CH(Me)CH$_2$CO$_2$iPr,
—C(O)CH(Me)CH$_2$CO$_2$tBu,
—C(O)CH(Me)CH(Me)CO$_2$H,
—C(O)CH(Me)CH(Me)CO$_2$Me,
—C(O)CH(Me)CH(Me)CO$_2$Et,
—C(O)CH(Me)CH(Me)CO$_2$iPr,
—C(O)CH(Me)CH(Me)CO$_2$tBu, —C(O)CH(Me)C(Me)₂CO₂H,
—C(O)CH(Me)C(Me)₂CO₂Me,
—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H,
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr, —C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me, —CH$_2$CH$_2$CO$_2$Et,
—CH$_2$CH$_2$C(O)NH$_2$,
—CH$_2$CH$_2$C(O)NHMe,
—CH$_2$CH$_2$C(O)NMe$_2$,
—CH$_2$CH$_2$-5-tetrazolyl,
—CH$_2$CH$_2$S(O)$_2$Me,
—CH$_2$CH$_2$S(O)Me,
—CH$_2$CH$_2$S(O)$_2$Et,
—CH$_2$CH$_2$S(O) Et,
—CH$_2$CH$_2$S(O)iPr,
—CH$_2$CH$_2$S(O)$_2$iPr,
—CH$_2$CH$_2$S(O)tBu,
—CH$_2$CH$_2$S(O)$_2$tBu,
—CH$_2$CH$_2$S(O)NH$_2$,
—CH$_2$CH$_2$S(O)NHMe,
—CH$_2$CH$_2$S(O)NMe$_2$,
—CH$_2$CH$_2$S(O)$_2$NH$_2$,
—CH$_2$CH$_2$S(O)$_2$NHMe,
—CH$_2$CH$_2$S(O)$_2$NMe$_2$,
—CH$_2$CH$_2$CH$_2$S(O)Me,
—CH$_2$CH$_2$CH$_2$S(O)Et,
—CH$_2$CH$_2$CH$_2$S(O)$_2$Me,
—CH$_2$CH$_2$CH$_2$S(O)$_2$Et,
—CH(Me)CH$_2$C(O)OH,
—C(Me)$_2$CH$_2$C(O)OH,
-5-tetrazolyl,

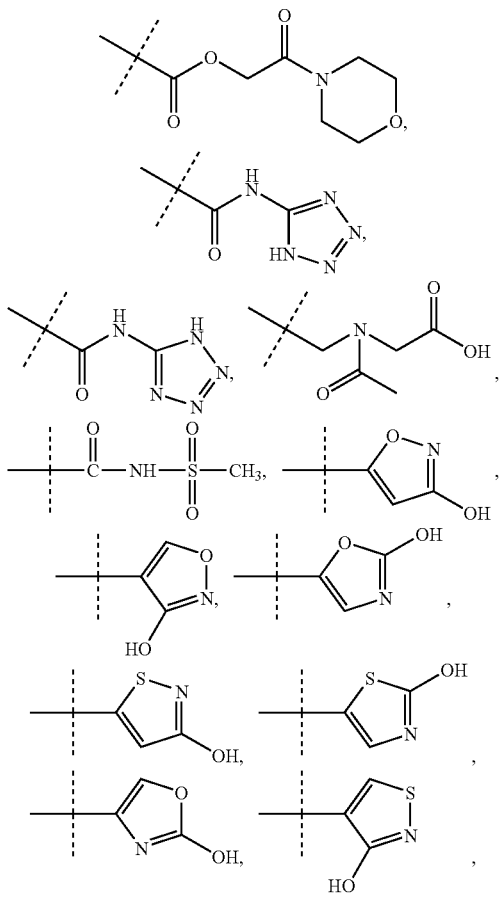

-continued

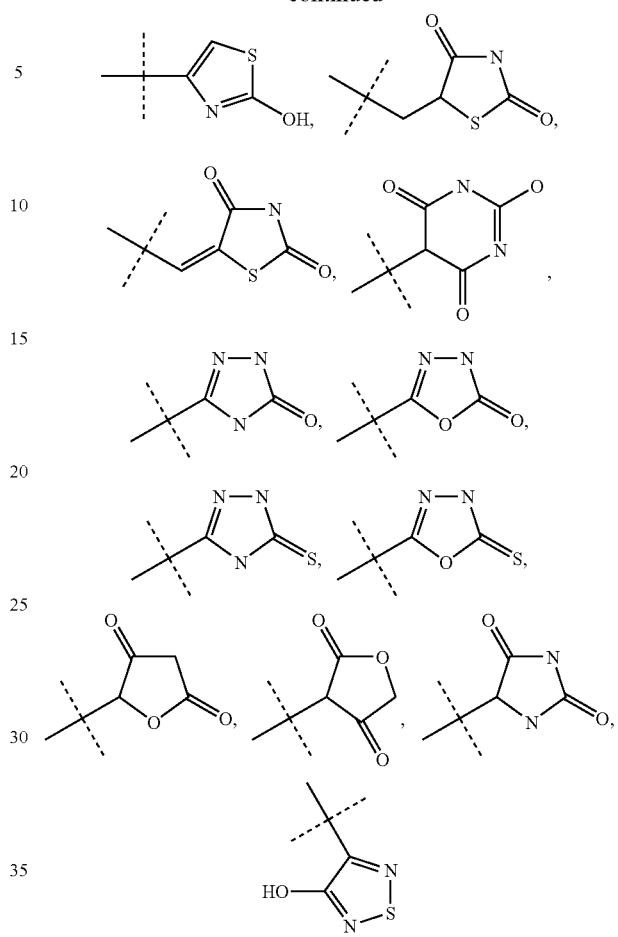

-1,3,4-oxadiazolin-2-one-5-yl,
-imidazolidine-2,4-dione-5-yl,
-isoxazol-3-ol-yl, or
-1,3,4-oxadiazolin-2-thione-5-yl;

provided that RB is substituted at either the 6 or 7 position of the benzofuran ring, except that RB is substituted only at the 7 position of the benzofuran ring when $Z_{FB}$ is at the 6 position; and provided that -(L$_{FB}$)-Z$_{FB}$ is substituted at either the 5 or 6 position of the benzofuran ring; and provided that RB is substituted at either the 6 or 7 position of the benzofuran ring, except that RB is substituted only at the 7 position of the benzofuran ring when the group -(L$_{FB}$)-Z$_{FB}$ is at the 6 position; and provided that RB' is substituted at either the 4 or 5 position of the benzofuran ring, except that RB' is substituted only at the 5 position of the benzofuran ring when the group -(L$_{FB}$)-Z$_{FB}$ is at the 6 position of the phenyl ring; ring; and provided that RP is substituted at either the 2, or 5 or 6 position of the phenyl ring.

The compounds of the invention with vitamin receptor modulating (VDRM) activity are represented by formula (IB) or a pharmaceutically acceptable salt or a prodrug derivative thereof:

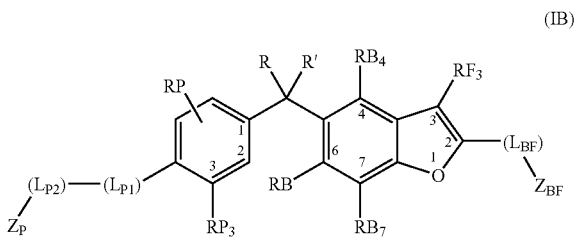

(IB)

wherein the variables R, R', RP, RP$_3$, Z$_P$, RB$_7$, RB, RB$_4$, RF$_3$, and Z$_{BF}$ are as hereinafter defined.

wherein

R and R' are independently C$_1$-C$_5$ alkyl, C$_1$-C$_5$ fluoroalkyl, or together R and R' form a substituted or unsubstituted, saturated or unsaturated carbocyclic ring having from 3 to 8 carbon atoms;

RP, RB$_4$, RF$_3$ and RB are independently selected from the group consisting of hydrogen, halo, C$_1$-C$_5$ alkyl, C$_1$-C$_5$ fluoroalkyl, —O—C$_1$-C$_5$ alkyl, —S—C$_1$-C$_5$ alkyl, —O—C$_1$-C$_5$ fluoroalkyl, —CN, —NO$_2$, acetyl, —S—C$_1$-C$_5$ fluoroalkyl, C$_2$-C$_5$ alkenyl, C$_3$-C$_5$ cycloalkyl, and C$_3$-C$_5$ cycloalkenyl;

RP$_3$ and RB$_7$ are independently selected from hydrogen, halo, C$_1$-C$_5$ alkyl, C$_1$-C$_5$ fluoroalkyl, —O—C$_1$-C$_5$ alkyl, —S—C$_1$-C$_5$ alkyl, —O—C$_1$-C$_5$ fluoroalkyl, —CN, —NO$_2$, acetyl, —S—C$_1$-C$_5$ fluoroalkyl, C$_2$-C$_5$ alkenyl, C$_3$-C$_5$ cycloalkyl, or C$_3$-C$_5$ cycloalkenyl;

(L$_{P1}$), (L$_{P2}$), and (L$_{BF}$) are divalent linking groups independently selected from the group consisting of

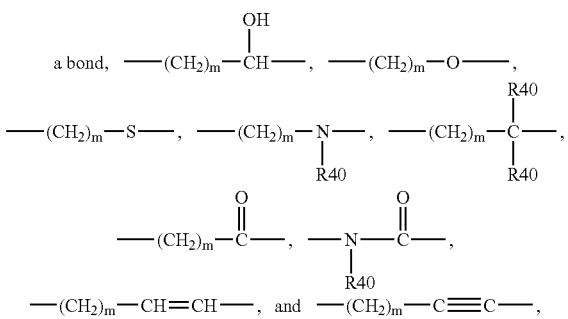

where m is 0, 1, or 2, and each R40 is independently hydrogen, C$_1$-C$_5$ alkyl, or C$_1$-C$_5$ fluoroalkyl;

Z$_P$ is branched C$_3$-C$_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
1-hydroxycycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
2-oxocyclohexyloxy
2-oxocyclohexylmethyl
3-methyl-2-oxocyclohexyloxy
3-methyl-2-oxocyclohexylmethyl
3,3-dimethyl-2-oxocyclohexyloxy
3,3-dimethyl-2-oxocyclohexylmethyl
2-hydroxycyclohexyloxy
2-hydroxycyclohexylmethyl
3-methyl-2-hydroxycyclohexyloxy
3-methyl-2-hydroxycyclohexylmethyl
3,3-dimethyl-2-hydroxycyclohexyloxy
3,3-dimethyl-2-hydroxycyclohexylmethyl
1-hydroxycycloheptyl, or
1-hydroxycyclooctyl;

provided, however, that when
Z$_P$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl, or
1-hydroxy-2-methyl-1-(methylethyl)propyl;
then (L$_{P1}$) and (L$_{P2}$) combine as a bond;

Z$_P$ is selected from
—O—(C$_1$-C$_5$ alkyl),
—O—(C$_2$-C$_5$ alkenyl),
—O—(C$_3$-C$_5$ cycloalkyl),
—O—(C$_3$-C$_5$ cycloalkenyl),
—O—(C$_1$-C$_5$ hydroxyalkyl),
—O—(C$_1$-C$_5$ fluoroalkyl),
—O—(C$_1$-C$_5$ alkyl)-phenyl,
—O—(C$_1$-C$_5$ alkyl)-(O)—(C$_1$-C$_5$ alkyl), —O—($C_1$-$C_5$ alkyl) $NH_2$,
—O—($C_1$-$C_5$ alkyl)-NH—($C_1$-$C_5$ alkyl)$_2$,
—O—($C_1$-$C_5$ alkyl)-C(O)—$NH_2$,
—O—($C_1$-$C_5$ alkyl)-C(O)—NH—($C_1$-$C_5$ alkyl),
—O—($C_1$-$C_5$ alkyl)-C(O)—N—($C_1$-$C_5$ alkyl)$_2$,
—O—($C_1$-$C_5$ alkyl)-C(O)—OH,
—O—($C_1$-$C_5$ alkyl)-C(O)—NH-5-tetrazolyl,
—O—($C_1$-$C_5$ alkyl)-C(O)—($C_1$-$C_5$ alkyl),
—O—($C_1$-$C_5$ alkyl)-C(O)—(O—$C_1$-$C_5$ alkyl),
—O—($C_1$-$C_5$ alkyl)-$NH_2$,
—O—($C_1$-$C_5$ alkyl)-NH—($C_1$-$C_5$ alkyl),
—O—($C_1$-$C_5$ alkyl)-N—($C_1$-$C_5$ alkyl)$_2$,
—O—($C_1$-$C_5$ alkyl)-NH—$SO_2$—($C_1$-$C_5$ alkyl),
—O—($C_1$-$C_5$ alkyl)-N-pyrrolidin-2-one,
—O—($C_1$-$C_5$ alkyl)-N-pyrrolidine,
—O—($C_1$-$C_5$ alkyl)-(1-methylpyrrolidin-2-one-3-yl),
—O—($C_1$-$C_5$ alkyl)-$SO_2$—($C_1$-$C_5$ alkyl,)
—O—($C_1$-$C_5$ alkyl)-$SO_2$—$NH_2$,
—O—($C_1$-$C_5$ alkyl)-$SO_2$—NH—($C_1$-$C_5$ alkyl),
—O—($C_1$-$C_5$ alkyl)-$SO_2$—N—($C_1$-$C_5$ alkyl)$_2$,
—O—($C_1$-$C_5$ alkyl)-$SO_2$—($C_1$-$C_5$ alkyl),
—O—($C_1$-$C_5$ alkyl)-S(O)—($C_1$-$C_5$ alkyl,)
—O—($C_1$-$C_5$ alkyl)-S(O)—$NH_2$,
—O—($C_1$-$C_5$ alkyl)-S(O)—NH—($C_1$-$C_5$ alkyl),
—O—($C_1$-$C_5$ alkyl)-S(O)—N—($C_1$-$C_5$ alkyl)$_2$,
—O—($C_1$-$C_5$ alkyl)-S(O)—($C_1$-$C_5$ alkyl),
—O—($C_1$-$C_5$ alkyl)-P(O)—(O—$C_1$-$C_5$ alkyl)$_2$,
—O—($C_1$-$C_5$ alkyl)-5-tetrazolyl,
—O—$CH_2$—$CO_2H$,
—O—$CH_2$-5-tetrazolyl,
—O—($C_1$-$C_5$ alkyl),
—O—C(O)—$NH_2$,
—O—C(O)—N—($CH_3$)$_2$,
—O—C(S)—N—($CH_3$)$_2$,
—O—C(O)—O—($C_1$-$C_5$ alkyl),
—O-(5-tetrazolyl),
—O—$SO_2$—($C_1$-$C_5$ alkyl,)
—O—$SO_2$—$NH_2$,
—O—$SO_2$—NH—($C_1$-$C_5$ alkyl),
—O—$SO_2$—N—($C_1$-$C_5$ alkyl)$_2$,
—O—S(O)—($C_1$-$C_5$ alkyl,)
—O—S(O)—$NH_2$,
—O—S(O)—NH—($C_1$-$C_5$ alkyl),
—O—S(O)—N—($C_1$-$C_5$ alkyl)$_2$,
—S—($C_1$-$C_5$ alkyl),
—S—($C_2$-$C_5$ alkenyl),
—S—($C_3$-$C_5$ cycloalkyl),
—S—($C_3$-$C_5$ cycloalkenyl),
—S—($C_1$-$C_5$ fluoroalkyl),
—S—($C_1$-$C_5$ hydroxyalkyl),
—S—($C_1$-$C_5$ alkyl)-phenyl,
—S—($C_1$-$C_5$ alkyl)-O—($C_1$-$C_5$ alkyl),
—S—($C_1$-$C_5$ alkyl)-C(O)—OH,
—S—($C_1$-$C_5$ alkyl)-C(O)—($C_1$-$C_5$ alkyl),
—S—($C_1$-$C_5$ alkyl)-C(O)—O—($C_1$-$C_5$ alkyl),
—S—($C_1$-$C_5$ alkyl)-C(O)—$NH_2$,
—S—($C_1$-$C_5$ alkyl)C(O)—NH—($C_1$-$C_5$ alkyl),
—S—($C_1$-$C_5$ alkyl)-C(O)—N—($C_1$-$C_5$ alkyl)$_2$,
—S—($C_1$-$C_5$ alkyl) $NH_2$,
—S—($C_1$-$C_5$ alkyl)-NH—($C_1$-$C_5$ alkyl),
—S—($C_1$-$C_5$ alkyl)-N—($C_1$-$C_5$ alkyl)$_2$,
—S—($C_1$-$C_5$ alkyl)-NH—$SO_2$—($C_1$-$C_5$ alkyl),
—S—($C_1$-$C_5$ alkyl)-N-pyrrolidin-2-one,
—S—($C_1$-$C_5$ alkyl)-N-pyrrolidine,
—S—($C_1$-$C_5$ alkyl)-(1-methylpyrrolidin-2-one-3-yl),
—S—($C_1$-$C_5$ alkyl)-$SO_2$—($C_1$-$C_5$ alkyl),
—S—($C_1$-$C_5$ alkyl)-$SO_2$—$NH_2$,
—S—($C_1$-$C_5$ alkyl)-$SO_2$—NH—($C_1$-$C_5$ alkyl),
—S—($C_1$-$C_5$ alkyl)-$SO_2$—N—($C_1$-$C_5$ alkyl)$_2$,
—S—($C_1$-$C_5$ alkyl)-$SO_2$—($C_1$-$C_5$ alkyl),
—S—($C_1$-$C_5$ alkyl)-P(O)—(O—$C_1$-$C_5$ alkyl)$_2$,
—S—($C_1$-$C_5$ alkyl)-5-tetrazolyl,
—S—($C_1$-$C_5$ alkyl)-S(O)—($C_1$-$C_5$ alkyl),
—S—($C_1$-$C_5$ alkyl)-S(O)—$NH_2$,
—S—($C_1$-$C_5$ alkyl)-S(O)—NH—($C_1$-$C_5$ alkyl),
—S—($C_1$-$C_5$ alkyl)-S(O)—N—($C_1$-$C_5$ alkyl)$_2$,
—S—($C_1$-$C_5$ alkyl)-S(O)—($C_1$-$C_5$ alkyl),
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—$NH_2$,
—$SO_2$—NH—($C_1$-$C_5$ alkyl),
—$SO_2$—NH—$CH_2$—C(O)OH,
—$SO_2$—NH—$CH_2$—C(O)(O—$C_1$-$C_5$ alkyl),
—$SO_2$—NH—($C_1$-$C_5$ alkyl)-C(O)OH,
—$SO_2$—NH—($C_1$-$C_5$ alkyl)-C(O)(O—$C_1$-$C_5$ alkyl),
—$SO_2$—NHC(O)—($C_3$-$C_6$ cycloalkyl),
—$SO_2$—NH—C(O)—($C_1$-$C_5$ alkyl),
—$SO_2$—N—($C_1$-$C_5$ alkyl)$_2$,
—$SO_2$—($C_1$-$C_5$ alkyl)-O—($C_1$-$C_5$ alkyl),
—$SO_2$—($C_1$-$C_5$ alkyl)-C(O)—($C_1$-$C_5$ alkyl),
—$SO_2$—($C_1$-$C_5$ alkyl) $NH_2$,
—$SO_2$—($C_1$-$C_5$ alkyl)-NH—($C_1$-$C_5$ alkyl),
—$SO_2$—($C_1$-$C_5$ alkyl)-N—($C_1$-$C_5$ alkyl)$_2$,
—$SO_2$—($C_1$-$C_5$ alkyl)-C(O)—$NH_2$,
—$SO_2$—($C_1$-$C_5$ alkyl)-C(O)—NH—($C_1$-$C_5$ alkyl),
—$SO_2$—($C_1$-$C_5$ alkyl)-C(O)—N—($C_1$-$C_5$ alkyl)$_2$,
—$SO_2$—($C_1$-$C_5$ alkyl)-NH—$SO_2$—($C_1$-$C_5$ alkyl),
—$SO_2$—($C_1$-$C_5$ alkyl)-N-pyrrolidin-2-one,
—$SO_2$—($C_1$-$C_5$ alkyl)-N-pyrrolidine,
—$SO_2$—($C_1$-$C_5$ alkyl)-(1-methylpyrrolidin-2-one-3-yl),
—$SO_2$—($C_1$-$C_5$ alkyl)-C(O)—O—($C_1$-$C_5$ alkyl),
—$SO_2$—($C_1$-$C_5$ alkyl)-C(O)—OH,
—$SO_2$—($C_1$-$C_5$ alkyl)-5-tetrazolyl,
—$SO_2$—($C_1$-$C_5$ alkyl)-$SO_2$—($C_1$-$C_5$ alkyl),
—$SO_2$—($C_1$-$C_5$ alkyl)-$SO_2$—$NH_2$,
—$SO_2$—($C_1$-$C_5$ alkyl)-$SO_2$—NH—($C_1$-$C_5$ alkyl),
—$SO_2$—($C_1$-$C_5$ alkyl)-$SO_2$—N—($C_1$-$C_5$ alkyl)$_2$,
—$SO_2$—($C_1$-$C_5$ alkyl)-$SO_2$—($C_1$-$C_5$ alkyl),
—$SO_2$—($C_1$-$C_5$ alkyl)-P(O)—(O—$C_1$-$C_5$ alkyl)$_2$,
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—N=CHN($C_1$-$C_5$ alkyl) 2,
—S(O)—$NH_2$,
—S(O)—NH—($C_1$-$C_5$ alkyl),
—S(O)—NH—$CH_2$—C(O)OH
—S(O)—NH—($C_1$-$C_5$ alkyl)-C(O)OH,
—S(O)—NH—$CH_2$—C(O)(O—$C_1$-$C_5$ alkyl),
—S(O)—NH—($C_1$-$C_5$ alkyl)-C(O)(O—$C_1$-$C_5$ alkyl),
—S(O)HC(O)—($C_3$-$C_6$ cycloalkyl),
—S(O)—NH—C(O)—($C_1$-$C_5$ alkyl),
—S(O)—N—($C_1$-$C_5$ alkyl)$_2$,
—S(O)—($C_1$-$C_5$ alkyl)-O—($C_1$-$C_5$ alkyl),
—S(O)—($C_1$-$C_5$ alkyl)-C(O)—($C_1$-$C_5$ alkyl),
—S(O)—($C_1$-$C_5$ alkyl)-C(O)—(O—$C_1$-$C_5$ alkyl), —S(O)—(C$_1$-C$_5$ alkyl)-NH—(C$_1$-C$_5$ alkyl),
—S(O)—(C$_1$-C$_5$ alkyl)-N—(C$_1$-C$_5$ alkyl)$_2$,
—S(O)—(C$_1$-C$_5$ alkyl)-C(O)—NH$_2$,
—S(O)—(C$_1$-C$_5$ alkyl)-C(O)—NH—(C$_1$-C$_5$ alkyl),
—S(O)—(C$_1$-C$_5$ alkyl)-C(O)—N—(C$_1$-C$_5$ alkyl)$_2$,
—S(O)—(C$_1$-C$_5$ alkyl)-NH—SO$_2$—(C$_1$-C$_5$ alkyl),
—S(O)—(C$_1$-C$_5$ alkyl)-NH—S(O)—(C$_1$-C$_5$ alkyl),
—S(O)—(C$_1$-C$_5$ alkyl)-N-pyrrolidin-2-one,
—S(O)—(C$_1$-C$_5$ alkyl)-N-pyrrolidine,
—S(O)—(C$_1$-C$_5$ alkyl)-(1-methylpyrrolidin-2-one-3-yl),
—S(O)—(C$_1$-C$_5$ alkyl)-C(O)—(O—C$_1$-C$_5$ alkyl),
—S(O)—(C$_1$-C$_5$ alkyl)-C(O)—OH,
—S(O)—(C$_1$-C$_5$ alkyl)-5-tetrazolyl,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-SO$_2$—NH$_2$,
—S(O)—(C$_1$-C$_5$ alkyl)-S(O)—NH$_2$,
—S(O)—(C$_1$-C$_5$ alkyl)-SO$_2$—NH—(C$_1$-C$_5$ alkyl),
—S(O)—(C$_1$-C$_5$ alkyl)-S(O)—NH—(C$_1$-C$_5$ alkyl),
—S(O)—(C$_1$-C$_5$ alkyl)-SO$_2$—N—(C$_1$-C$_5$ alkyl)$_2$,
—S(O)—(C$_1$-C$_5$ alkyl)-S(O)—N—(C$_1$-C$_5$ alkyl)$_2$,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-P(O)—(O—C$_1$-C$_5$ alkyl)$_2$,
—S(O)—N=CHN(C$_1$-C$_5$ alkyl)$_2$,
—NHC(S)NH$_2$,
—NHC(S)NH—(C$_1$-C$_5$ alkyl),
—NHC(S)N—(C$_1$-C$_5$ alkyl)$_2$,
—NHC(S)NH—(C$_2$-C$_5$ alkenyl),
—NHC(S)NH—(C$_3$-C$_5$ cycloalkyl),
—NHC(S)NH—(C$_3$-C$_5$ cycloalkenyl),
—NHC(S)NH—(C$_1$-C$_5$ fluoroalkyl),
—NHC(S)NH—C$_1$-C$_5$ hydroxyalkyl,
—NHC(S)NH—(C$_1$-C$_5$ fluoroalkyl)
—NHC(S)NH-phenyl,
—NHC(S)NH—(C$_1$-C$_5$ alkyl)-C(O)—OH,
—NHC(S)NH—(C$_1$-C$_5$ alkyl)-O—(C$_1$-C$_5$ alkyl),
—NHC(S)NH—(C$_1$-C$_5$ alkyl)-C(O)—(C$_1$-C$_5$ alkyl),
—NHC(S)NH—(C$_1$-C$_5$ alkyl)-C(O)—(O—C$_1$-C$_5$ alkyl),
—NHC(S)NH—(C$_1$-C$_5$ alkyl)-NH$_2$,
—NHC(S)NH—(C$_1$-C$_5$ alkyl)-NH—(C$_1$-C$_5$ alkyl),
—NHC(S)NH—(C$_1$-C$_5$ alkyl)-N—(C$_1$-C$_5$ alkyl)$_2$,
—NHC(S)NH—(C$_1$-C$_5$ alkyl)-C(O)—NH$_2$,
—NHC(S)NH—(C$_1$-C$_5$ alkyl)-C(O)—NH—(C$_1$-C$_5$ alkyl),
—NHC(S)NH—(C$_1$-C$_5$ alkyl)-C(O)—N—(C$_1$-C$_5$ alkyl)$_2$,
—NHC(S)NH—(C$_1$-C$_5$ alkyl)-NH—SO$_2$—(C$_1$-C$_5$ alkyl),
—NHC(S)NH—(C$_1$-C$_5$ alkyl)-NH—S(O)—(C$_1$-C$_5$ alkyl),
—NHC(S)NH—(C$_1$-C$_5$ alkyl)-N-pyrrolidin-2-one,
—NHC(S)NH—(C$_1$-C$_5$ alkyl)-N-pyrrolidine,
—NHC(S)NH—(C$_1$-C$_5$ alkyl)-(1-methylpyrrolidin-2-one-3-yl),
—NHC(S)NH—(C$_1$-C$_5$ alkyl)-5-tetrazolyl,
—NHC(S)NH—(C$_1$-C$_5$ alkyl)-SO$_2$—(C$_1$-C$_5$ alkyl),
—NHC(S)NH—(C$_1$-C$_5$ alkyl)-SO$_2$—NH$_2$,
—NHC(S)NH—(C$_1$-C$_5$ alkyl)-SO$_2$—NH—(C$_1$-C$_5$ alkyl),
—NHC(S)NH—(C$_1$-C$_5$ alkyl)-SO$_2$—N—(C$_1$-C$_5$ alkyl)$_2$,
—NHC(S)NH—(C$_1$-C$_5$ alkyl)-S(O)—(C$_1$-C$_5$ alkyl),
—NHC(S)NH—(C$_1$-C$_5$ alkyl)-S(O)—NH$_2$,
—NHC(S)NH—(C$_1$-C$_5$ alkyl)-S(O)—NH—(C$_1$-C$_5$ alkyl),
—NHC(S)NH—(C$_1$-C$_5$ alkyl)-S(O)—N—(C$_1$-C$_5$ alkyl)$_2$,
—NHC(S)NH—(C$_1$-C$_5$ alkyl)-P(O)—(O—C$_1$-C$_5$ alkyl)$_2$,
—NHC(O)NH$_2$,
—NHC(O)NH—(C$_1$-C$_5$ alkyl),
—NHC(O)N—(C$_1$-C$_5$ alkyl)$_2$,
—NHC(O)NH—(C$_2$-C$_5$ alkenyl),
—NHC(O)NH—(C$_3$-C$_5$ cycloalkyl),
—NHC(O)NH—(C$_3$-C$_5$ cycloalkenyl),
—NHC(O)NH—(C$_1$-C$_5$ hydroxyalkyl),
—NHC(O)NH—(C$_1$-C$_5$ fluoroalkyl),
—NHC(O)NH-phenyl,
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-O—(C$_1$-C$_5$ alkyl),
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-C(O)—NH$_2$,
—NHC(O)NH—(C$_1$-C$_5$ alkyl)-C(O)—NH—(C$_1$-C$_5$ alkyl),
—NHC(O)NH—(C$_1$-C$_5$ alkyl)-C(O)—N—(C$_1$-C$_5$ alkyl)$_2$,
—NHC(O)NH—(C$_1$-C$_5$ alkyl)-C(O)—(C$_1$-C$_5$ alkyl),
—NHC(O)NH—(C$_1$-C$_5$ alkyl)-NH—SO$_2$—(C$_1$-C$_5$ alkyl),
—NHC(O)NH—(C$_1$-C$_5$ alkyl)-N-pyrrolidin-2-one,
—NHC(O)NH—(C$_1$-C$_5$ alkyl)-N-pyrrolidine,
—NHC(O)NH—(C$_1$-C$_5$ alkyl)-(1-methylpyrrolidin-2-one-3-yl),
—NHC(O)NH—(C$_1$-C$_5$ alkyl)-C(O)—OH,
—NHC(O)NH—(C$_1$-C$_5$ alkyl)-C(O)—O—(C$_1$-C$_5$ alkyl),
—NHC(O)NH—(C$_1$-C$_5$ alkyl)-5-tetrazolyl,
—NHC(O)NH—(C$_1$-C$_5$ alkyl)-SO$_2$—(C$_1$-C$_5$ alkyl),
—NHC(O)NH—(C$_1$-C$_5$ alkyl)-SO$_2$—NH$_2$,
—NHC(O)NH—(C$_1$-C$_5$ alkyl)-SO$_2$—NH—(C$_1$-C$_5$ alkyl),
—NHC(O)NH—(C$_1$-C$_5$ alkyl)-SO$_2$—N—(C$_1$-C$_5$ alkyl)$_2$,
—NHC(O)NH—(C$_1$-C$_5$ alkyl)-P(O)—O—(C$_1$-C$_5$ alkyl)$_2$,
—NH$_2$,
—NH—(C$_1$-C$_5$ alkyl),
—NH—CH$_2$—C(O)OH,
—N—(C$_1$-C$_5$ alkyl)$_2$,
—NH—C(O)—NH$_2$,
—NH—C(O)—NH—(C$_1$-C$_5$ alkyl),
—NH—C(O)—N—(C$_1$-C$_5$ alkyl)$_2$,
—NH—C(O)—(C$_1$-C$_5$ alkyl),
—NH—SO$_2$—(C$_1$-C$_5$ alkyl),
—NH—S(O)—(C$_1$-C$_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me,
—C(O)CH$_2$CH$_2$S(O)Et,
—C(O)CH$_2$CH$_2$S(O)$_2$Me,
—C(O)CH$_2$CH$_2$S(O)$_2$Et,
—C(O)CH(Me)CH$_2$CO$_2$H,
—C(O)CH(Me)CH$_2$CO$_2$Me,
—C(O)CH(Me)CH$_2$CO$_2$Et,
—C(O)CH(Me)CH$_2$CO$_2$iPr,
—C(O)CH(Me)CH$_2$CO$_2$tBu,
—C(O)CH(Me)CH(Me)CO$_2$H,
—C(O)CH(Me)CH(Me)CO$_2$Me,
—C(O)CH(Me)CH(Me)CO$_2$Et,
—C(O)CH(Me)CH(Me)CO$_2$iPr,
—C(O)CH(Me)CH(Me)CO$_2$tBu,
—C(O)CH(Me)C(Me)$_2$CO$_2$H,
—C(O)CH(Me)C(Me)$_2$CO$_2$Me,
—C(O)CH(Me)C(Me)$_2$CO$_2$Et,
—C(O)CH(Me)C(Me)$_2$CO$_2$iPr, —C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH-CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H,
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me, —C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)N—,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂, —CH$_2$CH$_2$-5-tetrazolyl,
—CH$_2$CH$_2$S(O)$_2$Me,
—CH$_2$CH$_2$S(O)Me,
—CH$_2$CH$_2$S(O)$_2$Et,
—CH$_2$CH$_2$S(O) Et,
—CH$_2$CH$_2$S(O)iPr,
—CH$_2$CH$_2$S(O)$_2$iPr,
—CH$_2$CH$_2$S(O)tBu,
—CH$_2$CH$_2$S(O)$_2$tBu,
—CH$_2$CH$_2$S(O)NH$_2$,
—CH$_2$CH$_2$S(O)NHMe,
—CH$_2$CH$_2$S(O)NMe$_2$,
—CH$_2$CH$_2$S(O)$_2$NH$_2$,
—CH$_2$CH$_2$S(O)$_2$NHMe —CH$_2$CH$_2$S(O)$_2$NMe$_2$,
—CH$_2$CH$_2$CH$_2$S(O)Me,
—CH$_2$CH$_{21}$CH$_2$S(O)Et,
—CH$_2$CH$_2$CH$_2$S(O)$_2$Me,
—CH$_2$CH$_2$CH$_2$S(O)$_2$Et,
—CH(Me)CH$_2$C(O)OH,
—C(Me)$_2$CH$_2$C(O)OH,
-5-tetrazolyl,

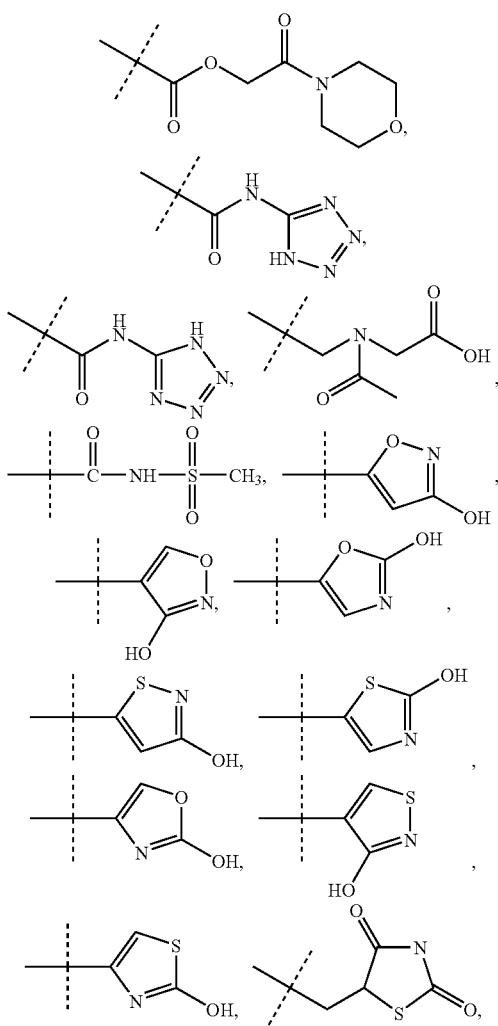

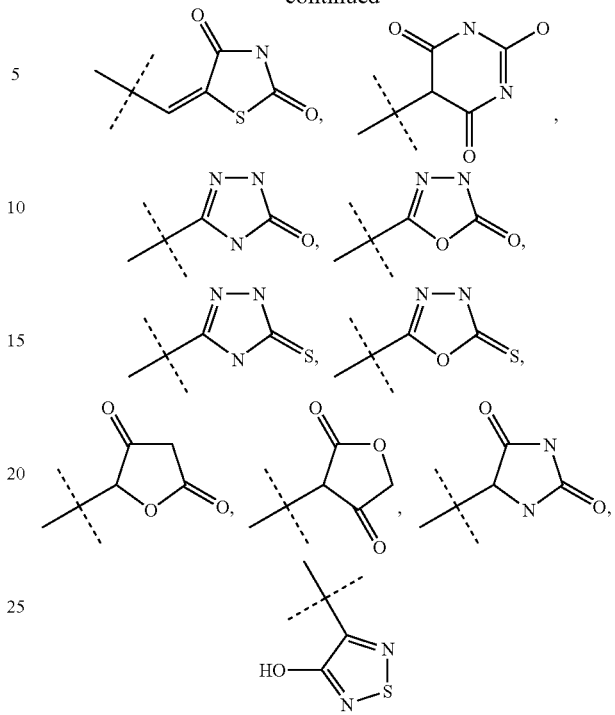

-1,3,4-oxadiazolin-2-one-5-yl,
-imidazolidine-2,4-dione-5-yl,
-isoxazol-3-ol-yl, or
-1,3,4-oxadiazolin-2-thione-5-yl;
provided that RP is substituted at either the 2, 5, or, 6 position of the phenyl ring.

The compounds of the invention with vitamin receptor modulating (VDRM) activity are represented by formula (IC) or a pharmaceutically acceptable salt or a prodrug derivative thereof:

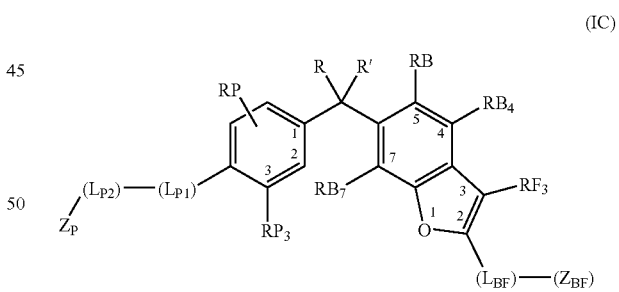

(IC)

wherein
R and R' are independently C$_1$-C$_5$ alkyl, C$_1$-C$_5$ fluoroalkyl, or together R and R' form a substituted or unsubstituted, saturated or unsaturated carbocyclic ring having from 3 to 8 carbon atoms;
RP, RB$_4$, RF$_3$ and RB are independently selected from the group consisting of hydrogen, halo, C$_1$-C$_5$ alkyl, C$_1$-C$_5$ fluoroalkyl, —O—C$_1$-C$_5$ alkyl, —S—C$_1$-C$_5$ alkyl, —O—C$_1$-C$_5$ fluoroalkyl, —CN, —NO$_2$, acetyl, —S—C$_1$-C$_5$ fluoroalkyl, C$_2$-C$_5$ alkenyl, C$_3$-C$_5$ cycloalkyl, and C$_3$-C$_5$ cycloalkenyl;
RP$_3$ and RB$_7$ are independently selected from hydrogen, halo, C$_1$-C$_5$ alkyl, C$_1$-C$_5$ fluoroalkyl, —O—C$_1$-C$_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, or $C_3$-$C_5$ cycloalkenyl;

($L_{P1}$), ($L_{P2}$), and ($L_{BF}$) are divalent linking groups independently selected from the group consisting of

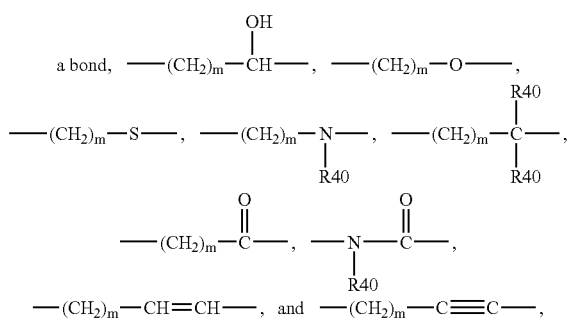

where m is 0, 1, or 2, and each R40 is independently hydrogen, $C_1$-$C_5$ alkyl, or $C_1$-$C_5$ fluoroalkyl;

$Z_P$ is
branched $C_3$-$C_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
1-hydroxycycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
2-oxocyclohexyloxy
2-oxocyclohexylmethyl
3-methyl-2-oxocyclohexyloxy
3-methyl-2-oxocyclohexylmethyl
3,3-dimethyl-2-oxocyclohexyloxy
3,3-dimethyl-2-oxocyclohexylmethyl
2-hydroxycyclohexyloxy
2-hydroxycyclohexylmethyl
3-methyl-2-hydroxycyclohexyloxy
3-methyl-2-hydroxycyclohexylmethyl
3,3-dimethyl-2-hydroxycyclohexyloxy
3,3-dimethyl-2-hydroxycyclohexylmethyl
1-hydroxycycloheptyl, or
1-hydroxycyclooctyl;

provided, however, that when
$Z_P$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl, or
1-hydroxy-2-methyl-1-(methylethyl)propyl;
then ($L_{P1}$) and ($L_{P2}$) combine as a bond;

$Z_{BF}$ is selected from
—O—($C_1$-$C_5$ alkyl),
—O—($C_2$-$C_5$ alkenyl),
—O—($C_3$-$C_5$ cycloalkyl),
—O—($C_3$-$C_5$ cycloalkenyl),
—O—($C_1$-$C_5$ hydroxyalkyl),
—O—($C_1$-$C_5$ fluoroalkyl),
—O—($C_1$-$C_5$ alkyl)-phenyl,
—O—($C_1$-$C_5$ alkyl)-(O)—($C_1$-$C_5$ alkyl),
—O—($C_1$-$C_5$ alkyl) $NH_2$,
—O—($C_1$-$C_5$ alkyl)-NH—($C_1$-$C_5$ alkyl)$_2$,
—O—($C_1$-$C_5$ alkyl)-C(O)—$NH_2$,
—O—($C_1$-$C_5$ alkyl)-C(O)—NH—($C_1$-$C_5$ alkyl),
—O—($C_1$-$C_5$ alkyl)-C(O)—N—($C_1$-$C_5$ alkyl)$_2$,
—O—($C_1$-$C_5$ alkyl)-C(O)—OH,
—O—($C_1$-$C_5$ alkyl)-C(O)—NH-5-tetrazolyl,
—O—($C_1$-$C_5$ alkyl)-C(O)—($C_1$-$C_5$ alkyl),
—O—($C_1$-$C_5$ alkyl)-C(O)—(O—$C_1$-$C_5$ alkyl),
—O—($C_1$-$C_5$ alkyl)-$NH_2$,
—O—($C_1$-$C_5$ alkyl)-NH—($C_1$-$C_5$ alkyl),
—O—($C_1$-$C_5$ alkyl)-N—($C_1$-$C_5$ alkyl)$_2$,
—O—($C_1$-$C_5$ alkyl)-NH—$SO_2$—($C_1$-$C_5$ alkyl),
—O—($C_1$-$C_5$ alkyl)-N-pyrrolidin-2-one,
—O—($C_1$-$C_5$ alkyl)-N-pyrrolidine,
—O—($C_1$-$C_5$ alkyl)-(1-methylpyrrolidin-2-one-3-yl),
—O—($C_1$-$C_5$ alkyl)-$SO_2$—($C_1$-$C_5$ alkyl,)
—O—($C_1$-$C_5$ alkyl)-$SO_2$—$NH_2$,
—O—($C_1$-$C_5$ alkyl)-$SO_2$—NH—($C_1$-$C_5$ alkyl),
—O—($C_1$-$C_5$ alkyl)-$SO_2$—N—($C_1$-$C_5$ alkyl)$_2$,
—O—($C_1$-$C_5$ alkyl)-$SO_2$—($C_1$-$C_5$ alkyl),
—O—($C_1$-$C_5$ alkyl)-S(O)—($C_1$-$C_5$ alkyl,)
—O—($C_1$-$C_5$ alkyl)-S(O)—$NH_2$,
—O—($C_1$-$C_5$ alkyl)-S(O)—NH—($C_1$-$C_5$ alkyl),
—O—($C_1$-$C_5$ alkyl)-S(O)—N—($C_1$-$C_5$ alkyl)$_2$,
—O—($C_1$-$C_5$ alkyl)-S(O)—($C_1$-$C_5$ alkyl),
—O—($C_1$-$C_5$ alkyl)-P(O)—(O—$C_1$-$C_5$ alkyl)$_2$, —O—(C₁-C₅ alkyl)-5-tetrazolyl,
—O—CH₂—CO₂H,
—O—CH₂-5-tetrazolyl,
—O—(C₁-C₅ alkyl),
—O—C(O)—NH₂,
—O—C(O)—N—(CH₃)₂,
—O—C(S)—N—(CH₃)₂,
—O—C(O)—O—(C₁-C₅ alkyl),
—O-(5-tetrazolyl),
—O—SO₂—(C₁-C₅ alkyl,)
—O—SO₂—NH₂,
—O—SO₂—NH—(C₁-C₅ alkyl),
—O—SO₂—N—(C₁-C₅ alkyl)₂,
—O—S(O)—(C₁-C₅ alkyl,)
—O—S(O)—NH₂,
—O—S(O)—NH—(C₁-C₅ alkyl),
—O—S(O)—N—(C₁-C₅ alkyl)₂,
—S—(C₁-C₅ alkyl),
—S—(C₂-C₅ alkenyl),
—S—(C₃-C₅ cycloalkyl),
—S—(C₃-C₅ cycloalkenyl),
—S—(C₁-C₅ fluoroalkyl),
—S—(C₁-C₅ hydroxyalkyl),
—S—(C₁-C₅ alkyl)-phenyl,
—S—(C₁-C₅ alkyl)-O—(C₁-C₅ alkyl),
—S—(C₁-C₅ alkyl)-C(O)—OH,
—S—(C₁-C₅ alkyl)-C(O)—(C₁-C₅ alkyl),
—S—(C₁-C₅ alkyl)-C(O)—O—(C₁-C₅ alkyl),
—S—(C₁-C₅ alkyl)-C(O)—NH₂,
—S—(C₁-C₅ alkyl)-C(O)—NH—(C₁-C₅ alkyl),
—S—(C₁-C₅ alkyl)-C(O)—N—(C₁-C₅ alkyl)₂,
—S—(C₁-C₅ alkyl) NH₂,
—S—(C₁-C₅ alkyl)-NH—(C₁-C₅ alkyl),
—S—(C₁-C₅ alkyl)-N—(C₁-C₅ alkyl)₂,
—S—(C₁-C₅ alkyl)-NH—SO₂—(C₁-C₅ alkyl),
—S—(C₁-C₅ alkyl)-N-pyrrolidin-2-one,
—S—(C₁-C₅ alkyl)-N-pyrrolidine,
—S—(C₁-C₅ alkyl)-(1-methylpyrrolidin-2-one-3-yl),
—S—(C₁-C₅ alkyl)-SO₂—(C₁-C₅ alkyl),
—S—(C₁-C₅ alkyl)-SO₂—NH₂,
—S—(C₁-C₅ alkyl)-SO₂—NH—(C₁-C₅ alkyl),
—S—(C₁-C₅ alkyl)-SO₂—N—(C₁-C₅ alkyl)₂,
—S—(C₁-C₅ alkyl)-SO₂—(C₁-C₅ alkyl),
—S—(C₁-C₅ alkyl)-P(O)—(O—C₁-C₅ alkyl)₂,
—S—(C₁-C₅ alkyl)-5-tetrazolyl,
—S—(C₁-C₅ alkyl)-S(O)—(C₁-C5 alkyl),
—S—(C₁-C₅ alkyl)-S(O)—NH₂,
—S—(C₁-C₅ alkyl)-S(O)—NH—(C₁-C₅ alkyl),
—S—(C₁-C₅ alkyl)-S(O)—N—(C₁-C₅ alkyl)₂,
—S—(C₁-C₅ alkyl)-S(O)—(C₁-C₅ alkyl),
—SO₂—(C₁-C₅ alkyl),
—SO₂—(C₂-C₅ alkenyl),
—SO₂—(C₃-C₅ cycloalkyl),
—SO₂—(C₃-C₅ cycloalkenyl),
—SO₂—(C₁-C₅ hydroxyalkyl),
—SO₂—(C₁-C₅ fluoroalkyl),
—SO₂—(C₁-C₅)-phenyl,
—SO₂—NH₂,
—SO₂—NH—(C₁-C₅ alkyl),
—SO₂—NH—CH₂—C(O)OH,
—SO₂—NH—CH₂—C(O)(O—C₁-C₅ alkyl),
—SO₂—NH—(C₁-C₅ alkyl)-C(O)OH,
—SO₂—NH—(C₁-C₅ alkyl)-C(O)(O—C₁-C₅ alkyl),
—SO₂—NHC(O)—(C₃-C₆ cycloalkyl),
—SO₂—NH—C(O)—(C₁-C₅ alkyl),
—SO₂—N—(C₁-C₅ alkyl)₂,
—SO₂—(C₁-C₅ alkyl)-O—(C₁-C₅ alkyl), —SO₂—(C₁-C₅ alkyl)-C(O)—(C₁-C₅ alkyl),
—SO₂—(C₁-C₅ alkyl) NH₂,
—SO₂—(C₁-C₅ alkyl)-NH—(C₁-C₅ alkyl),
—SO₂—(C₁-C₅ alkyl)-N—(C₁-C₅ alkyl)₂,
—SO₂—(C₁-C₅ alkyl)-C(O)—NH₂,
—SO₂—(C₁-C₅ alkyl)-C(O)—NH—(C₁-C₅ alkyl),
—SO₂—(C₁-C₅ alkyl)-C(O)—N—(C₁-C₅ alkyl)₂,
—SO₂—(C₁-C₅ alkyl)-NH—SO₂—(C₁-C₅ alkyl),
—SO₂—(C₁-C₅ alkyl)-N-pyrrolidin-2-one,
—SO₂—(C₁-C₅ alkyl)-N-pyrrolidine,
—SO₂—(C₁-C₅ alkyl)-(1-methylpyrrolidin-2-one-3-yl),
—SO₂—(C₁-C₅ alkyl)-C(O)—O—(C₁-C₅ alkyl),
—SO₂—(C₁-C₅ alkyl)-C(O)—OH,
—SO₂—(C₁-C₅ alkyl)-5-tetrazolyl,
—SO₂—(C₁-C₅ alkyl)-SO₂—(C₁-C₅ alkyl),
—SO₂—(C₁-C₅ alkyl)-SO₂—NH₂,
—SO₂—(C₁-C₅ alkyl)-SO₂—NH—(C₁-C₅ alkyl),
—SO₂—(C₁-C₅ alkyl)-SO₂—N—(C₁-C₅ alkyl)₂,
—SO₂—(C₁-C₅ alkyl)-SO₂—(C₁-C₅ alkyl),
—SO₂—(C₁-C₅ alkyl)-P(O)—(O—C₁-C₅ alkyl)₂,
—SO₂—(C₁-C₅ alkyl),
—SO₂—(C₂-C₅ alkenyl),
—SO₂—(C₃-C₅ cycloalkyl),
—SO₂—(C₃-C₅ cycloalkenyl),
—SO₂—(C₁-C₅ hydroxyalkyl),
—SO₂—(C₁-C₅ fluoroalkyl),
—SO₂—(C₁-C₅)-phenyl,
—SO₂—N=CHN(C₁-C₅ alkyl) 2,
—S(O)—NH₂,
—S(O)—NH—(C₁-C₅ alkyl),
—S(O)—NH—CH₂—C(O)OH
—S(O)—NH—(C₁-C₅ alkyl)-C(O)OH,
—S(O)—NH—CH₂—C(O)(O—C₁-C₅ alkyl),
—S(O)—NH—(C₁-C₅ alkyl)-C(O)(O—C₁-C₅ alkyl),
—S(O)HC(O)—(C₃-C₆ cycloalkyl),
—S(O)—NH—C(O)—(C₁-C₅ alkyl),
—S(O)—N—(C₁-C₅ alkyl)₂,
—S(O)—(C₁-C₅ alkyl)-O—(C₁-C₅ alkyl),
—S(O)—(C₁-C₅ alkyl)-C(O)—(C₁-C₅ alkyl),
—S(O)—(C₁-C₅ alkyl)-C(O)—(O—C₁-C₅ alkyl),
—S(O)—(C₁-C₅ alkyl)-NH—(C₁-C₅ alkyl),
—S(O)—(C₁-C₅ alkyl)-N—(C₁-C₅ alkyl)₂,
—S(O)—(C₁-C₅ alkyl)-C(O)—NH₂,
—S(O)—(C₁-C₅ alkyl)-C(O)—NH—(C₁-C₅ alkyl),
—S(O)—(C₁-C₅ alkyl)-C(O)—N—(C₁-C₅ alkyl)₂,
—S(O)—(C₁-C₅ alkyl)-NH—SO₂—(C₁-C₅ alkyl),
—S(O)—(C₁-C₅ alkyl)-NH—S(O)—(C₁-C₅ alkyl),
—S(O)—(C₁-C₅ alkyl)-N-pyrrolidin-2-one,
—S(O)—(C₁-C₅ alkyl)-N-pyrrolidine,
—S(O)—(C₁-C₅ alkyl)-(1-methylpyrrolidin-2-one-3-yl),
—S(O)—(C₁-C₅ alkyl)-C(O)—(O—C₁-C₅ alkyl),
—S(O)—(C₁-C₅ alkyl)-C(O)—OH,
—S(O)—(C₁-C₅ alkyl)-5-tetrazolyl,
—S(O)—(C₁-C₅ alkyl)-SO₂—(C₁-C₅ alkyl),
—S(O)—(C₁-C₅ alkyl)-S(O)—(C₁-C₅ alkyl),
—S(O)—(C₁-C₅ alkyl)-SO₂—NH₂,
—S(O)—(C₁-C₅ alkyl)-S(O)—NH₂,
—S(O)—(C₁-C₅ alkyl)-SO₂—NH—(C₁-C₅ alkyl),
—S(O)—(C₁-C₅ alkyl)-S(O)—NH—(C₁-C₅ alkyl),
—S(O)—(C₁-C₅ alkyl)-SO₂—N—(C₁-C₅ alkyl)₂,
—S(O)—(C₁-C₅ alkyl)-S(O)—N—(C₁-C₅ alkyl)₂,
—S(O)—(C₁-C₅ alkyl)-SO₂—(C₁-C₅ alkyl),
—S(O)—(C₁-C₅ alkyl)-S(O)—(C₁-C₅ alkyl),
—S(O)—(C₁-C₅ alkyl)-P(O)—(O—C₁-C₅ alkyl)₂,
—S(O)—N=CHN(C₁-C₅ alkyl)₂,
—NHC(S)NH₂,
—NHC(S)NH—(C₁-C₅ alkyl), —NHC(S)N—($C_1$-$C_5$ alkyl)$_2$,
—NHC(S)NH—($C_2$-$C_5$ alkenyl),
—NHC(S)NH—($C_3$-$C_5$ cycloalkyl),
—NHC(S)NH—($C_3$-$C_5$ cycloalkenyl),
—NHC(S)NH—($C_1$-$C_5$ fluoroalkyl),
—NHC(S)NH—$C_1$-$C_5$ hydroxyalkyl,
—NHC(S)NH—($C_1$-$C_5$ fluoroalkyl) —NHC(S)NH-phenyl,
—NHC(S)NH—($C_1$-$C_5$ alkyl)-C(O)—OH,
—NHC(S)NH—($C_1$-$C_5$ alkyl)-O—($C_1$-$C_5$ alkyl),
—NHC(S)NH—($C_1$-$C_5$ alkyl)-C(O)—($C_1$-$C_5$ alkyl),
—NHC(S)NH—($C_1$-$C_5$ alkyl)-C(O)—(O—$C_1$-$C_5$ alkyl),
—NHC(S)NH—($C_1$-$C_5$ alkyl)-NH$_2$,
—NHC(S)NH—($C_1$-$C_5$ alkyl)-NH—($C_1$-$C_5$ alkyl),
—NHC(S)NH—($C_1$-$C_5$ alkyl)-N—($C_1$-$C_5$ alkyl)$_2$,
—NHC(S)NH—($C_1$-$C_5$ alkyl)-C(O)—NH$_2$,
—NHC(S)NH—($C_1$-$C_5$ alkyl)-C(O)—NH—($C_1$-$C_5$ alkyl),
—NHC(S)NH—($C_1$-$C_5$ alkyl)-C(O)—N—($C_1$-$C_5$ alkyl)$_2$,
—NHC(S)NH—($C_1$-$C_5$ alkyl)-NH—SO$_2$—($C_1$-$C_5$ alkyl),
—NHC(S)NH—($C_1$-$C_5$ alkyl)-NH—S(O)—($C_1$-$C_5$ alkyl),
—NHC(S)NH—($C_1$-$C_5$ alkyl)-N-pyrrolidin-2-one,
—NHC(S)NH—($C_1$-$C_5$ alkyl)-N-pyrrolidine,
—NHC(S)NH—($C_1$-$C_5$ alkyl)-(1-methylpyrrolidin-2-one-3-yl),
—NHC(S)NH—($C_1$-$C_5$ alkyl)-5-tetrazolyl,
—NHC(S)NH—($C_1$-$C_5$ alkyl)-SO$_2$—($C_1$-$C_5$ alkyl),
—NHC(S)NH—($C_1$-$C_5$ alkyl)-SO$_2$—NH$_2$,
—NHC(S)NH—($C_1$-$C_5$ alkyl)-SO$_2$—NH—($C_1$-$C_5$ alkyl),
—NHC(S)NH—($C_1$-$C_5$ alkyl)-SO$_2$—N—($C_1$-$C_5$ alkyl)$_2$,
—NHC(S)NH—($C_1$-$C_5$ alkyl)-S(O)—($C_1$-$C_5$ alkyl),
—NHC(S)NH—($C_1$-$C_5$ alkyl)-S(O)—NH$_2$,
—NHC(S)NH—($C_1$-$C_5$ alkyl)-S(O)—NH—($C_1$-$C_5$ alkyl),
—NHC(S)NH—($C_1$-$C_5$ alkyl)-S(O)—N—($C_1$-$C_5$ alkyl)$_2$,
—NHC(S)NH—($C_1$-$C_5$ alkyl)-P(O)—(O—$C_1$-$C_5$ alkyl)$_2$,
—NHC(O)NH$_2$,
—NHC(O)NH—($C_1$-$C_5$ alkyl),
—NHC(O)N—($C_1$-$C_5$ alkyl)$_2$,
—NHC(O)NH—($C_2$-$C_5$ alkenyl),
—NHC(O)NH—($C_3$-$C_5$ cycloalkyl),
—NHC(O)NH—($C_3$-$C_5$ cycloalkenyl),
—NHC(O)NH—($C_1$-$C_5$ hydroxyalkyl),
—NHC(O)NH—($C_1$-$C_5$ fluoroalkyl),
—NHC(O)NH-phenyl,
—NHC(O)NH—($C_1$-$C_5$ alkyl)-NH$_2$,
—NHC(O)NH—($C_1$-$C_5$ alkyl)-NH—($C_1$-$C_5$ alkyl),
—NHC(O)NH—($C_1$-$C_5$ alkyl)-N—($C_1$-$C_5$ alkyl)$_2$,
—NHC(O)NH—($C_1$-$C_5$ alkyl)-O—($C_1$-$C_5$ alkyl),
—NHC(O)NH—($C_1$-$C_5$ alkyl)-NH$_2$,
—NHC(O)NH—($C_1$-$C_5$ alkyl)-NH—($C_1$-$C_5$ alkyl),
—NHC(O)NH—($C_1$-$C_5$ alkyl)-N—($C_1$-$C_5$ alkyl)$_2$,
—NHC(O)NH—($C_1$-$C_5$ alkyl)-C(O)—NH$_2$,
—NHC(O)NH—($C_1$-$C_5$ alkyl)-C(O)—NH—($C_1$-$C_5$ alkyl),
—NHC(O)NH—($C_1$-$C_5$ alkyl)-C(O)—N—($C_1$-$C_5$ alkyl)$_2$,
—NHC(O)NH—($C_1$-$C_5$ alkyl)-C(O)—($C_1$-$C_5$ alkyl),
—NHC(O)NH—($C_1$-$C_5$ alkyl)-NH—SO$_2$—($C_1$-$C_5$ alkyl),
—NHC(O)NH—($C_1$-$C_5$ alkyl)-N-pyrrolidin-2-one,
—NHC(O)NH—($C_1$-$C_5$ alkyl)-N-pyrrolidine,
—NHC(O)NH—($C_1$-$C_5$ alkyl)-(1-methylpyrrolidin-2-one-3-yl),
—NHC(O)NH—($C_1$-$C_5$ alkyl)-C(O)—OH,
—NHC(O)NH—($C_1$-$C_5$ alkyl)-C(O)—O—($C_1$-$C_5$ alkyl),
—NHC(O)NH—($C_1$-$C_5$ alkyl)-5-tetrazolyl,
—NHC(O)NH—($C_1$-$C_5$ alkyl)-SO$_2$—($C_1$-$C_5$ alkyl),
—NHC(O)NH—($C_1$-$C_5$ alkyl)-SO$_2$—NH$_2$,
—NHC(O)NH—($C_1$-$C_5$ alkyl)-SO$_2$—NH—($C_1$-$C_5$ alkyl),
—NHC(O)NH—($C_1$-$C_5$ alkyl)-SO$_2$—N—($C_1$-$C_5$ alkyl)$_2$,
—NHC(O)NH—($C_1$-$C_5$ alkyl)-P(O)—O—($C_1$-$C_5$ alkyl)$_2$,
—NH$_2$,
—NH—($C_1$-$C_5$ alkyl),
—NH—CH$_2$—C(O)OH,
—N—($C_1$-$C_5$ alkyl)$_2$,
—NH—C(O)—NH$_2$,
—NH—C(O)—NH—($C_1$-$C_5$ alkyl),
—NH—C(O)—N—($C_1$-$C_5$ alkyl)$_2$,
—NH—C(O)—($C_1$-$C_5$ alkyl),
—NH—SO$_2$—($C_1$-$C_5$ alkyl),
—NH—S(O)—($C_1$-$C_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me,
—C(O)CH$_2$CH$_2$S(O)Et,
—C(O)CH$_2$CH$_2$S(O)$_2$Me,
—C(O)CH$_2$CH$_2$S(O)$_2$Et,
—C(O)CH(Me)CH$_2$CO$_2$H,
—C(O)CH(Me)CH$_2$CO$_2$Me,
—C(O)CH(Me)CH$_2$CO$_2$Et,
—C(O)CH(Me)CH$_2$CO$_2$iPr,
—C(O)CH(Me)CH$_2$CO$_2$tBu,
—C(O)CH(Me)CH(Me)CO$_2$H,
—C(O)CH(Me)CH(Me)CO$_2$Me,
—C(O)CH(Me)CH(Me)CO$_2$Et,
—C(O)CH(Me)CH(Me)CO$_2$iPr,
—C(O)CH(Me)CH(Me)CO$_2$tBu,
—C(O)CH(Me)C(Me)$_2$CO$_2$H,
—C(O)CH(Me)C(Me)$_2$CO$_2$Me,
—C(O)CH(Me)C(Me)$_2$CO$_2$Et,
—C(O)CH(Me)C(Me)$_2$CO$_2$iPr,
—C(O)CH(Me)C(Me)$_2$CO$_2$tBu,
—C(O)CH(Me)CH(Et)CO$_2$H,
—C(O)CH(Me)CH(Et)CO$_2$Me,
—C(O)CH(Me)CH(Et)CO$_2$Et,
—C(O)CH(Me)CH(Et)CO$_2$iPr,
—C(O)CH(Me)CH(Et)CO$_2$tBu,
—C(O)C(O)OH,
—C(O)C(O)NH$_2$,
—C(O)C(O)NHMe,
—C(O)C(O)NMe$_2$,
—C(O)NH$_2$,
—C(O)NMe$_2$,
—C(O)NH—CH$_2$—C(O)OH,
—C(O)NH—CH$_2$—C(O)OMe,
—C(O)NH—CH$_2$—C(O)OEt,
—C(O)NH—CH$_2$—C(O)OiPr,
—C(O)NH—CH$_2$—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)$_2$-C(O)OH,
—C(O)NH—C(Me)$_2$-C(O)OMe,
—C(O)NH—C(Me)$_2$-C(O)OEt,
—C(O)NH—C(Me)$_2$-C(O)iPr,
—C(O)NH—C(Me)$_2$-C(O)tBu, —C(O)NH-CMe(Et)-C(O)OH,
—C(O)NH—CH(F)—C(O)OH,
—C(O)NH—CH(CF$_3$)—C(O)OH,
—C(O)NH—CH(OH)—C(O)OH,
—C(O)NH—CH(cyclopropyl)-C(O)OH,
—C(O)NH—C(Me)$_2$-C(O)OH,
—C(O)NH—C(Me)$_2$-C(O)OH,
—C(O)NH—CF(Me)-C(O)OH,
—C(O)NH—C(Me)(CF$_3$)—C(O)OH,
—C(O)NH—C(Me)(OH)—C(O)OH,
—C(O)NH—C(Me)(cyclopropyl)CO$_2$H,
—C(O)NMe-CH$_2$—C(O)OH,
—C(O)NMe-CH$_2$—C(O)OMe,
—C(O)NMe-CH$_2$—C(O)OEt,
—C(O)NMe-CH$_2$—C(O)OiPr,
—C(O)NMe-CH$_2$—C(O)tBu,
—C(O)NMe-CH$_2$—C(O)OH,
—C(O)NMe-CH(Me)-C(O)OH,
—C(O)NMe-CH(F)—C(O)OH,
—C(O)NMe-CH(CF$_3$)—C(O)OH,
—C(O)NMe-CH(OH)—C(O)OH,
—C(O)NMe-CH(cyclopropyl)-C(O)OH,
—C(O)NMe-C(Me)$_2$-C(O)OH,
—C(O)NMe-CF(Me)-C(O)OH,
—C(O)NMe-C(Me)(CF$_3$)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO$_2$Me,
—C(O)—NH-5-tetrazolyl,
—C(O)NHS(O)Me,
—C(O)NHS(O)Et,
—C(O)NHSO$_2$Me,
—C(O)NHSO$_2$Et,
—C(O)NHS(O)iPr,
—C(O)NHSO$_2$iPr,
—C(O)NHS(O)tBu,
—C(O)NHSO$_2$tBu,
—C(O)NHCH$_2$S(O)Me,
—C(O)NHCH$_2$S(O)Et,
—C(O)NHCH$_2$SO$_2$Me,
—C(O)NHCH$_2$SO$_2$Et,
—C(O)NHCH$_2$CH$_2$S(O)Me,
—C(O)NHCH$_2$CH$_2$S(O)Et,
—C(O)NHCH$_2$CH$_2$SO$_2$Me,
—C(O)NHCH$_2$CH$_2$SO$_2$Et,
—C(O)N(Me)S(O)Me,
—C(O)N(Me)SO$_2$Me,
—C(O)—N(Me)-5-tetrazolyl,
—C(O)N(Me)S(O)Me,
—C(O)N(Me)S(O)Et,
—C(O)N(Me)SO$_2$Me,
—C(O)N(Me)SO$_2$Et,
—C(O)N(Me)S(O)iPr,
—C(O)N(Me))SO$_2$iPr,
—C(O)N(Me))S(O)tBu,
—C(O)N(Me)SO$_2$tBu,
—C(O)N(Me)CH$_2$S(O)Me,
—C(O)N(Me)CH$_2$S(O)Et,
—C(O)N(Me)CH$_2$SO$_2$Me,
—C(O)N(Me)CH$_2$SO$_2$Et,
—C(O)N(Me)CH$_2$CH$_2$S(O)Me,
—C(O)N(Me)CH$_2$CH$_2$S(O)Et,
—C(O)N(Me)CH$_2$CH$_2$SO$_2$Me,
—C(O)N(Me)CH$_2$CH$_2$SO$_2$Et,
—CH$_2$CO$_2$H,
—CH$_2$-5-tetrazolyl,
—CH$_2$CO$_2$Me,
—CH$_2$CO$_2$Et,
—CH$_2$NHS(O)Me,
—CH$_2$NHS(O)Et,
—CH$_2$NHSO$_2$Me,
—CH$_2$NHSO$_2$Et,
—CH$_2$NHS(O)iPr,
—CH$_2$NHSO$_2$iPr,
—CH$_2$NHS(O)tBu,
—CH$_2$NHSO$_2$tBu,
—CH$_2$NHCH$_2$CH$_2$SO$_2$CH$_3$,
—CH$_2$NH(CH$_2$CO$_2$H),
—CH$_2$N(C(O)Me)(CH$_2$CO$_2$H),
—CH$_2$—N-pyrrolidin-2-one,
—CH$_2$-(1-methylpyrrolidin-2-one-3-yl),
—CH$_2$S(O)Me,
—CH$_2$S(O)Et,
—CH$_2$S(O)$_2$Me,
—CH$_2$S(O)$_2$Et,
—CH$_2$S(O)iPr,
—CH$_2$S(O)$_2$iPr,
—CH$_2$S(O)tBu,
—CH$_2$S(O)$_2$tBu,
—CH$_2$CO$_2$H, CH$_2$C(O)NH$_2$,
—CH$_2$C(O)NMe$_2$,
—CH$_2$C(O)NHMe,
—CH$_2$C(O)—N-pyrrolidine,
—CH$_2$S(O)$_2$Me, CH$_2$S(O)Me,
—CH(OH)CO$_2$H,
—CH(OH)C(O)NH$_2$,
—CH(OH)C(O)NHMe,
—CH(OH)C(O)NMe$_2$,
—CH(OH)C(O)NEt$_2$,
—CH$_2$CH$_2$CO$_2$H,
—CH$_2$CH$_2$CO$_2$Me,
—CH$_2$CH$_2$CO$_2$Et,
—CH$_2$CH$_2$C(O)NH$_2$,
—CH$_2$CH$_2$C(O)NHMe,
—CH$_2$CH$_2$C(O)NMe$_2$,
—CH$_2$CH$_2$-5-tetrazolyl,
—CH$_2$CH$_2$S(O)$_2$Me,
—CH$_2$CH$_2$S(O)Me,
—CH$_2$CH$_2$S(O)$_2$Et,
—CH$_2$CH$_2$S(O) Et,
—CH$_2$CH$_2$S(O)iPr,
—CH$_2$CH$_2$S(O)$_2$iPr,
—CH$_2$CH$_2$S(O)tBu,
—CH$_2$CH$_2$S(O)$_2$tBu,
—CH$_2$CH$_2$S(O)NH$_2$,
—CH$_2$CH$_2$S(O)NHMe,
—CH$_2$CH$_2$S(O)NMe$_2$,
—CH$_2$CH$_2$S(O)$_2$NH$_2$,
—CH$_2$CH$_2$S(O)$_2$NHMe
—CH$_2$CH$_2$S(O)$_2$NMe$_2$,
—CH$_2$CH$_2$CH$_2$S(O)Me,
—CH$_2$CH$_2$CH$_2$S(O)Et,
—CH$_2$CH$_2$CH$_2$S(O)$_2$Me,
—CH$_2$CH$_2$CH$_2$S(O)$_2$Et,
—CH(Me)CH$_2$C(O)OH, —C(Me)$_2$CH$_2$C(O)OH,
—C(O)OH,
-5-tetrazolyl,

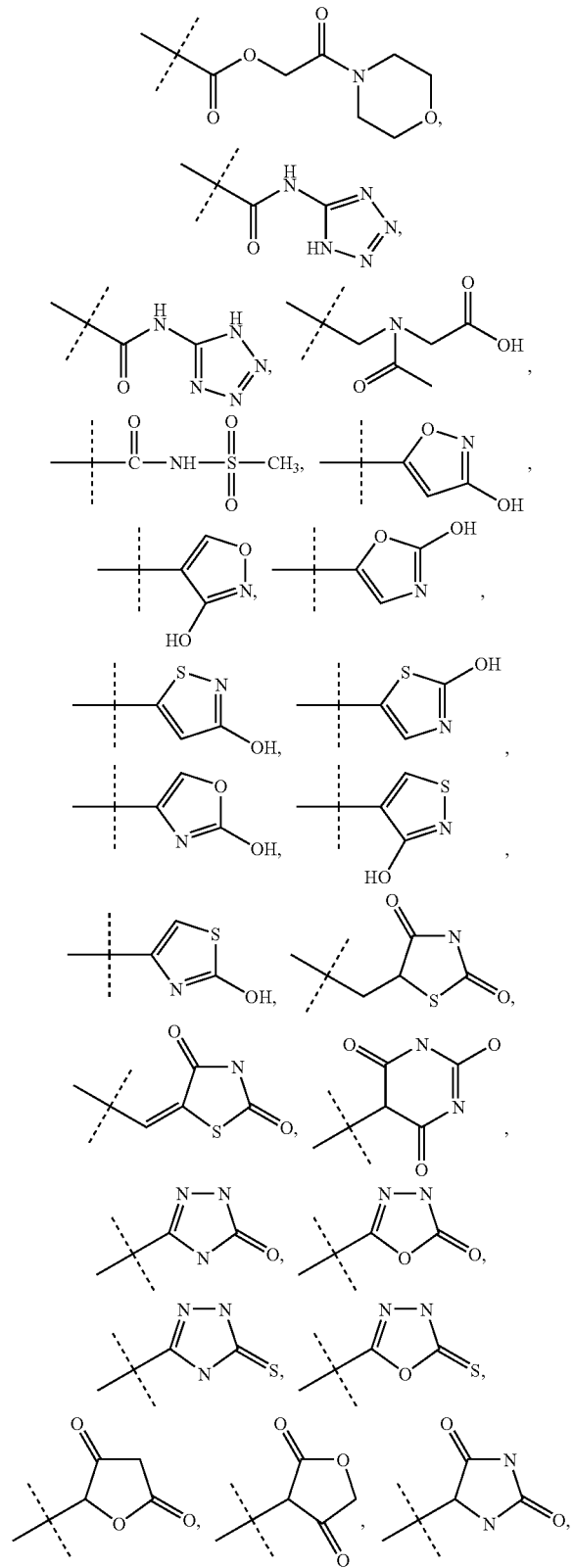

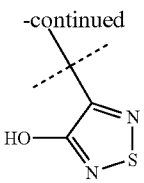

-1,3,4-oxadiazolin-2-one-5-yl,
-imidazolidine-2,4-dione-5-yl,
-isoxazol-3-ol-yl, or
-1,3,4-oxadiazolin-2-thione-5-yl;
provided that RP is substituted at either the 2, 5, or 6 position of the phenyl ring.

Preferred Embodiments of the Invention

The compound of Formula IA having as preferred substituents;
R and R' are independently methy or ethyl;
RP and RT$_3$ are independently, hydrogen or methyl;
RP$_3$ and RB are independently hydrogen, methyl, ethyl, —O-methyl, or cyclopropyl,
(L$_{P1}$) and (L$_{TB}$) divalent linking groups are both bonds;
(L$_{P2}$) is a bond, —CH$_2$—, —CH(OH)—, or —C(Me)OH—;
Z$_P$ is 1,1-dimethylethyl; 1-hydroxycyclopentyl, 1-hydroxycyclohexyl, 3-ethyl-3-hydroxypentyl, 3-ethyl-3-hydroxypentenyl, 3-ethyl-3-hydroxypentynyl;
Z$_{FB}$ is
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me,
—C(O)CH$_2$CH$_2$S(O)Et,
—C(O)CH$_2$CH$_2$S(O)$_2$Me,
—C(O)CH$_2$CH$_2$S(O)$_2$Et,
—C(O)CH(Me)CH$_2$CO$_2$H,
—C(O)CH(Me)CH$_2$CO$_2$Me,
—C(O)CH(Me)CH$_2$CO$_2$Et,
—C(O)CH(Me)CH$_2$CO$_2$iPr,
—C(O)CH(Me)CH$_2$CO$_2$tBu,
—C(O)CH(Me)CH(Me)CO$_2$H,
—C(O)CH(Me)CH(Me)CO$_2$Me,
—C(O)CH(Me)CH(Me)CO$_2$Et,
—C(O)CH(Me)CH(Me)CO$_2$iPr,
—C(O)CH(Me)CH(Me)CO$_2$tBu,
—C(O)CH(Me)C(Me)$_2$CO$_2$H,
—C(O)CH(Me)C(Me)$_2$CO$_2$Me,
—C(O)CH(Me)C(Me)$_2$CO$_2$Et,
—C(O)CH(Me)C(Me)$_2$CO$_2$iPr,
—C(O)CH(Me)C(Me)$_2$CO$_2$tBu,
—C(O)CH(Me)CH(Et)CO$_2$H,
—C(O)CH(Me)CH(Et)CO$_2$Me,
—C(O)CH(Me)CH(Et)CO$_2$Et,
—C(O)CH(Me)CH(Et)CO$_2$iPr,
—C(O)CH(Me)CH(Et)CO$_2$tBu,
—C(O)C(O)OH,
—C(O)C(O)NH$_2$,
—C(O)C(O)NHMe,
—C(O)C(O)NMe$_2$, —C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH-CMe(Et)-C(O)OH,
—C(O)NH—CH(F)—C(O)COH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O) Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂, —$CH_2CH_2S(O)NHMe$,
—$CH_2CH_2S(O)NMe_2$,
—$CH_2CH_2S(O)_2NH_2$,
—$CH_2CH_2S(O)_2NHMe$,
—$CH_2CH_2S(O)_2NMe_2$,
—$CH_2CH_2CH_2S(O)Me$,
—$CH_2CH_2CH_2S(O)Et$,
—$CH_2CH_2CH_2S(O)_2Me$, or
—$CH_2CH_2CH_2S(O)_2Et$.

The compound of formula IB or formula IC having as preferred substituents;

R and R' are independently methy or ethyl;

RP, RB, $RB_4$, and $RF_3$ are independently, hydrogen or methyl;

$RP_3$ and $RB_7$ are independently hydrogen, methyl, ethyl, —O-methyl, or cyclopropyl;

$(L_{P1})$ and $(L_{BF})$ divalent linking groups are both bonds;

$(L_{P2})$ is a bond, —$CH_2$—, —CH(OH)—, or —C(Me)OH—;

$Z_P$ is 1,1-dimethylethyl; 1-hydroxycyclopentyl, 1-hydroxycyclohexyl, 3-ethyl-3-hydroxypentyl, 3-ethyl-3-hydroxypentenyl, 3-ethyl-3-hydroxypentynyl;

$Z_{BF}$ is
—$CO_2H$,
—$CO_2Me$,
—$CO_2Et$,
—$C(O)CH_2S(O)Me$,
—$C(O)CH_2S(O)Et$,
—$C(O)CH_2S(O)_2Me$,
—$C(O)CH_2S(O)_2Et$,
—$C(O)CH_2CH_2S(O)Me$,
—$C(O)CH_2CH_2S(O)Et$,
—$C(O)CH_2CH_2S(O)_2Me$,
—$C(O)CH_2CH_2S(O)_2Et$,
—$C(O)CH(Me)CH_2CO_2H$,
—$C(O)CH(Me)CH_2CO_2Me$,
—$C(O)CH(Me)CH_2CO_2Et$,
—$C(O)CH(Me)CH_2CO_2iPr$,
—$C(O)CH(Me)CH_2CO_2tBu$,
—$C(O)CH(Me)CH(Me)CO_2H$,
—$C(O)CH(Me)CH(Me)CO_2Me$,
—$C(O)CH(Me)CH(Me)CO_2Et$,
—$C(O)CH(Me)CH(Me)CO_2iPr$,
—$C(O)CH(Me)CH(Me)CO_2tBu$,
—$C(O)CH(Me)C(Me)_2CO_2H$,
—$C(O)CH(Me)C(Me)_2CO_2Me$,
—$C(O)CH(Me)C(Me)_2CO_2Et$,
—$C(O)CH(Me)C(Me)_2CO_2iPr$,
—$C(O)CH(Me)C(Me)_2CO_2tBu$,
—$C(O)CH(Me)CH(Et)CO_2H$,
—$C(O)CH(Me)CH(Et)CO_2Me$,
—$C(O)CH(Me)CH(Et)CO_2Et$,
—$C(O)CH(Me)CH(Et)CO_2iPr$,
—$C(O)CH(Me)CH(Et)CO_2tBu$,
—$C(O)C(O)OH$,
—$C(O)C(O)NH_2$,
—$C(O)C(O)NHMe$,
—$C(O)C(O)NMe_2$,
—$C(O)NH_2$,
—$C(O)NMe_2$,
—C(O)NH—$CH_2$—C(O)OH,
—C(O)NH—$CH_2$—C(O)OMe,
—C(O)NH—$CH_2$—C(O)OEt,
—C(O)NH—$CH_2$—C(O)OiPr,
—C(O)NH—$CH_2$—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—$C(Me)_2$-C(O)OH,
—C(O)NH—$C(Me)_2$-C(O)OMe,
—C(O)NH—$C(Me)_2$-C(O)OEt,
—C(O)NH—$C(Me)_2$-C(O)iPr,
—C(O)NH—$C(Me)_2$-C(O)tBu,
—C(O)NH-CMe(Et)-C(O)OH,
—C(O)NH—CH(F)—C(O)OH,
—C(O)NH—$CH(CF_3)$—C(O)OH,
—C(O)NH—CH(OH)—C(O)OH,
—C(O)NH—CH(cyclopropyl)-C(O)OH,
—C(O)NH—$C(Me)_2$-C(O)OH,
—C(O)NH—$C(Me)_2$-C(O)OH,
—C(O)NH—CF(Me)-C(O)OH,
—C(O)NH—$C(Me)(CF_3)$—C(O)OH,
—C(O)NH—C(Me)(OH)—C(O)OH,
—C(O)NH—$C(Me)(cyclopropyl)CO_2H$
—C(O)NMe-$CH_2$—C(O)OH,
—C(O)NMe-$CH_2$—C(O)OMe,
—C(O)NMe-$CH_2$—C(O)OEt,
—C(O)NMe-$CH_2$—C(O)OiPr,
—C(O)NMe-$CH_2$—C(O)tBu,
—C(O)NMe-$CH_2$—C(O)OH,
—C(O)NMe-CH(Me)-C(O)OH,
—C(O)NMe-CH(F)—C(O)OH,
—C(O)NMe-$CH(CF_3)$—C(O)OH,
—C(O)NMe-CH(OH)—C(O)OH,
—C(O)NMe-CH(cyclopropyl)-C(O)OH,
—C(O)NMe-$C(Me)_2$-C(O)OH,
—C(O)NMe-CF(Me)-C(O)OH,
—C(O)NMe-$C(Me)(CF_3)$—C(O)OH,
—C(O)NMe-C(Me)(OH)—C(O)OH,
—C(O)NMe-C(Me)(cyclopropyl)-C(O)OH,
—C(O)NHS(O))Me,
—$C(O)NHSO_2Me$,
—C(O)—NH-5-tetrazolyl,
—C(O)NHS(O)Me,
—C(O)NHS(O)Et,
—$C(O)NHSO_2Me$,
—$C(O)NHSO_2Et$,
—C(O)NHS(O)iPr,
—$C(O)NHSO_2iPr$,
—C(O)NHS(O)tBu,
—$C(O)NHSO_2tBu$,
—$C(O)NHCH_2S(O)Me$,
—$C(O)NHCH_2S(O)Et$,
—$C(O)NHCH_2SO_2Me$,
—$C(O)NHCH_2SO_2Et$,
—$C(O)NHCH_2CH_2S(O)Me$,
—$C(O)NHCH_2CH_2S(O)Et$,
—$C(O)NHCH_2CH_2SO_2Me$,
—$C(O)NHCH_2CH_2SO_2Et$,
—C(O)N(Me)S(O)Me,
—$C(O)N(Me)SO_2Me$,
—C(O)—N(Me)-5-tetrazolyl,
—C(O)N(Me)S(O)Me,
—C(O)N(Me)S(O)Et,
—$C(O)N(Me)SO_2Me$,
—$C(O)N(Me)SO_2Et$,
—C(O)N(Me)S(O)iPr,
—$C(O)N(Me))SO_2iPr$,
—C(O)N(Me))S(O)tBu,
—$C(O)N(Me)SO_2tBu$,
—$C(O)N(Me)CH_2S(O)Me$, —C(O)N(Me)CH$_2$S(O)Et,
—C(O)N(Me)CH$_2$SO$_2$Me,
—C(O)N(Me)CH$_2$SO$_2$Et,
—C(O)N(Me)CH$_2$CH$_2$S(O)Me,
—C(O)N(Me)CH$_2$CH$_2$S(O)Et,
—C(O)N(Me)CH$_2$CH$_2$SO$_2$Me,
—C(O)N(Me)CH$_2$CH$_2$SO$_2$Et,
—CH$_2$CO$_2$H,
—CH$_2$-5-tetrazolyl,
—CH$_2$CO$_2$Me,
—CH$_2$CO$_2$Et,
—CH$_2$NHS(O)Me,
—CH$_2$NHS(O)Et,
—CH$_2$NHSO$_2$Me,
—CH$_2$NHSO$_2$Et,
—CH$_2$NHS(O)iPr,
—CH$_2$NHSO$_2$iPr,
—CH$_2$NHS(O)tBu,
—CH$_2$NHSO$_2$tBu,
—CH$_2$NHCH$_2$CH$_2$SO$_2$CH$_3$,
—CH$_2$NH(CH$_2$CO$_2$H),
—CH$_2$N(C(O)Me)(CH$_2$CO$_2$H),
—CH$_2$—N-pyrrolidin-2-one,
—CH$_2$-(1-methylpyrrolidin-2-one-3-yl),
—CH$_2$S(O)Me,
—CH$_2$S(O)Et,
—CH$_2$S(O)$_2$Me,
—CH$_2$S(O)$_2$Et,
—CH$_2$S(O)iPr,
—CH$_2$S(O)$_2$iPr,
—CH$_2$S(O)tBu,
—CH$_2$S(O)$_2$tBu,
—CH$_2$CO$_2$H, CH$_2$C(O)NH$_2$,
—CH$_2$C(O)NMe$_2$,
—CH$_2$C(O)NHMe,
—CH$_2$C(O)—N-pyrrolidine,
—CH$_2$S(O)$_2$Me, CH$_2$S(O)Me,
—CH(OH)CO$_2$H,
—CH(OH)C(O)NH$_2$,
—CH(OH)C(O)NHMe,
—CH(OH)C(O)NMe$_2$,
—CH(OH)C(O)NEt$_2$,
—CH$_2$CH$_2$CO$_2$H,
—CH$_2$CH$_2$CO$_2$Me,
—CH$_2$CH$_2$CO$_2$Et,
—CH$_2$CH$_2$C(O)NH$_2$,
—CH$_2$CH$_2$C(O)NHMe,
—CH$_2$CH$_2$C(O)NMe$_2$,
—CH$_2$CH$_2$-5-tetrazolyl,
—CH$_2$CH$_2$S(O)$_2$Me,
—CH$_2$CH$_2$S(O)Me,
—CH$_2$CH$_2$S(O)$_2$Et,
—CH$_2$CH$_2$S(O) Et,
—CH$_2$CH$_2$S(O)iPr,
—CH$_2$CH$_2$S(O)$_2$iPr,
—CH$_2$CH$_2$S(O)tBu,
—CH$_2$CH$_2$S(O)$_2$tBu,
—CH$_2$CH$_2$S(O)NH$_2$,
—CH$_2$CH$_2$S(O)NHMe,
—CH$_2$CH$_2$S(O)NMe$_2$,
—CH$_2$CH$_2$S(O)$_2$NH$_2$,
—CH$_2$CH$_2$S(O)$_2$NHMe —CH$_2$CH$_2$S(O)$_2$NMe$_2$,
—CH$_2$CH$_2$CH$_2$S(O)Me,
—CH$_2$CH$_2$CH$_2$S(O)Et,
—CH$_2$CH$_2$CH$_2$S(O)$_2$Me, or
—CH$_2$CH$_2$CH$_2$S(O)$_2$Et.

Particularly preferred compounds of the invention and salts and prodrug derivatives are represented by formulae C1 to C39 as follows:

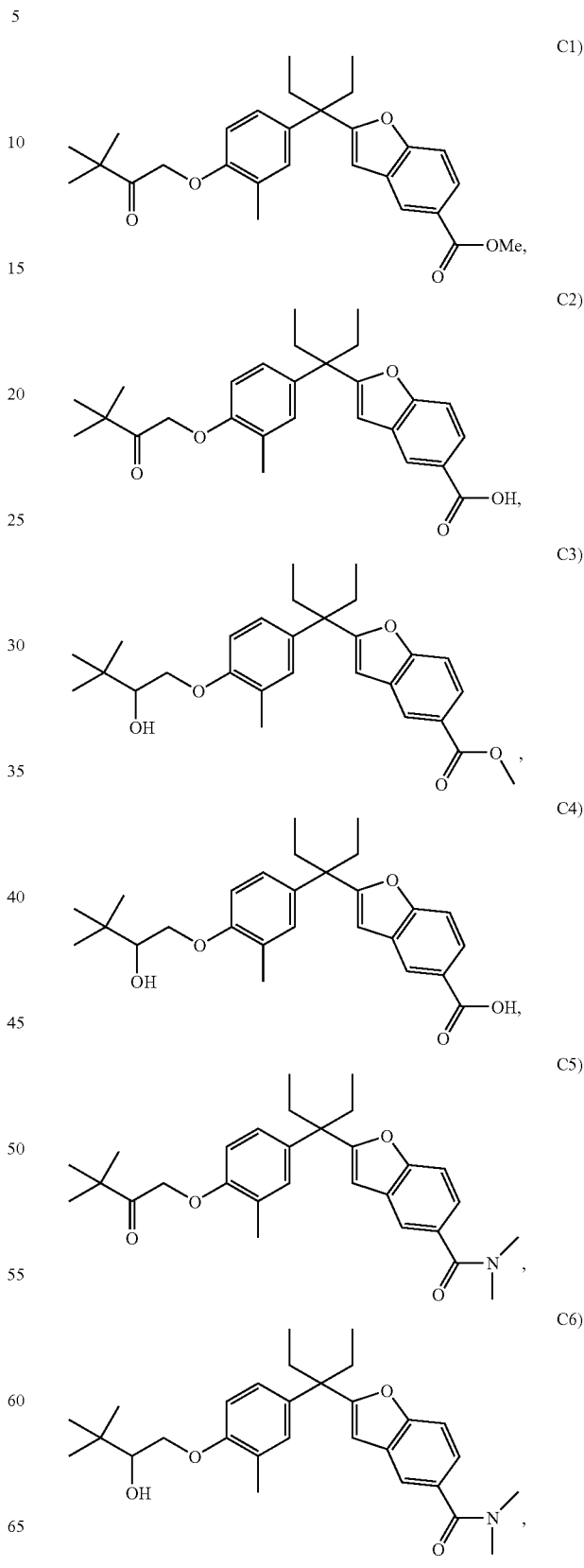

-continued
C7)
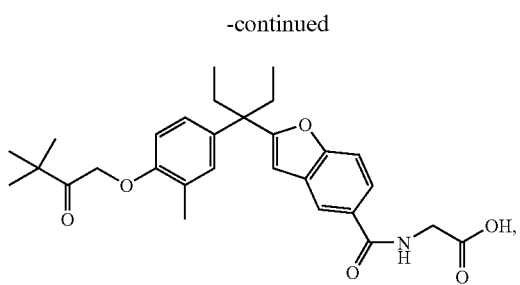
C8)
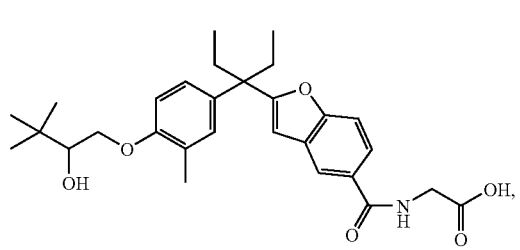
C9)
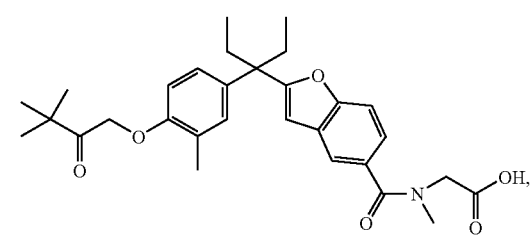
C10)
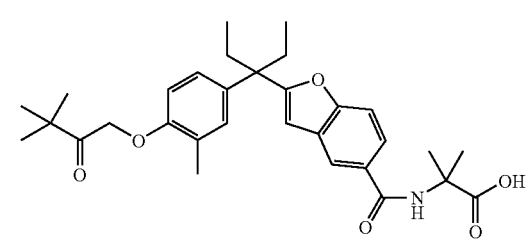
C11)
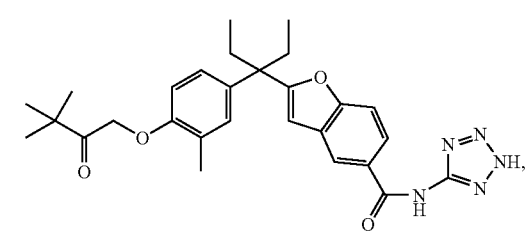
C13)
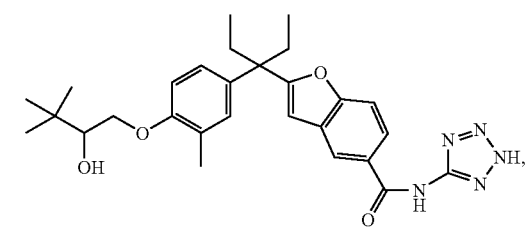
-continued
C14)
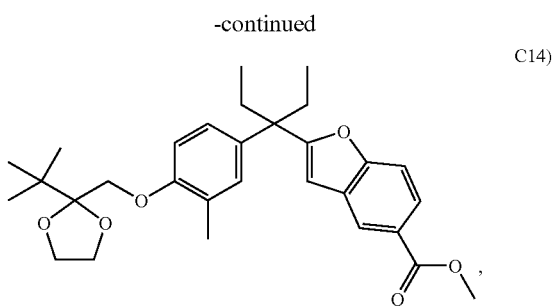
C15)
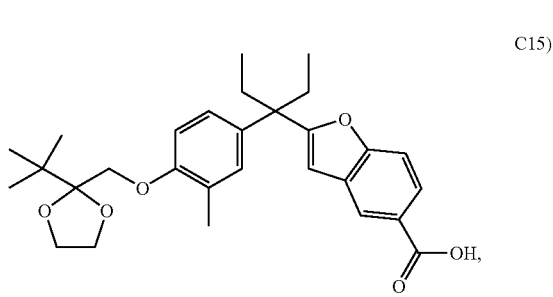
C16)
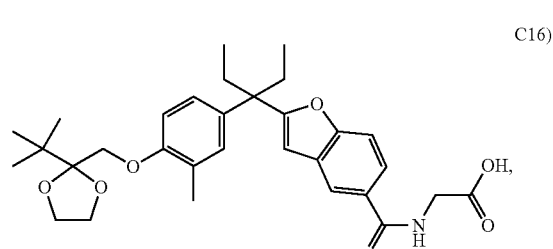
C17)
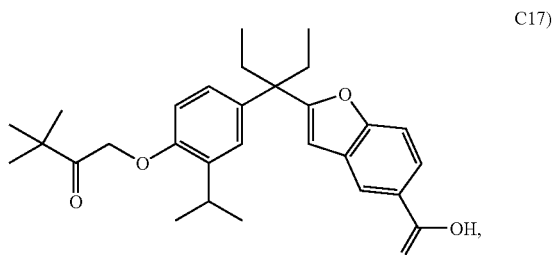
C18)
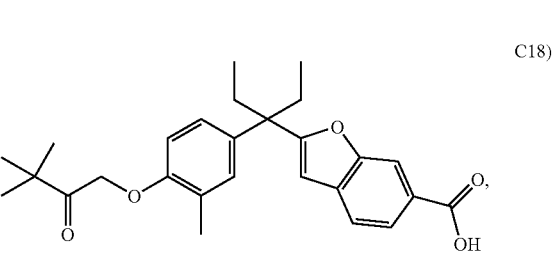
C19)
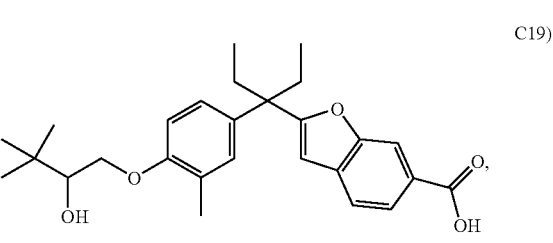

-continued
C20)
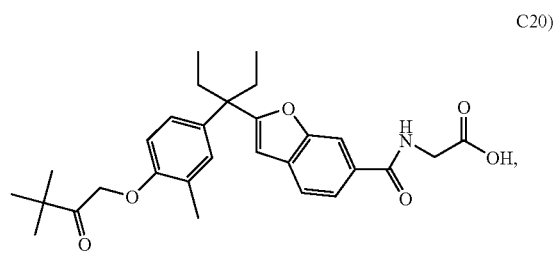
C21)
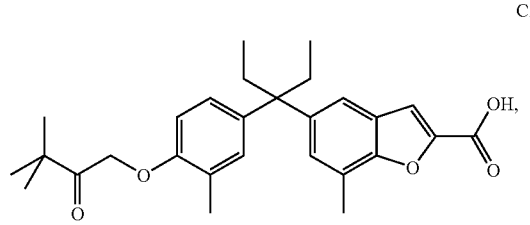
C22)
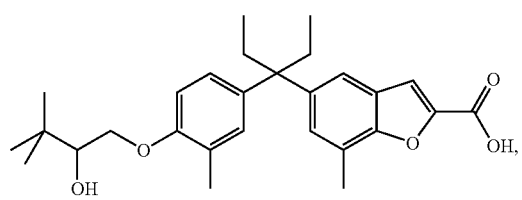
C23)
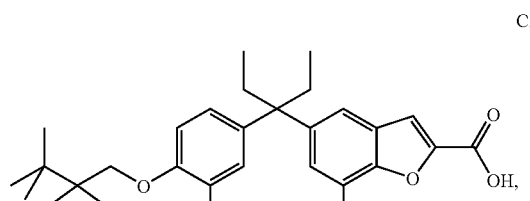
C24)
C25)
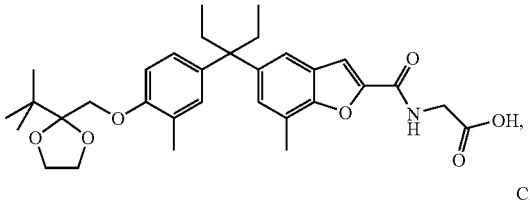
C26)
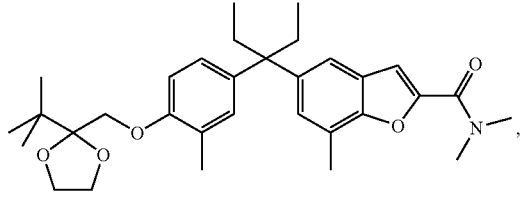
-continued
C27)
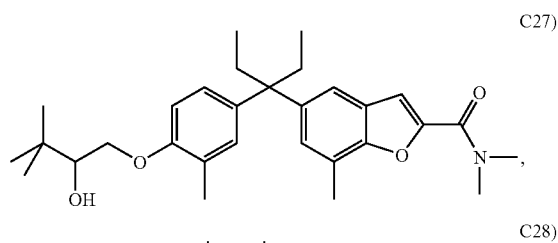
C28)
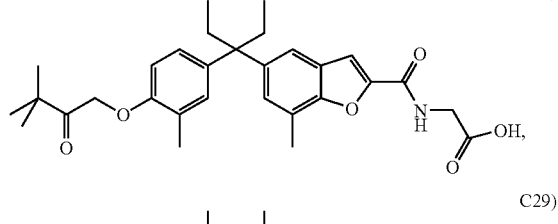
C29)
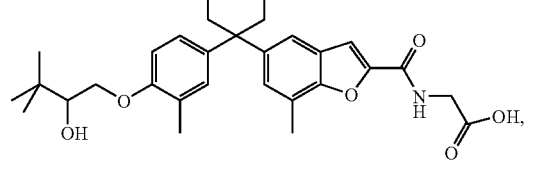
C30)
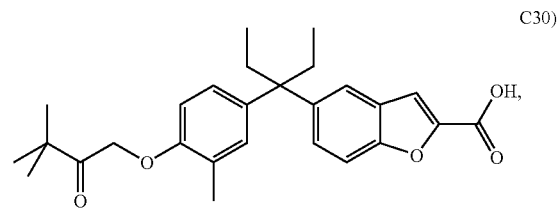
C31)
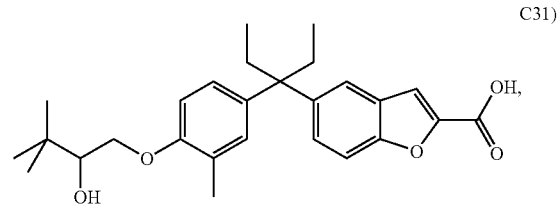
C32)
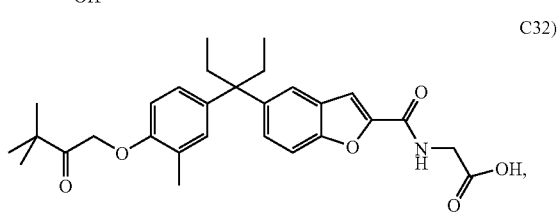
C33)
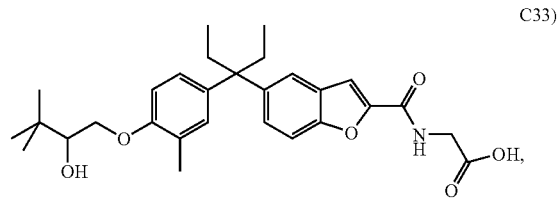
C34)
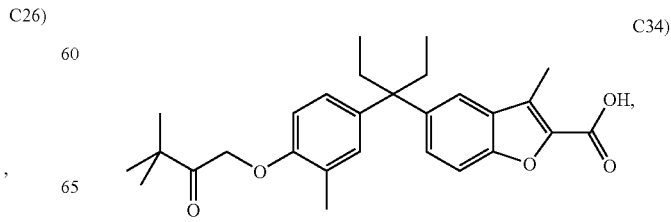

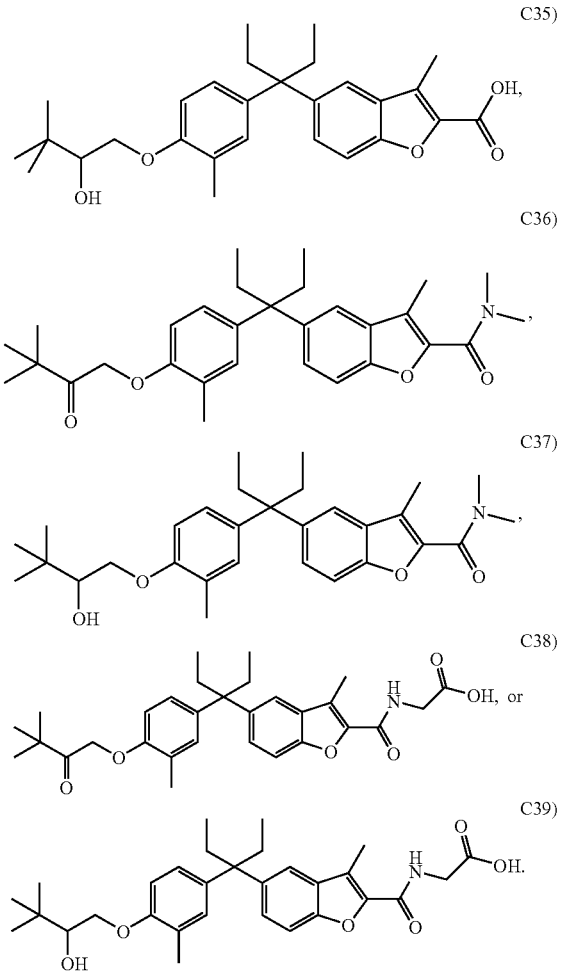

Particularly preferred is the compound represented by the structural formula AA or a pharmaceutically acceptable salt or prodrug thereof:

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the organic layer is $MgSO_4$/$Na_2SO_4$ dried is defined as stirring the solution with a dessicant for 5-15 m and filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo −25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

For HPLC, the conditions listed are for the analytical trace only. For Preparative HPLC, the eluent is similar to analytical HPLC eluent.

Thin layer chromatography is performed with silica gel plates with UV and/or appropriate staining solution.

NMR spectra are obtained with either 300 or 400 mHz spectrometer.

NMR data is listed to denote spectrum is consistent with assigned structure.

"NMR" notation without data denotes spectrum is consistent with assigned structure.

HRMS—high resolution mass spectrum
ES-MS—electrospray mass spectrum
Abbreviations:
Aq—aqueous
d—day
eq—equivalent
h—hour
m—minute
satd—saturated
disp—dispersion
quant—quantitative
rt for retention time (both small caps to minimize confusion with RT)
RT—room temperature Chemical Definitions:
BF3-OEt2—boron trifluoride etherate
BnBr—benzyl bromide
CH2Cl2-dichloromethane
CH3CN—acetonitrile
CO—carbon monoxide
CsF—cesium fluoride
DMAP—4-(dimethylamino)pyridine
DMF—N,N-dimethylformamide
DMSO—dimethylsulfoxide
DPPB—1,4-bis(diphenylphosphino)butane
DPPF—dichloro[1,1'-bis(diphenylphosphino)ferrocene
EDCI—3-Ethyl-1-[3-(dimethylamino)propyl]carbodiimide hydrochloride
Et3N—triethylamine
EtMgBr—ethyl magnesium bromide
EtOAc—ethyl acetate
EtOH—ethanol
H2—hydrogen pressure
H2NCH2CO2Me—methyl glycinate
Hept—heptane
Hex—hexanes
HN(OMe)Me —N-methyl-O-methyl hydroxylamine
HNMe2—dimethyl amine
HATU—O-(7-azabenzotriazol-1-yl)-N,N,N',N'-tetramethyluronium hexafluorophosphate
HOAT—7-aza-1-hydroxybenzotriazole
HOBT—1-hydroxybenzotriazole
K2CO3-potassium carbonate
KI—potassium iodine
KOH—potassium hydroxide
LAH—lithium aluminum hydride
LiHMDS—lithium hexamethyldisilazide
Lindlar catalyst—Pd—$CaCO_3$—PbO
LiOH—lithium hydroxide
mCPBA—meta-chloroperbenzoic acid
MeI—methyl iodide
MeOH—methanol NaBH4—sodium borohydride
MgSO4—magnesium sulfate
NaH—sodium hydride
NaHCO3—sodium bicarbonate
NaI—sodium iodide
Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)$_2$—palladium (II) acetate
Pd(TPP)$_4$—palladium tetrakistriphenylphosphine
Pd—C—palladium on carbon
Pd—C/H2—palladium on carbon with hydrogen pressure
pTSA—para-toluenesulfonic acid
Pyr—pyridine
Red-Al—sodium bis(2-methoxyethoxy)aluminum hydride
R2MgBr—alkyl magnesium bromide
R3MgBr—alkyl magnesium bromide
R5MgBr—alkyl magnesium bromide
R3S(O)$_2$Cl—alkylsulfonyl chloride
R2S(O)$_2$NH$_2$-alkylsulfonamide
TBSCl—tert-butyldimethylsilyl chloride
tBuC(O)CH$_2$Br—1-bromopinacolone
Tf2O—triflic anhydride
TFA—trifluoroacetic acid
THF—tetrahydrofuran
Ti(OiPr)4—titanium tetraisopropoxide
TMS-acetylene—trimethylsilyl acetylene
TPAP—tetrapropylammonium perruthenate
Zn(OTf)2—zinc trifluoromethane sulfonate General Procedures Scheme I

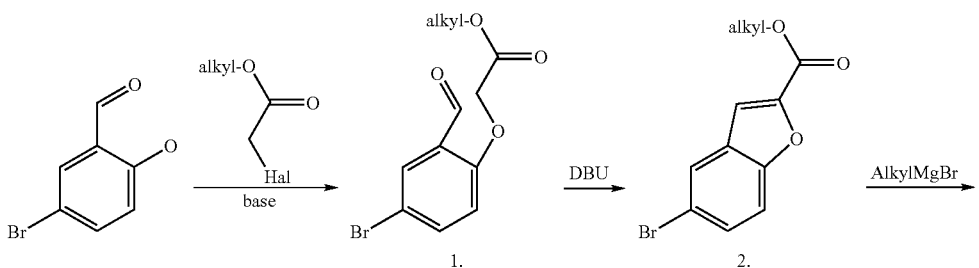

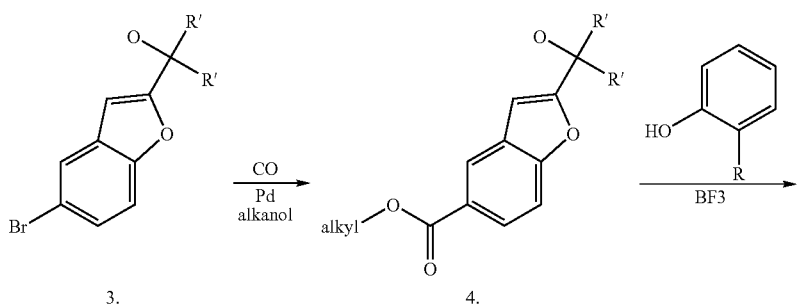

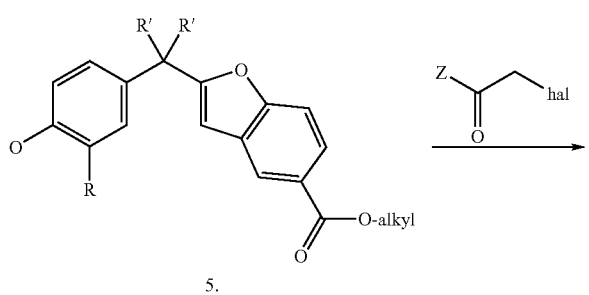

-continued
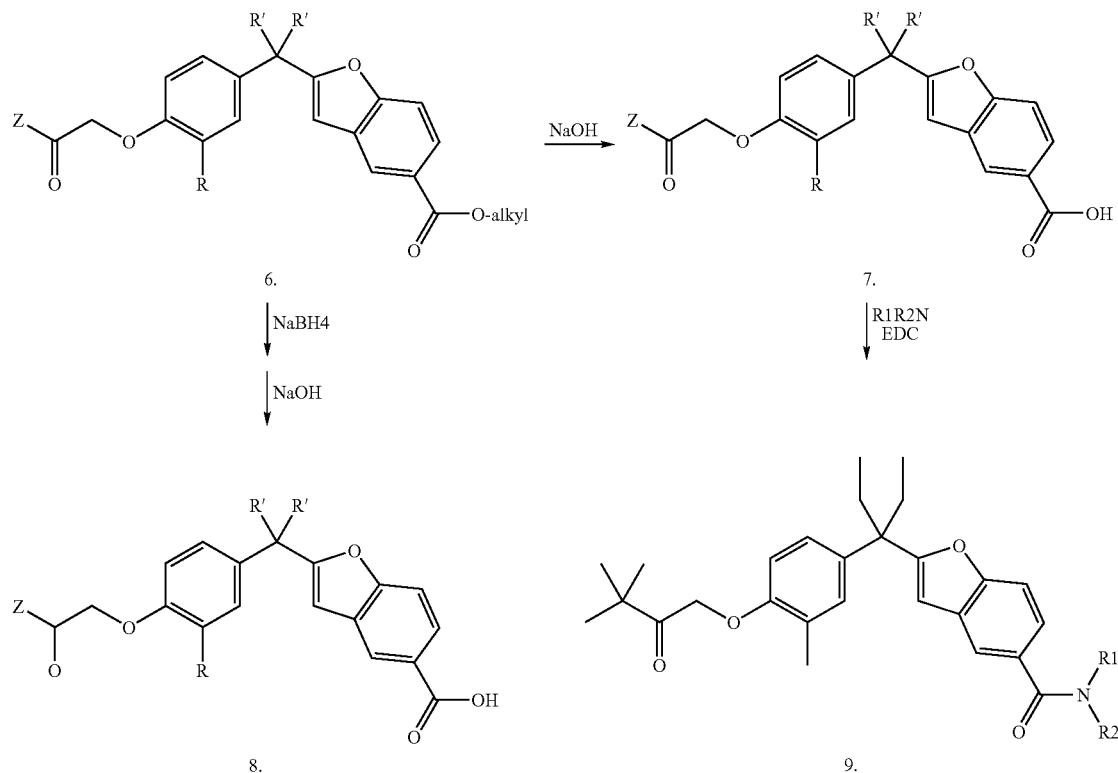
Scheme II
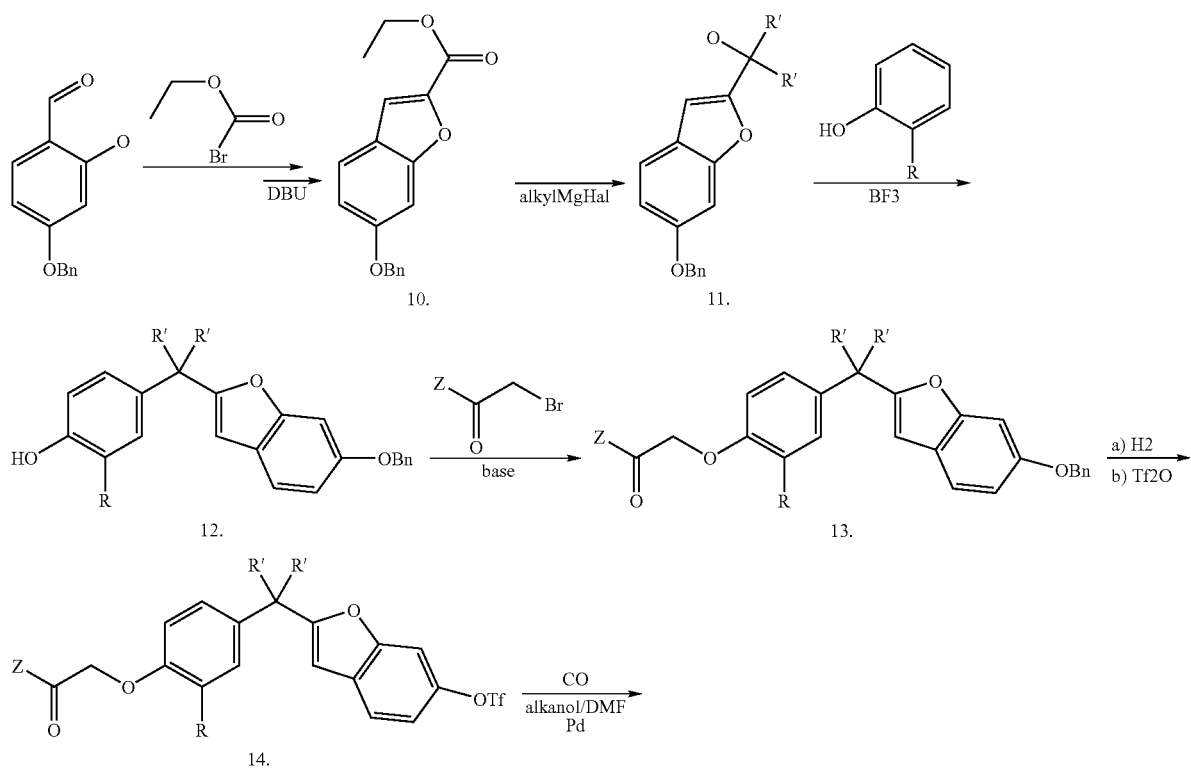

-continued
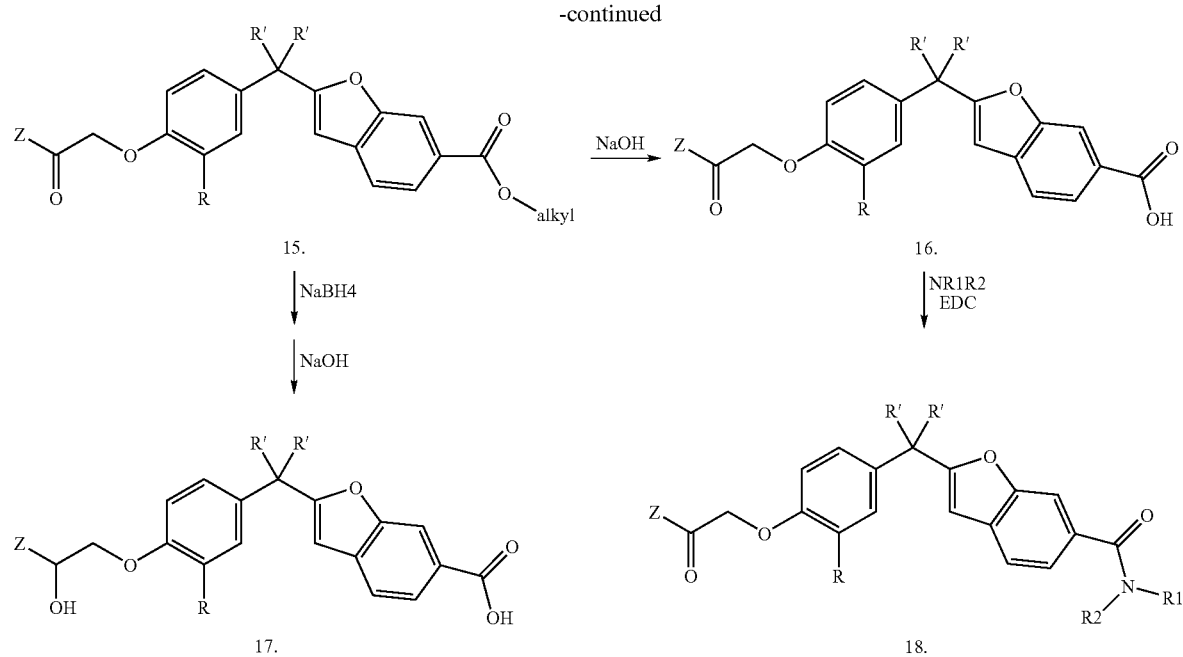
Scheme III
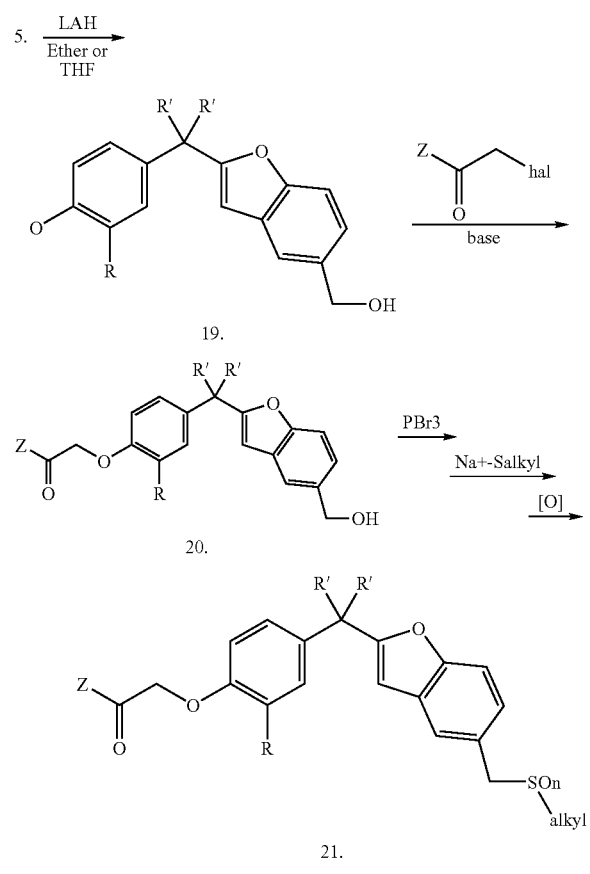
Scheme IV
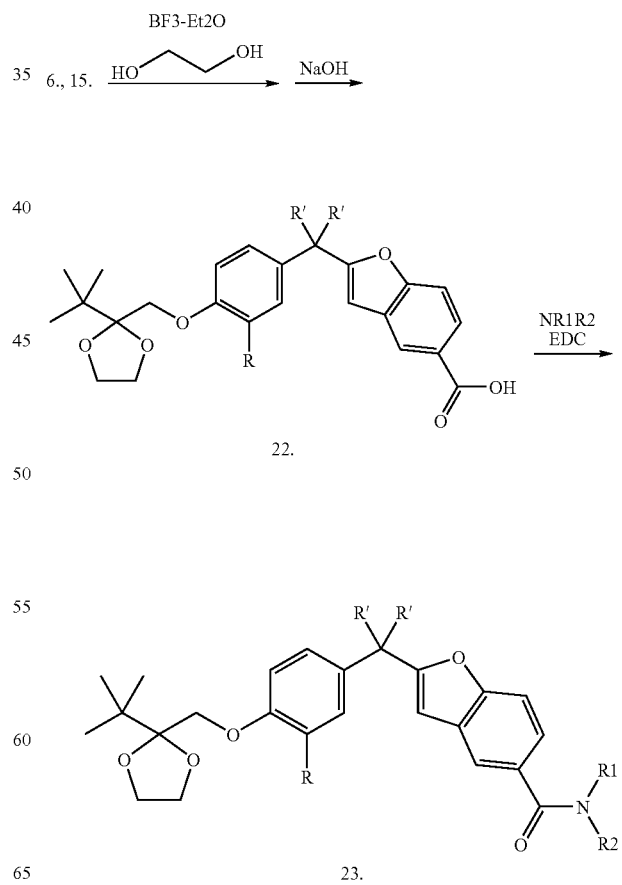

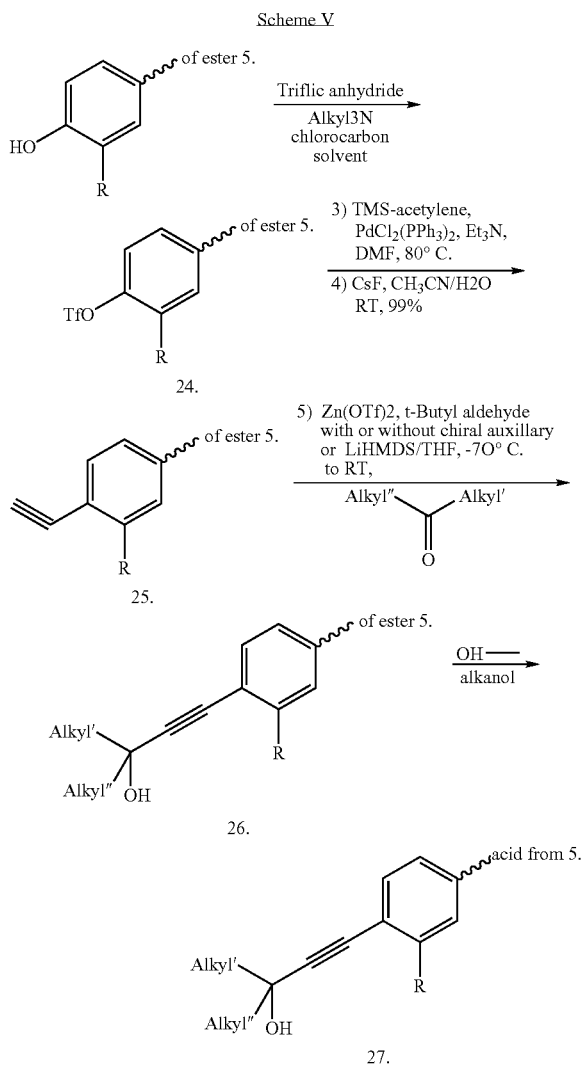

the acid 8. The diarylmethane 6. is also saponified with lithium, sodium, or potassium hydroxide in an alkanol from room temperature to the reflux temperature of the mixture to give the acid 7. Both acid 7. and acid 8. are converted to the amides, e.g., amide 9. with a coupling reagent, e.g., EDC, and a primary or secondary amine.

Scheme II. 4-Benzyloxy-2-hydroxybenzaldehyde is alkylated with an alpha-haloacetate analogous to compound 1. above and cyclized analogous to compound 2. above to give benzofuran 10. Benzofuran 10. is reacted with an excess of Grignard reagent analogous to compound 3. above to give the tert-carbinol 11. The carbinol 11. is alkylated with an alpha-halo ketone or ester in base and a polar aprotic solvent to give diarylmethane 13. The protecting group of diarylmethane 13. is removed by hydrogenation in the presence of catalyst, e.g., pd on carbon, and the free hydroxyl converted to the triflate 14. with triflic anhydride and base in THF or a chlorocarbon solvent. The triflate 14. is reacted with carbon monoxide (1-1000 psi) in the presence of a palladium catalyst, e.g., $Pd(OAc)_2$ and DPPF (0.01 to 0.9 equivalents) from room temperature to 160° C. for 30 min to 48 h in an alkanol with DMF to produce the ester 15. Ester 15. is reduced with lithium, sodium, or potassium borohydride or cyanoborohydride in alkanol or THF to give the intermediate carbinol, which is saponified with lithium, sodium, or potassium hydroxide in an alkanol from room temperature to the reflux temperature of the mixture to give the acid 17. The ester 15. is also saponified with lithium, sodium, or potassium hydroxide in an alkanol from room temperature to the reflux temperature of the mixture to give the acid 16. Both acid 17. and acid 16. are converted to the amides, e.g., amide 18. with a coupling reagent, e.g., EDC, and a primary or secondary amine.

Scheme III. Diarylmethane 5. is reduced with, e.g., LAH in ether or THF to the methanol 19. Methanol 19. is alkylated with an alpha-halo ketone or ester in base and a polar aprotic solvent to give methanol 20. Methanol 20. is converted to the primary halide with, e.g., $PBr_3$, and the primary halide is displaced with a sodium, lithium, or potassium -Salkyl in a polar aprotic solvent to give a thioether intermediate that is oxidized, e.g., hydrogen peroxide in alkanol or MCPBA, to the sulfoxide or sulfone 21.

Scheme IV. Esters 6. and 15. from Schemes I. and II. are ketalized with, e.g., ethylene glycol in the presence of a Lewis acid, e.g., boron trifluoride etherate (0.01 to 1 equivalents) followed by saponification with lithium, sodium, or potassium hydroxide in an alkanol from room temperature to the reflux temperature of the mixture to give the acids 22. The acids 22. are converted to the amides 23. with a coupling reagent, e.g., EDC, and a primary or secondary amine. Alternately, amides 23. are derived by ketalizing amides 9. and 18. with, e.g., ethylene glycol in the presence of a Lewis acid, e.g., boron trifluoride etherate (0.01 to 1 equivalents).

Scheme V. Ester 5. from Scheme I is converted to the triflate 24. with triflic anhydride and base in a chlorocarbon solvent. The triflate 24. is coupled to TMS-acetylene in the presence of a palladium catalyst, e.g., $PdCl2(PPh3)_2$ (0.01 to 10%) in a polar aprotic solvent, e.g., acetonitrile from room temperature to 150 C. to give the TMS protected acetylene as an intermediate, that is deprotected with fluoride ion in THF to give acetylene 25. Acetylene 25. is deprotonated with, e.g., LiHMDS and treated with a ketone to produce the carbinol 26. The carbinol 26. is saponified with lithium, potassium, or sodium hydroxide in alkanol to give the acid 27. Acid 27. is converted to amides with a coupling reagent, e.g., EDC, and a primary or secondary amine.

Scheme I. 5-Bromo-2-hydroxy-benzaldehyde is alkylated with a 2-haloacetate ester in a polar aprotic solvent, e.g., acetone or acetonitrile and base, e.g., potassium carbonate at from room temperature to the reflux temperature of the mixture for 30 min to 48 h to give the aldehyde 1. Aldehyde 1. is cyclized with a base or DBU in a polar aprotic solvent at from 100 to 160° C. for 30 min to 48 h to produce the furanyl ester 2. Furanyl ester 2. is reacted with an excess of alkyl Grignard reagent (2 to 5 equivalents) in diethylether or THF to produce the tert-carbinol 3. Carbinol 3. is reacted with carbon monoxide (1-1000 psi) in the presence of a palladium catalyst, e.g., $Pd(OAc)_2$ and DPPF (0.01 to 0.9 equivalents) from room temperature to 160° C. for 30 min to 48 h in an alkanol with DMF to produce the ester 4. Ester 4. is treated with an ortho-substituted phenol in the presence of a Lewis acid, e.g., boron trifluoride etherate (0.01 to 5 equivalents) to give the diarylmethane 5. Diarylmethane 5. is alkylated with an alpha-halo ketone or ester to give the diarylmethane 6. The diarylmethane 6. is reduced % with lithium, sodium, or potassium borohydride or cyanoborohydride in alkanol or THF to give the intermediate carbinol, which is saponified with lithium, sodium, or potassium hydroxide in an alkanol from room temperature to the reflux temperature of the mixture to give Each of the free acids produced in each of the above schemes (3., 4., 5., 8., 9., 14., 15., 22., 23., and 28.) are converted to lower alkanol esters and lower alkyl secondary or tertiary carboxamides using reactions well known to those skilled in the art.

Example 11

Preparation of 2-{1-[4-(3,3-dimethyl-2-oxo-butoxy)-3-methyl-phenyl]-ethylpropyl}-benzofuran-5-carboxylic acid methyl ester

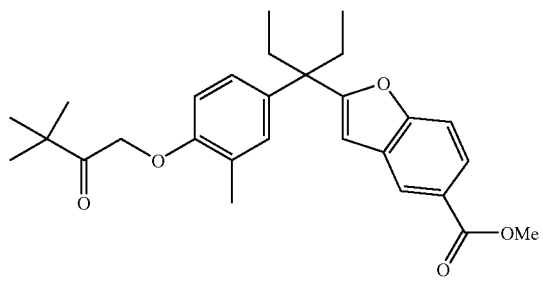

A. 5-Bromo-benzofuran-2-carboxylic acid ethyl ester.

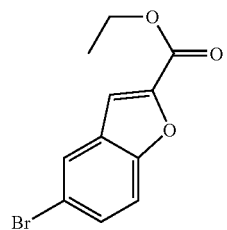

To a solution of 5-bromo-2-hydroxy-benzaldehyde (50.9 g, 253.2 mmol) and ethyl bromoacetate (46.5 g, 278.5 mmol) in acetone (300 mL) is added K$_2$CO$_3$ (45.4 g, 329 mmol). The suspension is stirred for 16 h at RT, and the solid is filtered. The filtrate is concentrated to a residue and dissolved in DMF (100 mL), DBU (38.5 g, 253 mmol) is added and the solution is heated to 140° C. for 2 h. The reaction mixture is cooled down and poured into water (500 mL) and extracted with EtOAc (300 mL, 100 mL). The organic layer is dried over Na$_2$SO$_4$, concentrated, purified on column chromatography (10% EtOAc/Hex), to give the title compound as an oil (41.6 g, 60%)

H-NMR (ppm, CDCl$_3$) δ: 7.81 (1H, d, J=1.8 Hz), 7.54 (1H, dd, J=1.8, 8.8 Hz), 7.47 (1H, d, J=9.2 Hz), 7.44 (1H, s), 4.47 (2H, q, J=7.0 Hz), 1.44 (3H, t, J=7.0 Hz).

B. 3-(5-Bromo-benzofuran-2-yl)-pentan-3-ol.

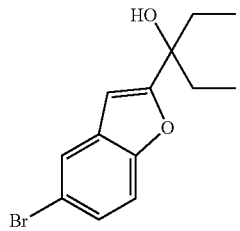

To a stirred solution of 5-bromo-benzofuran-2-carboxylic acid ethyl ester (24.3 g, 90.3 mmol) in THF (300 mL) at −40° C. is added ethyl magnesium bromide (90.3 mL, 3.0 M). The reaction is allowed to warm to RT and stirred for 2 h before quenched with water and HCl (1.0 M) till pH~2. The THF is removed in vacuum and the mixture is extracted with EtOAc (200 mL, 100 mL). The organic layer is dried over Na$_2$SO$_4$, concentrated, purified on column chromatography (10-15% EtOAc/Hex), to give the title compound as an oil (22.4 g, 88%)

H-NMR (ppm, CDCl$_3$) δ: 7.64 (1H, d, J=1.3 Hz), 7.32 (1H, d, J=2.2 Hz), 7.31 (1H, s), 6.57 (1H, s), 2.00-1.86 (4H, m), 0.86 (6H, t, J=7.5 Hz).

C. 2-(1-Ethyl-1-hydroxy-propyl)-benzofuran-5-carboxylic acid methyl ester.

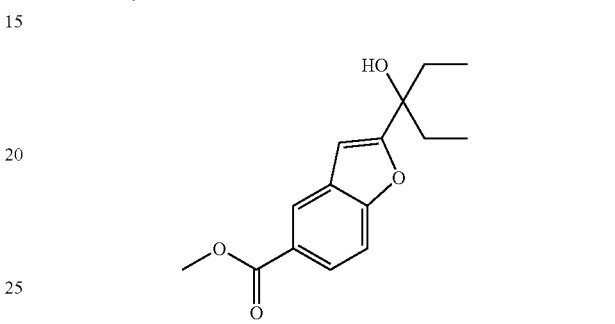

A solution of 3-(5-bromo-benzofuran-2-yl)-pentan-3-ol (22.4 g, 79.2 mmol) in DMSO (544 mL) and MeOH (360 mL) is treated with Pd(OAc)$_2$ (3.63 g), DPPF (13.1 g) and Et$_3$N (62 mL). The mixture is stirred under CO (100 psi) at 80° C. for 16 h. The MeOH is removed in vacuum and residue is poured into water (2000 mL) and extracted with EtOAc (2×200 mL). The organic layer is dried over Na$_2$SO$_4$, concentrated, purified on column chromatography (15-20% EtOAc/Hex), to give the title compound as an oil (11.35 g, 77%) and recovered starting material (6.50 g).

H-NMR (ppm, CDCl$_3$) δ: 8.25 (1H, d, J=1.3 Hz), 7.97 (1H, dd, J=1.8, 8.4 Hz), 7.45 (1H, d, J=8.8 Hz), 6.68 (1H, s), 3.94 (3H, s), 2.02-1.88 (4H, m), 0.88 (6H, t, J=7.5 Hz).

D. 2-[1-Ethyl-1-(4-hydroxy-3-methyl-phenyl)-propyl]-benzofuran-5-carboxylic acid methyl ester.

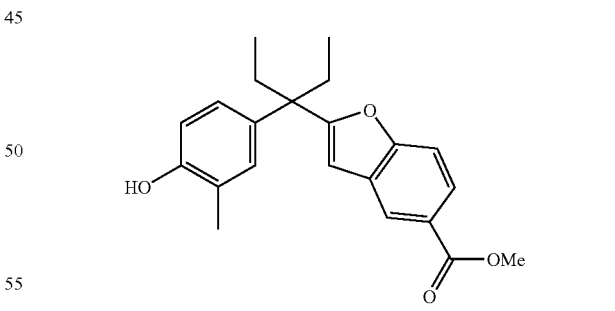

To a mixture of 2-(1-ethyl-1-hydroxy-propyl)-benzofuran-5-carboxylic acid methyl ester (6.01 g, 22.9 mmol) and o-cresol (3.71 g, 34.4 mmol) in CH$_2$Cl$_2$ (150 mL) at −78° C. is added BF$_3$-Et$_2$O (1.63 ml, 11.5 mol). After stirring for 5 min, the reaction mixture is allowed to warm up to 0° C. over 30 min. The reaction is quenched with water (50 mL) and extracted with CH$_2$Cl$_2$ (50 mL). The organic layer is dried over Na$_2$SO$_4$, concentrated, purified on column chromatography (15-20% EtOAc/Hex) to afford the title compound (7.38 g, 91%).

H-NMR (ppm, CDCl$_3$) δ: 8.25 (1H, d, J=1.3 Hz), 7.90 (1H, dd, J=1.8, 8.8 Hz), 7.34 (1H, d, J=8.4 Hz), 6.96 (1H, d, J=1.3 Hz), 6.92 (1H, dd, J=2.2, 7.9 Hz), 6.70 (1H, d, J=8.4 Hz), 6.66 (1H, s), 3.94 (3H, s), 2.21 (3H, s), 2.22-2.04 (4H, m), 0.72 (6H, t, J=7.5 Hz).

MS (ES) m/e: 353.1 (M+1), 351.1 (M−1)

E. 2-{1-[4-(3,3-Dimethyl-2-oxo-butoxy)-3-methyl-phenyl]-ethylpropyl}-benzofuran-5-carboxylic acid methyl ester.

A solution of 2-[1-ethyl-1-(4-hydroxy-3-methyl-phenyl)-propyl]-benzofuran-5-carboxylic acid methyl ester (4.25 g, 12.1 mmol) and 1-bromopinacolone (2.70 g, 15.1 mmol) in acetone (80 mL) is treated with K$_2$CO$_3$ (3.33 g, 24.1 mmol) and stirred at RT for 18 h. The solid is filtered and the filtrate is concentrated, the residue is purified on column chromatography with 10-15% EtOAc/Hexane to provide the title compound (4.90 g, 90%).

H-NMR (ppm, CDCl$_3$) δ: 8.25 (1H, s), 7.90 (1H, dd, J=1.8, 8.8 Hz), 7.36 (1H, d, J=8.8 Hz), 7.00 (1H, s), 6.94 (1H, d, J=8.3 Hz), 6.66 (1H, s), 6.52 (1H, d, J=8.8 Hz), 4.84 (2H, s), 3.94 (3H, s), 2.26 (3H, s), 2.19 (2H, q, J=7.4 Hz), 2.10 (2H, q, J=7.4 Hz), 1.25 (9H, s), 0.72 (6H, t, J=7.4 Hz).

MS (ES) m/e: 353.1 (M+1), 351.1 (M−1)

Example 2

Preparation of 2-{1-[4-(3,3-dimethyl-2-oxo-butoxy)-3-methyl-phenyl]-ethylpropyl}-benzofuran-5-carboxylic acid

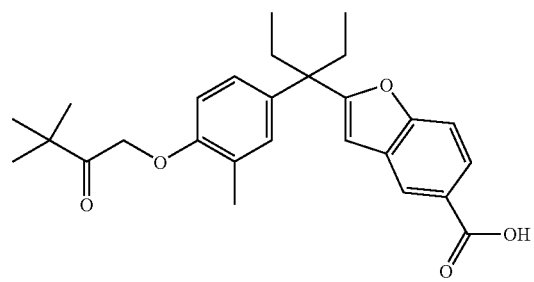

A solution of 2-{1-[4-(3,3-dimethyl-2-oxo-butoxy)-3-methyl-phenyl]-ethylpropyl}-benzofuran-5-carboxylic acid methyl ester (5.30 g, 11.8 μmmol) in methanol (30.0 mL) and THF (30.0 mL) is treated with NaOH (2.0 M, 60 mL). The resulting mixture is stirred at RT for 16 h. The mixture is concentrated and neutralized with HCl (5 N) till pH~3, and extracted with EtOAc (2×100 mL). The organic layer is dried over Na$_2$SO$_4$, concentrated to afford the title compound (4.85 g, 94%).

H-NMR (ppm, CDCl$_3$) δ: 8.34 (1H, d, J=1.8 Hz), 7.99 (1H, dd, J=1.8, 8.8 Hz), 7.38 (1H, d, J=8.8 Hz), 7.00 (1H, d, J=1.8 Hz), 6.95 (1H, dd, J=2.2, 8.4 Hz), 6.69 (1H, s), 6.54 (1H, d, J=8.4 Hz), 4.84 (2H, s), 2.26 (3H, s), 2.24-2.06 (4H, m), 1.26 (9H, s), 0.73 (6H, t, J=7.5 Hz).

MS (ES) m/e: 435.3 (M−1)

Example 3

Preparation of 2-{1-ethyl-1-[4-(2-hydroxy-3,3-dimethyl-butoxy)-3-methyl-phenyl]-propyl}-benzofuran-5-carboxylic acid methyl ester

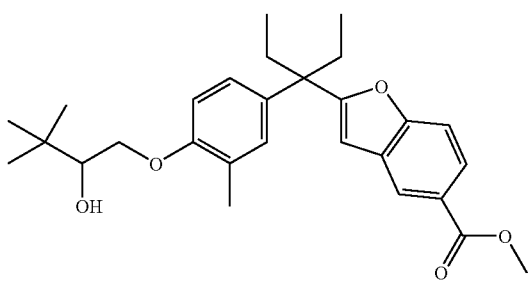

A solution of 2-{1-[4-(3,3-dimethyl-2-oxo-butoxy)-3-methyl-phenyl]-ethylpropyl}-benzofuran-5-carboxylic acid methyl ester (1.70 g, 3.77 mmol) in THF (40 mL) at RT is treated with NaBH$_4$ (286 mg, 7.54 mmol). The resulting mixture is stirred for 2 h and quenched with HCl (1 N, 8.0 mL), THF is removed in vacuum and the aqueous layer is extracted with EtOAc (2×40 mL). The combined organic layers are dried over Na$_2$SO$_4$, concentrated, purified on column chromatography (20% EtOAc/Hex) to afford the racemic intermediate alcohol (1.40 g, 82%). MS (ES) m/e: 453.2 (M+1)

Example 4

Preparation of 2-{1-Ethyl-1-[4-(2-hydroxy-3,3-dimethyl-butoxy)-3-methyl-phenyl]-propyl}-benzofuran-5-carboxylic acid

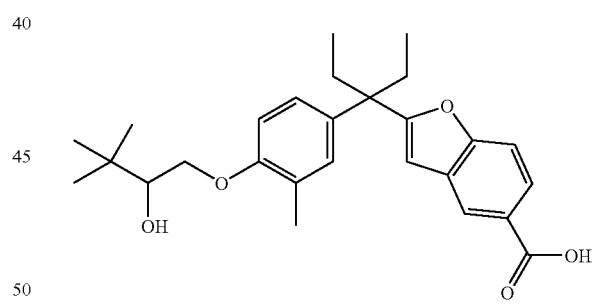

A solution of 2-{1-ethyl-1-[4-(2-hydroxy-3,3-dimethyl-butoxy)-3-methyl-phenyl]-propyl}-benzofuran-5-carboxylic acid methyl ester (555 mg, 1.226 mmol) in methanol (3.0 mL) and THF (3.0 mL) and is treated with NaOH (2.0 M, 6.0 mL). The resulting mixture is stirred at RT for 18 h. The mixture is concentrated and neutralized with HCl (1 N) till pH~2, and extracted with EtOAc (3×10 mL). The organic layer is dried over Na$_2$SO$_4$, concentrated to afford the title compound (530 mg, 99%).

H-NMR (ppm, CDCl$_3$) δ: 8.11 (1H, s), 7.99 (1H, dd, J=1.3, 8.4 Hz), 7.56 (1H, d, J=7.5 Hz), 7.01 (2H, m), 6.74 (1H, d, J=8.4 Hz), 6.68 (1H, s), 4.11 (1H, dd, J=2.6, 9.2 Hz), 3.88 (1H, t, J=9.2 Hz), 3.73 (1H, dd, J=2.6, 8.8 Hz), 2.20 (3H, s), 2.25-2.06 (4H, m), 1.02 (9H, s), 0.74 (6H, t, J=7.5 Hz).

MS (ES) m/e: 437.4 (M−1), 439.4 (M+1)

Example 5

Preparation of 2-{1-[4-(3,3-Dimethyl-2-oxo-butoxy)-3-methyl-phenyl]-1-ethyl-propyl}-benzofuran-5-carboxylic acid dimethylamide

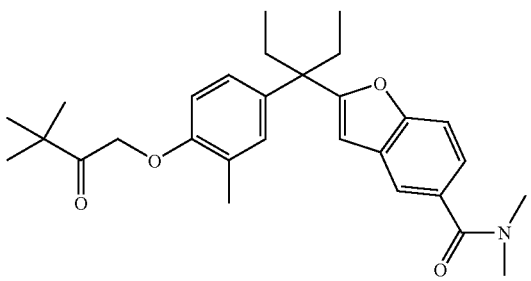

A solution of 2-{1-[4-(3,3-dimethyl-2-oxo-butoxy)-3-methyl-phenyl]-ethylpropyl}-benzofuran-5-carboxylic acid (260 mg, 0.596 mmol) in CH₂Cl₂ (5.0 mL) is treated with DMAP (218 mg, 1.79 mmol) and EDC (172 mg, 0.895 mmol). The mixture is stirred for 15 min at RT before the addition of dimethylamine hydrochloride (73 mg, 0.895 mmol). The reaction is stirred for 18 h and quenched with aqueous NH₄Cl (5.0 mL). The organic layer is loaded on silica gel column and purified with 50% EtOAc/Hex to afford the title compound (82 mg, 30%).

H-NMR (ppm, CDCl₃) δ: 7.60 (1H, d, J=1.8 Hz), 7.32 (1H, d, J=8.4 Hz), 7.24 (1H, dd, J=1.8, 8.4 Hz), 6.98 (1H, s), 6.95 (1H, dd, J=2.2, 8.4 Hz), 6.62 (1H, s), 6.52(1H, d, J=8.4 Hz), 4.83 (2H, s), 3.08 (6H, br s), 2.25 (3H, s), 2.18 (2H, q, J=7.4 Hz), 2.08 (2H, q, J=7.4 Hz), 1.25 (9H, s), 0.72 (6H, t, J=7.5 Hz).

MS (ES) m/e: 464.2 (M+1)

Example 6

Preparation of 2-{1-Ethyl-1-[4-(2-hydroxy-3,3-dimethyl-butoxy)-3-methyl-phenyl]-propyl}-benzofuran-5-carboxylic acid dimethylamide

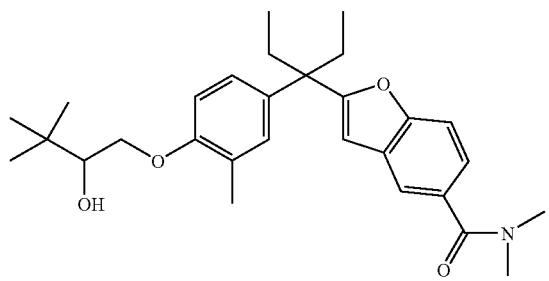

A solution of 2-{1-[4-(3,3-dimethyl-2-oxo-butoxy)-3-methyl-phenyl]-1-ethyl-propyl}-benzofuran-5-carboxylic acid dimethylamide (45 mg, 0.0972) in THF (5.0 mL) at RT is treated with NaBH₄ (7 mg, 0.194 mmol). The resulting mixture is stirred for 1 hour. The reaction is quenched with water (1.0 mL) and extracted with EtOAc (2×20 mL). The organic layer is dried over Na₂SO₄, concentrated, purified on column chromatography (20% EtOAc/Hex) to afford the title compound (45 mg, 99%).

H-NMR (ppm, CDCl₃) δ: 7.55 (1H, d, J=1.3 Hz), 7.29 (1H, d, J=8.4 Hz), 7.19 (1H, dd, J=1.8, 8.4 Hz), 6.97-6.94 (2H, m), 6.69 (1H, d, J=8.4 Hz), 6.59 (1H, s), 4.05 (1H, dd, J=2.6, 9.2 Hz), 3.88 (1H, t, J=9.2 Hz), 3.73 (1H, dd, J=2.6, 8.4 Hz), 3.08 (6H, br s), 2.15 (3H, s), 2.20-2.00 (4H, m), 0.96 (9H, s), 0.68 (6H, t, J=7.5 Hz).

MS (ES) m/e: 466.2 (M+1)

Example 7

Preparation of [(2-{1-[4-(3,3-Dimethyl-2-oxo-butoxy)-3-methyl-phenyl]-1-ethylpropyl}-benzofuran-5-carbonyl)-amino]-acetic acid

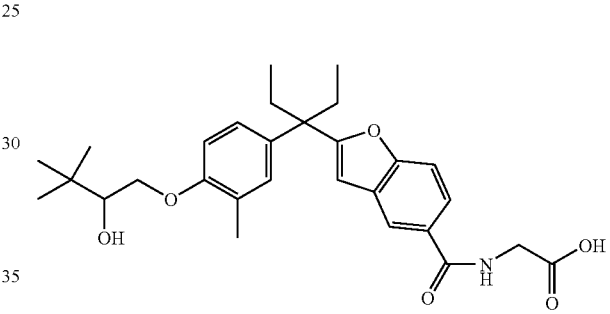

A solution of 2-{1-[4-(3,3-dimethyl-2-oxo-butoxy)-3-methyl-phenyl]-ethylpropyl}-benzofuran-5-carboxylic acid (190 mg, 0.436 mmol) in CH₂Cl₂ (5.0 mL) is treated with DMAP (106 mg, 0.872 mmol) and EDC (133 mg, 0.698 mmol). The mixture is stirred for 10 min at RT before the addition of glycine methyl ester hydrochloride (82 mg, 0.654 mmol). The reaction is stirred for 12 h and quenched with water (5.0 mL). The organic layer is loaded on silica gel column and purified with 20-50% EtOAc/Hex to afford the intermediate amide ester.

The intermediate is dissolved in methanol (1.0 mL) and THF (1.0 mL) and is treated with NaOH (2.0 M, 2.0 mL). The resulting mixture is stirred at RT for 18 h. The mixture is concentrated and neutralized with HCl (1 N) till pH~3, and extracted with EtOAc (3×10 mL). The organic layer is dried over Na₂SO₄, concentrated to afford the title compound (150 mg, 70%).

H-NMR (ppm, CDCl₃) δ: 8.03 (1H, s), 7.66 (1H, dd, J=1.8, 8.8 Hz), 7.36 (1H, d, J=8.4 Hz), 6.99 (1H, d, J=2.2 Hz), 6.95 (1H, dd, J=2.2, 8.8 Hz), 6.72 (1H, t, J=4.8 Hz), 6.66 (1H, s), 6.53 (1H, d, J=8.4 Hz), 4.84 (2H, s), 4.33 (2H, d, J=4.8 Hz), 2.25 (3H, s), 2.20 (2H, q, J=7.4 Hz), 2.12 (2H, q, J=7.4 Hz), 1.25 (9H, s), 0.72 (6H, t, J=7.5 Hz).

MS (ES) m/e: 492.3 (M−1), 494.3 (M+1)

Example 8

Preparation of [(2-{1-Ethyl-1-[4-(2-hydroxy-3,3-dimethyl-butoxy)-3-methyl-phenyl]-propyl}-benzofuran-5-carbonyl)-amino]-acetic acid

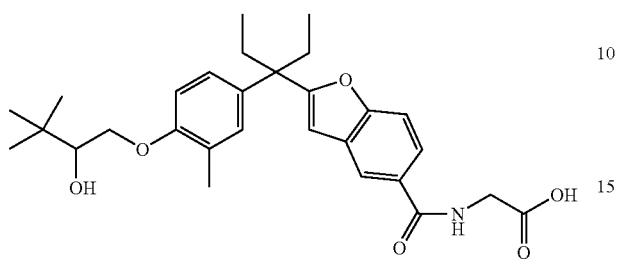

A solution of [(2-{1-[4-(3,3-dimethyl-2-oxo-butoxy)-3-methyl-phenyl]-1-ethylpropyl}-benzofuran-5-carbonyl)-amino]-acetic acid (74 mg, 0.150 mmol) in THF (5.0 mL) at RT is treated with NaBH$_4$ (11 mg, 0.300 mmol). The resulting mixture is stirred for 4 hour. The reaction is quenched with HCl (1.0 N, 1.0 mL) and extracted with EtOAc (2×20 mL). The organic layer is dried over Na$_2$SO$_4$, concentrated to afford the title compound (65 mg, 88%).

H-NMR (ppm, CDCl$_3$) δ: 7.99 (1H, d, J=1.8 Hz), 7.63 (1H, dd, J=1.8, 8.4 Hz), 7.32 (1H, d, J=8.4 Hz), 6.96-6.93 (2H, m), 6.69 (1H, d, J=8.4 Hz), 6.63 (1H, s), 4.04 (2H, s), (1H, dd, J=2.7, 9.7 Hz), 3.82 (1H, t, J=8.8 Hz), 3.63 (1H, dd, J=2.6, 8.4 Hz), 2.13 (3H, s), 2.20-2.00 (4H, m), 0.95 (9H, s), 0.68 (6H, t, J=7.5 Hz).

MS (ES) m/e: 494.2 (M−1), 496.2 (M+1)

Example 9

Preparation of [(2-{1-[4-(3,3-Dimethyl-2-oxo-butoxy)-3-methyl-phenyl]-1-ethylpropyl}-benzofuran-5-carbonyl)-amino]-acetic acid

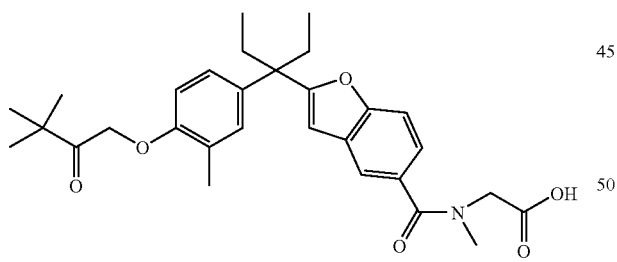

A solution of 2-{1-[4-(3,3-dimethyl-2-oxo-butoxy)-3-methyl-phenyl]-ethylpropyl}-benzofuran-5-carboxylic acid (110 mg, 0.252 mmol) in CH$_2$Cl$_2$ (5.0 mL) is treated with DMAP (92 mg, 0.756 mmol) and EDC (73 mg, 0.378 mmol). The mixture is stirred for 10 min at RT before the addition of sarcosine ethyl ester hydrochloride (58 mg, 0.378 mmol). The reaction is stirred for 12 h and is loaded on silica gel column and purified with 20-50% EtOAc/Hex to afford the intermediate amide ester.

The intermediate is dissolved in methanol (2.0 mL) and THF (2.0 mL) and is treated with NaOH (2.0 M, 4.0 mL). The resulting mixture is stirred at RT for 18 h. The mixture is concentrated and neutralized with HCl (1 N) till pH~3, and extracted with EtOAc (3×10 mL). The organic layer is dried over Na$_2$SO$_4$, concentrated to afford the title compound (95 mg, 74%).

MS (ES) m/e: 506.3 (M−1), 508.2 (M+1)

Example 10

Preparation of 2-[(2-{1-[4-(3,3-Dimethyl-2-oxo-butoxy)-3-methyl-phenyl]-1-ethyl-propyl}-benzofuran-5-carbonyl)-amino]-2-methyl-propionic acid

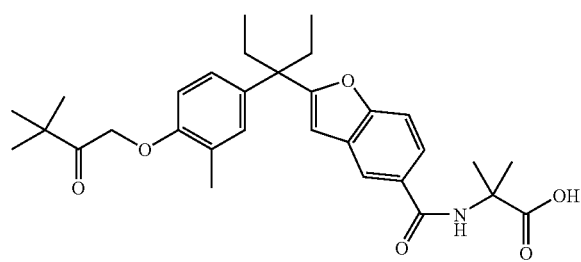

A solution of 2-{1-[4-(3,3-dimethyl-2-oxo-butoxy)-3-methyl-phenyl]-ethylpropyl}-benzofuran-5-carboxylic acid (110 mg, 0.252 mmol) in CH$_2$Cl$_2$ (5.0 mL) is treated with DMAP (92 mg, 0.756 mmol) and EDC (73 mg, 0.378 mmol). The mixture is stirred for 10 min at RT before the addition of ethyl, 2-amino-2-methylpropionate, hydrochloride (58 mg, 0.378 mmol). The reaction is stirred for 12 h and is loaded on silica gel column and purified with 20-50% EtOAc/Hex to afford the intermediate amide ester.

The intermediate is dissolved in methanol (2.0 mL) and THF (2.0 mL) and is treated with NaOH (2.0 M, 4.0 mL). The resulting mixture is stirred at RT for 18 h. The mixture is concentrated and neutralized with HCl (1 N) till pH~3, and extracted with EtOAc (3×10 mL). The organic layer is dried over Na$_2$SO$_4$, concentrated to afford the title compound (95 mg, 72%).

MS (ES) m/e: 520.3 (M−1), 522.2 (M+1)

Example 11

Preparation of 2-{1-[4-(3,3-dimethyl-2-oxo-butoxy)-3-methyl-phenyl]-1-ethyl-propyl}-benzofuran-5-carboxylic acid (2H-tetrazol-5-yl)-amide

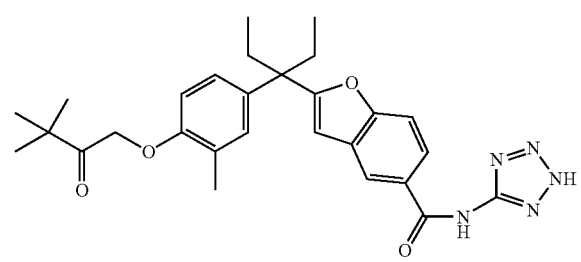

A solution of 2-{1-[4-(3,3-dimethyl-2-oxo-butoxy)-3-methyl-phenyl]-ethylpropyl}-benzofuran-5-carboxylic acid (190 mg, 0.436 mmol) in CH$_2$Cl$_2$ (5.0 mL) is treated with DMAP (106 mg, 0.872 mmol) and EDC (133 mg, 0.698 mmol). The mixture is stirred for 15 min at RT before the addition of 2H-tetrazol-5-ylamine (57 mg, 0.654 mmol). The reaction is stirred for 12 h and the mixture is loaded on silica gel column and purified with 10-20% MeOH/EtOAc to afford the title compound (41 mg, 19%).

H-NMR (ppm, CDCl$_3$) δ: 8.25 (1H, d, J=1.3 Hz), 7.92 (1H, dd, J=1.8, 8.8 Hz), 7.36 (1H, d, J=8.4 Hz), 6.99 (1H, d, J=2.2 Hz), 6.94 (1H, dd, J=2.2, 8.4 Hz), 6.67 (1H, s), 6.52 (1H, d, J=8.8 Hz), 4.84 (2H, s), 2.26 (3H, s), 2.20 (2H, q, J=7.4 Hz), 2.10 (2H, q, J=7.4 Hz), 1.26 (9H, s), 0.72 (6H, t, J=7.5 Hz).

Example 12

Preparation of 2-{1-[4-(3,3-Dimethyl-2-oxo-butoxy)-3-ethyl-phenyl]-ethylpropyl}-benzofuran-5-carboxylic acid

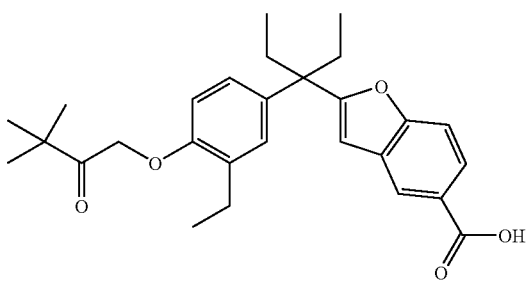

A. 2-[1-ethyl-1-(3-ethyl-4-hydroxy-phenyl)-propyl]-benzofuran-5-carboxylic acid methyl ester.

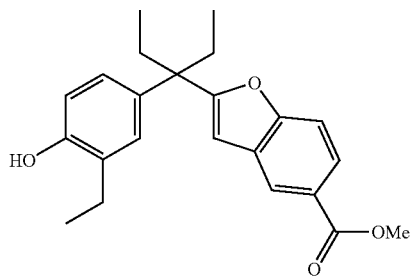

2-(1-Ethyl-1-hydroxy-propyl)-benzofuran-5-carboxylic acid methyl ester (1.01 g, 3.85 mmol) and 2-ethylphenol (0.706 g, 5.77 mmol) and BF$_3$-Et$_2$O (273 mg, 1.925 mmol) are reacted analogous to step D to give the title compound (1.30 g, 92%).

H-NMR (ppm, CDCl$_3$) δ: 8.25 (1H, d, J=1.8 Hz), 7.92 (1H, dd, J=1.8, 8.8 Hz), 7.34 (1H, d, J=8.8 Hz), 6.96 (1H, d, J=2.2 Hz), 6.90 (1H, dd, J=2.6, 8.4 Hz), 6.69 (1H, d, J=8.4 Hz), 6.66 (1H, s), 3.94 (3H, s), 2.60 (2H, q, J=7.5 Hz), 2.19 (2H, q, J=7.4 Hz), 2.10 (2H, q, J=7.4 Hz), 1.20 (3H, t, J=7.5 Hz), 0.72 (6H, t, J=7.5 Hz).

B. 2-{1-[4-(3,3-Dimethyl-2-oxo-butoxy)-3-ethyl-phenyl]-ethylpropyl}-benzofuran-5-carboxylic acid methyl ester.

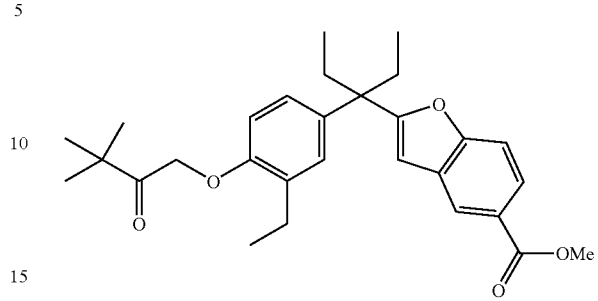

2-[1-Ethyl-1-(4-hydroxy-3-ethyl-phenyl)-propyl]-benzofuran-5-carboxylic acid methyl ester (1.30 g, 3.55 mmol) and 1-bromopinacolone (0.953 g, 5.33 mmol) and K$_2$CO$_3$ (0.98 g, 7.10 mmol) are reacted analogous to Example 1E to give the title compound (1.64 g, 99%).

H-NMR (ppm, CDCl$_3$) δ: 8.25 (1H, d, J=1.8 Hz), 7.92 (1H, dd, J=1.8, 8.4 Hz), 7.34 (1H, d, J=8.8 Hz), 7.02 (1H, d, J=2.6 Hz), 6.93 (1H, dd, J=2.6, 8.4 Hz), 6.66 (1H, s), 6.54 (1H, d, J=8.4 Hz), 4.83 (2H, s), 3.94 (3H, s), 2.66 (2H, q, J=7.5 Hz), 2.19 (2H, q, J=7.4 Hz), 2.10 (2H, q, J=7.4 Hz), 1.24 (9H, s), 1.19 (3H, t, J=7.5 Hz), 0.72 (6H, t, J=7.5 Hz).

C. 2-{1-[4-(3,3-Dimethyl-2-oxo-butoxy)-3-ethyl-phenyl]-ethylpropyl}-benzofuran-5-carboxylic acid.

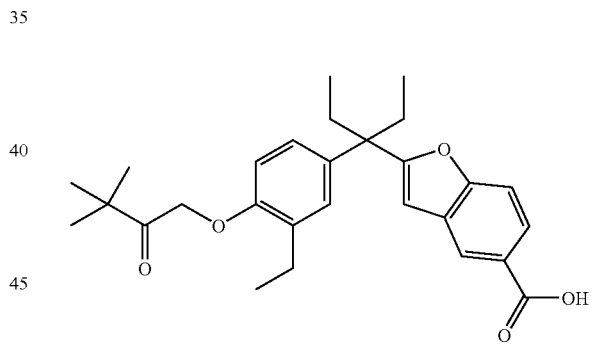

A solution of 2-{1-[4-(3,3-dimethyl-2-oxo-butoxy)-3-ethyl-phenyl]-ethylpropyl}-benzofuran-5-carboxylic acid methyl ester (1.64 g, 3.53 mmol) in methanol (5.0 mL) and THF (5.0 mL) is treated with NaOH (2.0 M, 10 mL). The resulting mixture is stirred at RT for 12 h. The mixture is concentrated and neutralized with HCl (5 N) until pH~3, and extracted with EtOAc (3×30 mL). The organic layer is dried over Na$_2$SO$_4$, concentrated to afford the title compound (1.57 g, 99%).

H-NMR (ppm, CDCl$_3$) δ: 8.34 (1H, d, J=1.8 Hz), 7.98 (1H, dd, J=1.8, 8.4 Hz), 7.38 (1H, d, J=8.4 Hz), 7.03 (1H, d, J=2.2 Hz), 6.93 (1H, dd, J=2.6, 8.4 Hz), 6.69 (1H, s), 6.55 (1H, d, J=8.8 Hz), 4.85 (2H, s), 2.67 (2H, q, J=7.5 Hz), 2.20 (2H, q, J=7.4 Hz), 2.10 (2H, q, J=7.4 Hz), 1.26 (9H, s), 1.19 (3H, t, J=7.5 Hz), 0.74 (6H, t, J=7.5 Hz).

MS (ES) m/e: 468.3 (M+18), 449.3 (M−1).

Example 13

2-{1-Ethyl-1-[4-(2-hydroxy-3,3-dimethyl-butoxy)-3-methyl-phenyl]-propyl}-benzofuran-5-carboxylic acid (2H-tetrazol-5-yl)-amide

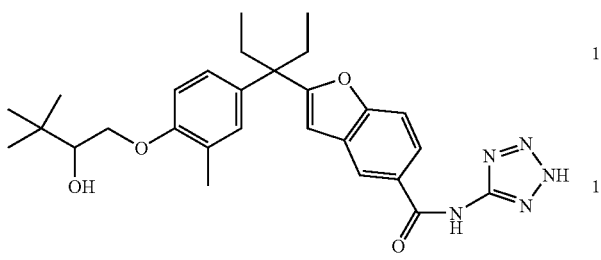

A solution of 2-{1-[4-(3,3-dimethyl-2-oxo-butoxy)-3-methyl-phenyl]-1-ethyl-propyl}-benzofuran-5-carboxylic acid (2H-tetrazol-5-yl)-amide (90 mg, 0.179 mmol) in THF (5.0 mL) at RT is treated with NaBH$_4$ (20 mg, 0.537 mmol). The resulting mixture is stirred for 30 min. The reaction is quenched with water (1.0 mL) and extracted with EtOAc (2×20 mL). The organic layer is dried over Na$_2$SO$_4$, concentrated to afford the title compound (35 mg, 39%).

H-NMR (ppm, CDCl$_3$) δ: 8.28 (1H, s), 7.92 (1H, d, 8.4 Hz), 7.46 (1H, d, J=8.8 Hz), 7.02 (1H, d, J=8.4 Hz), 6.99 (1H, s), 6.84 (1H, s), 6.81 (1H, d, J=8.4 Hz), 4.10(1H, dd, J=2.2, 9.2 Hz), 3.88 (1H, t, J=8.6 Hz), 3.62 (1H, dd, J=2.6, 7.9 Hz), 2.18 (3H, s), 2.28-2.12 (4H, m), 1.00 (9H, s), 0.73 (6H, t, J=7.5 Hz).

MS (ES) m/e: 506.3 (M+1)

Example 14

Preparation of 2-{-[4-(2-tert-butyl-[1,3]dioxolan-2-ylmethoxy)-3-methyl-phenyl]-1-ethyl-propyl}-benzofuran-5-carboxylic acid methyl ester

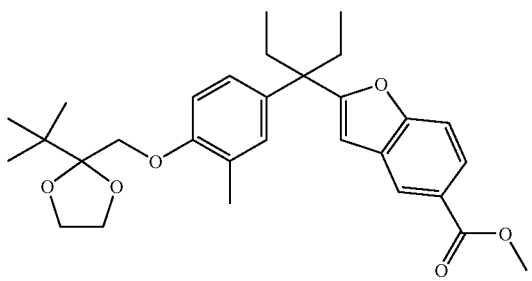

A solution of 2-{1-[4-(3,3-dimethyl-2-oxo-butoxy)-3-methyl-phenyl]-ethylpropyl}-benzofuran-5-carboxylic acid methyl ester (2.25 g, 4.99 mmol) in ethylene glycol (5.0 mL) is treated with BF$_3$-Et$_2$O (3.0 mL). The mixture is stirred for 16 h at 80° C. It was cooled down to RT, diluted with CH$_2$Cl$_2$ (50 mL) and washed with water (50 mL). The organic layer is concentrated and purified on silica gel column with 6% EtOAc/Hex to afford the product as an oil (1.51 g, 61%).

H-NMR (ppm, CDCl$_3$) δ: 8.25 (1H, d, J=1.3 Hz), 7.91 (1H, dd, J=1.8, 8.4 Hz), 7.35 (1H, d, J=8.4 Hz), 7.00 (1H, dd, J=1.8, 8.4 Hz), 6.96 (1H, d, J=1.3 Hz), 6.73 (1H, d, J=8.4 Hz), 6.66 (1H, d, J=1.3 Hz), 4.24 (2H, m), 4.09 (2H, s), 4.02 (2H, m), 3.94 (3H, s), 2.20 (3H, s), 2.19 (2H, q, J=7.4 Hz), 2.10 (2H, q, J=7.4 Hz), 1.05 (9H, s), 0.72 (6H, t, J=7.4 Hz).

Example 15

Preparation of 2-{1-[4-(2-tert-Butyl-[1,3]dioxolan-2-ylmethoxy)-3-methyl-phenyl]-1-ethyl-propyl}-benzofuran-5-carboxylic acid

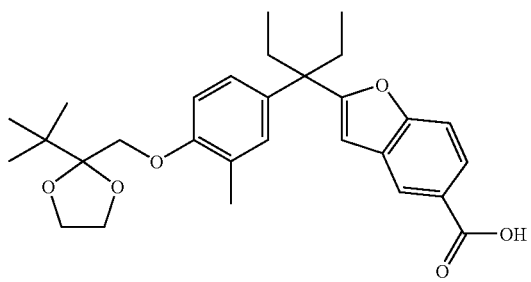

A solution of 2-{1-[4-(2-tert-butyl-[1,3]dioxolan-2-ylmethoxy)-3-methyl-phenyl]-1-ethyl-propyl}-benzofuran-5-carboxylic acid methyl ester (1.51 g, 3.05 mmol) in methanol (5.0 mL) and THF (5.0 mL) and is treated with NaOH (2.0 M, 10 mL). The resulting mixture is stirred at RT for 2 h. The mixture is concentrated and neutralized with HCl (1 N) till pH~3, and extracted with EtOAc (3×50 mL). The organic layer is dried over Na$_2$SO$_4$, concentrated to afford the title compound (1.43 g, 95%).

H-NMR (ppm, CDCl$_3$) δ: 8.25 (1H, d, J=1.3 Hz), 7.91 (1H, dd, J=1.8, 8.4 Hz), 7.35 (1H, d, J=8.4 Hz), 7.00 (1H, dd, J=1.8, 8.4 Hz), 6.96 (1H, d, J=1.3 Hz), 6.73 (1H, d, J=8.4 Hz), 6.66 (1H, d, J=1.3 Hz), 4.24 (2H, m), 4.09 (2H, s), 4.02 (2H, m), 2.20 (3H, s), 2.19 (2H, q, J=7.4 Hz), 2.10 (2H, q, J=7.4 Hz), 1.05 (9H, s), 0.72 (6H, t, J=7.4 Hz).

MS (ES) m/e: 479.2 (M−1)

Example 16

Preparation of [(2-{1-[4-(2-tert-butyl-[1,3]dioxolan-2-ylmethoxy)-3-methyl-phenyl]-1-ethyl-propyl}-benzofuran-5-carbonyl)-amino]-acetic acid

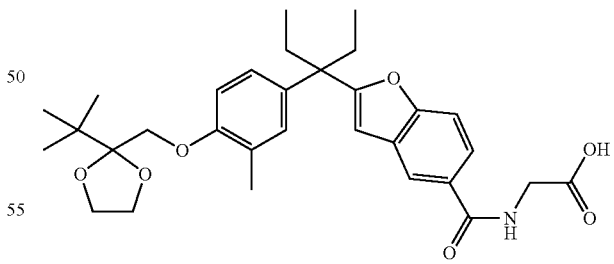

2-{1-[4-(2-tert-butyl-[1,3]dioxolan-2-ylmethoxy)-3-methyl-phenyl]-1-ethyl-propyl}-benzofuran-5-carboxylic acid (125 mg, 0.260 mmol), EDC (75 mg, 0.391 mmol), DMAP (95 mg, 0.781 mmol), and glycine methyl ester hydrochloride (49 mg, 0.39 mmol) are reacted to produce the intermediate followed by hydrolysis analogous to Example 1, step K to give title compound (125 mg, 90%).

H-NMR (ppm, CDCl$_3$) δ: 8.02 (1H d, J=1.8 Hz), 7.66 (1H, dd, J=1.3, 8.8 Hz), 7.35 (1H, d, J=8.8 Hz), 7.00 (1H, dd, J=2.6, 8.4 Hz), 6.96 (1H, d, J=2.2 Hz), 6.73 (1H, d, J=8.4 Hz), 6.66 (1H, s), 4.28 (2H, d, J=4.0 Hz), 4.24 (2H, m), 4.10 (2H, s), 4.02 (2H, m), 2.20 (3H, s), 2.19 (2H, q, J=7.4 Hz), 2.10 (2H, q, J=7.4 Hz), 1.06 (9H, s), 0.72 (6H, t, J=7.4 Hz).

MS (ES) m/e: 538.2 (M+1), 536.2 (M−1).

Example 17

Preparation of 2-{1-[4-(3,3-dimethyl-2-oxo-butoxy)-3-isopropyl-phenyl]-ethylpropyl}-benzofuran-5-carboxylic acid

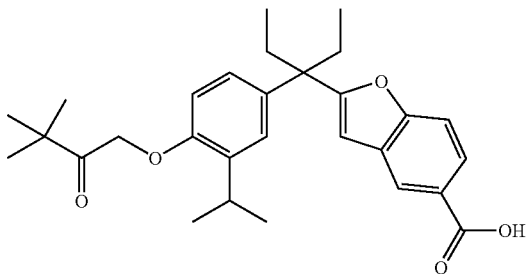

A. 2-[1-Ethyl-1-(4-hydroxy-3-isopropyl-phenyl)-propyl]-benzofuran-5-carboxylic acid methyl ester.

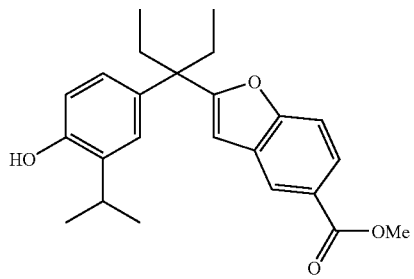

2-(1-Ethyl-1-hydroxy-propyl)-benzofuran-5-carboxylic acid methyl ester (0.92 g, 3.507 mmol) and 2-isopropylphenol (0.716 g, 5.26 mmol) and BF$_3$-Et$_2$O (249 mg, 1.753 mmol) are reacted analogous to Example 1D to give the title compound (1.25 g, 94%).

H-NMR (ppm, CDCl$_3$) δ: 8.25 (1H, d, J=1.3 Hz), 7.92 (1H, dd, J=1.8, 8.8 Hz), 7.35 (1H, d, J=8.4 Hz), 7.06 (1H, d, J=2.2 Hz), 6.88 (1H, dd, J=2.6, 8.4 Hz), 6.66 (1H, d, J=8.4 Hz), 6.65 (1H, s), 3.94 (3H, s), 3.21 (1H, q, J=7.0 Hz), 2.19 (2H, q, J=7.4 Hz), 2.10 (2H, q, J=7.4 Hz), 1.20 (6H, d, J=7.0 Hz), 0.72 (6H, t, J=7.5 Hz).

B. 2-{1-[4-(3,3-Dimethyl-2-oxo-butoxy)-3-isopropyl-phenyl]-ethylpropyl}-benzofuran-5-carboxylic acid methyl ester.

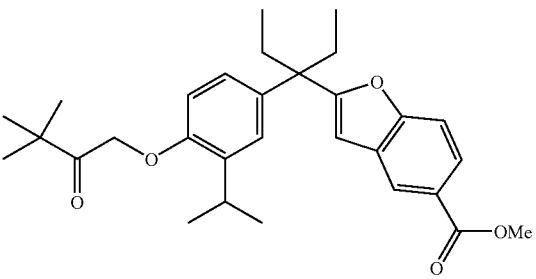

2-[1-Ethyl-1-(4-hydroxy-3-isopropyl-phenyl)-propyl]-benzofuran-5-carboxylic acid methyl ester (1.25 g, 3.28 mmol) and 1-bromopinacolone (0.882 g, 4.93 mmol) and K$_2$CO$_3$ (0.91 g, 6.57 mmol) are reacted analogous to Example 1E to give the title compound (1.55 g, 99%).

H-NMR (ppm, CDCl$_3$) δ: 8.25 (1H, d, J=1.8 Hz), 7.92 (1H, dd, J=1.8, 8.8 Hz), 7.35 (1H, d, J=8.8 Hz), 7.09 (1H, d, J=2.2 Hz), 6.90 (1H, dd, J=2.2, 8.4 Hz), 6.65 (1H, s), 6.54 (1H, d, J=8.4 Hz), 4.84 (1H, s), 3.93 (3H, s), 3.40 (1H, q, J=7.0 Hz), 2.20 (2H, q, J=7.4 Hz), 2.10 (2H, q, J=7.4 Hz), 1.25 (9H, s), 1.20 (6H, d, J=7.0 Hz), 0.72 (6H, t, J=7.5 Hz).

C. 2-{1-[4-(3,3-Dimethyl-2-oxo-butoxy)-3-isopropyl-phenyl]-ethylpropyl}-benzofuran-5-carboxylic acid.

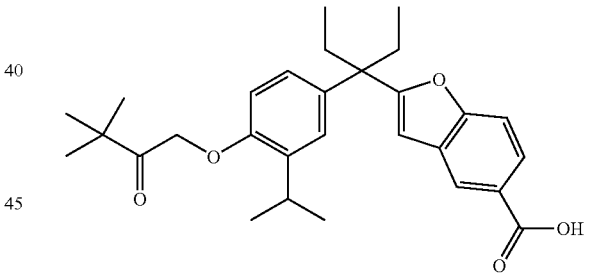

A solution of 2-{1-[4-(3,3-dimethyl-2-oxo-butoxy)-3-isopropyl-phenyl]-ethylpropyl}-benzofuran-5-carboxylic acid methyl ester (1.55 g, 3.24 mmol) in methanol (5.0 mL) and THF (5.0 mL) is treated with NaOH (2.0 M, 10 mL). The resulting mixture is stirred at RT for 12 h. The mixture is concentrated and neutralized with HCl (5 N) till pH~3, and extracted with EtOAc (3×30 mL). The organic layer is dried over Na$_2$SO$_4$, concentrated to afford the title compound (1.49 g, 99%).

H-NMR (ppm, CDCl$_3$) δ: 8.34 (1H, d, J=1.3 Hz), 8.00 (1H, dd, J=1.8, 8.8 Hz), 7.40 (1H, d, J=8.8 Hz), 7.10 (1H, d, J=2.2 Hz), 6.92 (1H, dd, J=2.2, 8.4 Hz), 6.69 (1H, s), 6.54 (1H, d, J=8.8 Hz), 4.84 (1H, s), 3.40 (1H, q, J=7.0 Hz), 2.20 (2H, q, J=7.4 Hz), 2.10 (2H, q, J=7.4 Hz), 1.25 (9H, s), 1.20 (6H, d, J=7.0 Hz), 0.72 (6H, t, J=7.5 Hz).

MS (ES) m/e: 482.3 (M+18), 463.3 (M−1).

Example 18

Preparation of 2-{1-[4-(3,3-dimethyl-2-oxo-butoxy)-3-methyl-phenyl]-1-ethyl-propyl}-benzofuran-6-carboxylic acid

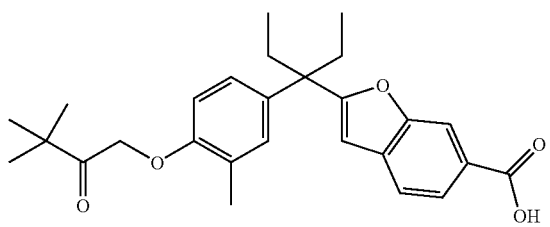

A. 6-Benzyloxy-benzofuran-2-carboxylic acid ethyl ester

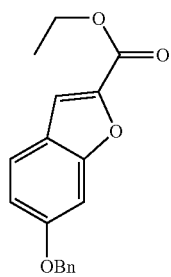

A solution of 4-benzyloxy-2-hydroxybenzaldehyde (7.90 g, 25.1 mmol) in acetone is treated with ethyl bromoacetate (5.79 g, 34.7 mmol) and potassium carbonate (7.98 g, 57.8 mmol). The mixture is stirred for 48 h at RT and filtered and concentrated, purified on column with 20% EtOAc/Hex to afford the intermediate ether (7.90 g, 87%).

The intermediate is dissolved in DMF (40 mL) and treated with DBU (3.83 g, 25.1 mmol). The mixture is stirred at 140° C. for 2 h, cooled down, poured into water (500 mL) and extracted with EtOAc (2×100 mL). The organic layer is dried over $Na_2SO_4$, concentrated, purified on column chromatography (10-15% EtOAc/Hex) to afford the title compound (5.80 g, 78%).

H-NMR (ppm, $CDCl_3$) δ: 7.53 (1H, d, J=8.8 Hz), 7.46 (1H, s), 7.46 (1H, s), 7.44-7.32 (4H, m), 7.12 (1H, d, J=2.2 Hz), 7.02 (1H, dd, J=2.2, 8.4 Hz), 5.12 (2H, s), 4.43 (2H, q, J=7.0 Hz), 1.42 (3H, t, J=7.0 Hz).

B. 3-(6-Benzyloxy-benzofuran-2-yl)-pentan-3-ol. (PF1-A03671-050)

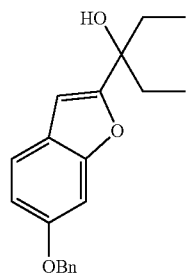

6-Benzyloxy-benzofuran-2-carboxylic acid ethyl ester (5.80 g, 19.6 mmol) and ethyl magnesium bromide (20 mL, 3.0 M) are reacted analogous to Example 1B to give the title compound as a pale yellow oil (5.47 g, 90%).

H-NMR (ppm, $CDCl_3$) δ 7.45 (1H, s), 7.47-7.33 (5H, m), 7.06 (1H, d, J=2.2 Hz), 6.93 (1H, dd, J=2.2, 9.0 Hz), 6.53 (1H, s), 5.11 (2H, s), 2.00-1.86 (4H, m), 0.88 (6H, t, J=7.5 Hz).

C. 4-[1-(6-Benzyloxy-benzofuran-2-yl)-1-ethyl-propyl]-2-methyl-phenol.

3-(6-Benzyloxy-benzofuran-2-yl)-pentan-3-ol (5.40 g, 17.4 mmol) and o-cresol (3.76 g, 34.8 mmol) and $BF_3$—$OEt_2$ (2.47 g, 17.4 mmol) are reacted analogous to Example 1D to give the title compound as a pale yellow oil (5.50 g, 79%).

H-NMR (ppm, $CDCl_3$) δ: 7.47-7.33 (5H, m), 6.99-6.90 (5H, m), 6.67 (1H, d, J=7.9 Hz), 6.54 (1H, s), 5.06 (2H, s), 2.21 (3H, s), 2.18 (2H, q, J=7.5 Hz), 2.06 (2H, q, J=7.5 Hz), 0.88 (6H, t, J=7.5 Hz).

E. 1-{4-[1-(6-Benzyloxy-benzofuran-2-yl)-1-ethyl-propyl]-2-methyl-phenoxy}-3,3-dimethyl-butan-2-one.

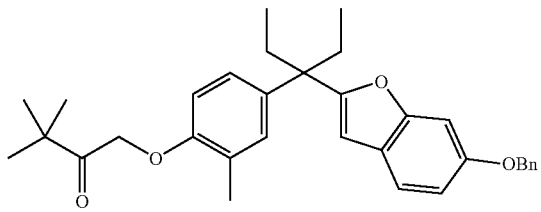

4-[1-(6-Benzyloxy-benzofuran-2-yl)-1-ethyl-propyl]-2-methyl-phenol (5.50 g, 13.7 mmol) and 1-bromopinacolone (4.92 g, 27.5 mmol) and $K_2CO_3$ (3.80 g, 27.5 mmol) are reacted analogous to Example 1E to give the title compound as a pale yellow oil (5.90 g, 86%).

H-NMR (ppm, $CDCl_3$) δ: 7.46-7.32 (6H, m), 7.02 (1H, d, J=1.8 Hz), 6.99 (1H, d, J=2.2 Hz), 6.97 (1H, dd, J=2.2, 8.8 Hz), 6.91 (1H, dd, J=2.2, 8.8 Hz), 6.54 (1H, s), 6.52 (1H, d, J=7.0 Hz), 5.07 (2H, s), 4.84 (2H, s), 2.27 (3H, s), 2.18 (2H, q, J=7.5 Hz), 2.07 (2H, q, J=7.5 Hz), 1.27 (9H, s), 0.73 (6H, t, J=7.5 Hz).

F. 1-{4-[1-Ethyl-1-(6-hydroxy-benzofuran-2-yl)-propyl]-2-methyl-phenoxy}-3,3-dimethyl-butan-2-one.

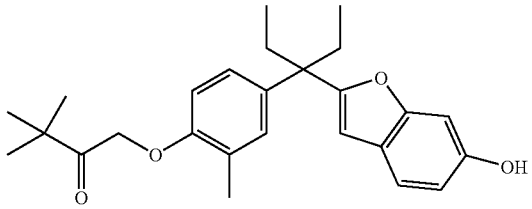

A solution of 1-{4-[1-(6-benzyloxy-benzofuran-2-yl)-1-ethyl-propyl]-2-methyl-phenoxy}-3,3-dimethyl-butan-2-one (5.90 g, 11.8 mmol) in EtOAc (20.0 mL) is added a slurry of Pd—C (590 mg, 10%) in MeOH (20.0 mL) at RT. The resulting mixture is stirred under hydrogen balloon pressure for 2 h. The mixture is filtered through a pad of celite and the filtrate is concentrated, the residue is purified with 20-30% EtOAc/Hex to afford the title compound (4.35 g, 90%).

H-NMR (ppm, CDCl$_3$) δ: 7.34 (1H, d, J=8.4 Hz), 6.99 (1H, d, J=1.8 Hz), 6.95 (1H, dd, J=2.6, 8.4 Hz), 6.83 (1H, d, J=2.2 Hz), 6.72 (1H, dd, J=2.6, 8.4 Hz), 6.52 (1H, d, J=7.0 Hz), 6.51 (1H, s), 4.82 (2H, s), 2.25 (3H, s), 2.16 (2H, q, J=7.5 Hz), 2.07 (2H, q, J=7.5 Hz), 1.25 (9H, s), 0.73 (6H, t, J=7.5 Hz).

G. Trifluoromethanesulfonic acid 2-{1-[4-(3,3-dimethyl-2-oxo-butoxy)-3-methyl-phenyl]-1-ethyl-propyl}-benzofuran-6-yl ester.

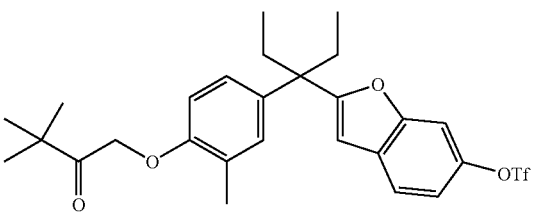

A solution of 1-{4-[1-ethyl-1-(6-hydroxy-benzofuran-2-yl)-propyl]-2-methyl-phenoxy}-3,3-dimethyl-butan-2-one (4.35 g, 10.6 mmol) and 2,6-lutidine (2.48 mL, 21.3 mmol) in CH$_2$Cl$_2$ (100 mL) at −78° C. is added trifluoromethanesulfonic anhydride (2.69 mL, 15.9 mmol). The resulting mixture is stirred while allowed to warmed up to 0° C. over 60 min. The reaction is quenched with water (25 mL) and the aqueous layer is extracted with CH$_2$Cl$_2$ (100 mL). The combined organic layer is dried over Na$_2$SO$_4$, concentrated and purified on column chromatography (10% EtOAc/Hex) to afford the title compound (4.95 g, 86%).

H-NMR (ppm, CDCl$_3$) δ: 7.53 (1H, d, J=8.8 Hz), 7.29 (1H, d, J=2.2 Hz), 7.12 (1H, dd, J=2.2, 8.4 Hz), 6.99 (1H, d, J=1.8 Hz), 6.94 (1H, dd, J=2.2, 8.4 Hz), 6.63 (1H, s), 6.54 (1H, d, J=8.8 Hz), 4.84 (2H, s), 2.27 (3H, s), 2.18 (2H, q, J=7.5 Hz), 2.07 (2H, q, J=7.5 Hz), 1.25 (9H, s), 0.72 (6H, t, J=7.5 Hz).

H. 2-{1-[4-(3,3-Dimethyl-2-oxo-butoxy)-3-methyl-phenyl]-1-ethyl-propyl}-benzofuran-6-carboxylic acid methyl ester.

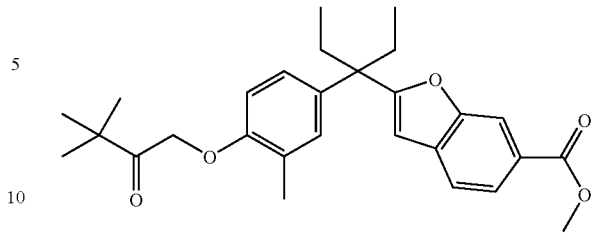

A solution of trifluoromethanesulfonic acid 2-{1-[4-(3,3-dimethyl-2-oxo-butoxy)-3-methyl-phenyl]-1-ethyl-propyl}-benzofuran-6-yl ester (4.90 g, 9.06 mmol) in DMSO (15 mL) and MeOH (10 mL) is treated with Pd(OAc)$_2$ (0.202 g), DPPB (0.455 g) and Et$_3$N (6.6 mL). The mixture is stirred under CO (100 psi) at 80° C. for 4 h. The reaction mixture is concentrated and poured into water (200 mL) and extracted with EtOAc (2×100 mL). The organic layer is dried over Na$_2$SO$_4$, concentrated, purified on column chromatography (10-20% EtOAc/Hex), to give the title compound as an oil (3.80 g, 93%).

H-NMR (ppm, CDCl$_3$) δ: 8.03 (1H, s), 7.91 (1H, dd, J=1.8, 8.4 Hz), 7.54 (1H, d, J=7.5 Hz), 6.99 (1H, d, J=1.8 Hz), 6.95 (1H, dd, J=2.2, 8.4 Hz), 6.64 (1H, s), 6.54 (1H, d, J=8.8 Hz), 4.83 (2H, s), 3.91 (3H, s), 2.26 (3H, s), 2.20 (2H, q, J=7.5 Hz), 2.10 (2H, q, J=7.5 Hz), 1.25 (9H, s), 0.72 (6H, t, J=7.5 Hz).

I. 2-{1-[4-(3,3-Dimethyl-2-oxo-butoxy)-3-methyl-phenyl]-1-ethyl-propyl}-benzofuran-6-carboxylic acid.

2-{1-[4-(3,3-dimethyl-2-oxo-butoxy)-3-methyl-phenyl]-1-ethyl-propyl}-benzofuran-6-carboxylic acid methyl ester (2.90 g, 6.436 mmol) is hydrolyzed analogous to Example 2 to give the title compound as a pale yellow oil (2.17 g, 77%).

H-NMR (ppm, CDCl$_3$) δ: 8.09 (1H, s), 7.96 (1H, dd, J=1.8, 8.4 Hz), 7.57 (1H, d, J=8.4 Hz), 7.00 (1H, d, J=1.8 Hz), 6.96 (1H, dd, J=2.4, 8.8 Hz), 6.66 (1H, s), 6.54 (1H, d, J=8.8 Hz), 4.84 (2H, s), 2.26 (3H, s), 2.22 (2H, q, J=7.5 Hz), 2.12 (2H, q, J=7.5 Hz), 1.25 (9H, s), 0.73 (6H, t, J=7.5 Hz).

MS (ES) m/e: 454.0 (M+18), 435.1 (M−1)

Example 19

Preparation of 2-{1-Ethyl-1-[4-(2-hydroxy-3,3-dimethyl-butoxy)-3-methyl-phenyl]-propyl}-benzofuran-6-carboxylic acid

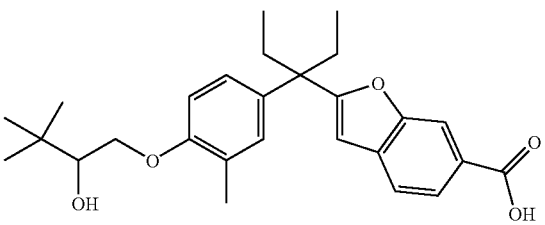

A solution of 2-{1-[4-(3,3-dimethyl-2-oxo-butoxy)-3-methyl-phenyl]-1-ethyl-propyl}-benzofuran-6-carboxylic acid (110 mg, 0.252 mmol) in THF (5.0 mL) at RT is treated with NaBH$_4$ (19 mg, 0.505 mmol). The resulting mixture is stirred for 1 h and is quenched with water (1.0 mL) and extracted with EtOAc (3×30 mL). The organic layer is dried over Na$_2$SO$_4$, concentrated to afford the title compound (105 mg, 95%).

H-NMR (ppm, CDCl₃) δ: 7.96 (1H, s), 7.84 (1H, d, J=8.4 Hz), 7.47 (1H, d, J=7.9 Hz), 6.94 (1H, dd, J=2.4, 8.8 Hz), 6.91 (1H, s), 6.66 (1H, d, J=8.8 Hz), 6.60 (1H, s), 4.02 (1H, dd, J=2.6, 9.2 Hz), 3.80 (1H, d, J=8.4 Hz), 3.60 (1H, dd, J=2.6, 8.4 Hz), 2.26 (3H, s), 2.22 (2H, q, J=7.5 Hz), 2.12 (2H, q, J=7.5 Hz), 0.95 (9H, s), 0.65 (6H, t, J=7.5 Hz).

MS (ES) m/e: 456.0 (M+18), 437.1 (M−1)

Example 20

Preparation of [(2-{1-[4-(3,3-Dimethyl-2-oxo-butoxy)-3-methyl-phenyl]-1-ethyl-propyl}-benzofuran-6-carbonyl)-amino]-acetic acid

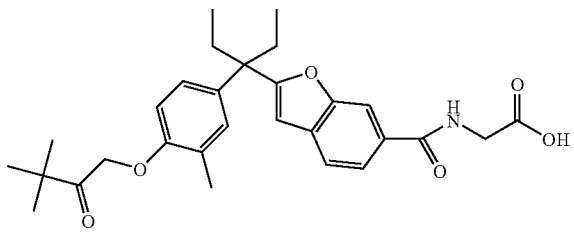

A solution of 2-{1-[4-(3,3-dimethyl-2-oxo-butoxy)-3-methyl-phenyl]-ethylpropyl}-benzofuran-6-carboxylic acid (880 mg, 2.016 mmol) in CH₂Cl₂ (40 mL) is treated with DMAP (740 mg, 6.047 mmol) and EDC (580 mg, 3.024 mmol). The mixture is stirred for 10 min at RT before the addition of glycine methyl ester hydrochloride (380 mg, 3.024 mmol). The reaction is stirred for 12 h and quenched with water (5.0 mL). The organic layer is loaded on silica gel column and purified with 20-50% EtOAc/Hex to afford the intermediate amide ester (790 mg, 77%).

The intermediate (180 mg, 0.355 mmol) is dissolved in methanol (3.0 mL) and THF (3.0 mL) and is treated with NaOH (2.0 M, 6.0 mL). The resulting mixture is stirred at 40° C. for 3 h. The mixture is concentrated and neutralized with HCl (1 N) till pH~3, and extracted with EtOAc (3×30 mL). The organic layer is dried over Na₂SO₄, concentrated and purified with 2% HOAc in 50% EtOAc/Hex to afford the title compound (45 mg, 26%).

H-NMR (ppm, CDCl₃) δ: 7.81 (1H, s), 7.66 (1H, dd, J=1.8, 8.4 Hz), 7.55 (1H, d, J=8.4 Hz), 6.99 (1H, d, J=1.8 Hz), 6.93 (1H, dd, J=2.2, 8.8 Hz), 6.79 (1H, t, J=4.8 Hz), 6.64 (1H, s), 6.53 (1H, d, J=8.8 Hz), 4.84 (2H, s), 4.28 (2H, d, J=4.8 Hz), 2.25 (3H, s), 2.20 (2H, q, J=7.4 Hz), 2.12 (2H, q, J=7.4 Hz), 1.25 (9H, s), 0.72 (6H, t, J=7.5 Hz).

MS (ES) m/e: 494.2 (M+1)

Example 21

Preparation of 5-{1-[4-(3,3-dimethyl-2-oxo-butoxy)-3-methyl-phenyl]-1-ethyl-propyl}-7-methyl-benzofuran-2-carboxylic acid

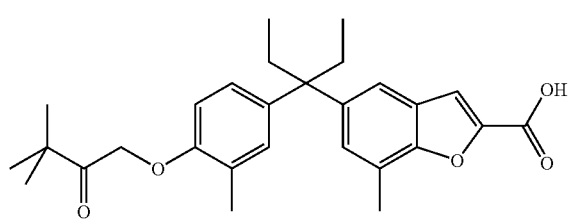

A. 5-(1-Ethyl-1-hydroxy-propyl)-2-hydroxy-3-methyl-benzaldehyde.

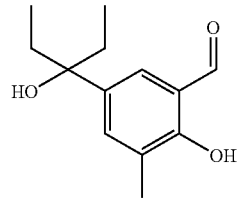

A solution of 4-(1-ethyl-1-hydroxy-propyl)-2-methyl-phenol (8.12 g, 41.8 mmol) in acetonitrile (200 mL) is added MgCl₂ (5.97 g, 62.7 mmol) and triethyl amine (20.5 mL, 146 mmol). The mixture is treated with paraformaldehyde (8.16 g, 271 mmol) and heated at 80° C. for 2 h. The reaction mixture is cooled to RT and quenched with HCl (1 N, 50 mL), the acetonitrile is removed in vacuum and the aqueous layer extracted with EtOAc (2×100 mL). The organic layer is dried over Na₂SO₄, concentrated, purified on column chromatography (10-20% EtOAc/Hex) to afford the title compound (6.52 g, 70%).

H-NMR (ppm, CDCl₃) δ: 11.1 (1H, s), 9.87 (1H, s), 7.44 (1H, d, J=2.6 Hz), 7.35 (1H, d, J=2.2 Hz), 2.28 (3H, s), 1.83 (4H, dq, J=7.0 Hz), 0.78 (6H, t, J=7.5 Hz).

MS (ES) m/e: 223.0 (M+1), 221.1 (M−1)

B. 5-(1-Ethyl-1-hydroxy-propyl)-7-methyl-benzofuran-2-carboxylic acid ethyl ester.

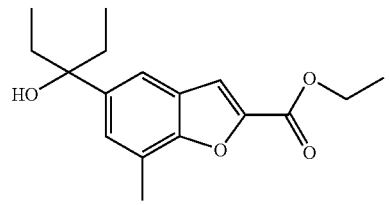

A solution of 5-(1-ethyl-1-hydroxy-propyl)-2-hydroxy-3-methyl-benzaldehyde (6.52 g, 29.3 mmol) in acetone (100 mL) is treated with ethyl bromoacetate (7.33 g, 43.9 mmol) and potassium carbonate (8.09 g, 58.7 mmol). The mixture is stirred for 2 h at RT and filtered and concentrated to afford the intermediate ether.

The intermediate is dissolved in DMF (100 mL) and treated with DBU (10 mL). The mixture is stirred at 140° C. for 60 min, cooled down, poured into water (400 mL) and extracted with EtOAc (2×100 mL). The organic layer is dried over Na₂SO₄, concentrated, purified on column chromatography (10-15% EtOAc/Hex) to afford the title compound (7.90 g, 93%).

H-NMR (ppm, CDCl₃) δ: 7.52 (1H, d, J=1.8 Hz), 7.23 (1H, dd, J=0.9, 1.8 Hz), 4.44 (2H, q, J=7.0 Hz), 2.58 (3H, s), 1.94-1.82 (4H, m), 0.77 (6H, t, J=7.5 Hz).

C. 5-[1-Ethyl-1-(4-hydroxy-3-methyl-phenyl)-propyl]-7-methyl-benzofuran-2-carboxylic acid ethyl ester (PF1-A03671-100)

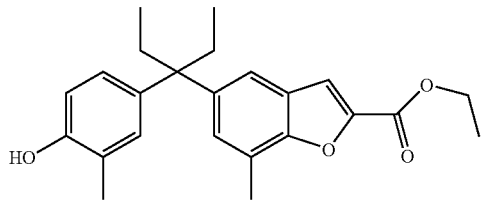

5-(1-Ethyl-1-hydroxy-propyl)-7-methyl-benzofuran-2-carboxylic acid ethyl ester (7.90 g, 27.2 mmol) and o-cresol (5.88 g, 54.4 mmol) and BF$_3$-Et$_2$O (3.86 g, 27.2 mmol) are reacted analogous to Example 1D to give the title compound (5.55 g, 54%).

H-NMR (ppm, CDCl$_3$) δ: 7.46 (1H, s), 7.39 (1H, d, J=1.8 Hz), 6.92 (1H, d, J=1.8 Hz), 6.88 (1H, d, J=2.2 Hz), 6.84 (1H, dd, J=2.2, 8.4 Hz), 6.67 (1H, d, J=8.0 Hz), 4.42 (2H, q, J=7.0 Hz), 2.46 (3H, s), 2.20 (3H, s), 2.10 (4H, q, J=7.5 Hz), 1.42 (3H, t, J=7.0 Hz), 0.61 (6H, t, J=7.5 Hz).

MS (ES) m/e: 381.2 (M+1), 379.2 (M−1)

E. 5-{1-[4-(3,3-Dimethyl-2-oxo-butoxy)-3-methyl-phenyl]-1-ethyl-propyl}-7-methyl-benzofuran-2-carboxylic acid ethyl ester.

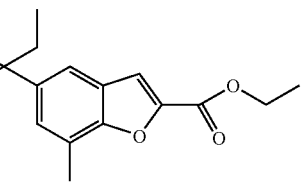

5-[1-Ethyl-1-(4-hydroxy-3-methyl-phenyl)-propyl]-7-methyl-benzofuran-2-carboxylic acid ethyl ester (5.55 g, 14.6 mmol) and 1-bromopinacolone (3.92 g, 21.9 mmol) and K$_2$CO$_3$ (6.04 g, 43.8 mmol) are reacted analogous to Example 1E to give the title compound as a pale yellow oil (5.00 g, 72%).

H-NMR (ppm, CDCl$_3$) δ: 7.46 (1H, s), 7.39 (1H, d, J=1.3 Hz), 6.92-6.88 (3H, m), 6.50 (1H, d, J=8.8 Hz), 4.84 (2H, s), 4.42 (2H, q, J=7.0 Hz), 2.47 (3H, s), 2.24 (3H, s), 2.10 (4H, q, J=7.0 Hz), 1.42 (3H, t, J=7.0 Hz), 1.26 (9H, s), 0.61 (6H, t, J=7.5 Hz).

MS (ES) m/e: 479.2 (M+1)

F. 5-{1-[4-(3,3-Dimethyl-2-oxo-butoxy)-3-methyl-phenyl]-1-ethyl-propyl}-7-methyl-benzofuran-2-carboxylic acid.

5-{1-[4-(3,3-Dimethyl-2-oxo-butoxy)-3-methyl-phenyl]-1-ethyl-propyl}-7-methyl-benzofuran-2-carboxylic acid ethyl ester (1.80 g, 3.76 mmol) is hydrolyzed analogous to Example 2 to give the title compound (1.68 g, 99%).

H-NMR (ppm, CDCl$_3$) δ: 7.60 (1H, s), 7.43 (1H, d, J=1.3 Hz), 6.95 (1H, s), 6.90 (1H, s), 6.88 (1H, d, J=2.2 Hz), 6.50 (1H, d, J=8.8 Hz), 4.85 (2H, s), 2.47 (3H, s), 2.23 (3H, s), 2.10 (4H, q, J=7.5 Hz), 1.26 (9H, s), 0.61 (6H, t, J=7.5 Hz).

MS (ES) m/e: 449.2 (M−1)

Example 22

Preparation of 5-{1-Ethyl-1-[4-(2-hydroxy-3,3-dimethyl-butoxy)-3-methyl-phenyl]-propyl}-7-methyl-benzofuran-2-carboxylic acid

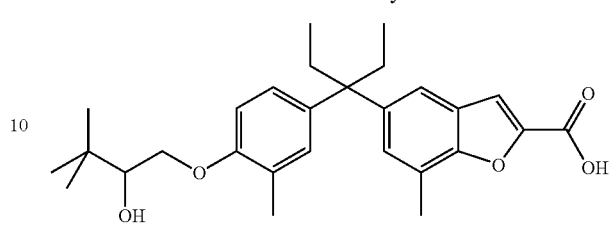

A solution of 5-{1-[4-(3,3-dimethyl-2-oxo-butoxy)-3-methyl-phenyl]-1-ethyl-propyl}-7-methyl-benzofuran-2-carboxylic acid (250 mg, 0.555 mmol) in THF (10 mL) at RT is treated with NaBH$_4$ (42 mg, 1.11 mmol). The resulting mixture is stirred for 60 min and is quenched with HCl (1.0 N, 5.0 mL) and extracted with EtOAc (2×30 mL). The organic layer is dried over Na$_2$SO$_4$, concentrated to afford the title compound (170 mg, 68%).

H-NMR (ppm, CDCl$_3$) δ: 7.62 (1H, s), 7.43 (1H, d, J=1.8 Hz), 6.96 (2H, m), 6.89 (1H, d, J=1.8 Hz), 6.71 (1H, d, J=8.5 Hz), 4.10 (1H, dd, J=2.6, 9.2 Hz), 3.86 (1H, t, J=9.2 Hz), 3.72 (1H, dd, J=2.6, 9.2 Hz), 2.48 (3H, s), 2.18 (3H, s), 2.10 (4H, q, J=7.0 Hz), 1.02 (9H, s), 0.61 (6H, t, J=7.5 Hz).

MS (ES) m/e: 451.2 (M−1)

Example 23

Preparation of 5-{1-[4-(2-tert-Butyl-[1,3]dioxolan-2-ylmethoxy)-3-methyl-phenyl]-1-ethylpropyl}-7-methyl-benzofuran-2-carboxylic acid

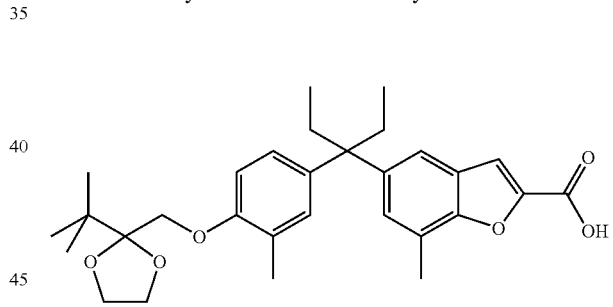

A. 5-{1-[4-(2-tert-Butyl-[1,3]dioxolan-2-ylmethoxy)-3-methyl-phenyl]-1-ethyl-propyl}-7-methyl-benzofuran-2-carboxylic acid ethyl ester.

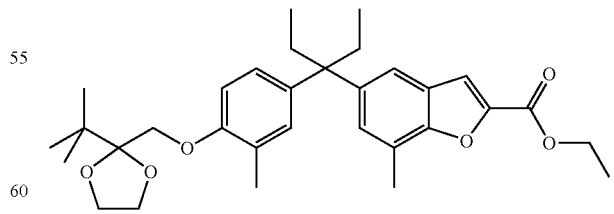

A solution of 5-{1-[4-(3,3-dimethyl-2-oxo-butoxy)-3-methyl-phenyl]-1-ethyl-propyl}-7-methyl-benzofuran-2-carboxylic acid ethyl ester (506 mg, 1.06 mmol) in ethylene glycol (5.0 mL) is treated with BF$_3$-Et$_2$O (3.0 ml). The reaction mixture is heated to 80° C. and stirred for 3 h. The reaction is quenched with water (20 mL) and extracted with CH₂Cl₂ (30×2 mL). The organic layer is dried over Na₂SO₄, concentrated, purified on column chromatography (8% EtOAc/Hex) to afford the title compound (550 mg, 99%).

H-NMR (ppm, CDCl₃) δ: 7.46 (1H, s), 7.39 (1H, d, J=1.3 Hz), 6.95 (1H, dd, J=2.2, 6.6 Hz), 6.91 (1H, m), 6.86 (1H, d, J=1.8 Hz), 6.69 (1H, d, J=8.3 Hz), 4.42 (1H, q, J=7.0 Hz), 4.25 (2H, m), 4.11 (2H, s), 4.02 (2H, m), 2.47 (3H, s), 2.18 (3H, s), 2.10 (4H, q, J=7.0 Hz), 1.42 (3H, t, J=7.0 Hz), 1.07 (9H, s), 0.61 (6H, t, J=7.5 Hz).

MS (ES) m/e: 523.2 (M+1)

B. 5-{1-[4-(2-tert-Butyl-[1,3]dioxolan-2-ylmethoxy)-3-methyl-phenyl]-1-ethylpropyl}-7-methyl-benzofuran-2-carboxylic acid.

5-{1-[4-(2-tert-Butyl-[1,3]dioxolan-2-ylmethoxy)-3-methyl-phenyl]-1-ethyl-propyl}-7-methyl-benzofuran-2-carboxylic acid ethyl ester (0.550 g, 1.05 mmol) is hydrolyzed analogous to Example 2 to give the title compound (0.48 g, 91%).

H-NMR (ppm, CDCl₃) δ: 7.59 (1H, s), 7.42 (1H, d, J=1.3 Hz), 6.94 (2H, m), 6.91 (1H, m), 6.86 (1H, d, J=1.8 Hz), 6.69 (1H, d, J=8.8 Hz), 4.25 (2H, m), 4.10 (2H, s), 4.03 (2H, m), 2.47 (3H, s), 2.17 (3H, s), 2.10 (4H, q, J=7.0 Hz), 1.06 (9H, s), 0.61 (6H, t, J=7.5 Hz).

MS (ES) m/e: 493.2 (M−1)

Example 24

Preparation of [(5-{1-[4-(2-tert-butyl-[1,3]dioxolan-2-ylmethoxy)-3-methyl-phenyl]-1-ethyl-propyl}-7-methyl-benzofuran-2-carbonyl)-amino]-acetic acid

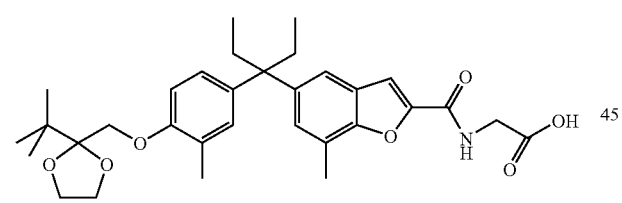

5-{1-[4-(2-tert-Butyl-[1,3]dioxolan-2-ylmethoxy)-3-methyl-phenyl]-1-ethylpropyl}-7-methyl-benzofuran-2-carboxylic acid (180 mg, 0.364 mmol), EDC (105 mg, 0.546 mmol), DMAP (133 mg, 1.09 mmol, and glycine methyl ester hydrochloride (68 mg, 0.55 mmol) are reacted to produce the intermediate followed by hydrolysis analogous to Example 7 to give title compound (195 mg, 97%).

H-NMR (ppm, CDCl₃) δ 7.48 (1H, s), 7.40 (1H, br s), 7.13 (1H, t, J=5.3 Hz), 6.95 (1H, d, J=8.8 Hz), 6.90(1H, s), 6.85 (1H, s), 6.70 (1H, d, J=8.8 Hz), 4.34 (2H, d, J=5.3 Hz), 4.25 (2H, t, J=6.2 Hz), 4.10 (2H, s), 4.03 (2H, t, J=6.2 Hz), 2.43 (3H, s), 2.17 (3H, s), 2.10 (4H, q, J=7.0 Hz), 1.06 (9H, s), 0.61 (6H, t, J=7.5 Hz).

MS (ES) m/e: 552.2 (M+1), 550.2 (M−1)

Example 25

Preparation of 5-{1-[4-(2-tert-Butyl-[1,3]dioxolan-2-ylmethoxy)-3-methyl-phenyl]-1-ethyl-propyl}-7-methyl-benzofuran-2-carboxylic acid dimethylamide

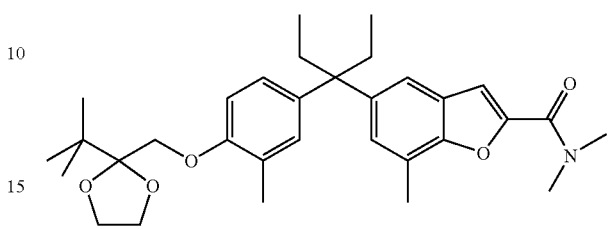

5-{1-[4-(2-tert-Butyl-[1,3]dioxolan-2-ylmethoxy)-3-methyl-phenyl]-1-ethylpropyl}-7-methyl-benzofuran-2-carboxylic acid A solution of 5-{1-[4-(2-tert-butyl-[1,3]dioxolan-2-ylmethoxy)-3-methyl-phenyl]-1-ethylpropyl}-7-methyl-benzofuran-2-carboxylic acid (160 mg, 0.323 mmol) in CH₂Cl₂ (10 mL) is treated with DMAP (118 mg, 0.970 mmol) and EDC (93 mg, 0.485 mmol). The mixture is stirred for 15 min at RT before the addition of dimethylamine hydrochloride (40 mg, 0.485 mmol). The reaction is stirred for 18 h and quenched with aqueous NH₄Cl (5.0 mL). The organic layer is loaded on silica gel column and purified with 50% EtOAc/Hex to afford the title compound (148 mg, 88%).

H-NMR (ppm, CDCl₃) δ: 7.37 (1H, d, J=1.8 Hz), 7.27 (1H, s), 6.95 (1H, d, J=8.4 Hz), 6.88(2H, m), 6.69 (1H, d, J=8.4 Hz), 4.25 (2H, t, J=6.2 Hz), 4.10 (2H, s), 4.03 (2H, t, J=6.2 Hz), 3.26 (6H, br s), 2.43 (3H, s), 2.18 (3H, s), 2.10 (4H, q, J=7.0 Hz), 1.06 (9H, s), 0.61 (6H, t, J=7.5 Hz).

MS (ES) m/e: 522.3 (M+1)

Example 26

5-{1-[4-(3,3-Dimethyl-2-oxo-butoxy)-3-methyl-phenyl]-1-ethyl-propyl}-7-methyl-benzofuran-2-carboxylic acid dimethylamide

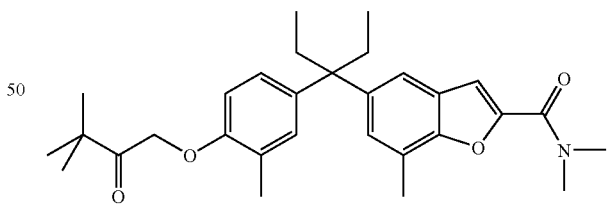

5-{1-[4-(3,3-Dimethyl-2-oxo-butoxy)-3-methyl-phenyl]-1-ethyl-propyl}-7-methyl-benzofuran-2-carboxylic acid (270 mg, 0.599 mmol) in CH₂Cl₂ (10 mL) and DMAP (220 mg, 1.80 mmol), EDC (172 mg, 0.898 mmol), and dimethyl amine hydrochloride (73 mg, 0.90 mmol) are reacted analogous to Example 5 to yield title compound (280 mg, 98%).

H-NMR (ppm, CDCl₃) δ 7.37 (1H, s), 7.28 (1H, s), 6.90 (3H, m), 6.50 (1H, d, J=8.8 Hz), 4.84 (2H, s), 3.26 (6H, br s), 2.43 (3H, s), 2.24 (3H, s), 2.10 (4H, q, J=7.0 Hz), 1.26 (9H, s), 0.61 (6H, t, J=7.5 Hz).

MS (ES) m/e: 478.3 (M+1)

Example 27

Preparation of 5-{1-Ethyl-1-[4-(2-hydroxy-3,3-dimethyl-butoxy)-3-methyl-phenyl]-propyl}-7-methyl-benzofuran-2-carboxylic acid dimethylamide

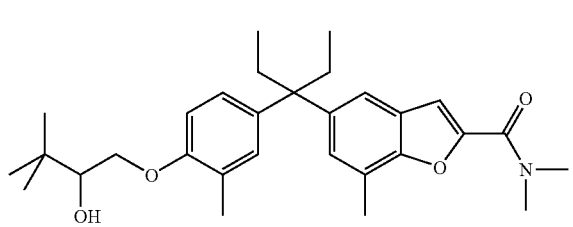

5-{1-[4-(3,3-Dimethyl-2-oxo-butoxy)-3-methyl-phenyl]-1-ethyl-propyl}-7-methyl-benzofuran-2-carboxylic acid dimethylamide (215 mg, 0.451 mmol) is reduced with NaBH₄ (34 mg, 0.901 mmol) analogous to Example 3 to give the title product (130 mg, 60%).

H-NMR (ppm, CDCl₃) δ: 7.37 (1H, d, J=1.3 Hz), 7.30 (1H, s), 6.95 (1H, dd, J=2.6, 8.3 Hz), 6.88 (2H, m), 6.70 (1H, d, J=8.4 Hz), 4.08 (1H, dd, J=2.6, 6.6 Hz), 3.86 (1H, t, J=9.2 Hz), 3.72 (1H, dd, J=2.6, 9.2 Hz), 3.26 (6H, br s), 2.42 (3H, s), 2.16 (3H, s), 2.10 (4H, q, J=7.0 Hz), 1.01 (9H, s), 0.61 (6H, t, J=7.5 Hz).

MS (ES) m/e: 480.3 (M+1)

Example 28

Preparation of [(5-{1-[4-(3,3-dimethyl-2-oxo-butoxy)-3-methyl-phenyl]-1-ethyl-propyl}-7-methyl-benzofuran-2-carbonyl)-amino]-acetic acid

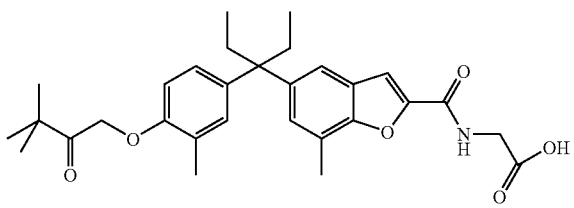

lp;1p

5-{1-[4-(3,3-Dimethyl-2-oxo-butoxy)-3-methyl-phenyl]-1-ethyl-propyl}-7-methyl-benzofuran-2-carboxylic acid (360 mg, 0.799 mmol) in CH₂Cl₂ (10 ml) and DMAP (293 mg, 2.40 mmol), EDC (230 mg, 1.20 mmol), and glycine methyl ester hydrochloride (150 mg, 1.20 mmol) are reacted and hydrolyzed analogous to Example 7 to yield title compound (395 mg, 97%).

H-NMR (ppm, CDCl₃) δ: 7.49 (1H, s), 7.40 (1H, d, J=1.8 Hz), 7.13 (1H, t, J=5.3 Hz), 6.90(3H, m), 6.50 (1H, d, J=9.2 Hz), 4.82 (2H, s), 4.33 (1H, d, J=5.3 Hz), 2.46 (3H, s), 2.24 (3H, s), 2.10 (4H, q, J=7.0 Hz), 1.26 (9H, s), 0.61 (6H, t, J=7.5 Hz).

MS (ES) m/e: 508.3 (M+1), 506.3 (M−1)

Example 29

Preparation of [(5-{1-Ethyl-1-[4-(2-hydroxy-3,3-dimethyl-butoxy)-3-methyl-phenyl]-propyl}-7-methyl-benzofuran-2-carbonyl)-amino]-acetic acid

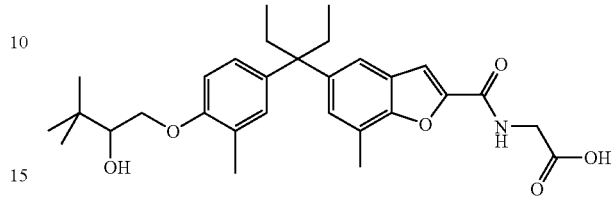

[(5-{1-[4-(3,3-Dimethyl-2-oxo-butoxy)-3-methyl-phenyl]-1-ethyl-propyl}-7-methyl-benzofuran-2-carbonyl)-amino]-acetic acid (210 mg, 0.414 mmol) is reduced with NaBH₄ (31 mg, 0.827 mmol) analogous to Example 3 to give the title product (210 mg, 100%).

H-NMR (ppm, CDCl₃) δ: 7.49 (1H, s), 7.40 (1H, d, J=1.8 Hz), 7.13 (1H, t, J=5.3 Hz), 6.90(3H, m), 6.50 (1H, d, J=9.2 Hz), 4.34 (2H, d, J=5.3 Hz), 4.10 (1H, dd, J=2.6, 9.2 Hz), 3.86 (1H, t, J=9.2 Hz), 3.72 (1H, dd, J=2.6, 9.2 Hz), 2.44 (3H, s), 2.17 (3H, s), 2.10 (4H, q, J=7.0 Hz), 1.02 (9H, s), 0.61 (6H, t, J=7.5 Hz).

MS (ES) m/e: 510.2 (M+1), 508.2 (M−1)

Example 30

Preparation of 5-{1-[4-(3,3-dimethyl-2-oxo-butoxy)-3-methyl-phenyl]-1-ethyl-propyl}-benzofuran-2-carboxylic acid

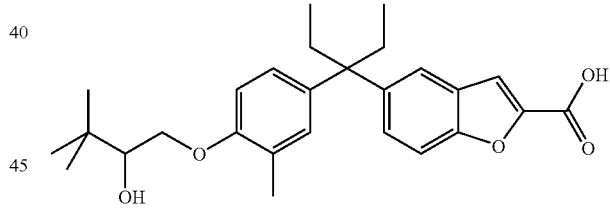

A. 5-(1-Ethyl-propenyl)-2-hydroxy-benzaldehyde.

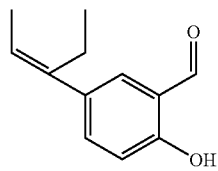

To a stirred solution of 4-hydroxy-benzoic acid methyl ester (13.8 g, 90.7 mmol) in THF (600 mL) at −78° C. is added ethylmagnesium bromide (121 mL, 3.0 M). The reaction is allowed to warm to RT and stirred for one hour before quenched with water and HCl (1.0 M) till pH~3. The THF is removed under vacuum and the mixture is extracted with EtOAc (2×200 mL). The organic layer is dried over Na₂SO₄, concentrated to give the intermediate olefin phenol as an oil.

The intermediate is dissolved in acetonitrile (600 mL) and MgCl₂ (12.1 g, 127 mmol) and Et₃N (38.1 mL, 272 mmol) is added. The mixture is treated with paraformaldehyde (16.3 g, 544 mmol) and heated at 80° C. for 2 h. The reaction mixture is cooled to RT and quenched with HCl (1 N, 100 mL), removed the acetonitrile under vacuum and extracted with EtOAc (2×200 mL). The organic layer is dried over Na₂SO₄, concentrated, purified on column chromatography (10-15% EtOAc/Hex) to afford the title compound (15.5 g, 90%).

H-NMR (ppm, CDCl₃), δ: 10.89 (1H, s), 9.89 (1H, s), 7.53 (1H, dd, J=2.6, 8.8 Hz), 7.49 (1H, d, J=2.6 Hz), 6.88 (1H, d, J=8.8 Hz), 5.70 (1H, q, J=7.0 Hz), 2.52 (2H, q, J=7.5 Hz), 1.82 (3H, d, J=6.6 Hz), 0.99 (3H, t, J=7.5 Hz).

MS (ES) m/e: 189.1 (M−1)

B. 5-(1-Ethyl-propenyl)-benzofuran-2-carboxylic acid ethyl ester.

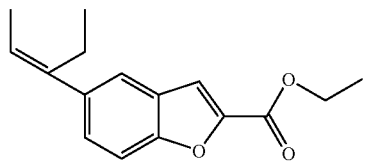

A solution of 5-(1-ethyl-propenyl)-2-hydroxy-benzaldehyde (15.5 g, 81.5 mmol) in acetone (300 mL) is treated with ethyl bromoacetate (15.0 g, 89.6 mmol) and potassium carbonate (16.9 g, 122 mmol). The mixture is stirred for 2 h at RT and filtered and concentrated to afford the intermediate ether.

The intermediate is dissolved in DMF (200 mL) and treated with DBU (2.48 g, 16.3 mmol). The mixture is stirred at 140° C. for 2 h, cooled down to RT, poured into water (400 mL) and extracted with EtOAc (2×200 mL). The organic layer is dried over Na₂SO₄, concentrated, purified on column chromatography (10-15% EtOAc/Hex) to afford the title compound (18.8 g, 89%).

MS (ES) m/e: 259.1 (M+1)

C. 5-[1-Ethyl-1-(4-hydroxy-3-methyl-phenyl)-propyl]-benzofuran-2-carboxylic acid ethyl ester.

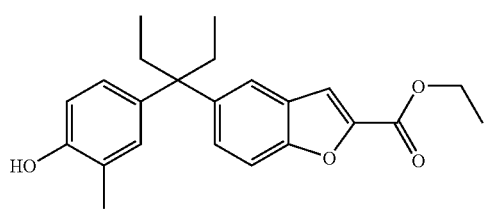

5-(1-Ethyl-1-hydroxy-propyl)-benzofuran-2-carboxylic acid ethyl ester (5.70 g, 22.1 mmol) and o-cresol (2.86 g, 26.5 mmol) and BF₃-Et₂O (3.13 g, 22.1 mmol) are reacted analogous to Example 1D to give the title compound (7.10 g, 88%).

MS (ES) m/e: 367.2 (M+1), 365.2 (M−1)

D. 5-{1-[4-(3,3-Dimethyl-2-oxo-butoxy)-3-methyl-phenyl]-1-ethyl-propyl}-benzofuran-2-carboxylic aci ethyl ester.

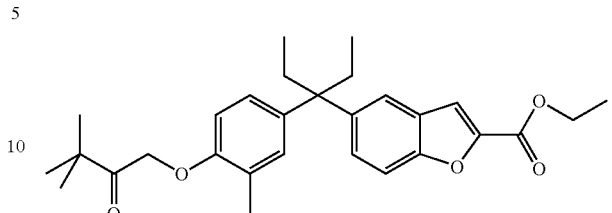

5-[1-Ethyl-1-(4-hydroxy-3-methyl-phenyl)-propyl]-benzofuran-2-carboxylic acid ethyl ester (7.10 g, 19.4 mmol) and 1-bromopinacolone (4.17 g, 23.3 mmol) and K₂CO₃ (5.35 g, 38.8 mmol) are reacted analogous to Example 1E to give the title compound as a pale yellow oil (7.60 g, 84%).

H-NMR (ppm, CDCl₃) δ: 7.61 (1H, s), 7.51 (1H, s), 7.43 (1H, d, J=8.8 Hz), 7.18 (1H, dd, J=1.6, 8.8 Hz), 6.92 (2H, m), 6.52 (1H, d, J=8.8 Hz), 4.87 (2H, s), 4.47 (2H, q, J=7.0 Hz), 2.26 (3H, s), 2.14 (4H, q, J=7.0 Hz), 1.46 (3H, t, J=7.0 Hz), 1.29 (9H, s), 0.65 (6H, t, J=7.5 Hz).

MS (ES) m/e: 464.6 (M+1)

E. 5-{1-[4-(3,3-Dimethyl-2-oxo-butoxy)-3-methyl-phenyl]-1-ethyl-propyl}-benzofuran-2-carboxylic acid.

5-{1-[4-(3,3-Dimethyl-2-oxo-butoxy)-3-methyl-phenyl]-1-ethyl-propyl}-benzofuran-2-carboxylic acid ethyl ester (0.68 g, 1.46 mmol) is hydrolyzed analogous to Example 2 to give the title compound (0.63 g, 99%).

H-NMR (ppm, CDCl₃) δ: 7.64 (2H, m), 7.44 (1H, d, J=8.4 Hz), 7.19 (1H, dd, J=1.6, 8.8 Hz), 6.92 (2H, m), 6.52 (1H, d, J=8.8 Hz), 4.87 (2H, s), 2.26 (3H, s), 2.14 (4H, q, J=7.0 Hz), 1.29 (9H, s), 0.65 (6H, t, J=7.5 Hz).

MS (ES) m/e: 435.2 (M−1), 454.2 (M+18).

Example 31

Preparation of 5-{1-ethyl-1-[4-(2-hydroxy-3,3-dimethyl-butoxy)-3-methyl-phenyl]-propyl}-benzofuran-2-carboxylic acid

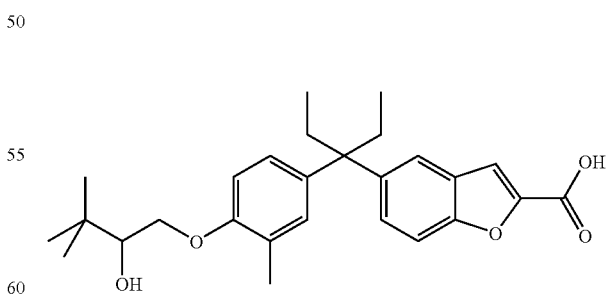

5-{1-[4-(3,3-Dimethyl-2-oxo-butoxy)-3-methyl-phenyl]-1-ethyl-propyl}-benzofuran-2-carboxylic acid (0.22 g, 0.504 mmol) is reduced with NaBH₄ (57 mg, 1.51 mmol) analogous to Example 3 to give the title product (210 mg, 95%).

MS (ES) m/e: 437.3 (M−1), 456.3 (M+18).

Example 32

Preparation of [(5-{1-[4-(3,3-dimethyl-2-oxo-butoxy)-3-methyl-phenyl]-1-ethyl-propyl}-benzofuran-2-carbonyl)-amino]-acetic acid

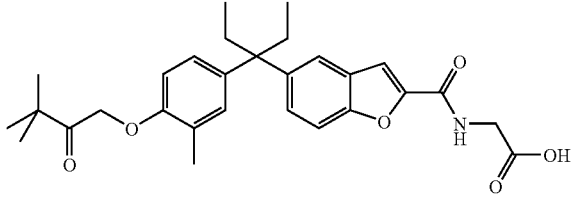

5-{1-[4-(3,3-Dimethyl-2-oxo-butoxy)-3-methyl-phenyl]-1-ethyl-propyl}-benzofuran-2-carboxylic acid (730 mg, 1.672 mmol) in $CH_2Cl_2$ (30 mL) and DMAP (612 mg, 5.02 mmol), EDC (481 mg, 2.51 mmol), and glycine methyl ester hydrochloride (313 mg, 2.51 mmol) are reacted and hydrolyzed analogous to Example 7 to yield title compound (401 mg, 47%).

MS (ES) m/e: 494.1 (M+1), 492.2 (M−1)

Example 33

Preparation of [(5-{1-ethyl-1-[4-(2-hydroxy-3,3-dimethyl-butoxy)-3-methyl-phenyl]-propyl}-benzofuran-2-carbonyl)-amino]-acetic acid

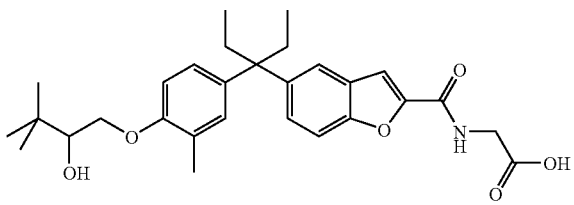

[(5-{1-[4-(3,3-Dimethyl-2-oxo-butoxy)-3-methyl-phenyl]-1-ethyl-propyl}-benzofuran-2-carbonyl)-amino]-acetic acid (52 mg, 0.105 mmol) is reduced with $NaBH_4$ (12 mg, 0.316 mmol) analogous to Example 3 to give the title product (45 mg, 86%).

MS (ES) m/e: 496.2 (M+1), 494.3 (M−1)

Example 34

Preparation of 5-{1-[4-(3,3-Dimethyl-2-oxo-butoxy)-3-methyl-phenyl]-1-ethyl-propyl}-3-methyl-benzofuran-2-carboxylic acid

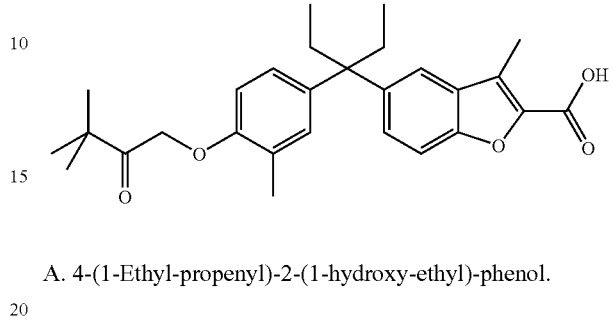

A. 4-(1-Ethyl-propenyl)-2-(1-hydroxy-ethyl)-phenol.

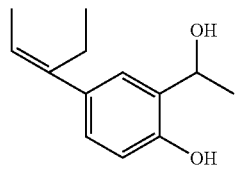

To a stirred solution of 5-(1-ethyl-propenyl)-2-hydroxy-benzaldehyde (6.80 g, 35.7 mmol) in THF (120 mL) at −78° C. is added methylmagnesium bromide (36.0 mL, 3.0 M). The reaction is allowed to warm to RT and stirred for 10 min before quenched with water and HCl (1.0 M) till pH∼3. The THF is evaporated and the mixture is extracted with EtOAc (2×100 mL). The organic layer is dried over $Na_2SO_4$, concentrated and purified on column chromatography (15% EtOAc/Hex) to afford the title compound (7.05 g, 95%).

H-NMR (ppm, $CDCl_3$), (major isomer) δ: 7.83 (1H, br s), 7.15 (1H, dd, J=2.2, 8.3 Hz), 6.96 (1H, d, J=2.2 Hz), 6.82 (1H, d, J=8.3 Hz), 5.62 (1H, q, J=7.0 Hz), 5.07 (1H, q, J=6.6 Hz), 2.47 (2H, q, J=7.5 Hz), 1.78 (3H, d, J=7.0 Hz), 1.62 (3H, d, J=6.6 Hz), 0.98 (3H, t, J=7.5 Hz).

MS (ES) m/e: 205.2 (M−1)

B. 1-[2-Acetyl-4-(1-ethyl-propenyl)-phenoxy]-3,3-dimethyl-butan-2-one.

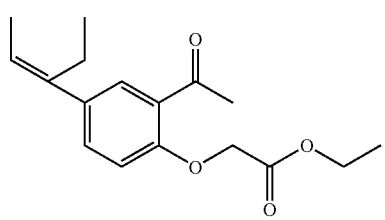

To a solution of 4-(1-ethyl-propenyl)-2-(1-hydroxy-ethyl)-phenol (7.05 g, 34.2 mmol) and ethyl bromoacetate (7.14 g, 42.8 mmol) in acetone (100 mL) is added $K_2CO_3$ (9.43 g, 68.3 mmol). The suspension is stirred for 16 h at RT, and the solid is filtered. The filtrate is concentrated and purified on column chromatography (15-20% EtOAc/Hex) to afford the intermediate compound (9.20 g).

The intermediate (9.20 g, 31.5 mmol) is dissolved in $CH_2Cl_2$ (200 mL) and treated with Dess-Martin reagent (1.4 g, 31.5 mmol). The mixture is stirred at RT for one hour and quenched with aqueous Na₂S₂O₃ (100 mL). The organic layer is concentrated and purified on column chromatography (10-15% EtOAc/Hex) to afford the title compound (4.80 g, 52%).

H-NMR (ppm, CDCl₃), (major isomer) δ: 7.73 (1H, d, J=2.6 Hz), 7.40 (1H, dd, J=2.6, 8.8 Hz), 6.77 (1H, d, J=8.8 Hz), 5.68 (1H, q, J=7.0 Hz), 4.71 (2H, s), 4.29 (2H, q, J=7.0 Hz), 2.71 (3H, s), 2.48 (2H, q, J=7.5 Hz), 1.78 (3H, d, J=6.6 Hz), 1.62 (3H, d, J=6.6 Hz), 1.31 (3H, t, J=7.0 Hz), 0.98 (3H, t, J=7.5 Hz).

C. 5-(1-Ethyl-propenyl)-3-methyl-benzofuran-2-carboxylic acid ethyl ester (PF1-A03671-106)

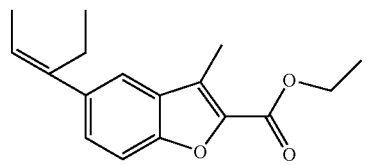

A solution of 1-[2-acetyl-4-(1-ethyl-propenyl)-phenoxy]-3,3-dimethyl-butan-2-one (4.80 g, 16.5 mmol) in DMF (40 mL) is treated with DBU (2.51 g, 16.5 mmol) and the solution is heated to 140° C. for 2 h. The reaction mixture is cooled down and poured into water (400 mL) and extracted with EtOAc (2×100 mL). The organic layer is dried over Na₂SO₄, concentrated, purified on column chromatography (5% EtOAc/Hex) to give the title compound as an oil (3.20 g, 71%)

H-NMR (ppm, CDCl₃), (major isomer) δ: 7.52 (1H, br s), 7.44 (1H, d, J=0.9 Hz), 7.43 (1H, d, J=1.8 Hz), 5.70 (1H, q, J=7.0 Hz), 4.29 (2H, q, J=7.0 Hz), 2.60 (3H, s), 2.58 (2H, q, J=7.5 Hz), 1.84 (3H, d, J=7.0 Hz), 1.62 (3H, d, J=6.6 Hz), 1.45 (3H, t, J=7.0 Hz), 1.00 (3H, t, J=7.5 Hz).

D. 5-[1-Ethyl-1-(4-hydroxy-3-methyl-phenyl)-propyl]-3-methyl-benzofuran-2-carboxylic acid ethyl ester.

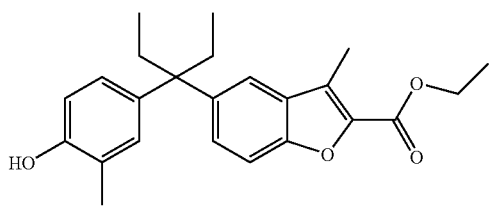

5-(1-Ethyl-propenyl)-3-methyl-benzofuran-2-carboxylic acid ethyl ester (3.20 g, 11.7 mmol) and o-cresol (1.91 g, 17.6 mmol) and BF₃-Et₂O (1.66 g, 11.7 mmol) are reacted analogous to Example 1D to give the title compound (4.04 g, 91%).

H-NMR (ppm, CDCl₃) δ: 7.53 (1H, d, J=1.8 Hz), 7.34 (1H, d, J=8.8 Hz), 7.13 (1H, dd, J=1.8, 8.8 Hz), 6.88 (2H, m), 6.67 (1H, d, J=8.0 Hz), 4.44 (2H, q, J=7.0 Hz), 2.60 (3H, s), 2.20 (3H, s), 2.14 (4H, q, J=7.5 Hz), 1.42 (3H, t, J=7.5 Hz), 0.61 (6H, t, J=7.5 Hz).

MS (ES) m/e: 381.2 (M+1), 379.2 (M−1)

E. 5-{1-[4-(3,3-Dimethyl-2-oxo-butoxy)-3-methyl-phenyl]-1-ethyl-propyl}-3-methyl-benzofuran-2-carboxylic acid ethyl ester.

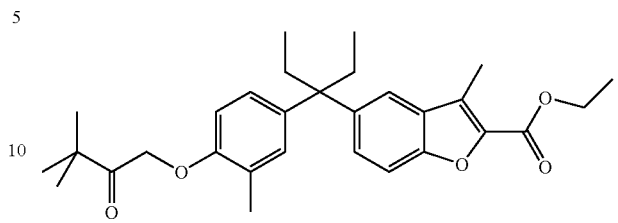

5-[1-Ethyl-1-(4-hydroxy-3-methyl-phenyl)-propyl]-3-methyl-benzofuran-2-carboxylic acid ethyl ester (4.04 g, 10.6 mmol) and 1-bromopinacolone (2.66 g, 14.9 mmol) and K₂CO₃ (2.91 g, 21.2 mmol) are reacted analogous to Example 1E to give the title compound as a pale yellow oil (4.77 g, 94%).

H-NMR (ppm, CDCl₃) δ: 7.52 (1H, d, J=1.8 Hz), 7.36 (1H, d, J=8.8 Hz), 7.12 (1H, dd, J=1.8, 8.8 Hz), 6.90 (2H, m), 6.51 (1H, d, J=9.2 Hz), 4.84 (2H, s), 4.45 (2H, q, J=7.0 Hz), 2.60 (3H, s), 2.23 (3H, s), 2.13 (4H, q, J=7.5 Hz), 1.44 (3H, t, J=7.5 Hz), 1.26 (9H, s), 0.61 (6H, t, J=7.5 Hz).

MS (ES) m/e: 479.2 (M+1)

F. 5-{1-[4-(3,3-Dimethyl-2-oxo-butoxy)-3-methyl-phenyl]-1-ethyl-propyl}-3-methyl-benzofuran-2-carboxylic acid.

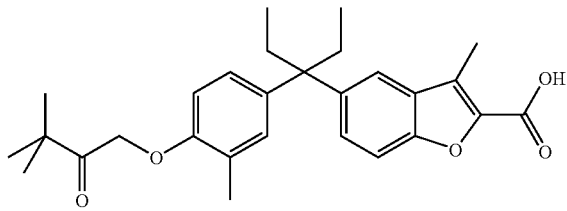

5-{1-[4-(3,3-Dimethyl-2-oxo-butoxy)-3-methyl-phenyl]-1-ethyl-propyl}-3-methyl-benzofuran-2-carboxylic acid ethyl ester (4.77 g, 9.97 mmol) is hydrolyzed analogous to Example 2 to give the title compound (4.40 g, 98%).

H-NMR (ppm, CDCl₃) δ: 7.55 (1H, d, J=1.8 Hz), 7.38 (1H, d, J=8.8 Hz), 7.16 (1H, dd, J=1.8, 8.8 Hz), 6.90 (2H, m), 6.51 (H, d, J=9.2 Hz), 4.84 (2H, s), 2.64 (3H, s), 2.23 (3H, s), 2.12 (4H, q, J=7.0 Hz), 1.26 (9H, s), 0.63 (6H, t, J=7.5 Hz).

MS (ES) m/e: 449.2 (M−1)

Example 35

Preparation of 5-{1-Ethyl-1-[4-(2-hydroxy-3,3-dimethyl-butoxy)-3-methyl-phenyl]-propyl}-3-methyl-benzofuran-2-carboxylic acid

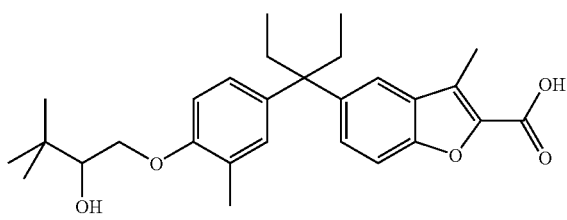

5-{1-[4-(3,3-Dimethyl-2-oxo-butoxy)-3-methyl-phenyl]-1-ethyl-propyl}-3-methyl-benzofuran-2-carboxylic acid (170 mg g, 0.378 mmol) is reduced with NaBH$_4$ (29 mg, 0.756 mmol) analogous to Example 3 to give the title product (120 mg, 71%).

H-NMR (ppm, CDCl$_3$) δ: 7.56 (1H, s), 7.35 (1H, d, J=8.8 Hz), 7.13 (1H, d, J=9.2 Hz), 6.97 (1H, dd, J=1.8, 8.4 Hz), 6.89 (1H, s), 6.70 (1H, d, J=8.4 Hz), 4.10 (1H, dd, J=2.6, 7.0 Hz), 3.88 (1H, t, J=8.8 Hz), 3.71 (1H, dd, J=2.2, 8.4 Hz), 2.64 (3H, s), 2.17 (3H, s), 2.14 (4H, q, J=7.5 Hz), 1.02 (9H, s), 0.63 (6H, t, J=7.0 Hz).

MS (ES) m/e: 451.2 (M−1)

Example 36

Preparation of 5-{1-[4-(3,3-dimethyl-2-oxo-butoxy)-3-methyl-phenyl]-1-ethyl-propyl}-3-methyl-benzofuran-2-carboxylic acid dimethylamide

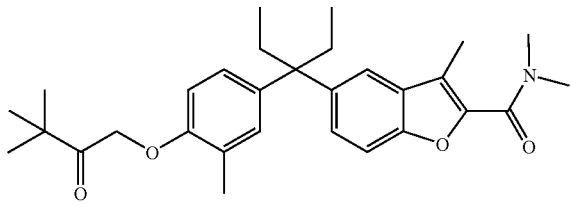

5-{1-[4-(3,3-Dimethyl-2-oxo-butoxy)-3-methyl-phenyl]-1-ethyl-propyl}-3-methyl-benzofuran-2-carboxylic acid (520 mg, 1.154 mmol), DMAP (422 mg, 3.46 mmol), EDC (332 mg, 1.73 mmol), and dimethyl amine hydrochloride (141 mg, 1.73 mmol) are reacted analogous to Example 1, step I to give the title product (205 mg, 37%).

H-NMR (ppm, CDCl$_3$) δ: 7.47 (1H, d, J=1.3 Hz), 7.46 (1H, d, J=8.8 Hz), 7.05 (1H, dd, J=1.8, 8.8 Hz), 6.90 (2H, m), 6.50 (1H, d, J=9.2 Hz), 4.84 (2H, s), 3.18 (6H, br s), 2.46 (3H, s), 2.24 (3H, s), 2.12 (4H, q, J=7.0 Hz), 1.26 (9H, s), 0.63 (6H, t, J=7.5 Hz).

MS (ES) m/e: 478.3 (M+1)

Example 37

Preparation of 5-{1-ethyl-1-[4-(2-hydroxy-3,3-dimethyl-butoxy)-3-methyl-phenyl]-propyl}-3-methyl-benzofuran-2-carboxylic acid dimethylamide

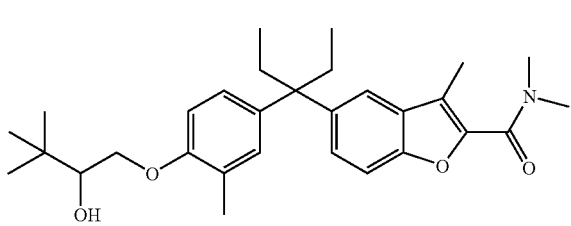

5-{1-[4-(3,3-Dimethyl-2-oxo-butoxy)-3-methyl-phenyl]-1-ethyl-propyl}-3-methyl-benzofuran-2-carboxylic acid dimethylamide (109 mg, 0.228) is reduced with NaBH$_4$ (17 mg, 0.457 mmol) analogous to Example 3 to give the title product (109 mg, 100%).

H-NMR (ppm, CDCl$_3$) δ: 7.48 (1H, d, J=1.8 Hz), 7.27 (1H, d, J=8.0 Hz), 7.05 (1H, dd, J=1.8, 8.8 Hz), 6.97 (1H, dd, J=1.8, 8.4 Hz), 6.95 (1H, d, J=1.8 Hz), 6.71 (1H, d, J=8.4 Hz), 4.08 (1H, dd, J=2.6, 7.0 Hz), 3.86 (1H, t, J=8.8 Hz), 3.71 (1H, dd, J=2.6, 8.8 Hz), 3.18 (6H, br s), 2.46 (3H, s), 2.17 (3H, s), 2.14 (4H, q, J=7.0 Hz), 1.02 (9H, s), 0.63 (6H, t, J=7.5 Hz).

MS (ES) m/e: 480.3 (M+1)

Example 38

Preparation of [(5-{1-[4-(3,3-dimethyl-2-oxo-butoxy)-3-methyl-phenyl]-1-ethyl-propyl}-3-methyl-benzofuran-2-carbonyl)-amino]-acetic acid

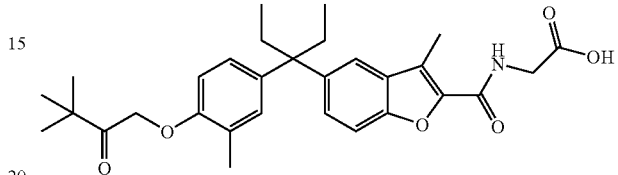

5-{1-[4-(3,3-Dimethyl-2-oxo-butoxy)-3-methyl-phenyl]-1-ethyl-propyl}-3-methyl-benzofuran-2-carboxylic acid (520 mg, 1.154 mmol) in CH$_2$Cl$_2$ (10 mL) and DMAP (422 mg, 3.46 mmol), EDC (332 mg, 1.73 mmol), and glycine methyl ester hydrochloride (217 mg, 1.73 mmol) are reacted and hydrolyzed analogous to Example 7 to yield title compound (390 mg, 100%).

H-NMR (ppm, CDCl$_3$) δ: 7.51 (1H, d, J=1.8 Hz), 7.26 (1H, d, J=8.8 Hz), 7.13 (1H, d, J=5.3 Hz), 7.09 (1H, dd, J=1.8, 8.8 Hz), 6.90 (2H, m), 6.50 (1H, d, J=8.8 Hz), 4.83 (2H, s), 4.29 (1H, d, J=5.3 Hz), 2.61 (3H, s), 2.22 (3H, s), 2.10 (4H, q, J=7.0 Hz), 1.25 (9H, s), 0.61 (6H, t, J=7.5 Hz).

MS (ES) m/e: 508.3 (M+1), 506.3 (M−1)

Example 39

Preparation of [(5-{1-ethyl-1-[4-(2-hydroxy-3,3-dimethyl-butoxy)-3-methyl-phenyl]-propyl}-3-methyl-benzofuran-2-carbonyl)-amino]-acetic acid

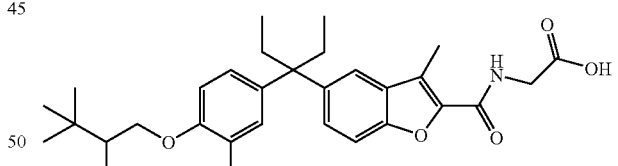

[(5-{1-[4-(3,3-Dimethyl-2-oxo-butoxy)-3-methyl-phenyl]-1-ethyl-propyl}-3-methyl-benzofuran-2-carbonyl)-amino]-acetic acid (190 mg, 0.375 mmol) is reduced with NaBH$_4$ (28 mg, 0.750 mmol) analogous to Example 3 to give the title product (190 mg, 100%).

H-NMR (ppm, CDCl$_3$) δ: 7.51 (1H, d, J=1.3 Hz), 7.26 (1H, d, J=8.2 Hz), 7.13 (1H, d, J=5.3 Hz), 7.09 (1H, dd, J=1.8, 8.8 Hz), 6.96 (1H, dd, J=2.3, 8.4 Hz), 6.87 (1H, d, J=2.2 Hz), 6.70 (1H, d, J=8.4 Hz), 4.30 (2H, d, J=5.3 Hz), 4.10 (1H, dd, J=2.6, 9.2 Hz), 3.86 (1H, t, J=8.6 Hz), 3.72 (1H, dd, J=2.2, 8.4 Hz), 2.61 (3H, s), 2.16 (3H, s), 2.12 (4H, q, J=7.0 Hz), 1.02 (9H, s), 0.61 (6H, t, J=7.5 Hz).

MS (ES) m/e: 510.3 (M+1), 508.3 (M−1).

Example 40

Preparation of methanesulfonic acid 2-{1-[4-(3,3-dimethyl-2-oxo-butoxy)-3-methyl-phenyl]-1-ethyl-propyl}-benzofuran-6-yl ester

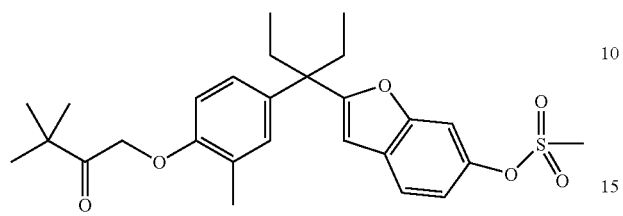

A solution of 1-{4-[1-ethyl-1-(6-hydroxy-benzofuran-2-yl)-propyl]-2-methyl-phenoxy}-3,3-dimethyl-butan-2-one (116 mg, 0.407 mmol) and Et$_3$N (0.20 mL) in CH$_2$Cl$_2$ (5.0 mL) at 0° C. is added methanesulfonic chloride (70 mg, 0.610 mmol). The resulting mixture is stirred for 30 min and quenched with MeOH (1.0 mL). The mixture is purified on column chromatography (25% EtOAc/Hex) to afford the title compound (185 mg, 93%).

H-NMR (ppm, CDCl$_3$) δ: 7.53 (1H, d, J=8.8 Hz), 7.33 (1H, d, J=2.4 Hz), 7.15 (1H, dd, J=2.4, 8.8 Hz), 7.03 (1H, d, J=2.0 Hz), 6.97 (1H, dd, J=2.4, 8.4 Hz), 6.65 (1H, s), 6.55 (1H, d, J=8.8 Hz), 4.87 (2H, s), 3.17 (3H, s), 2.30 (3H, s), 2.20 (2H, q, J=7.5 Hz), 2.12 (2H, q, J=7.5 Hz), 1.29 (9H, s), 0.75 (6H, t, J=7.5 Hz).

MS (ES) m/e: 504.2 (M+18).

Example 41

Preparation of methanesulfonic acid 2-{1-ethyl-1-[4-(2-hydroxy-3,3-dimethyl-butoxy)-3-methyl-phenyl]-propyl}-benzofuran-6-yl ester

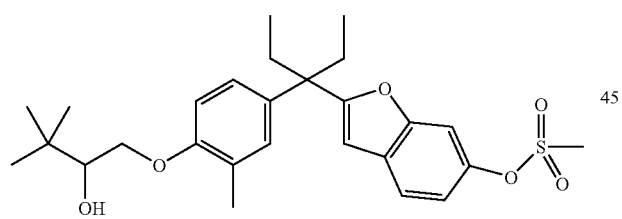

A solution of methanesulfonic acid 2-{1-[4-(3,3-dimethyl-2-oxo-butoxy)-3-methyl-phenyl]-1-ethyl-propyl}-benzofuran-6-yl ester (34 mg, 0.069) in THF (5.0 mL) at 0° C. is treated with NaBH$_4$ (13 mg, 0.349 mmol). The resulting mixture is stirred for 30 min at RT and quenched with HCl (1.0 N, 2.0 mL) and extracted with EtOAc (2×10 mL). The organic layer is dried over Na$_2$SO$_4$, concentrated to afford the title compound (30 mg, 88%).

H-NMR (ppm, CDCl$_3$) δ: 7.53 (1H, d, J=8.8 Hz), 7.33 (1H, d, J=1.6 Hz), 7.15 (1H, dd, J=2.4, 8.4 Hz), 7.05 (1H, d, J=2.4 Hz), 7.02 (1H, br s), 6.77 (1H, d, J=8.4 Hz), 6.65 (1H, s), 4.12 (1H, dd, J=2.8, 9.2 Hz), 3.90 (1H, d, J=8.8 Hz), 3.73 (1H, dd, J=2.8, 8.8 Hz), 3.17 (3H, s), 2.23 (3H, s), 2.23 (2H, q, J=7.5 Hz), 2.12 (2H, q, J=7.5 Hz), 1.05 (9H, s), 0.76 (6H, t, J=7.5 Hz).

MS (ES) m/e: 506.2 (M+18).

Example 42

2-[(2-{1-Ethyl-1-[4-(2-hydroxy-3,3-dimethyl-butoxy)-3-methyl-phenyl]-propyl}-benzofuran-5-carbonyl)-amino]-2-methyl-propionic acid

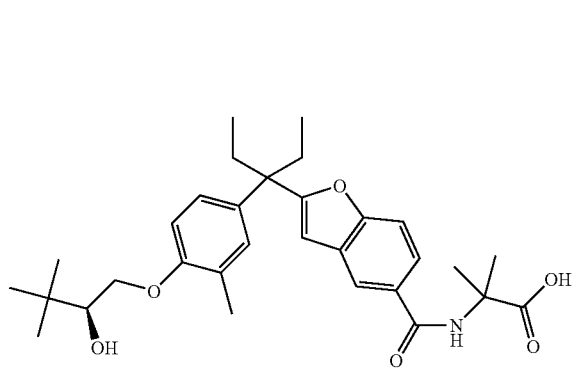

2-[(2-{1-[4-(3,3-Dimethyl-2-oxo-butoxy)-3-methyl-phenyl]-1-ethyl-propyl}-benzofuran-5-carbonyl)-amino]-2-methyl-propionic acid (Example 10) (47 mg, 0.090 mmol) in THF (2.0 mL) are reacted with NaBH$_4$ (7 mg, 0.18 mmol) analogous to Example 8 to yield title compound (45 mg, 96%). MS (ES) m/e: 522.3 (M−1), 524.3 (M+1)

Example 43

[(2-{1-Ethyl-1-[4-(2-hydroxy-3,3-dimethyl-butoxy)-3-methyl-phenyl]-propyl}-benzofuran-5-carbonyl)-methyl-amino]-acetic acid

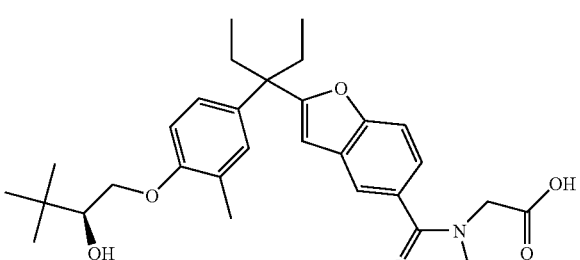

[(2-{1-[4-(3,3-Dimethyl-2-oxo-butoxy)-3-methyl-phenyl]-1-ethyl-propyl}-benzofuran-5-carbonyl)-methyl-amino]-acetic acid (Example 9) (47 mg, 0.093 mmol) in THF (2.0 mL) are reacted with NaBH$_4$ (7 mg, 0.18 mmol) analogous to Example 8 to yield title compound (35 mg, 74%). MS (ES) m/e: 508.3 (M−1), 510.3 (M+1)

Example 44

[(5-{1-Ethyl-1-[4-(2-hydroxy-3,3-dimethyl-butoxy)-3-methyl-phenyl]-propyl}-benzofuran-2-carbonyl)-methyl-amino]-acetic acid

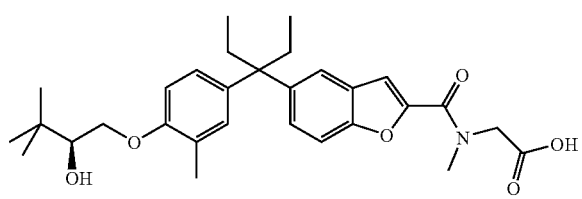

[(5-{1-[4-(3,3-Dimethyl-2-oxo-butoxy)-3-methyl-phenyl]-1-ethyl-propyl}-benzofuran-2-carbonyl)-methyl-amino]-acetic acid (130 mg, 0.256 mmol) in THF (2.0 mL) are reacted with NaBH$_4$ (19 mg, 0.513 mmol) analogous to Example 8 to yield title compound (120 mg, 92%). MS (ES) m/e: 508.3 (M−1), 510.3 (M+1)

Example 45

[(5-{1-Ethyl-1-[4-(2-hydroxy-3,3-dimethyl-butoxy)-3-methyl-phenyl]-propyl}-7-methyl-benzofuran-2-carbonyl)-methyl-amino]-acetic acid

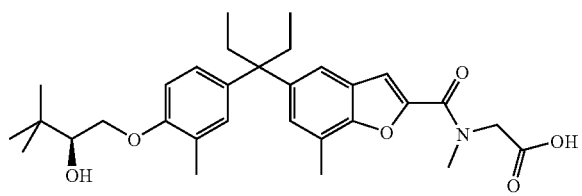

[(5-{1-[4-(3,3-Dimethyl-2-oxo-butoxy)-3-methyl-phenyl]-1-ethyl-propyl}-7-methyl-benzofuran-2-carbonyl)-methyl-amino]-acetic acid (310 mg, 0.594 mmol) in THF (2.0 mL) are reacted with NaBH$_4$ (45 mg, 1.19 mmol) analogous to Example 8 to yield title compound (300 mg, 97%). MS (ES) m/e: 522.3 (M−1), 524.3 (M+1)

Example 46

[(5-{1-[4-(3,3-Dimethyl-2-oxo-butoxy)-3-methyl-phenyl]-1-ethyl-propyl}-benzofuran-2-carbonyl)-methyl-amino]-acetic acid

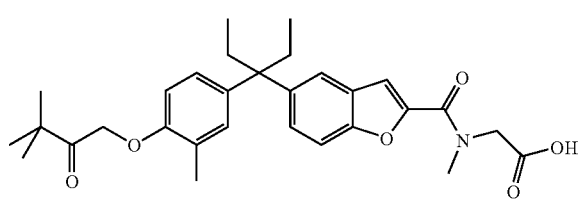

5-{1-[4-(3,3-Dimethyl-2-oxo-butoxy)-3-methyl-phenyl]-1-ethyl-propyl}-benzofuran-2-carboxylic acid (256 mg, 0.586 mmol) in CH$_2$Cl$_2$ (5 mL) and DMAP (215 mg, 1.76 mmol) and EDC (169 mg, 0.879 mmol) are reacted with sarcosine ethyl ester hydrochloride (135 mg, 0.879 mmol) and the intermediate ester is hydrolyzed analogous to Example 7 to yield title compound (260 mg, 88%). MS (ES) m/e: 506.2 (M−1), 508.2 (M+1)

Example 47

[(5-{1-[4-(3,3-Dimethyl-2-oxo-butoxy)-3-methyl-phenyl]-1-ethyl-propyl}-7-methyl-benzofuran-2-carbonyl)-methyl-amino]-acetic acid

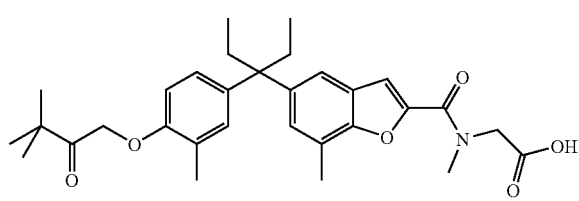

5-{1-[4-(3,3-Dimethyl-2-oxo-butoxy)-3-methyl-phenyl]-1-ethyl-propyl}-7-methyl-benzofuran-2-carboxylic acid (720 mg, 1.60 mmol) in CH$_2$Cl$_2$ (10 mL) and DMAP (586 mg, 4.80 mmol) and EDC (460 mg, 2.40 mmol) are reacted with sarcosine ethyl ester hydrochloride (368 mg, 2.40 mmol) and the intermediate ester is hydrolyzed analogous to Example 7 to yield title compound (610 mg, 73%). MS (ES) m/e: 520.3 (M−1), 522.3 (M+1)

Example 48

5-{1-ethyl-1-[4-(2-hydroxy-3,3-dimethyl-butoxy)-3-methyl-phenyl]-propyl}-benzofuran-2-carboxylic acid

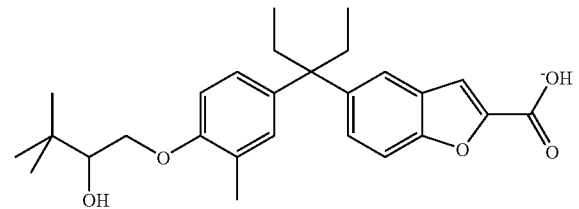

Step A. Preparation of racemic 5-{1-ethyl-1-[4-(2-hydroxy-3,3-dimethyl-butoxy)-3-methyl-phenyl]-propyl}-benzofuran-2-carboxylic acid ethyl ester.

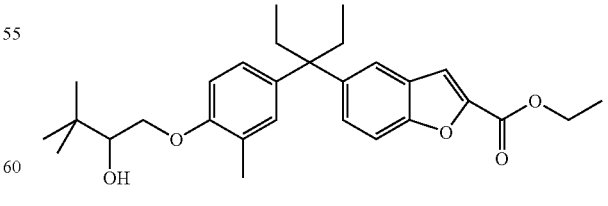

To a solution of 5-{1-[4-(3,3-dimethyl-2-oxo-butoxy)-3-methyl-phenyl]-1-ethyl-propyl}-benzofuran-2-carboxylic acid ethyl ester (6.80 g, 14.6 mmol) in THF (100 mL) at 0° C. is added NaBH$_4$ (0.556 g, 14.6 mmol). The mixture is stirred at room temperature for 30 minutes before quenching with 1

N HCl (30 mL). The mixture is concentrated and extracted with EtOAc (2×100 mL). The organic layer is dried over Na$_2$SO$_4$ and concentrated to give the racemic compound as an oil (6.50 g).

H-NMR (ppm, CDCl$_3$) δ: 7.61 (1H, s), 7.52 (1H, s), 7.43 (1H, d, J=8.8 Hz), 7.18 (1H, dd, J=1.6 Hz, 9.2 Hz), 7.00 (1H, dd, J=2.0 Hz, 8.8 Hz), 6.92 (1H, s), 6.75 (1H, d, J=8.0 Hz), 4.48 (2H, q, J=7.0 Hz), 4.14 (1H, dd, J=2.4, 8.8 Hz), 3.89 (1H, t, J=8.8 Hz), 3.72 (1H, dd, J=2.4, 8.8 Hz), 2.20 (3H, s), 2.18 (4H, q, J=7.0 Hz), 1.46 (3H, t, J=7.0 Hz), 1.05 (9H, s), 0.66 (6H, t, J=7.5 Hz).

Step B. Separation of enantiomers of 5-{1-ethyl-1-[4-(2-hydroxy-3,3-dimethyl-butoxy) -3-methyl-phenyl]-propyl}-benzofuran-2-carboxylic acid ethyl ester

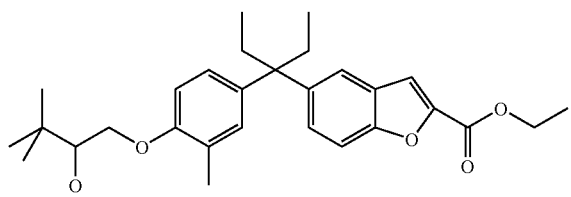

(enantiomer 1)
(enantiomer 2)

A mixture of racemic 5-{1-ethyl-1-[4-(2-hydroxy-3,3-dimethyl-butoxy)-3-methyl-phenyl]-propyl}-benzofuran-2-carboxylic acid ethyl ester (5.80 g) is chromatographed with Chiralpak AD column to give enantiomer 1, Example 48A (2.39 g, 41%) and enantiomer 2, Example 48B (2.21 g, 38%).

Enantiomer 1, Example 48A

HPLC: ChiralPak AD (4.6×150); 40% heptane/45% IPA/15% MeOH; 0.6 mL/min (flow rate); uv: 310 nm.

Rt=8.8 m.

NMR eq to Example 48 Step A.

Enantiomer 2, Example 48B

HPLC: ChiralPak AD (4.6×150); 40% heptane/45% IPA/15% MeOH; 0.6 mL/min (flow rate); uv: 310 nm.

Rt=18.5 m.

NMR eq to Example 48 Step A.

For enantiomer 1, the solution of enantiomer 1 (2.39 g, 5.12 mmol) in THF (5.0 mL) and MeOH (5.0 mL) is treated with NaOH (2.0 M, 10.0 mL). The mixture is stirred at room temperature for 16 hours before quenching with HCl (1 N, 22 mL). Remove the THF and MeOH under vacuum and the residue is extracted with EtOAc (2×50 mL). The combined is dried over Na$_2$SO$_4$, concentrated, to give the corresponding enantiomeric pure acid (2.20 g). NMR and MS are the same as those in Example 31.

Same procedure is applied for enantiomer 2 to obtain 1.91 g of the corresponding acid. NMR and MS are the same as those in Example 31.

Example 49

Preparation of methanesulfonic acid 2-{1-ethyl-1-[4-(2-hydroxy-3,3-dimethyl-butoxy)-3-methyl-phenyl]-propyl}-benzofuran-5-yl ester

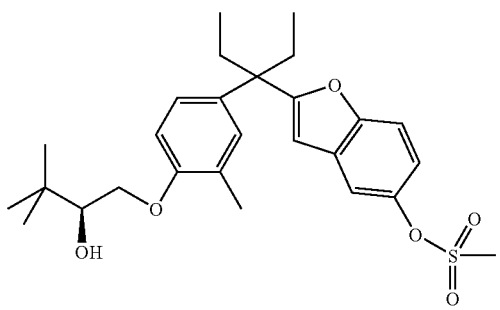

Step A: 5-Benzyloxy-benzofuran-2-carboxylic acid ethyl ester

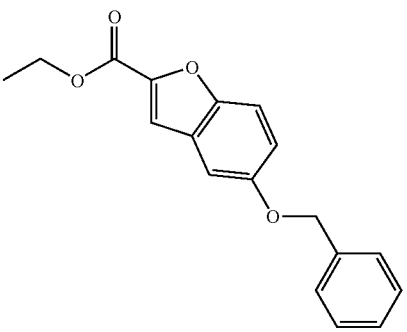

5-Benzyloxy-2-hydroxy-benzaldehyde ((21.5 g, 94.2 mmol) and ethyl bromoacetate (17.3 g, 103.6 mmol) and K$_2$CO$_3$ (19.5 g, 141.3 mmol) and DBU (14.3 g, 94.2 mmol) are reacted analogous to Example 18-A to give the title compound (23.5 g, 84%).

Step B. 3-(5-Benzyloxy-benzofuran-2-yl)-pentan-3-ol

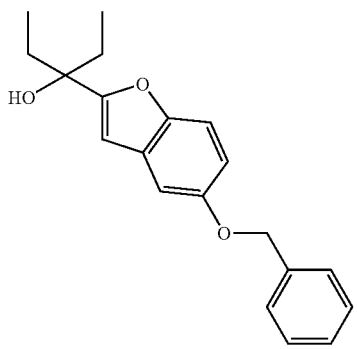

5-Benzyloxy-benzofuran-2-carboxylic acid ethyl ester (6.02 g, 20.3 mmol) and EtMgBr (20.3 mL, 3.0 M) in THF (100 mL) are reacted analogous to Example 18-B to give the title compound (6.10 g, 97%).

Step C: 4-[1-(5-Benzyloxy-benzofuran-2-yl)-1-ethyl-propyl]-2-methyl-phenol

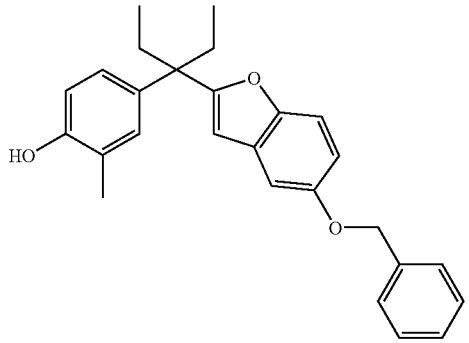

3-(5-Benzyloxy-benzofuran-2-yl)-pentan-3-ol (6.10 g, 19.7 mmol) and o-cresol (2.55 g, 23.6 mmol) and BF$_3$—OEt$_2$ (1.39 g, 9.83 mmol) in CH$_2$Cl$_2$ are reacted analogous to Example 18-C to give the title compound (4.05 g, 51%).

Step D. 1-{4-[1-(5-Benzyloxy-benzofuran-2-yl)-1-ethyl-propyl]-2-methyl-phenoxy}-3,3-dimethyl-butan-2-one

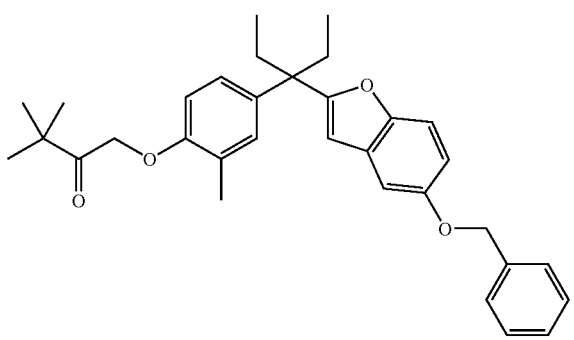

4-[1-(5-Benzyloxy-benzofuran-2-yl)-1-ethyl-propyl]-2-methyl-phenol (4.05 g, 10.1 mmol) and 1-bromopinacolone (2.17 g, 12.1 mmol) and K$_2$CO$_3$ (2.79 g, 20.2 mmol) in acetone (50 mL) are reacted analogous to Example 18-E to give the title compound (3.20 g, 63%).

Step E. 1-{4-[1-Ethyl-1-(5-hydroxy-benzofuran-2-yl)-propyl]-2-methyl-phenoxy}-3,3-dimethyl-butan-2-one

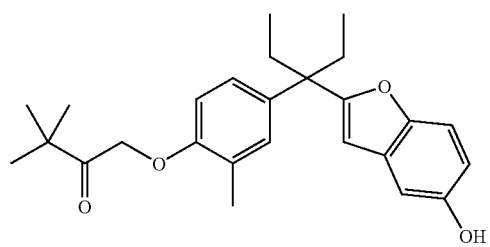

1-{4-[1-(5-Benzyloxy-benzofuran-2-yl)-1-ethyl-propyl]-2-methyl-phenoxy}-3,3-dimethyl-butan-2-one (3.20 g, 6.42 mmol) and Pd—C (0.20 g) are reacted under hydrogen analogous to Example 18-F to give the title compound (2.50 g, 95%).

Step F. Methanesulfonic acid 2-{1-[4-(3,3-dimethyl-2-oxo-butoxy)-3-methyl-phenyl]-1-ethyl-propyl}-benzofuran-5-yl ester

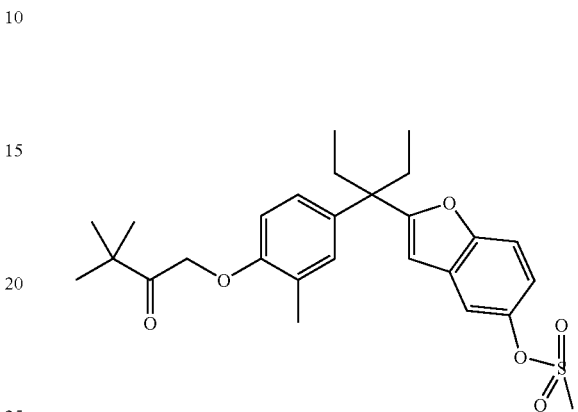

A solution of 1-{4-[1-ethyl-1-(5-hydroxy-benzofuran-2-yl)-propyl]-2-methyl-phenoxy}-3,3-dimethyl-butan-2-one (236 mg, 0.579 mmol) in CH$_2$Cl$_2$ (10 mL) was treated with methanesulfonic chloride (99 mg, 0.868 mmol) and Et$_3$N (0.40 mL). The mixture was stirred at 0° C. for 30 min, and the reaction is quenched with MeOH (1.0 mL). The mixture is purified with EtOAc/Hexanes (25%) to obtain the title compound (260 mg, 92%). MS (ES) m/e: 504.2 (M+18).

Step G. Methanesulfonic acid 2-{1-ethyl-1-[4-(2-hydroxy-3,3-dimethyl-butoxy)-3-methyl-phenyl]-propyl}-benzofuran-5-yl ester

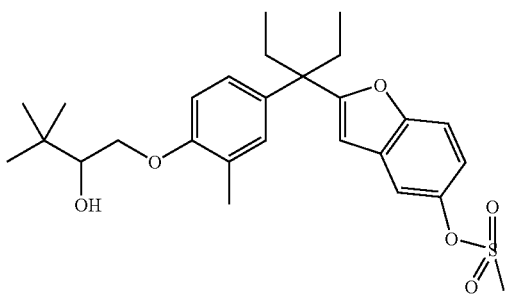

Methanesulfonic acid 2-{1-[4-(3,3-dimethyl-2-oxo-butoxy)-3-methyl-phenyl]-1-ethyl-propyl}-benzofuran-5-yl ester (100 mg, 0.206 mmol) and NaBH$_4$ (8.0 mg, 0.206 mmol) in THF (5.0 mL) are reacted analogous to Example 19 to give the title compound (100 mg, 100%). MS (ES) m/e: 506.2 (M+18).

Example 50

Preparation of 1-{4-[1-ethyl-1-(5-methanesulfonyl-methyl-benzofuran-2-yl)-propyl]-2-methyl-phenoxy}-3,3-dimethyl-butan-2-one

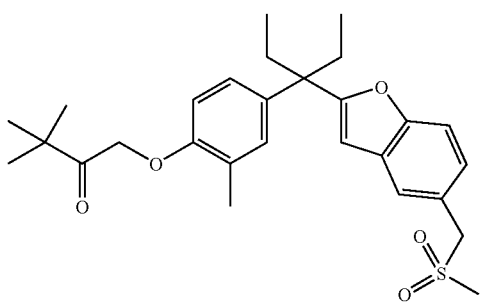

Step A: 4-[1-Ethyl-1-(5-hydroxymethyl-benzofuran-2-yl)-propyl]-2-methyl-phenol

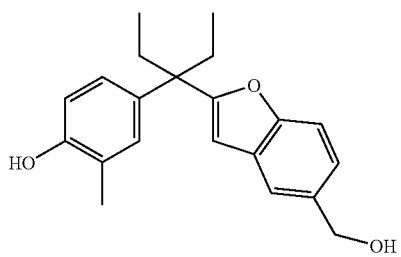

A solution of 2-[1-ethyl-1-(4-hydroxy-3-methyl-phenyl)-propyl]-benzofuran-5-carboxylic acid methyl ester (710 mg, 2.02 mmol) in THF (40 mL) at 0° C. are added with LAH (153 mg, 4.03 mmol) and the mixture are stirred for 30 minutes. The reaction is quenched with water (0.5 mL), then NaOH (5N, 3.0 mL) and stirred for 10 minutes. The organic layer is concentrated and loaded on column and purified with EtOAc/Hexanes (50%) to obtain the title compound (653 mg, 100%).

Step B. 1-{4-[1-Ethyl-1-(5-hydroxymethyl-benzofuran-2-yl)-propyl]-2-methyl-phenoxy}-3,3-dimethyl-butan-2-one

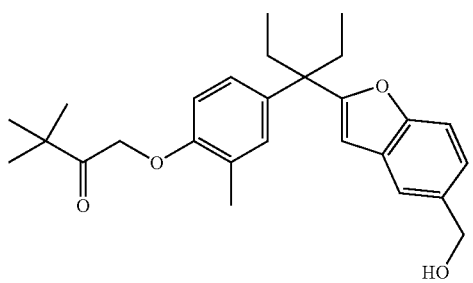

4-[1-Ethyl-1-(5-hydroxymethyl-benzofuran-2-yl)-propyl]-2-methyl-phenol (653 mg, 2.02 mmol) and 1-bromopinacolone (555 mg, 3.10 mmol) and $K_2CO_3$ (570 mg, 4.13 mmol) in acetone (40 mL) are reacted analogous to Example 18-E to give the title compound (870 mg, 100%).

Step C. 1-{4-[1-Ethyl-1-(5-methylsulfanylmethyl-benzofuran-2-yl)-propyl]-2-methyl-phenoxy}-3,3-dimethyl-butan-2-one

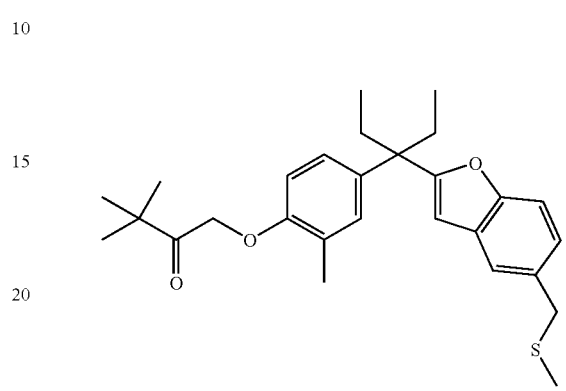

A solution of 1-{4-[1-ethyl-1-(5-hydroxymethyl-benzofuran-2-yl)-propyl]-2-methyl-phenoxy}-3,3-dimethyl-butan-2-one (210 mg, 0.497 mmol) in $Et_2O$ (3 mL) was treated with $PBr_3$ (148 mg, 0.547 mmol) at 0° C. for 60 minutes. The reaction is diluted with $Et_2O$ (30 mL) and quenched with water (2 mL), brine (2 mL). The organic layer is concentrated and dissolved in DMF (2 mL), treated with NaSMe (105 mg, 1.49 mmol) and stirred at 0° C. for 2 hours. It is loaded on column directly and purified with EtOAc/Hexanes (10%) to obtain the title compound (105 mg, 47%).

Step D. 1-{4-[1-Ethyl-1-(5-methanesulfonylmethyl-benzofuran-2-yl)-propyl]-2-methyl-phenoxy}-3,3-dimethyl-butan-2-one

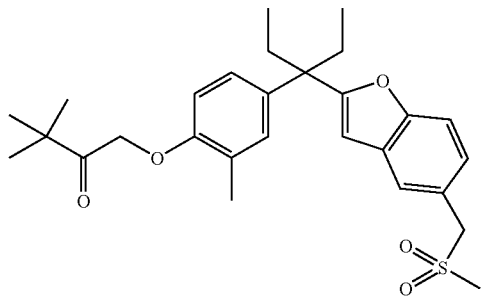

A solution of 1-{4-[1-ethyl-1-(5-methylsulfanylmethyl-benzofuran-2-yl)-propyl]-2-methyl-phenoxy}-3,3-dimethyl-butan-2-one (105 mg, 0.232 mmol) in $CH_2Cl_2$ (3 mL) was treated with mCPBA (133 mg, 0.464 mmol) at 0° C. for 60 minutes. The reaction mixture is loaded on column directly and purified with EtOAc/Hexanes (20%) to obtain the title compound (9 mg, 8%). MS (ES) m/e: 502.3 (M+18).

Example 51

Preparation of 6-{1-[4-(3,3-dimethyl-2-oxo-butoxy)-3-methyl-phenyl]-1-ethyl-propyl}-benzofuran-2-carboxylic acid

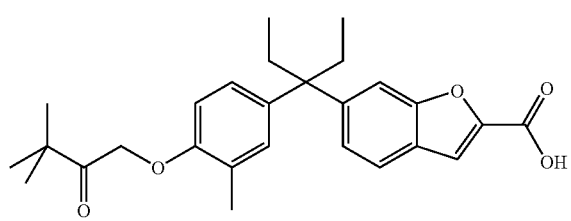

Step A. 4-(1-Ethyl-propenyl)-2-hydroxy-benzaldehyde

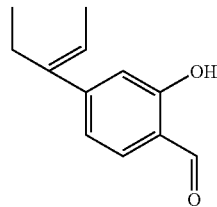

3-Hydroxybenzoic acid methyl ester (10.8 g, 71.0 mmol) and EtMgBr (3 M, 100 mL) in THF (200 mL) are reacted analogous to Example 30-A to give the intermediate, which is further treated with MgCl$_2$ (10.1 g, 106.5 mmol) and Et3N (35 mL, 249 mmol) and paraformaldehyde (13.9 g, 462 mmol) in acetonitrile (300 mL) analogous to Example 30-A to give the title compound (13.0 g, 96%).

Step B. 6-(1-Ethyl-propenyl)-benzofuran-2-carboxylic acid ethyl ester

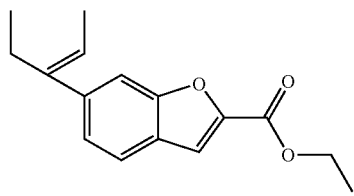

4-(1-Ethyl-propenyl)-2-hydroxy-benzaldehyde (9.00 g, 47.3 mmol) and ethyl bromoacetate (9.88 g, 59.1 mmol) and K$_2$CO$_3$ (13.1 g, 94.6 mmol) in acetone (100 mL) followed by DBU (mL) and DMF (40 mL) are reacted analogous to Example 30-B to give the title compound (9.40 g, 77%).

Step C. 6-[1-Ethyl-1-(4-hydroxy-3-methyl-phenyl)-propyl]-benzofuran-2-carboxylc acid ethyl ester

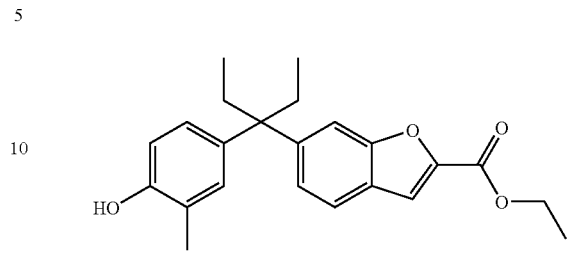

6-(1-Ethyl-propenyl)-benzofuran-2-carboxylic acid ethyl ester (2.01 g, 7.78 mmol) and o-cresol (1.26 g, 11.7 mmol) and BF$_3$—OEt$_2$ (1.10 g, 7.78 mmol) in CH$_2$Cl$_2$ are reacted analogous to Example 30-C to give the title compound (1.58 g, 55%).

Step D. 6-{1-[4-(3,3-Dimethyl-2-oxo-butoxy)-3-methyl-phenyl]-1-ethyl-propyl}-benzofuran-2-carboxylic acid ethyl ester

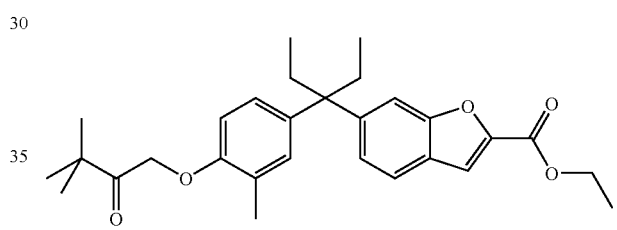

6-[1-Ethyl-1-(4-hydroxy-3-methyl-phenyl)-propyl]-benzofuran-2-carboxylic acid ethyl ester (1.58 g, 4.31 mmol) and 1-bromopinacolone (1.16 g, 6.47 mmol) and K$_2$CO$_3$ (1.78 g, 12.9 mmol) in acetone (50 mL) are reacted analogous to Example 30-D to give the title compound (1.80 g, 90%).

Step F. 6-{1-[4-(3,3-Dimethyl-2-oxo-butoxy)-3-methyl-phenyl]-1-ethyl-propyl}-benzofuran-2-carboxylic acid

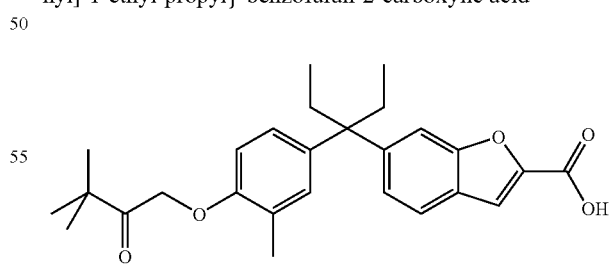

6-{1-[4-(3,3-Dimethyl-2-oxo-butoxy)-3-methyl-phenyl]-1-ethyl-propyl}-benzofuran-2-carboxylic acid ethyl ester (980 mg, 2.11 mmol) and NaOH (2 N, 10.0 mL) and MeOH (5.0 mL) and THF (5.0 mL) are reacted analogous to Example 2 to give the title compound (880 mg, 96%). MS (ES) m/e: 435.3 (M−1).

Example 52

Preparation of enantiomers of 5-{1-Ethyl-1-[4-(2-hydroxy-3,3-dimethyl-butoxy)-3-methyl-phenyl]-propyl}-7-methyl-benzofuran-2-carboxylic acid

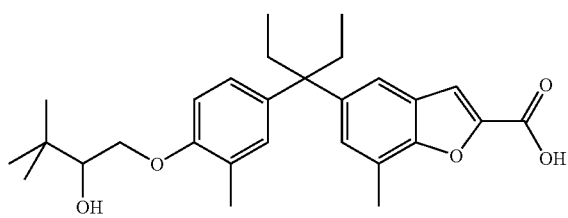

Step A: Preparation of racemic 5-{1-ethyl-1-[4-(2-hydroxy-3,3-dimethyl-butoxy)-3-methyl-phenyl]-propyl}-7-methyl-benzofuran-2-carboxylic acid ethyl ester

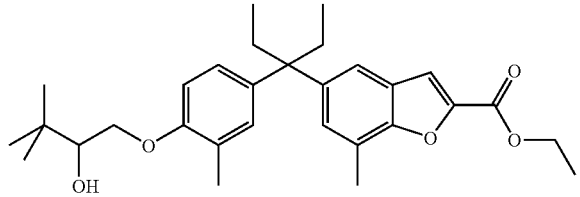

5-{1-[4-(3,3-Dimethyl-2-oxo-butoxy)-3-ethyl-phenyl]-1-ethyl-propyl}-7-methyl-benzofuran-2-carboxylic acid ethyl ester (1.87 g, 3.91 mmol) in THF (50 mL) is reacted with NaBH₄ (0.45 g, 11.7 mmol) analogous to Example 22 to obtain the title compound (1.28 g, 68%).

Step B: Preparation of enantiomers of 5-{1-ethyl-1-[4-(2-hydroxy-3,3-dimethyl-butoxy)-3-methyl-phenyl]-propyl}-7-methyl-benzofuran-2-carboxylic acid ethyl ester

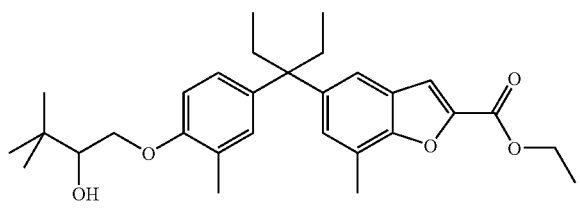

(enantiomer 1)
(enantiomer 2)

A mixture of racemic 5-{1-ethyl-1-[4-(2-hydroxy-3,3-dimethyl-butoxy)-3-methyl-phenyl]-propyl}-7-methyl-benzofuran-2-carboxylic acid ethyl ester (1.28 g, 2.66 mmol) is chromatographed with Chiralpak AD column to give enantiomer 1, Example 52A (0.544 g, 42%) and enantiomer 2, Example 52B (0.493 g, 38%).

Enantiomer 1, Example 52A
HPLC: ChiralPak AD (4.6×150); 60% heptane/40% IPA; 1.0 mL/min (flow rate); uv: 300 nm.
Rt=5.6 m.
NMR eq to Step A.
Enantiomer 2, Example 52B
HPLC: ChiralPak AD (4.6×150); 60% heptane/40% IPA; 1.0 ml/min (flow rate); uv: 300 nm.
Rt=8.5 m.
NMR eq to Step A.

Step C:
Enantiomer 1 (544 mg, 1.13 mmol) is hydrolyzed analogous to Example 4 to provide the corresponding acid (510 mg, 99%). NMR and MS are the same as those in Example 22.
Enantiomer 2 (493 mg, 1.03 mmol) is hydrolyzed analogous to Example 4 to provide the corresponding acid (460 mg, 99%). NMR and MS are the same as those in Example 22.

Example 53

Preparation of enantiomers of 2-{1-ethyl-1-[4-(2-hydroxy-3,3-dimethyl-butoxy)-3-methyl-phenyl]-propyl}-benzofuran-5-carboxylic acid

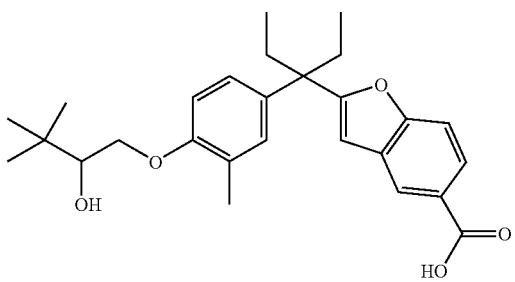

Step A: Preparation of enantiomers of 2-{1-ethyl-1-[4-(2-hydroxy-3,3-dimethyl-butoxy)-3-methyl-phenyl]-propyl}-benzofuran-5-carboxylic acid methyl ester

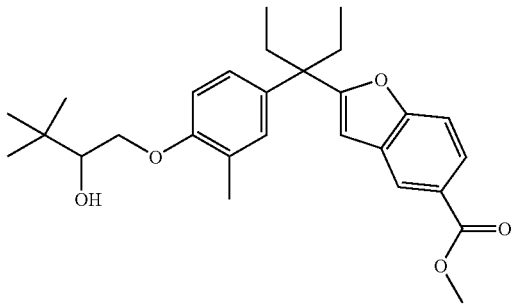

(enantiomer 1)
(enantiomer 2)

A mixture of racemic 2-{1-ethyl-1-[4-(2-hydroxy-3,3-dimethyl-butoxy)-3-methyl-phenyl]-propyl}-benzofuran-5-carboxylic acid methyl ester (1.40 g, 3.09 mmol) is chromatographed with Chiralpak AD column to give enantiomer 1, Example 53A (0.555 g, 40%) and enantiomer 2, Example 53B (0.600 g, 43%).

Enantiomer 1, Example 53A
HPLC: ChiralPak AD (4.6×150); 60% heptane/40% IPA; 1.0 mL/min (flow rate); uv: 260 nm.
Rt=8.5 m.
MS eq to Example 3.
Enantiomer 2, Example 53B
HPLC: ChiralPak AD (4.6×150); 60% heptane/40% IPA; 1.0 mL/min (flow rate); uv: 260 nm.
Rt=11.3 m.
MS eq to Example 3.

Step B:

Enantiomer 1 (555 mg, 1.23 mmol) is hydrolyzed analogous to Example 4 to provide the corresponding acid (530 mg, 99%). NMR and MS are eq to those in Example 4.

Enantiomer 2 (600 mg, 1.33 mmol) is hydrolyzed analogous to Example 4 to provide the corresponding acid (580 mg, 99%). NMR and MS are eq to those in Example 4.

Example 54

Preparation of enantiomers of 2-{1-ethyl-1-[4-(2-hydroxy-3,3-dimethyl-butoxy)-3-methyl-phenyl]-propyl}-benzofuran-6-carboxylic acid

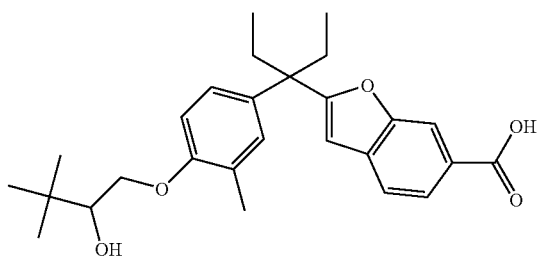

Step A: Preparation of acemic of 2-{1-ethyl-1-[4-(2-hydroxy-3,3-dimethyl-butoxy)-3-methyl-phenyl]-propyl}-benzofuran-6-carboxylic acid ethyl ester

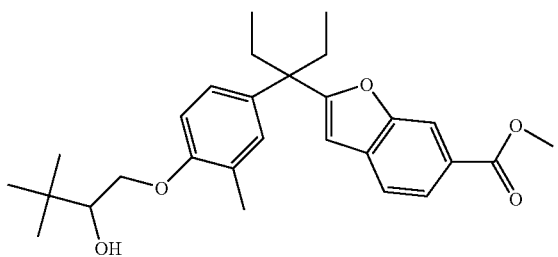

2-{1-[4-(3,3-Dimethyl-2-oxo-butoxy)-3-methyl-phenyl]-1-ethyl-propyl}-benzofuran-6-carboxylic acid methyl ester (0.88 g, 1.95 mmol) in THF (40 mL) is reacted with NaBH$_4$ (0.148 g, 3.91 mmol) analogous to Example 22 to obtain the title compound (0.78 g, 89%).

Step B: Preparation of enantiomers of 2-{1-ethyl-1-[4-(2-hydroxy-3,3-dimethyl-butoxy)-3-methyl-phenyl]-propyl}-benzofuran-6-carboxylic acid ethyl ester

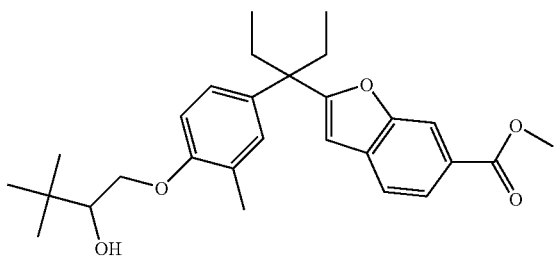

(enantiomer 1)
(enantiomer 2)

A mixture of racemic 2-{1-ethyl-1-[4-(2-hydroxy-3,3-dimethyl-butoxy)-3-methyl-phenyl]-propyl}-benzofuran-6-carboxylic acid methyl ester (0.78 g, 1.72 mmol) is chromatographed with Chiralpak AD column to give enantiomer 1, Example 54A (0.254 g, 33%) and enantiomer 2, Example 54B (0.266 g, 34%).

Enantiomer 1, Example 54A.

HPLC: ChiralPak AD (4.6×250); 80% heptane/20% IPA; 1.0 mL/min (flow rate); uv: 300 nm.

Rt=6.8 min.

NMR eq to Step A.

Enantiomer 2, Example 54B

HPLC: ChiralPak AD (4.6×150); 80% heptane/20% IPA; 1.0 mL/min (flow rate); uv: 300 nm.

Rt=12.6 min.

NMR eq to Step A.

Step C:

Enantiomer 1 (254 mg, 0.561 mmol) is hydrolyzed analogous to Example 4 to provide acid 2165210 (220 mg, 99%). NMR and MS are eq to those in Example 19.

Enantiomer 2 (266 mg, 0.588 mmol) is hydrolyzed analogous to Example 4 to provide acid 2165211 (258 mg, 99%). NMR and MS are eq to those in Example 19.

Example 55

Preparation of [(2-{1-[4-(3,3-Dimethyl-2-oxo-butoxy)-3-isopropyl-phenyl]-1-ethyl-propyl}-benzofuran-5-carbonyl)-methyl-amino]-acetic acid

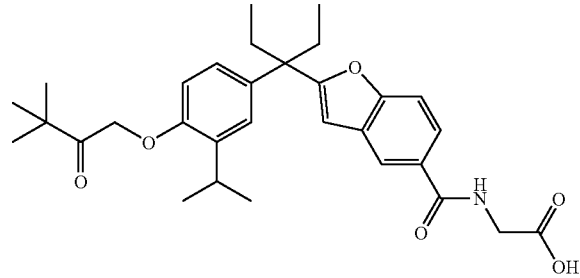

A solution of 2-{1-[4-(3,3-dimethyl-2-oxo-butoxy)-3-isopropyl-phenyl]-ethylpropyl}-benzofuran-5-carboxylic acid (200 mg, 0.430 mmol) (Example 17) in CH$_2$Cl$_2$ (5 ml) is treated with EDC (262 mg, 0.645 mmol) and DMAP (158 mg, 1.3 mmol). The mixture is stirred for 10 min at RT before the addition of sarcosine ethyl ester hydrochloride (100 mg, 0.645 mmol). The reaction is stirred for 12 hours and concentrated onto silica and purified with 25% EtOAc in Hexanes to afford the intermediate ester (75 mg, 30%). The intermediate (75 mg, 0.133 mmol) is dissolved in methanol (2 mL), and is treated with 2N NaOH (2 mL). The mixture is stirred at RT overnight. The mixture is concentrated and neutralized to pH 1 with 1N NaOH and extracted with EtOAc (3×10 mL) to afford the title compound (71 mg, 100%) MS (ES) m/e: 534.3 (M−1)

Example 56

Preparation of [(2-{1-[4-(3,3-Dimethyl-2-oxo-butoxy)-3-methyl-phenyl]-1-ethyl-propyl}-benzofuran-5-carbonyl)-amino]-acetic acid

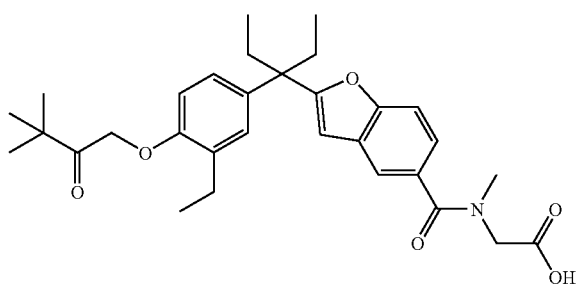

A Solution of 2-{1-[4-(3,3-Dimethyl-2-oxo-butoxy)-3-ethyl-phenyl]-ethylpropyl}-benzofuran-5-carboxylic acid (200 mg, 0.443 mmol) (Example 12) in dichloromethane (3 mL) is treated with EDC (270 mg, 0.665 mmol) and DMAP (162 mg, 1.33 mmol). The reaction is stirred for 10 minutes before addition of sarcosine ethyl ester hydrochloride (102 mg, 0.665 mmol). The reaction is stirred overnight, concentrated on silica and purified with 25% EtOAc to afford the intermediate (78 mg, 23%).

The intermediate is dissolved in THF (2 mL), MeOH (2 mL) and treated with 2N NaOH (2.5 mL). The reaction is stirred at RT overnight. The mixture is concentrated and neutralized to pH 1 with 1N NaOH and extracted with EtOAc (3×10 mL) to afford the title compound (77 mg, 80%) MS (ES) m/e: 506.2 (M−1)

Example 57

Preparation of [(6-{1-[4-(3,3-Dimethyl-2-oxo-butoxy)-3-methyl-phenyl]-1-ethyl-propyl}-benzofuran-2-carbonyl)-amino]-acetic acid

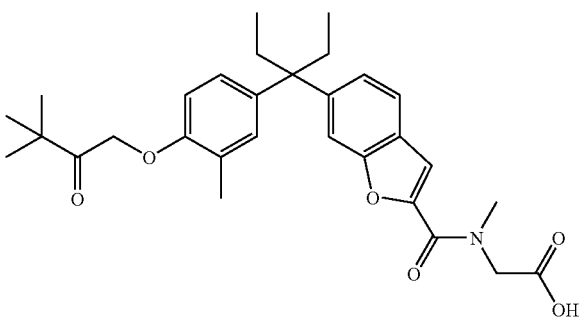

A solution of 6-{1-[4-(3,3-Dimethyl-2-oxo-butoxy)-3-methyl-phenyl]-1-ethyl-propyl}-benzofuran-2-carboxylic acid (200 mg, 430 mmol) in dichloromethane (4 mL) is treated with EDC (262 mg, 0.645 mmol) and DMAP (158 mg, 1.3 mmol). The reaction was stirred at RT for 10 minutes before addition of sarcosine ethyl ester hydrochloride (100 mg, 0.645 mmol). The reaction is stirred at RT overnight. The reaction is concentrated onto silica and purified 25% EtOAc in hexanes to (86 mg, 35%) of the intermediate. The intermediate is dissolved in MeOH (2 mL) and THF (2 mL), treated with 2N NaOH (2.5 mL) and stirred at RT overnight. The reaction is concentrated and acidified to pH 1 with 1 N HCl and extracted with EtOAc (3×10 mL) to yield (77 mg, 80%) MS (ES) m/e: 520.2 (M−1)

Example 58

Preparation of [(5-{1-[4-(3,3-Dimethyl-2-oxo-butoxy)-3-methyl-phenyl]-1-ethyl-propyl}-7-methyl-benzofuran-2-carbonyl)-methyl-amino]-acetic acid. (isomer 1)

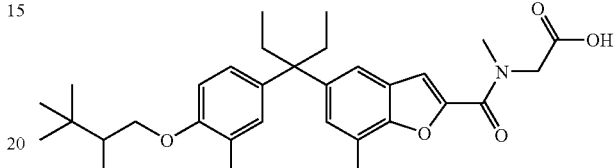

A solution of 5-{1-[4-(3,3-Dimethyl-2-oxo-butoxy)-3-methyl-phenyl]-1-ethyl-propyl}-7-methyl-benzofuran-2-carboxylic acid (ISOMER 1) (220 mg, 486 mmol)in DMF (5 mL) is treated with HATU (203 mg, 534 mmol) and DIEA (0.25 mL, 1.4 mmol). The reaction is stirred for 20 minutes before addition of sarcosine ethyl ester hydrochloride (100 mg, 0.583 mmol). The reaction is stirred overnight. The reaction is partitioned between EtOAc (25 mL) and 1N HCl (10 mL). The organics are washed with bicarb, brine (10 mL each) and dried. Purified 25% EtOAc in hexanes to yield (173 mg, 50%) of the intermediate.

The intermediate is dissolved in MeOH and THF (2 mL each) followed by treatment with 2N NaOH. The reaction is stirred overnight at RT. The reaction is concentrated and acidified to pH 1 with 1N HCl. The reaction is extracted with EtOAc (3×10 mL) to yield (118 mg, 72%). MS (ES) m/e: 522.3 (M−1)

Example 59

Preparation of [(2-{1-Ethyl-1-[4-(3-hydroxy-4,4-dimethyl-pentyl)-3-isopropyl-phenyl]-propyl}-benzofuran-5-carbonyl)-methyl-amino]-acetic acid

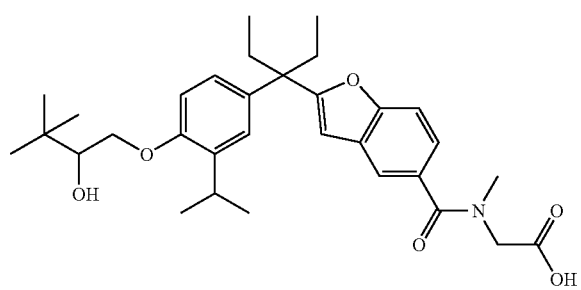

A solution of [(2-{1-[4-(4,4-Dimethyl-3-oxo-pentyl)-3-isopropyl-phenyl]-1-ethyl-propyl}-benzofuran-5-carbonyl)-methyl-amino]-acetic acid (27 mg, 0.05 mmol) (Example 55) in THF (2 mL) is treated with NaBH$_4$ (4 mg, 0.1 mmol) at room temp. The resulting mixture is stirred for 2 hours. The mixture is concentrated and neutralized to pH 3 and extracted with EtOAc (3×5 mL). The organic layer is dried over sodium sulfate, concentrated to afford the desired compound. (17 mg, 63%) MS (ES) m/e: 536.3 (M−1)

Example 60

Preparation of [(6-{1-Ethyl-1-[4-(2-hydroxy-3,3-dimethyl-butoxy)-3-methyl-phenyl]-propyl}-benzofuran-2-carbonyl)-methyl-amino]-acetic acid

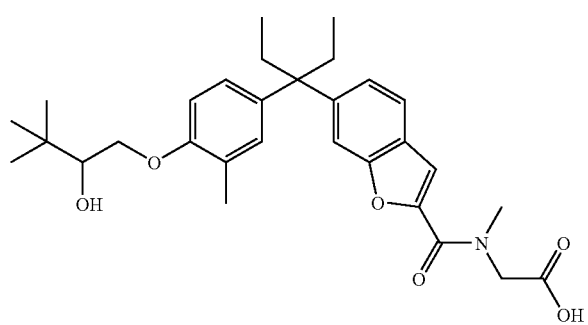

A solution of (6-{1-[4-(3,3-Dimethyl-2-oxo-butoxy)-3-methyl-phenyl]-1-ethyl-propyl}-benzofuran-2-carbonyl)-amino]-acetic acid (66 mg, 0.130 mmol) (Example 57) in THF (2 mL) is treated with NaBH$_4$ (11 mg, 0.26 mmol) at room temp. The resulting mixture is stirred for 2 hours. The mixture is concentrated and neutralized to pH 3 and extracted with EtOAc (3×5 mL). The organic layer is dried over sodium sulfate, concentrated to afford the desired compound (39 mg, 59%). MS (ES) m/e: 508.3 (M−1)

Example 61

Preparation of (2-{1-Ethyl-1-[3-ethyl-4-(2-hydroxy-3,3-dimethyl-butoxy)-phenyl]-propyl}-benzofuran-5-carbonyl)-methyl-amino]-acetic acid

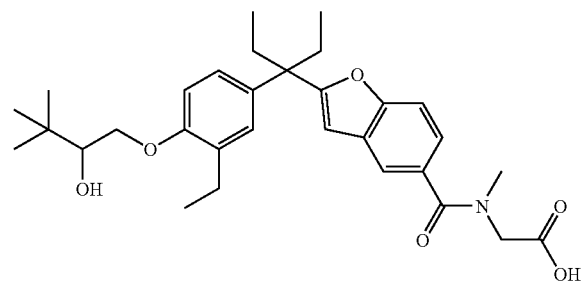

A solution of (2-{1-[4-(3,3-Dimethyl-2-oxo-butoxy)-3-methyl-phenyl]-1-ethyl-propyl}-benzofuran-5-carbonyl)-amino]-acetic acid (54 mg, 0.103 mmol) (Example 56) in THF (2 mL) is treated with NaBH$_4$ (8 mg, 0.08 mmol) at room temp. The resulting mixture is stirred for 2 hours. The mixture is concentrated and neutralized to pH 3 and extracted with EtOAc (3×5 mL). The organic layer is dried over sodium sulfate, concentrated to afford the desired compound (42 mg, 77%). MS (ES) m/e: 522.3 (M−1)

Example 62

Preparation of (2-{1-Ethyl-1-[4-(2-hydroxy-3,3-dimethyl-butoxy)-3-methyl-phenyl]-propyl}-benzofuran-5-carbonyl)-methyl-amino]-acetic acid (isomer 1)

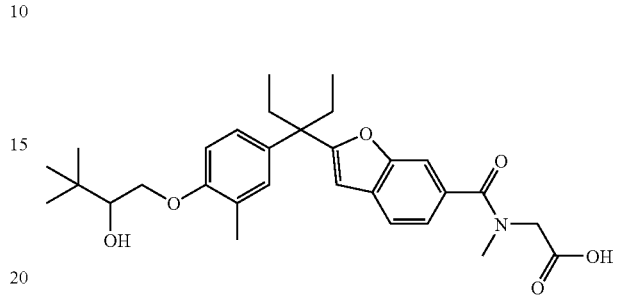

A solution of 2-{1-Ethyl-1-[4-(2-hydroxy-3,3-dimethyl-butoxy)-3-methyl-phenyl]-propyl}-benzofuran-5-carboxylic acid (150 mg, 0.342 mmol) in DMF (4 mL) is treated with HATU (142 mg, 0.376 mmol) and DIEA (0.3 mL, 1.0 mmol). The reaction is stirred for 20 minutes before addition of sarcosine ethyl ester hydrochloride (63 mg, 0.410 mmol). The reaction is stirred at RT overnight. The reaction is diluted with dichloromethane (50 mL) and is washed with 1N HCl, water, and brine (1×10 mL each). The organic layer is dried with sodium sulfate and purified on silica 75% EtOAc in hexanes to yield the desired intermediate (108 mg, 53%).

The intermediate (108 mg, 0.201 mmol) is dissolved in methanol (0.5 mL) and THF (0.5 mL) followed by addition of 2N NaOH (1 mL). The reaction is stirred overnight at RT. The reaction is acidified to pH 3 with 1N HCl and extracted with EtOAc (3×15 mL). The organic layer is washed with brine and dried to yield (72 mg, 71%) of the desired compound. MS (ES) m/e: 508.3 (M−1)

Example 63

Preparation of [(2-{1-Ethyl-1-[4-(2-hydroxy-3,3-dimethyl-butoxy)-3-methyl-phenyl]-propyl}-benzofuran-6-carbonyl)-methyl-amino]-acetic acid. (isomer 2)

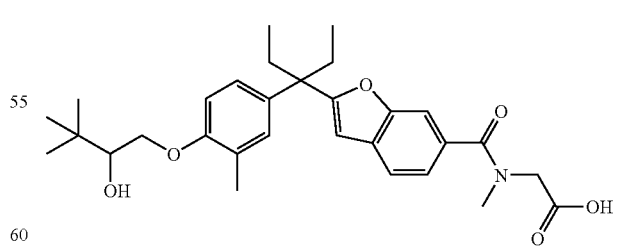

2-{1-Ethyl-1-[4-(2-hydroxy-3,3-dimethyl-butoxy)-3-methyl-phenyl]-propyl}-benzofuran-6-carboxylic acid (115 mg, 0.262 mmol), HATU (142 mg, 0.376 mmol), DIEA (0.3 ml, 1.02 mmol), and sarcosine ethyl ester hydrochloride (48 mg, 0.314 mmol) are reacted followed by base hydrolysis with 2N NaOH in an analogous manner to example 59 from to yield (66 mg, 25%) MS (ES) m/e: 508.2 (M−1)

Example 64

Preparation of [(2-{1-Ethyl-[4-(2-hydroxy-3,3-dimethyl-butoxy)-3-methyl-phenyl]-propyl}-benzofuran-5-carbonyl)-methyl-amino]-acetic acid (Isomer 1)

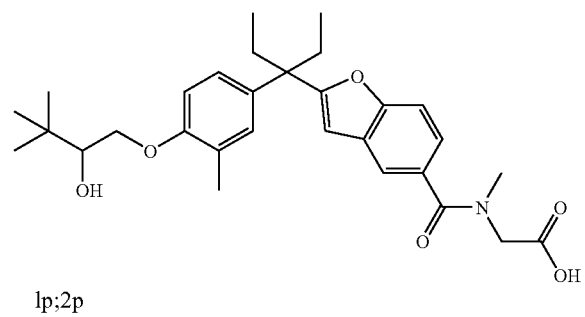

1p;2p

2-{1-Ethyl-1-[4-(2-hydroxy-3,3-dimethyl-butoxy)-3-methyl-phenyl]-propyl}-benzofuran-5-carboxylic acid (115 mg, 0.262 mmol), HATU (145 mg, 0.380 mmol), DIEA (0.35 ml, 2.07 mmol), and sarcosine ethyl ester hydrochloride (60 mg, 0.394 mmol) are reacted followed by base hydrolysis with 2N NaOH in an analogous manner to example 59 from to yield (89 mg, 64%) 596.3

Example 65

Preparation of [(2-{1-Ethyl-1-[4-(2-hydroxy-3,3-dimethyl-butoxy)-3-methyl-phenyl]-propyl}-benzofuran-5-carbonyl)-methyl-amino]-acetic acid (Isomer 2)

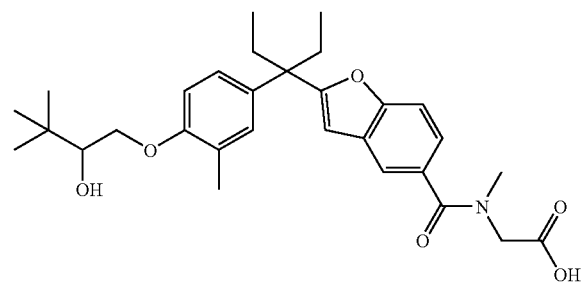

2-{1-Ethyl-1-[4-(2-hydroxy-3,3-dimethyl-butoxy)-3-methyl-phenyl]-propyl}-benzofuran-5-carboxylic acid (152 mg, 346 mmol) HATU (145 mg, 380 mmol) DIEA (0.35 ml, 2.07 mmol) and sarcosine ethyl ester hydrochloride (63 mg, 0.415 mmol) are reacted followed by base hydrolysis with 2N NaOH in an analogous manner to example E from to yield (78 mg, 56%). MS (ES) m/e: 508.3 (M−1)

Example 66

Preparation of [(5-{1-[(3,3-Dimethyl-2-oxo-butoxy)-3-methyl-phenyl]-1-ethyl-propyl}-7-methyl-benzofuran-2-carbonyl)-methyl-amino]-acetic acid. (isomer 2)

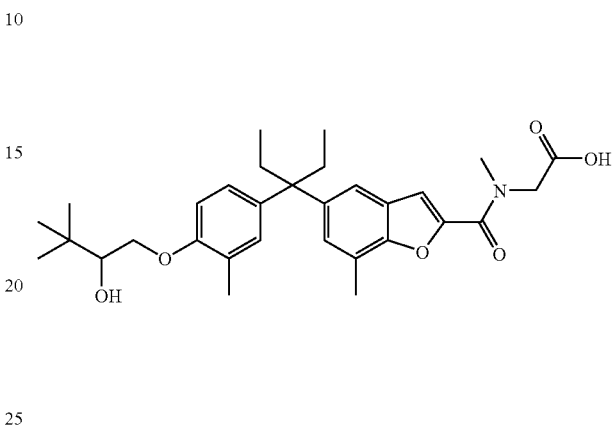

5-{1-Ethyl-1-[4-(2-hydroxy-3,3-dimethyl-butoxy)-3-methyl-phenyl]-propyl}-7-methyl-benzofuran-2-carboxylic acid (175 mg, 0.386 mmol) HATU, (162 mg, 0.425 mmol), DIEA (0.4 mL, 2.3 mmol) and sarcosine ethyl ester hydrochloride (72 mg, 0.463 mmol) is reacted analogous to Example 58 to yield (71 mg, 42%) MS (ES) m/e: 522.3 (M−1)

Example 67

Preparation of 5-{1-[4-(3,3-Dimethyl-2-oxo-cyclohexyloxy)-3-methyl-phenyl]-1-ethyl-propyl}-benzofuran-2-carboxylic acid. (racemic)

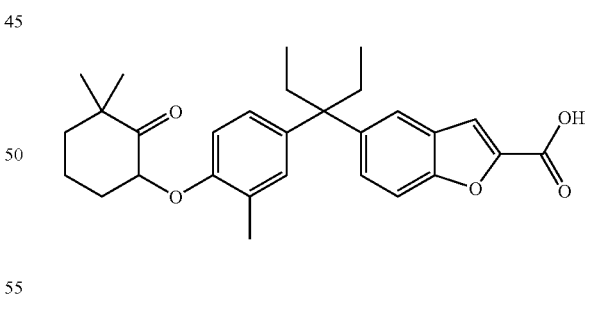

5-[1-Ethyl-1-(4-hydroxy-3-methyl-phenyl)-propyl]-7-methyl-benzofuran-2-carboxylic acid (619 mg, 1.7 mmol) (PF1-A05244-139), 2-bromo-4,4 dimethyl cyclohexanone (520 mg, 2.5 mmol) (JACS 74, 4331 (1952) and potassium carbonate (500 mg, 3.4 mmol) was made in an analogous manner to Example 30 part D followed by base hydrolysis with 2N NaOH analogous to Example 30 part E to yield (82 mg, 72%) MS (ES) m/e: 461.3 (M−1)

Example 68

Preparation of 5-{1-Ethyl-1-[3-methyl-4-(2-oxo-cyclohexyloxy)-phenyl]-propyl}-benzofuran-2-carboxylic acid

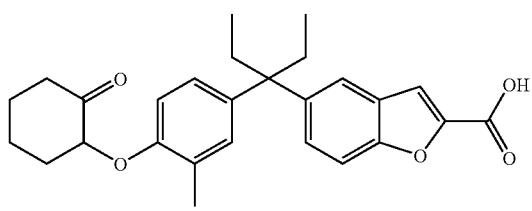

5-[1-Ethyl-1-(4-hydroxy-3-methyl-phenyl)-propyl]-7-methyl-benzofuran-2-carboxylic acid (1000 mg, 2.7 mmol), 2-chloro cyclohexanone (429 mg, 3.3 mmol) and potassium carbonate (759 mg, 5.5 mmol) was made in an analogous manner to Example 30 part D followed by base hydrolysis with 2N NaOH analogous to Example 30 part E to yield (60 mg, 30%) MS (ES) m/e: 433.3 (M−1)

Example 69

Preparation of 5-{1-Ethyl-1-[4-(2-hydroxy-cyclohexyloxy)-3-methyl-phenyl]-propyl}-benzofuran-2-carboxylic acid

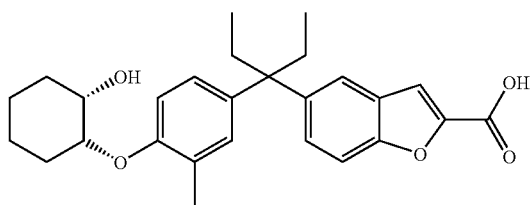

5-{1-Ethyl-1-[3-methyl-4-(2-oxo-cyclohexyloxy)-phenyl]-propyl}-benzofuran-2-carboxylic acid (357 mg, 0.822 mmol) (Example N) was reacted with sodium borohydride (68 mg, 1.6 mmol) in an analogous manner to Example 31 to yield (13 mg, 65% yield).
MS (ES) m/e: 435.2 (M−1)

Example 70

Preparation of 5-{1-Ethyl-1-[4-(2-hydroxy-3,3-dimethyl-cyclohexyloxy)-3-methyl-phenyl]-propyl}-benzofuran-2-carboxylic acid

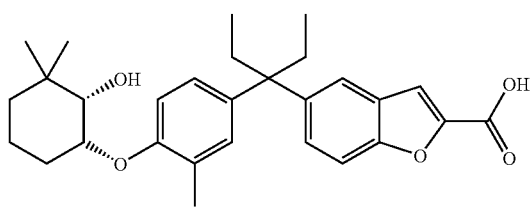

5-{1-[4-(3,3-Dimethyl-2-oxo-cyclohexyloxy)-3-methyl-phenyl]-1-ethyl-propyl}-benzofuran-2-carboxylic acid (200 mg, 0.432 mmol) (Example 67) is reacted with sodium borohydride (36 mg, 0.864 mmol) in an analogous manner to Example 31 to yield (13 mg, 64% yield). MS (ES) m/e: 563.3 (M−1)

Example 71

Preparation of diasteromers of 5-{1-Ethyl-1-[4-(2-hydroxy-3,3-dimethyl-cyclohexyloxy)-3-methyl-phenyl]-propyl}-benzofuran-2-carboxylic acid

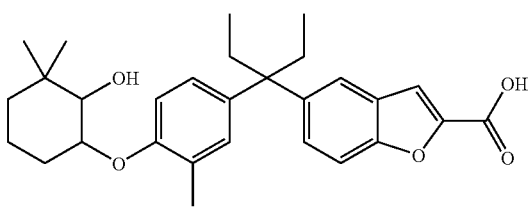

A mixture of racemic 5-{1-Ethyl-1-[4-(2-hydroxy-3,3-dimethyl-cyclohexyloxy)-3-methyl-phenyl]-propyl}-benzofuran-2-carboxylic acid ethyl ester, analogous to Example 30D is chromatographed with a ChiralPak AD column 4/1 heptane/IPA and hydrolyzed analogous to Example 30E to give enantiomer 1, Example 71A (13 mg, 62%)

MS (ES) m/e: 563.3 (M−1) enantiomer 2 Example 71B (4.6 mg, 21%) MS (ES) m/e: 563.3 (M−1), enantiomer 3 Example 71C (12 mg, 60%) MS (ES) m/e: 563.3 (M−1) and enantiomer 4 Example 71D (12 mg, 60%) MS (ES) m/e: 563.3 (M−1).

Example 72

Preparation of enantiomers 5-{1-Ethyl-1-[3-methyl-4-(2-oxo-cyclohexyloxy)-phenyl]-propyl}-benzofuran-2-carboxylic acid

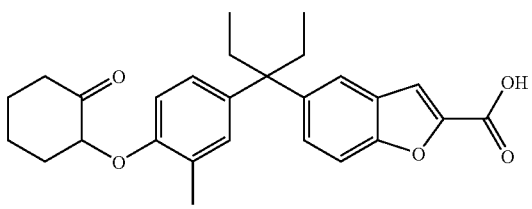

A mixture of racemic 5-{1-Ethyl-1-[3-methyl-4-(2-oxo-cyclohexyloxy)-phenyl]-propyl}-benzofuran-2-carboxylic acid ethyl ester analogous to Example 30D is chromatographed with a ChiralPak AD-H column 60% IPA in heptane and hydrolyzed analogous to Example 30E to give enantiomer 1 Example 72A (86 mg, 60%) and enantiomer 2 Example 72B (100 mg, 69%) MS (ES) m/e: 433.3 (M−1)

Example 73

Preparation of enantiomers 5-{1-[4-(3,3-Dimethyl-2-oxo-cyclohexyloxy)-3-methyl-phenyl]-1-ethyl-propyl}-7-methyl-benzofuran-2-carboxylic acid

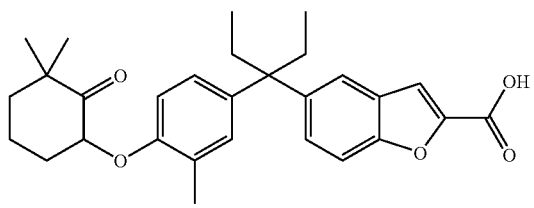

A mixture of racemic 5-{1-[4-(3,3-Dimethyl-2-oxo-cyclohexyloxy)-3-methyl-phenyl]-1-ethyl-propyl}-7-methyl-benzofuran-2-carboxylic acid ethyl ester analogous to Example 30D is chromatographed with a Chiracel OJ with 100% methanol and hydrolyzed with 2N NaOH analogous to Example 30E to give Enantomer 1 Example 73A (60 mg, 73%)

MS (ES) m/e: 461.2 (M−1) and Enantiomer 2 Example 73B (60 mg, 73%) MS (ES) m/e: 461.2 (M−1)

Example 74

Preparation of diasteromers of [(5-{1-Ethyl-1-[4-(2-hydroxy-3,3-dimethyl-cyclohexyloxy)-3-methyl-phenyl]-propyl}-benzofuran-2-carbonyl)-methyl-amino]-acetic acid

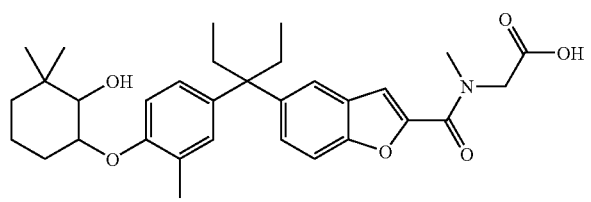

Example 71 5-{1-Ethyl-1-[4-(2-hydroxy-3,3-dimethyl-cyclohexyloxy)-3-methyl-phenyl]-propyl}-benzofuran-2-carboxylic acid (175 mg, 0.376 mmol) in dichloromethane (5 mL) is reacted with EDC (108 mg, 0.564 mmol), HOBT (55 mg, 0.395 mmol), triethylamine (0.2 ml, 1.5 mmol) and sarcosine ethyl ester hydrochloride (75 mg, 0.490 mmol) separately. The reactions are stirred overnight at RT. The reactions are diluted to 25 mL with dichloromethane and washed with 1N HCL, sat bicarb, and brine (1×10 mL) each followed by purification on silica with 30% ethyl acetate in hexanes to yield (100 mg, 66%) of each intermediate. MS (ES) m/e: 534.3 (M−1)

The intermediates are hydrolyzed with 2N NaOH in an analogous fashion to Example 30 part E to yield (80 mg, 82%) of each isomer.

Example 75

Preparation of [(5-{1-[4-(3,3-Dimethyl-2-oxo-cyclohexyloxy)-3-methyl-phenyl]-1-ethyl-propyl}-benzofuran-2-carbonyl)-methyl-amino]-acetic acid

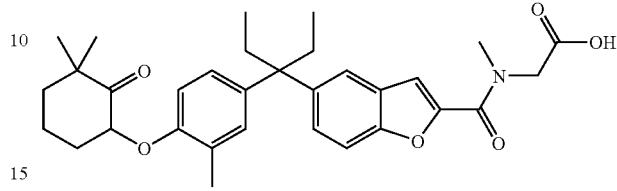

A solution of 5-{1-[4-(3,3-Dimethyl-2-oxo-cyclohexyloxy)-3-methyl-phenyl]-1-ethyl-propyl}-benzofuran-2-carboxylic acid (153 mg, 0.331 mmol) (from example R2), EDC (94 mg, 0.496 mmol), HOBT (47 mg, 0.347 mmol), triethylamine (0.2 ml, 1.3 mmol), and sarcosine ethyl ester hydrochloride (76 mg, 0.496 mmol) were reacted followed by base hydrolysis as in Example 74 to yield (55 mg, 34%) MS (ES) m/e: 532.3 (M−1)

Example 76

Preparation of [(5-{1-[4-(3,3-Dimethyl-2-oxo-cyclohexyloxy)-3-methyl-phenyl]-1-ethyl-propyl}-benzofuran-2-carbonyl)-methyl-amino]-acetic acid

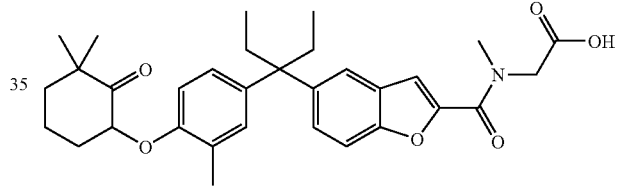

A solution of 5-{1-[4-(3,3-Dimethyl-2-oxo-cyclohexyloxy)-3-methyl-phenyl]-1-ethyl-propyl}-benzofuran-2-carboxylic acid (244 mg, 0.527 mmol) (from example 73A), EDC (151 mg, 0.791 mmol), HOBT (75 mg, 0.554 mmol), triethylamine (0.3 ml, 2.1 mmol), and sarcosine ethyl ester hydrochloride (105 mg, 0.685 mmol) were reacted followed by base hydrolysis as in Example 74 to yield (48 mg, 30%) MS (ES) m/e: 532.3 (M−1)

Example 77

Preparation of 2-[(5-{1-[4-(3,3-Dimethyl-2-oxo-cyclohexyloxy)-3-methyl-phenyl]-1-ethyl-propyl}-benzofuran-2-carbonyl)-methyl-amino]-3-methyl-butyric acid

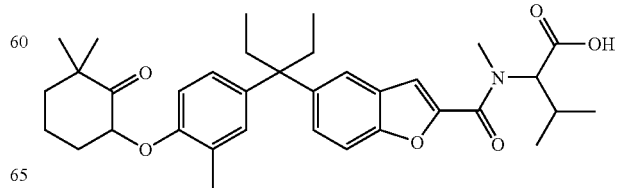

A solution of 5-{1-[4-(3,3-Dimethyl-2-oxo-cyclohexyloxy)-3-methyl-phenyl]-1-ethyl-propyl}-benzofuran-2-carboxylic acid (100 mg, 0.204 mmol) (from example 73A), EDC (58 mg, 0.306 mmol), HOBT (32 mg, 0.244 mmol), triethylamine (0.1 ml, 0.816 mmol), and L-valine methyl ester hydrochloride (41 mg, 0.244 mmol) were reacted followed by base hydrolysis as in Example 74 to yield (80 mg, 68%) MS (ES) m/e: 574.3 (M−1)

Compounds of the Invention—Salts, Stereoisomers & Prodrugs:

Salts of the compounds represented by formulae IA, IB, and IC are an additional aspect of the invention. The skilled artisan will also appreciate that the family of compounds of formulae IA, IB, and IC include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66:1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae IA or IB.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula IA, IB, or IC (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula IA, IB, or IC (in a medium such as dimethylformamide) 4-(2-chloroethyl)morpholine hydrochloride (available from Aldrich Chemical Co., Milwaukee, Wis. USA, Item No. C5,220-3). For example, prodrugs may be prepared by reaction of the sodium salt for a compound of Formula IA, IB, or IC with;

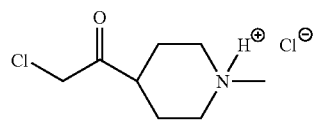

and sodium iodide to provide the ester prodrug pendent group

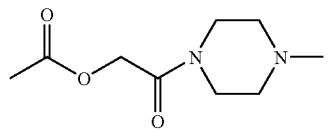

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —$CO_2H$) of a compound of Formulae IA, IB or IC with an alkyl iodide such as methyl iodide, ethyl iodide, n-propyl iodide, isopropyl iodide. Typical ester prodrug substituents are

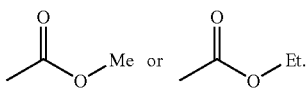

Pharmaceutical Formulations Containing the Novel Compounds of the Invention:

Pharmaceutical formulations of the invention are prepared by combining (e.g., mixing) a therapeutically effective amount of the compound of the invention (compounds of Formula IA, IB, or IC) together with a pharmaceutically acceptable carrier or diluent. The present pharmaceutical formulations are prepared by known procedures using well-known and readily available ingredients.

In making the compositions of the present invention, the compounds of the invention will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delivered to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets a compound of the invention I is mixed with a carrier having the necessary binding properties in suitable proportions and compacted in the shape and size desired. The powders and tablets preferably contain from about 1 to about 99 weight percent of the compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula IA, IB, or IC include, but are not limited to:

- disease states characterized by abnormal calcium regulation
- disease states characterized by abnormal cell proliferation
- disease states characterized by abnormal cell differentiation
- disease states characterized by abnormal immune response
- disease states characterized by abnormal dermatological conditions
- disease states characterized by neurodegenerative condition
- disease states characterized by inflammation
- disease states characterized by vitamin D sensitivity
- disease states characterized by hyperproliferative disorders.

Specific disease states benefited by treatment of the compounds of Formula I and II include, but are not limited to:

Acne
Actinic keratosis
Alopecia
Alzheimer's disease
Benign prostatic hyperplasia
Bladder cancer
Bone maintenance in zero gravity
Bone fracture healing
Breast cancer
Chemoprovention of Cancer
Crohn's disease
Colon cancer
Type I diabetes
Host-graft rejection
Hypercalcemia
Type II diabetes
Leukemia
Multiple sclerosis
Myelodysplastic syndrome
Insufficient sebum secretion
Osteomalacia
Osteoporosis
Insufficient dermal firmness
Insufficient dermal hydration
Psoriatic arthritis
Prostate cancer
Psoriasis
Renal osteodystrophy
Rheumatoid arthritis Scleroderma
Skin cancer
Systemic lupus erythematosus
Skin cell damage from Mustard vesicants
Ulcerative colitis
Vitiligo
Wrinkles Particularly preferred is the treatment of psoriasis and osteoporosis by administration to a mammal (including a human) of a therapeutically effective amount of compounds of Formulae IA, IB, or IC. By "pharmaceutically effective amount" it is meant that quantity of pharmaceutical agent corresponding to formulae IA, IB, or IC which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)
Prepare Polyethylene Glycol Ointment as follows:

| | |
|---|---|
| Polyethylene Glycol 3350 | 400 g. |
| Polyethylene Glycol 400 | 600 g. |
| To make | 1000 g. |

Heat the two ingredients on a water bath to 65C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as follows:

| | |
|---|---|
| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75C. The other ingredients, previously dissolved in the water are added, warmed to 75C, and the mixture stirred until it congeals.

For each of the above formulations the Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source:—United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, $13^{th}$ edition, 1994, published by McGraw Hill Publ., ISBN 0-07-032370-4, pgs. 2172-77; the disclosure of which is incorporated herein by reference.). Any one or combination of these conventional therapies may be used in combination with the method of treatment using compounds of Formulae IA, IB, or IC as taught herein. For example, in a method of treating osteoporosis, the vitamin D receptor modulator compounds of the invention may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
  Ingredient (A1): a vitamin D receptor modulator represented by formula (IA), (IB), or (IC), or a pharmaceutically acceptable salt or prodrug derivative thereof;
  Ingredient (B1):
    one or more co-agents that are conventional for treatment osteoporosis selected from the group consisting of:
      a. estrogens,
      b. androgens,
      c. calcium supplements,
      d. vitamin D metabolites,
      e. thiazide diuretics,
      f. calcitonin,
      g. bisphosphonates,
      h. SERMS, and
      i. fluorides.
  Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using compounds of Formulae IA, IB, or IC as taught herein. For example, in a method of treating osteoporosis, the vitamin D receptor modulator compounds of the invention (e.g., as defined by formula I) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating psoriasis comprising:
  Ingredient (A2): a vitamin D receptor modulator represented by formula (IA), (IB), or (IC), or a pharmaceutically acceptable salt or prodrug derivative thereof;
  Ingredient (B2):
    one or more co-agents that are conventional for treatment psoriasis selected from the group consisting of:
      a. topical glucocorticoids,
      b. salicylic acid, or
      c. crude coal tar.
  Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

TABLE 1

Summary of Experimental Results

| Test Cmpd.[1] | RXR-VDR heterodimer[2] EC$_{50}$ (nM) | VDR EC$_{50}$ (nM) (Caco-2 cells)[3] | OCN Promoter[4] EC$_{50}$ (nM) | Mouse Hypercal[5] μg/Kg/d |
|---|---|---|---|---|
| Ex. 1 | | | 1 | |
| Ex. 2 | 75 | 677 | 3 | >1000 |
| Ex. 4 | 0.4/19/127 | 312/368 | 0.5/7 | |
| Ex. 5 | 494/46 | 1199 | 106/79 | |
| Ex. 6 | 410/79 | | 68/47 | |
| Ex 7 | 31/3 | 412 | 0.4 | >300 |
| Ex. 8 | 6/2 | 120 | 0.6 | |
| Ex. 9 | 9 | | 7 | |
| Ex. 10 | 235 | | 275 | |
| Ex. 11 | 730 | 819 | 3/243 | >1000 |
| Ex. 12 | 43/1 | 515 | 0.7 | >1000 |
| Ex. 13 | 75/2 | 602 | 3 | |
| Ex 15 | 1354/627 | | 634 | |
| Ex 16 | 570/71 | | 27/44 | |
| Ex 17 | 16/252 | 589 | 7/15 | |
| Ex 18 | 132/9 | 472 | 2 | >300 |
| Ex 19 | 53/1 | 620 | 1.4/0.9 | |
| Ex 20 | 264/68 | 773 | 5/17 | |
| Ex 21 | 50/5 | 462 | 2/1 | >1000 |
| Ex 22 | 27 | | 1 | |
| Ex 23 | 660/320 | | 127/88 | |
| Ex 24 | 851 | | 431 | |
| Ex 25 | 67 | | 1000 | |
| Ex 26 | 983/81 | | 17 | |
| Ex 27 | 154/51 | | 9/17 | |
| Ex 28 | 300/20 | | 4 | >1000 |
| Ex 29 | 71 | | 3 | |
| Ex 30 | 37/3 | 364 | 0.3 | >1000 |
| Ex 31 | 12 | 279 | 0.5 | |
| Ex 32 | 31/4 | 385 | 1 | >300 |
| Ex 33 | 9 | 178 | 0.4 | |

TABLE 1-continued

Summary of Experimental Results

| Test Cmpd.[1] | RXR-VDR heterodimer[2] EC$_{50}$ (nM) | VDR EC$_{50}$ (nM) (Caco-2 cells)[3] | OCN Promoter[4] EC$_{50}$ (nM) | Mouse Hypercal[5] μg/Kg/d |
|---|---|---|---|---|
| Ex 34 | 622/33 | 896 | 13/21 | >3000 |
| Ex 35 | 836/83 | 753 | 13/21 | |
| Ex 36 | 536 | | 210 | |
| Ex 37 | 777/133 | 865 | 181/496 | |
| Ex 38 | 178/2 | 314 | 0.5 | >30 |
| Ex 39 | 138 | 419 | 0.4 | |
| Ex 40 | 80 | | 1/75 | |

TABLE 2

Summary of Experimental Results

| Test Cmpd.[1] | Kera. Prolif. IC$_{50}$ (nM) | IL-10. IC$_{50}$ (nM) |
|---|---|---|
| Ex. 1 | 71 | |
| Ex. 2 | 12 | 95/2000 |
| Ex. 4 | 3/62 | |
| Ex. 5 | | |
| Ex. 6 | | |
| Ex 7 | 5 | 24 |
| Ex. 8 | 0.3 | |
| Ex. 9 | 10 | |
| Ex. 10 | 215 | |
| Ex. 11 | 9 | >2000 |
| Ex. 12 | 16 | 49 |
| Ex. 13 | >1000 | |
| Ex 15 | | |
| Ex 16 | | |
| Ex 17 | 13 | 95 |
| Ex 18 | 25 | |
| Ex 19 | 8 | 34 |
| Ex 20 | 1000 | |
| Ex 21 | 18 | 80 |
| Ex 22 | 109 | |
| Ex 23 | | |
| Ex 24 | | |
| Ex 25 | 1000 | |
| Ex 26 | | |
| Ex 27 | >1000 | |
| Ex 28 | 11 | |
| Ex 29 | 414 | |
| Ex 30 | 9 | 25 |
| Ex 31 | 1 | 5.4 |
| Ex 32 | 10 | 51 |
| Ex 33 | | |
| Ex 34 | | |
| Ex 35 | 700 | |
| Ex 36 | | |
| Ex 37 | >1000 | |
| Ex 38 | 22 | |
| Ex 39 | 19 | |
| Ex 40 | | |

Table 3 of Experimental Results
(comparison compounds)

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| AA | 5.02 | 16 | 5 | 0.06 |
| BB | 10.32 | 169.81 | 8.24 | 20 |
| CC | 2427.7 | | 2680.9 | |
| DD | 109.44 | | 31.1 | 1000 |

-continued

Table 3 of Experimental Results (comparison compounds)

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] µg/Kg/d |
|---|---|---|---|---|
| EE | 429.99 | 891.16 | 341.25 | 1000 |
| FF | 3/1 | 57 | 0.28 | |

Table 4 of Experimental Results (comparison compounds)

| Test Cmpd.[1] | Kera. Prolif. IC$_{50}$ (nM) | IL-10 IC$_{50}$ (nM) |
|---|---|---|
| AA | 120 | 1.2 |
| BB | 10 | 28 |
| CC | — | — |
| DD | 1060 | |
| EE | | |
| FF | 103 | 0.5 |

Explanation of Table 5 and 6 Column Numerical Superscripts:

1. Test Compound numbers refer to the products of the corresponding Example Nos. that is, compounds within the scope of the invention 2. The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one "DD"=compound represented by the formula:

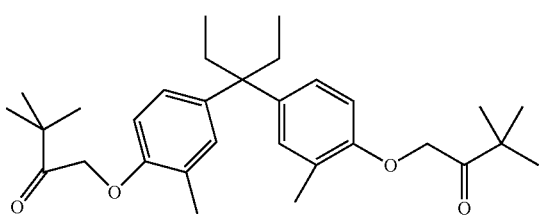

"EE"=compound represented by the formula:

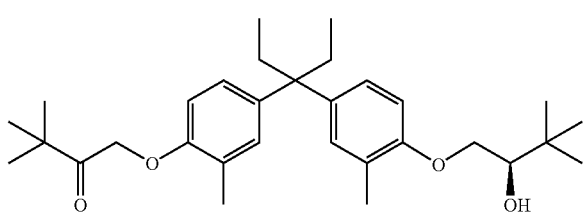

"FF"-=calcipotriol (structural formula below):

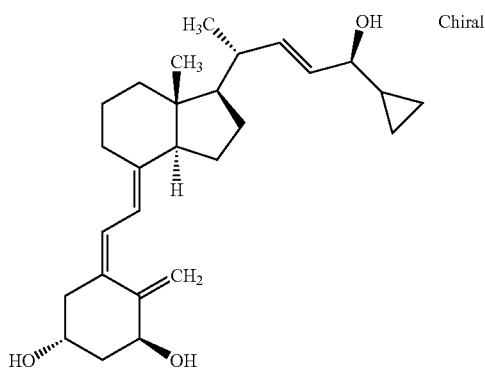

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR Heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (Osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 µg/kg/day. Preferred assay results are levels greater than 1000 µg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-10 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measure of the therapeutic index (bone efficacy vx. Hypervcalcemia) of compounds of the invention for treatment of osteoporosis is a numerical ratio calculated as follows:

Dose Threshold needed to induce hypercalcemia divided by Dose Threshold needed for bone efficacy An alternative measure of the therapeutic index (in vivo keratinocyte proliferation vs. hypercalcemia) of compounds of the invention for treatment of psoriasis is a numerical ratio calculated as follows:

Dose Threshold needed to induce hypercalcemia divided by Dose Threshold needed to induce keratinocyte proliferation For the above ratios, Dose Thresholds are determined from dose response curve data.

8. The CaT1 (Calcium Transporter 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Details of the Assay Methods:

(1) Materials and Method for RXR-VDR Heterodimerization Assay:

Transfection Method:
  FuGENE 6 Transfection Reagent (Roche Cat #1 814 443)

Growth Media:
  D-MEM High Glucose (Gibco BRL Cat #11054-020), 10% FBS, 1% antibiotic-antimycotic (Ab-Am)

FBS heat inactivated (Gibco BRL Cat #10092-147)

Ab-Am (Gibco BRL Cat #15240-062)

Cells:
  Grow SaOs-2 cells in T-152 $cm^2$ culture flasks in growth media.
  Keep the density at 5-6×$10^5$ cells/ml
  Passage cells 1:3 twice a week
  Add Trypsin EDTA (Gibco BRL Cat #25300-020) and incubate
  Resuspend cells in plating media and transfer into growth media.

Wash Media:
  HBSS Low Glucose Without Phenol Red (Gibco BRL Cat #14175-095), 1% Ab-Am Plating Media:
  D-MEM Low Glucose Without Phenol Red (Gibco BRL Cat #11054-020), 1% Ab-Am D-MEM Stripped FBS (Hyclone Cat#SH30068.03 Lot #AHM9371)

Ab-Am

Transfection/Treatment Media:
  D-MEM Low Glucose Without Phenol Red only

T-152 $cm^2$ Culture Flask:
  Use Corning Coastar T-152 $cm^2$ culture flask (Cat #430825) to grow the cells Flat well Plates:
  Use well plate to plate cells
  Use Deep well plate sterile to make up treatment media.

Luciferase Assay Reagent:
  Use Steady-Glo Luciferase Reagent from Promega (Cat #E2550) Consists of:

a. E2533 Assay Substrate, lyopholized product and b. E2543 Assay Buffer.
  Thaw at room temperature
  Store Cell Harvesting Aspirate media from culture flask, rinse cells with HBSS and aspirate.

Add trypsin and incubate.

When cells appear detached, resuspend cells in growth media.

Transfer into a new flask with fresh growth media for passaging the cells.

Plate well plates and two extra plates

A. Cell Count

Mix the cell suspension using pipette

Use Hematocytometer to count the cells

Load cell suspension onto the hemocytometer chamber

Count cells.

Plate Seeding:

Use plating media 10% Stripped FBS in D-MEM Low Glucose, Without Phenol Red, 1% Ab-Am Plate 14 plates @ 165 µl/well.

In sterile flask add cell suspension to plating media.

Mix.

Add cells/well.

Place the cells in the incubator.

Cells should be about 75% confluent prior to transfection.

DAY 2: Transfection

Step 1: DNA and Media

Add plain DMEM media to tubes for mixing the DNA

Add the Reporter gene pFR-LUC

Add the Gal4-RXR-DEF and VP16-VDR-LBD

Step 2: FuGENE and Media

Prepare plain DMEM media in a ubes for mixing FuGENE

Add FuGENE 6 Transfection Reagent

Incubate

Step 3: FuGENE, DNA and Media Complex

Add FuGENE Media complex from step 2 to DNA Media complex from step 1

Incubate

Step 4: FuGENE, DNA and Media Complex to-well plate

Add FuGENE-DNA-Media complex from step 3 to each plate

Incubate.

Day 3: Dosing

Treatment preparation

Allow for transfection time

Make a stock solution of the compounds in DMSO

Vortex until all the compounds has been dissolved.

Further dilute in D-MEM (Low Glucose—With out Phenol Red)

Add compounds in quadruplicate to give final volume

Incubate.

Day 4: Luciferase Assay

Read the plates after drug treatment

Remove part of media from all the wells and leave remainder

Add Steady-Glo Luciferase Reagent mixture/wells

Incubate

Count each well using a Luminescence counter, Top Count NXT by Packard

Set a delay between plates to reduce the background.

(2) Materials and Method for the Caco-2 Cell Assay:

Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal4-responsive reporter pFRLuc (150 ng, Stratagene, La Jolla Calif.) and the receptor expression vector pGal4-VDR-LBD (10 ng), along with Fugene 6 reagent (0.2 µl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for The OCN Promoter Assay:

The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J. Biol. Chem. 275, 999-1006, 2000). Confluent RG-15 cells maintained in DMEM/F-12 medium (3:1) containing 5% FBS, 300 µg/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 µl of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for the Mouse Hypercalcemia Assay:

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha$-25(OH)$_2$D$_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 µl keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 µl keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for Human IL-10 Induction Assay:

Isolation of Peripheral Blood Mononuclear Cells (PBMCs):
A. Collect 50 ml of human blood and dilute with media, RPMI-1640.
B. Prepare sterile tubes with ficol.
C. Add diluted blood to tubes.
D. Centrifuge.
E. Discard the top layer and collect the cells from middle layer.
F. Divide all cells into four tubes and add media.
G. Centrifuge.
H. Aspirate off media and resuspend.
I. Collect all cells
J. Centrifuge. at 1200 rpm for 10 minutes.
K. Resuspend in RPMI-1640 with 2% FBS and count cells
Stimulation of PBMC:
L. Prepare TPA in DMSO.
M. Dissolve PHA in water.
N. Plate TPA/PHA treated PBMCs in well plates.
O. Incubate.
Treatment:
P. Prepare all compound dilutions in plain RPMI-1640 media.
Q. Add diluted compound.
R. Incubate.
Sample Collection and Assay:
S. Remove all the cells by centrifugation and assay the supernatant for IL-10 by immunoassay.

1) T. Perform IL-1 assay using anti-human IL-10 antibody coated beads, as described by the manufacturer (Linco Research Inc., St. Charles, Mo.).

(8) CaT1 Assay

Human colon carcinoma, Caco-2 cells, maintained in DMEM (high glucose with 25 mM Hepes buffer; Invitrogen, Carlsbad, Calif.) supplemented with 10% fetal bovine serum (Invitrogen, Carlsbad, Calif.), are plated at 5500 cell per well in a 96-well plate in a total volume of 100 μl/well. The cells are kept in the 96-well plate for 6 days to differentiate them to small intestinal cells that express the calcium transporter, CaT1. On day 3 after plating, old media is removed and replaced with fresh media (150 μl/well). On day 6 the old media is removed and the cells are kept in treatment media (180 μl/well) that contained 10% charcoal stripped fetal bovine serum (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 μl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 μl quantitative RT-PCR reaction in a 384-well Taqman PCR plate consists of forward and reverse primers (900 nM), Taqman probe (200 nM), total RNA (4 μl form each well of the 96-well culture plate) and 10 μl of Taqman Universal PCR Master Mix (Roche Diagnostics, Indianapolis, Ind.). Reactions are incubated at 48° C. for 30 minutes, followed by 10 minutes at 95° C. and subjected to 40 cycles of PCR (95° C. for 15 seconds followed by 60° C. for 1 minute). GAPDH is used as an internal control and its primer and probe set are obtained commercially (Applied Biosystems, Foster City, Calif.).

We claim:

1. A compound represented by a formula below:

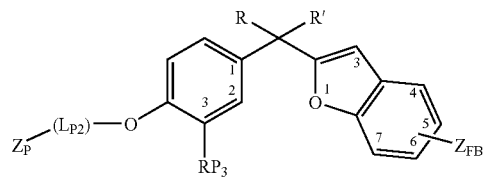

wherein
R and R' are independently $C_1$-$C_5$ alkyl, or together R and R' form a saturated carbocyclic ring having from 3 to 8 carbon atoms;
$RP_3$ is hydrogen or $C_1$-$C_5$ alkyl;
$(L_{P2})$ is

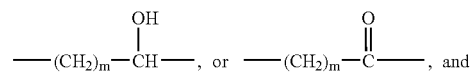

where m is 0, 1, or 2,
$Z_P$ is a branched $C_3$-$C_5$ alkyl;
$Z_{FB}$ is attached to the 5 or 6 position on the benzofuranyl ring and selected from:
—$CO_2H$
—$CO_2(C_1$-$C_5$ alkyl),
—$C(O)NMe_2$,
—$CO_2(C_1$-$C_5$ alkyl)-$NH_2$,
—C(O)NH—$CH_2$—C(O)OH,
—C(O)NH—$CH_2$—C(O)OMe,
—C(O)NH—$CH_2$—C(O)OEt,
—C(O)NH—$CH_2$—C(O)OiPr,
—C(O)NH—$CH_2$—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)$_2$-C(O)OH,
—C(O)NH—C(Me)$_2$-C(O)OMe,
—C(O)NH—C(Me)$_2$-C(O)OEt,
—C(O)NH—C(Me)$_2$-C(O)iPr,
—C(O)NH—C(Me)$_2$-C(O)tBu,
—C(O)NH-CMe(Et)-C(O)OH,
—C(O)NMe-$CH_2$—C(O)OH,
—C(O)NMe-$CH_2$—C(O)OMe,
—C(O)NMe-$CH_2$—C(O)OEt,
—C(O)NMe-$CH_2$—C(O)OiPr,
—C(O)NMe-$CH_2$—C(O)tBu,
—C(O)NMe-CH(Me)-C(O)OH,
C(O)—NH-5-tetrazolyl,
—O—$SO_2$—$C_1$-$C_5$ alkyl),
—$SO_2(C_1$-$C_5$ alkyl),
$CH_2S(O)_2Me$,
$CH_2S(O)_2Et$, and
$CH_2S(O)_2iPr$,
and a pharmaceutically acceptable salt thereof.

2. A compound selected from the following formulae (C1) to (C11) and (C13)-(C20) or a pharmaceutically acceptable salt thereof:

C1) 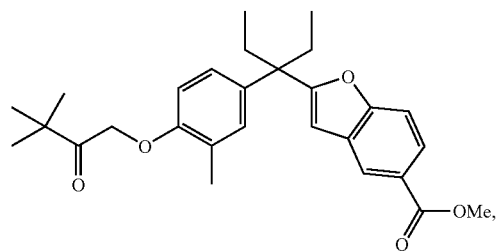
C2) 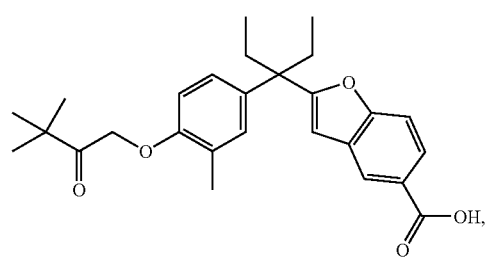
C3) 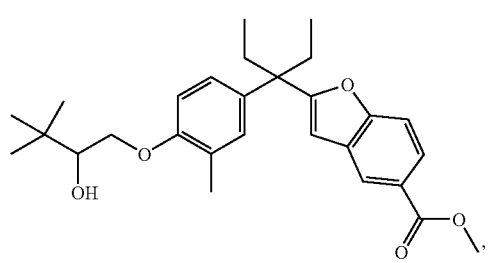
C4) 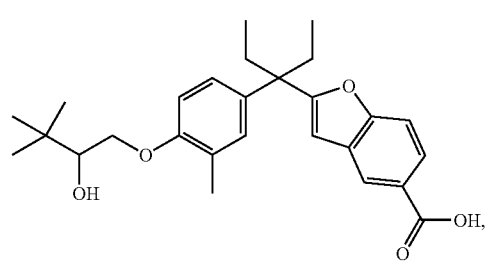
C5) 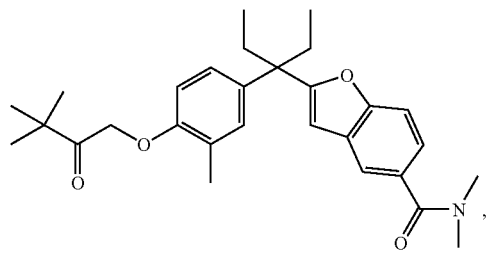
C6) 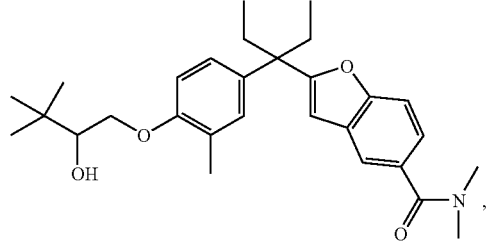
-continued
C7) 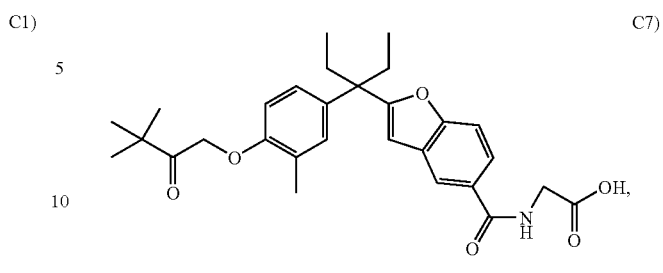
C8) 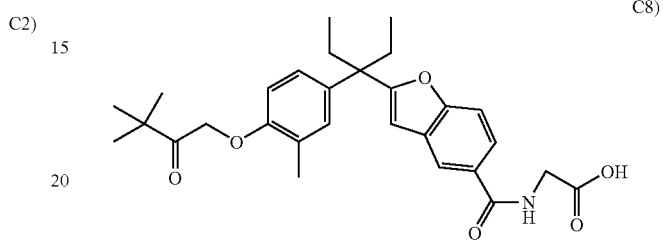
C9) 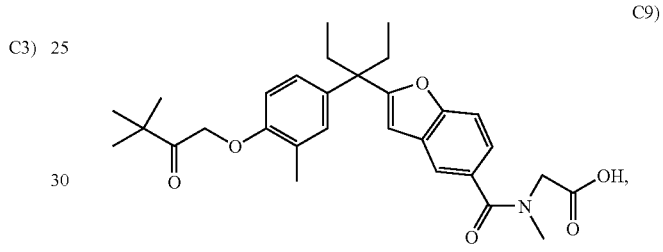
C10) 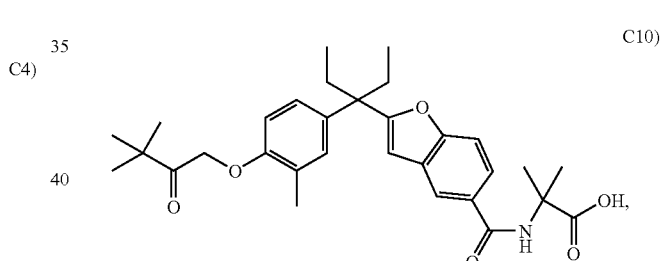
C11) 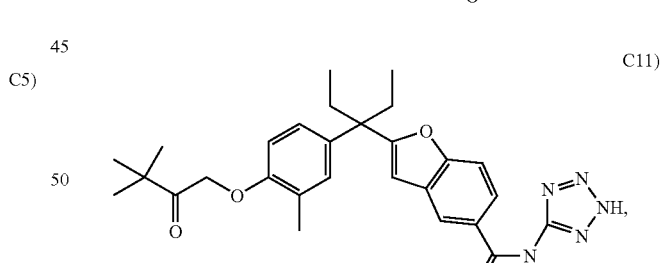
C13) 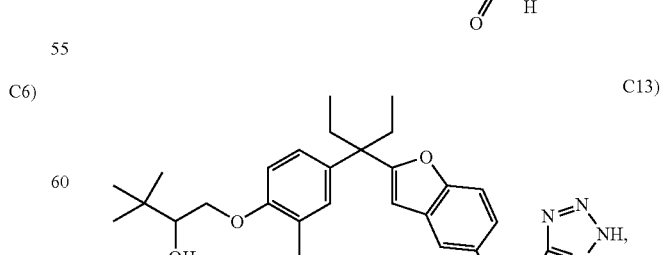

-continued
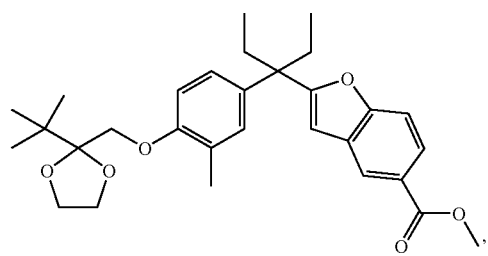
C14)
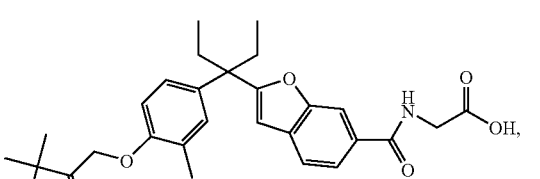
C20)
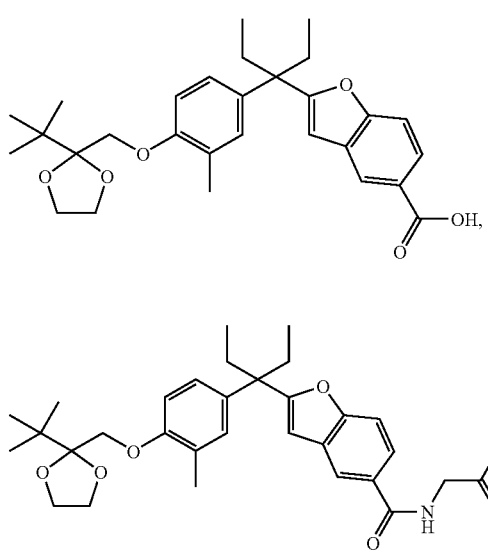
C-15)
C16)
C17)
3. A compound represented by the structural formula AA
(AA)
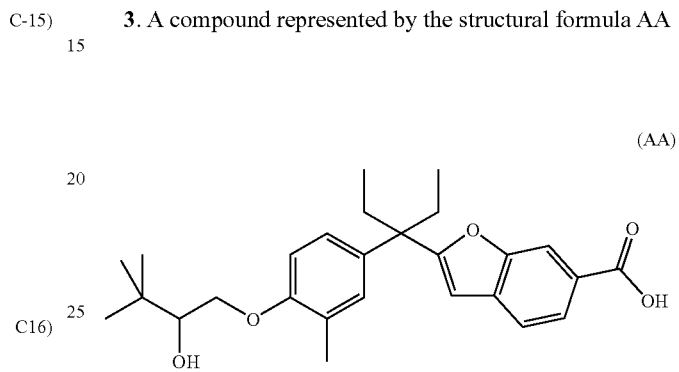
or a pharmaceutically acceptable salt thereof.
4. A compound selected from the group consisting of:
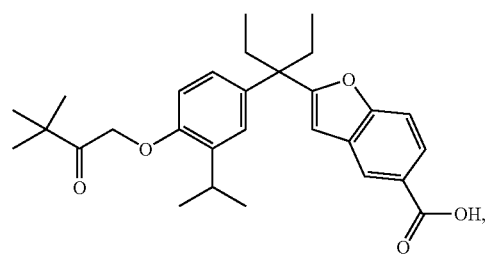
C17)
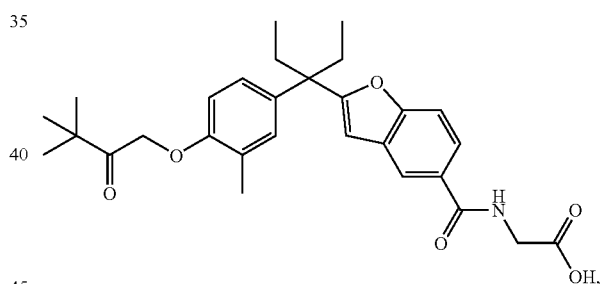
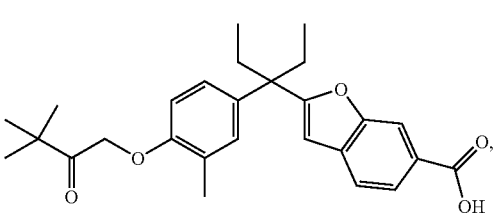
C18)
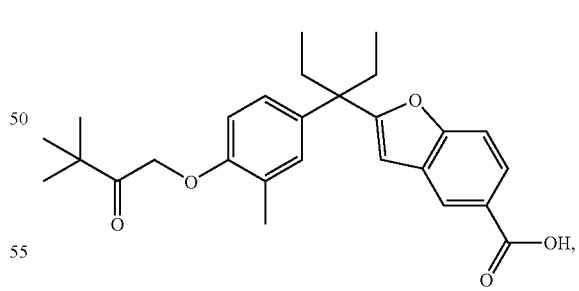
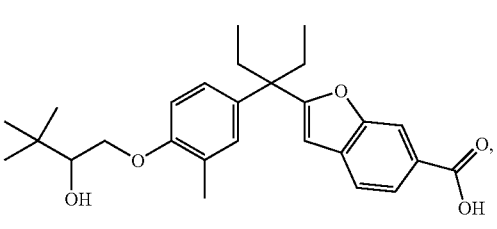
C19)
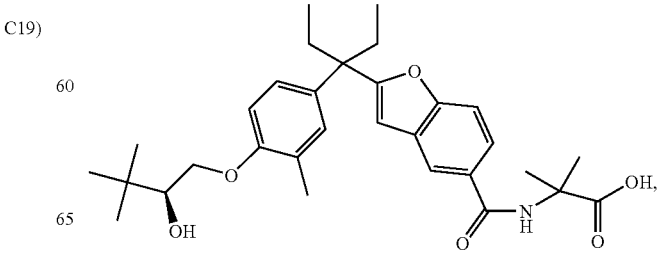

-continued
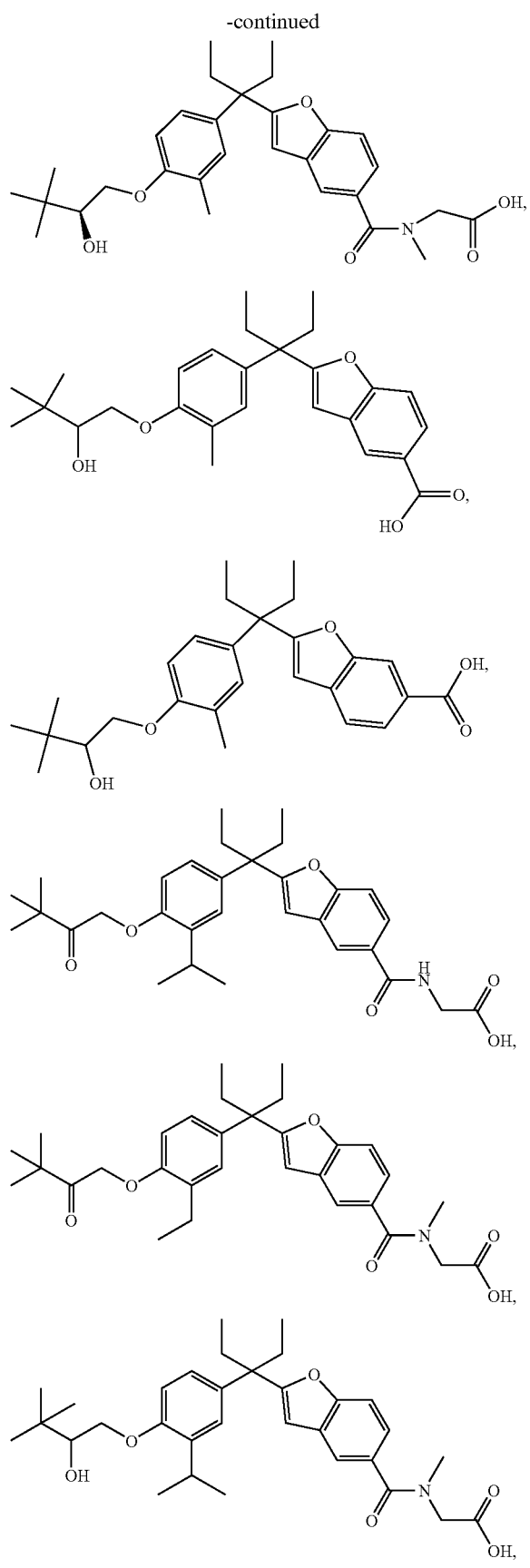
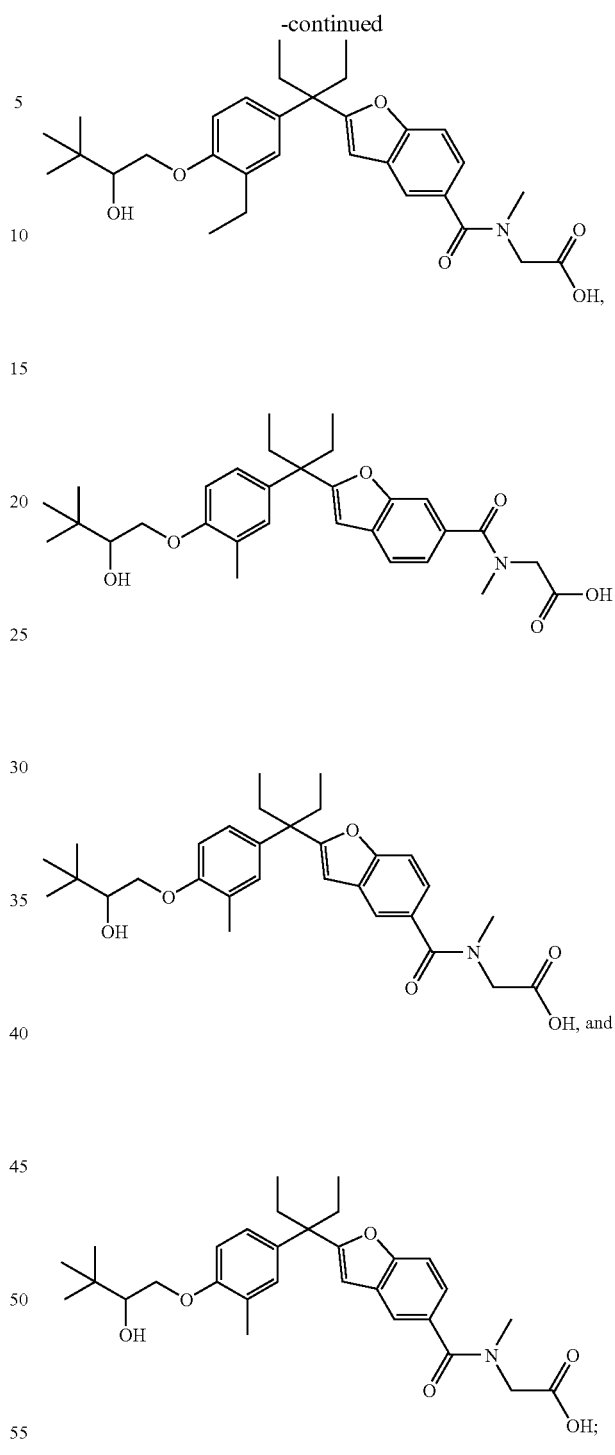
or a pharmaceutically acceptable salt thereof.
5. A compound according to claim 1 wherein ZFP includes a carboxyl group functionalized as a N,N-diethylglycolamido ester, or morpholinylethyl ester.
6. The salt derivative of the compound of claim 1 wherein the salt is sodium or potassium.

7. A compound represented by a formula:

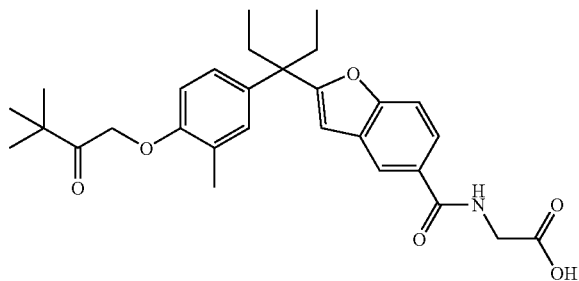

and pharmaceutically acceptable salts thereof.

8. A compound represented by a formula:

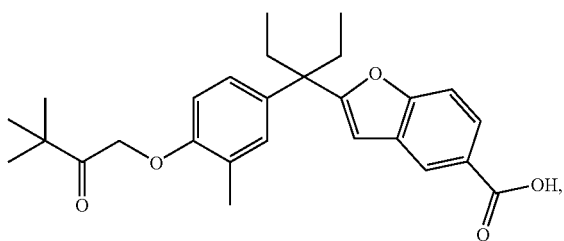

and pharmaceutically acceptable salts thereof.

9. A method of treating a mammal or alleviating the pathological effects of psoriasis in need thereof comprising administered a pharmaceutically effective amount of a compound of claim 7, or a pharmaceutically acceptable salt thereof.

10. A compound represented by a formula:

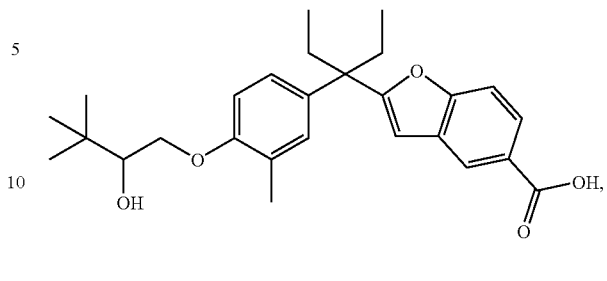

and pharmaceutically acceptable salts thereof.

11. A pharmaceutical formulation comprising the compound of claim 1 either with a pharmaceutically acceptable carrier or diluent.

12. A pharmaceutical formulation comprising the compound of claim 7 with a pharmaceutically acceptable carrier or diluent.

13. A pharmaceutical formulation comprising the compound of claim 8 with a pharmaceutically acceptable carrier or diluent.

14. A pharmaceutical formulation comprising the compound of claim 10 with a pharmaceutically acceptable carrier or diluent.

15. A method of treating a mammal for Osteoporosis or wherein the method comprises administering a pharmaceutically effective amount of at least one compound according to claim 1.

16. The method of claim 15 for the treatment of psoriasis.

17. The method of claim 15 for the treatment of osteoporosis.

* * * * *

UNITED STATES PATENT AND TRADEMARK OFFICE
CERTIFICATE OF CORRECTION

PATENT NO.        : 7,579,488 B2                                              Page 1 of 2
APPLICATION NO. : 10/579563
DATED             : August 25, 2009
INVENTOR(S)       : Jianliang Lu It is certified that error appears in the above-identified patent and that said Letters Patent is hereby corrected as shown below:

In Column 2 (Other Publications), Line 4, Delete "nonsecpsteroidal" and insert --nonsecosteroidal--.

In Claim 2, Column 140, Line 15-25 (Approx.), delete

" 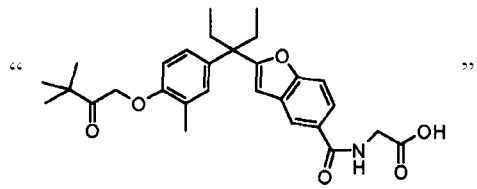 "

and insert

-- 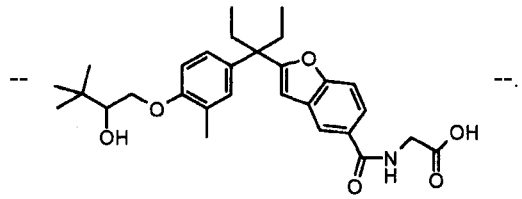 --.

Signed and Sealed this

Twenty-seventh Day of April, 2010

David J. Kappos
*Director of the United States Patent and Trademark Office*

CERTIFICATE OF CORRECTION (continued)
U.S. Pat. No. 7,579,488 B2

In Claim 2, Column 142, line 5-15, delete

" 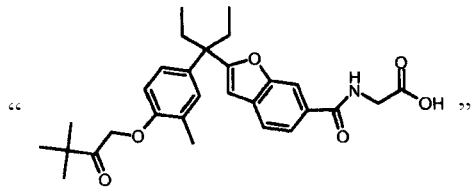 "

and insert

-- 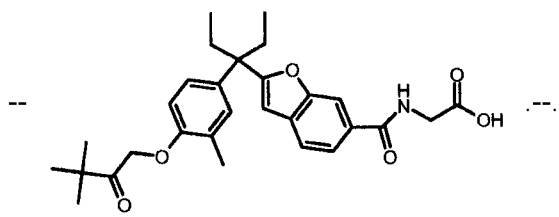 --.

In Claim 15, Column 144, line 27, after "or" insert --Psoriasis--.